US009410129B2

(12) United States Patent
Ranki et al.

(10) Patent No.: US 9,410,129 B2
(45) Date of Patent: Aug. 9, 2016

(54) RECOMBINANT SEROTYPE 5 (AD5) ADENOVIRAL VECTORS

(71) Applicant: Targovax Oy, Helsinki (FI)

(72) Inventors: Tuuli Ranki, Riihimaki (FI); Akseli Hemminki, Helsinki (FI); Vincenzo Cerullo, Helsinki (FI); Anniina Koski, Espoo (FI)

(73) Assignee: Targovax Oy, Helsinki (FI)

(*) Notice: Subject to any disclaimer, the term of this patent is extended or adjusted under 35 U.S.C. 154(b) by 0 days.

(21) Appl. No.: 14/359,141

(22) PCT Filed: Nov. 23, 2012

(86) PCT No.: PCT/FI2012/051162

§ 371 (c)(1),
(2) Date: May 19, 2014

(87) PCT Pub. No.: WO2013/076374

PCT Pub. Date: May 30, 2013

(65) Prior Publication Data

US 2015/0232811 A1 Aug. 20, 2015

Related U.S. Application Data

(60) Provisional application No. 61/563,634, filed on Nov. 25, 2011.

(30) Foreign Application Priority Data

Nov. 25, 2011 (FI) ..................................... 20116181

(51) Int. Cl.
*C12N 7/00* (2006.01)
*A61K 45/06* (2006.01)
*A61K 35/761* (2015.01)

(52) U.S. Cl.
CPC ................ *C12N 7/00* (2013.01); *A61K 35/761* (2013.01); *A61K 45/06* (2013.01); *C12N 2710/10021* (2013.01); *C12N 2710/10034* (2013.01)

(58) Field of Classification Search
None
See application file for complete search history.

(56) References Cited

U.S. PATENT DOCUMENTS

| | | | | |
|---|---|---|---|---|
| 6,339,068 | B1 * | 1/2002 | Krieg et al. ................. | 514/44 R |
| 2003/0138405 | A1 | 7/2003 | Fueyo et al. | |
| 2010/0166799 | A1 | 7/2010 | Hemminki et al. | |
| 2011/0053893 | A1 | 3/2011 | Wu et al. | |

FOREIGN PATENT DOCUMENTS

| | | |
|---|---|---|
| EP | 1990418 | 11/2008 |
| WO | 2009127666 | 1/2009 |
| WO | 2010072900 | 7/2010 |

OTHER PUBLICATIONS

Mastrangeli, et al. (1996) ""Sero-switch" adenovirus-mediated in vivo gene transfer: circumvention of anti-adenovirus humoral immune defenses against repeat adenovirus vector administration by changing the adenovirus serotype", Human Gene Therapy, 7(1): 79-87.*

Hoffman, et al. (2006) "Restriction of adenoviral replication to the transcriptional intersection of two different promoters for colorectal and pancreatic cancer treatment", Molecular Cancer Therapy, 5(2): 374-81.*

Pesonen, et al. (2012) "Integrin targeted oncolytic adenoviruses Ad5-D24-RGD and Ad5-RGD-D24-GMCSF for treatment of patients with advanced chemotherapy refractory solid tumors" International Journal of Cancer, 130: 1937-47.*

Kanerva, et al. (2002) "Targeting Adenovirus to the Serotype 3 Receptor Increases GeneTransfer Efficiency to Ovarian Cancer Cells", Clinical Cancer Research, 8: 275-80.*

Dmitriev, et al. (2002) "Engineering of Adenovirus Vectors Containing Heterologous Peptide Sequences in the C Terminus of Capsid Protein IX", Journal of Virology, 76(14): 6893-99.*

Kritz, et al. (2007) "Adenovirus 5 Fibers Mutated at the Putative HSPG-binding Site Show Restricted Retargeting with Targeting Peptides in the HI Loop", Molecular Therapy, 15(4): 741-49.*

Rein, et al. (2006) "Current developments in adenovirus-based cancer gene therapy" Future Oncology, 2(1): 137-43.*

Applicant's publication Cerullo, et al. (2012) "An Oncolytic Adenovirus Enhanced for Toll-like Receptor 9 Stimulation Increases Antitumor Immune Responses and Tumor Clearance", Molecular Therapy, 20(11); 2076-86 is made of record.*

Diaconu et al. "Immune Response is an Important Aspect of the Antitumor Effect Produced by a CD40L-Encoding Oncolytic Adenovirus", *Cancer Research*, vol. 72, No. 9, Mar. 6, 2012, pp. 2327-2338.

Tillman et al., "Adenoviral vectors targeted to CD40 enhance the efficacy of dendritic cell-based vaccination against human papillomavirus 16-induced tumor cells in a murine model", *Cancer Research*, American Association for Cancer Research, US, vol. 60, No. 19, Oct. 1, 2000, pp. 5456-5463.

Iacobelli-Martinez M. et al., "Preferential Activation of Toll-Like Receptor Nine by CD46-Utilizing Adenoviruses", *Journal of Virology*, vol. 81, No. 3, (Nov. 15, 2006), pp. 1305-1312.

Lei N. et al., "An oncolytic adenovirus expressing granulocyte macrophage colony-stimulating factor shows improved specificity and efficacy for treating human solid tumors", *Cancer Gene Therapy*, vol. 16, No. 1, (Aug. 1, 2008), pp. 33-43.

Wong, Han Hsi et al., "Oncolytic Viruses for Cancer Therapy: Overcoming the Obstacles", *Viruses*, vol. 2, No. 1, (Jan. 11, 2010), pp. 78-106.

Supplementary European Search Report issued in EP12852023 and mailed Jun. 22, 2015.

Elmetwali, et al. (2010) "CD40 ligand induced cytotoxicity in carcinoma cells is enhanced by inhibition of metalloproteinase cleavage and delivery via a conditionally-replicating adenovirus", Molecular Cancer, 9: 52, pp. 1-12.

Koski, et al. (2010) "Treatment of Cancer Patients With a Serotype 5/3 Chimeric Oncolytic Adenovirus Expressing GMCSF", Molecular Therapy, 18(10): 1874-84.

Stoff-Khalili, et al. (2006) "Combining high selectivity of replication via CSCR4 promoter with fiber chimerism for effective adenoviral oncolysis in breast cancer", International Journal of Cancer, 120: 935-41.

* cited by examiner

*Primary Examiner* — Robert M Kelly

(74) *Attorney, Agent, or Firm* — Cooley LLP; Matthew Pavao; Ivor Elrifi

(57) ABSTRACT

The invention relates to oncolytic adenovirus vectors and their uses in cancer therapy. The adenovirus vectors according to the invention have superior safety properties and have effective therapeutic activity. A production method for the inventive adenoviruses is also disclosed. The adenovirus vectors are useful in cancer therapy.

29 Claims, 34 Drawing Sheets

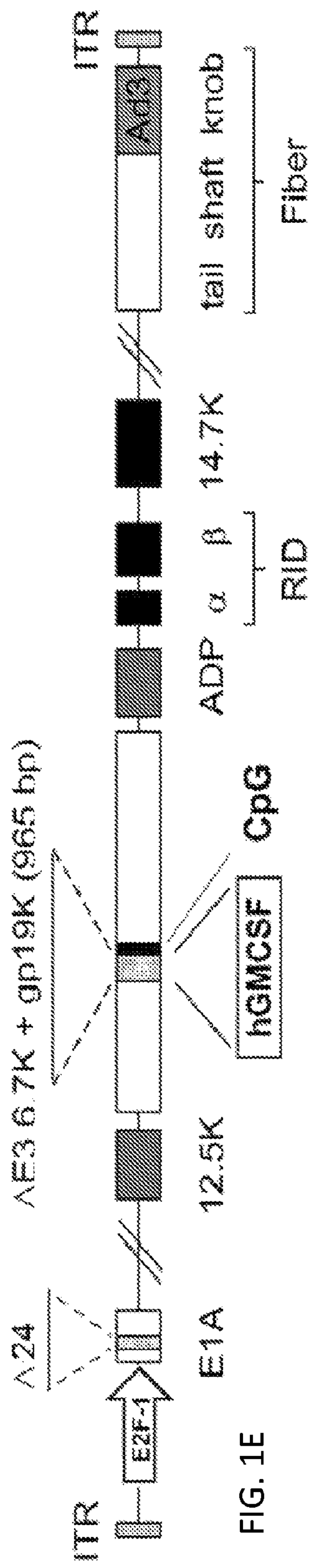
FIG. 1E
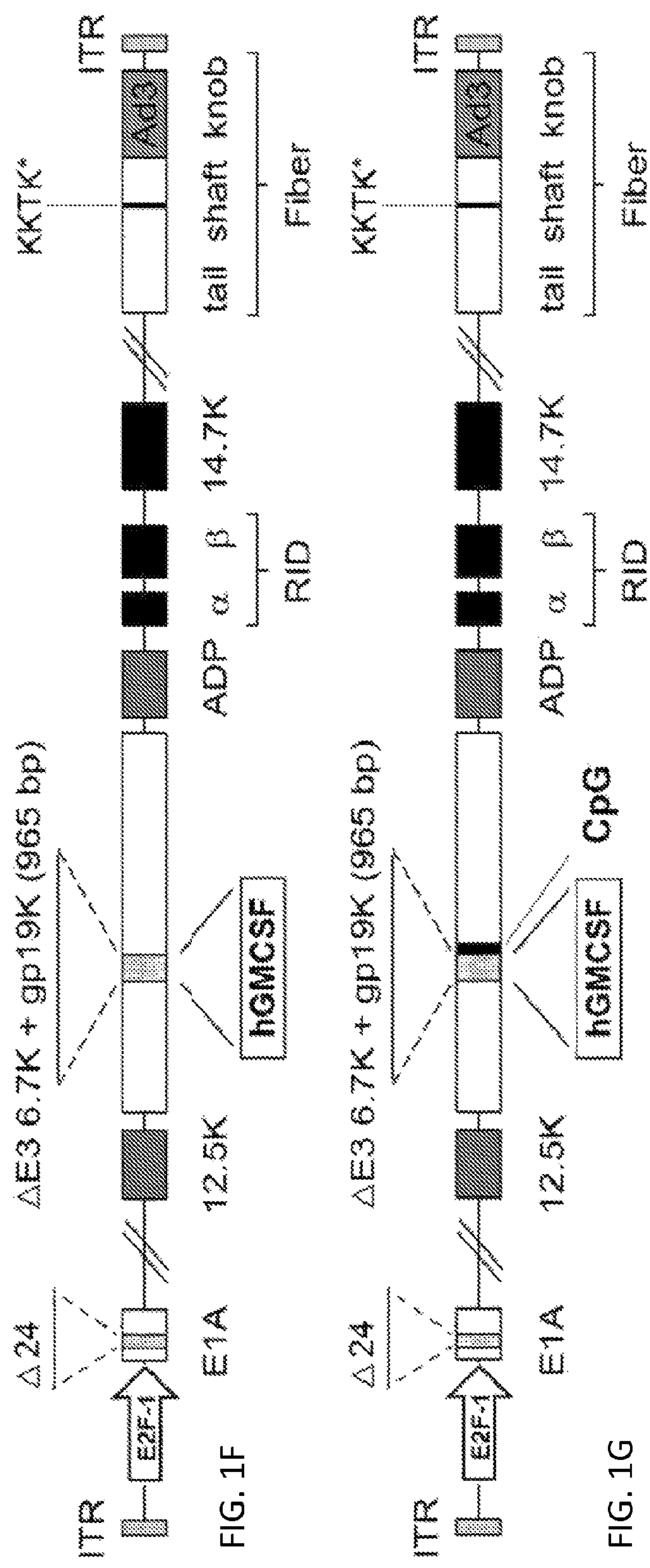
FIG. 1F
FIG. 1G

Change from pre-treatment value (%)
O314: Ca12-5
4
9
H344: CEA
3
7
10
R319: CEA
3
8
10
H344: Ca19-9
3
7
10
O351: Ca12-5
3
R342: Ca15-3
3
Weeks post-treatment

C

D

A

B

SEQUENCE LISTING

```
<160> NUMBER OF SEQ ID NOS: 29

<210> SEQ ID NO 1
<211> LENGTH: 36834
<212> TYPE: DNA
<213> ORGANISM: Artificial Sequence
<220> FEATURE:
<223> OTHER INFORMATION: The nucleotide sequence encoding the virus
      CGTG-601
<220> FEATURE:
<221> NAME/KEY: misc_feature
<222> LOCATION: (34564)..(34564)
<223> OTHER INFORMATION: n is a, c, g, or t

<400> SEQUENCE: 1

taacatcatc aataatatac cttattttgg attgaagcca atatgataat gagggggtgg      60

agtttgtgac gtggcgcggg gcgtgggaac ggggcgggtg acgtagtagt gtggcggaag     120

tgtgatgttg caagtgtggc ggaacacatg taagcgacgg atgtggcaaa agtgacgttt     180

ttggtgtgcg ccggtgtaca caggaagtga caattttcgc gcggttttag gcggatgttg     240

tagtaaattt gggcgtaacc gagtaagatt tggccatttt cgcgggaaaa ctgaataaga     300

ggaagtgaaa tctgaataat tttgtgttac tcatagcgcg taatactggt accgcggccg     360

ctggtaccat ccggacaaag cctgcgcgcg ccccgccccg ccattggccg taccgccccg     420

cgccgccgcc ccatcccgcc cctcgccgcc gggtccggcg cgttaaagcc aataggaacc     480

gccgccgttg ttcccgtcac ggccggggca gccaattgtg gcggcgctcg gcggctcgtg     540

gctctttcgc ggcaaaaagg atttggcgcg taaaagtggc cgggactttg caggcagcgg     600

cggccggggg cggagcggga tcgagccctc gccctcgagc tagaagcttg ttttctcctc     660

cgagccgctc cgacaccggg actgaaaatg agacatatta tctgccacgg aggtgttatt     720

accgaagaaa tggccgccag tcttttggac cagctgatcg aagaggtact ggctgataat     780

cttccacctc ctagccattt tgaaccacct acccttcacg aactgtatga tttagacgtg     840

acggccccg aagatcccaa cgaggaggcg gtttcgcaga tttttcccga ctctgtaatg     900

ttggcggtgc aggaagggat tgacttactc acttttccgc cggcgcccgg ttctccggag     960

ccgcctcacc tttcccggca gcccgagcag ccggagcaga gagccttggg tccggtttct    1020

atgccaaacc ttgtaccgga ggtgatcgat ccacccagtg acgacgagga tgaagagggt    1080

gaggagtttg tgttagatta tgtggagcac ccccgggcacg gttgcaggtc ttgtcattat    1140
```

-continued

```
caccggagga atacgggggga cccagatatt atgtgttcgc tttgctatat gaggacctgt   1200
ggcatgtttg tctacagtaa gtgaaaatta tgggcagtgg gtgatagagt ggtgggtttg   1260
gtgtggtaat ttttttttta atttttacag ttttgtggtt taaagaattt tgtattgtga   1320
tttttttaaa aggtcctgtg tctgaacctg agcctgagcc cgagccagaa ccggagcctg   1380
caagacctac ccgccgtcct aaaatggcgc ctgctatcct gagacgcccg acatcacctg   1440
tgtctagaga atgcaatagt agtacggata gctgtgactc cggtccttct aacacacctc   1500
ctgagataca cccggtggtc ccgctgtgcc ccattaaacc agttgccgtg agagttggtg   1560
ggcgtcgcca ggctgtggaa tgtatcgagg acttgcttaa cgagcctggg caacctttgg   1620
acttgagctg taaacgcccc aggccataag gtgtaaacct gtgattgcgt gtgtggttaa   1680
cgcctttgtt tgctgaatga gttgatgtaa gtttaataaa gggtgagata atgtttaact   1740
tgcatggcgt gttaaatggg gcggggctta aagggtatat aatgcgccgt gggctaatct   1800
tggttacatc tgacctcatg gaggcttggg agtgtttgga agatttttct gctgtgcgta   1860
acttgctgga acagagctct aacagtacct cttggttttg gaggtttctg tggggctcat   1920
cccaggcaaa gttagtctgc agaattaagg aggattacaa gtgggaattt gaagagcttt   1980
tgaaatcctg tggtgagctg tttgattctt tgaatctggg tcaccaggcg cttttccaag   2040
agaaggtcat caagactttg gatttttcca caccggggcg cgctgcggct gctgttgctt   2100
ttttgagttt tataaaggat aaatggagcg aagaaaccca tctgagcggg gggtacctgc   2160
tggattttct ggccatgcat ctgtggagag cggttgtgag acacaagaat cgcctgctac   2220
tgttgtcttc cgtccgcccg gcgataatac cgacggagga gcagcagcag cagcaggagg   2280
aagccaggcg gcggcggcag gagcagagcc catggaaccc gagagccggc ctggaccctc   2340
gggaatgaat gttgtacagg tggctgaact gtatccagaa ctgagacgca ttttgacaat   2400
tacagaggat gggcaggggc taaagggggt aaagagggag cggggggctt gtgaggctac   2460
agaggaggct aggaatctag cttttagctt aatgaccaga caccgtcctg agtgtattac   2520
ttttcaacag atcaaggata attgcgctaa tgagcttgat ctgctggcgc agaagtattc   2580
catagagcag ctgaccactt actggctgca gccaggggat gattttgagg aggctattag   2640
ggtatatgca aaggtggcac ttaggccaga ttgcaagtac aagatcagca aacttgtaaa   2700
tatcaggaat tgttgctaca tttctgggaa cggggccgag gtggagatag atacggagga   2760
tagggtggcc tttagatgta gcatgataaa tatgtggccg ggggtgcttg gcatggacgg   2820
ggtggttatt atgaatgtaa ggtttactgg ccccaatttt agcggtacgg ttttcctggc   2880
caataccaac cttatcctac acggtgtaag cttctatggg tttaacaata cctgtgtgga   2940
agcctggacc gatgtaaggg ttcggggctg tgccttttac tgctgctgga agggggtggt   3000
gtgtcgcccc aaaagcaggg cttcaattaa gaaatgcctc tttgaaaggt gtaccttggg   3060
tatcctgtct gagggtaact ccagggtgcg ccacaatgtg gcctccgact gtggttgctt   3120
catgctagtg aaaagcgtgg ctgtgattaa gcataacatg gtatgtggca actgcgagga   3180
cagggcctct cagatgctga cctgctcgga cggcaactgt cacctgctga agaccattca   3240
cgtagccagc cactctcgca aggcctggcc agtgtttgag cataacatac tgacccgctg   3300
ttccttgcat ttgggtaaca ggaggggggt gttcctacct taccaatgca atttgagtca   3360
cactaagata ttgcttgagc ccgagagcat gtccaaggtg aacctgaacg gggtgtttga   3420
catgaccatg aagatctgga aggtgctgag gtacgatgag acccgcacca ggtgcagacc   3480
ctgcgagtgt ggcggtaaac atattaggaa ccagcctgtg atgctggatg tgaccgagga   3540
```

```
gctgaggccc gatcacttgg tgctggcctg cacccgcgct gagtttggct ctagcgatga   3600
agatacagat tgaggtactg aaatgtgtgg gcgtggctta agggtgggaa agaatatata   3660
aggtgggggt cttatgtagt tttgtatctg ttttgcagca gccgccgccg ccatgagcac   3720
caactcgttt gatggaagca ttgtgagctc atatttgaca acgcgcatgc ccccatgggc   3780
cggggtgcgt cagaatgtga tgggctccag cattgatggt cgccccgtcc tgcccgcaaa   3840
ctctactacc ttgacctacg agaccgtgtc tggaacgccg ttggagactg cagcctccgc   3900
cgccgcttca gccgctgcag ccaccgcccg cgggattgtg actgactttg ctttcctgag   3960
cccgcttgca agcagtgcag cttcccgttc atccgcccgc gatgacaagt tgacggctct   4020
tttggcacaa ttggattctt tgacccggga acttaatgtc gtttctcagc agctgttgga   4080
tctgcgccag caggtttctg ccctgaaggc ttcctcccct cccaatgcgg tttaaaacat   4140
aaataaaaaa ccagactctg tttggatttg gatcaagcaa gtgtcttgct gtctttattt   4200
aggggttttg cgcgcgcggt aggcccggga ccagcggtct cggtcgttga gggtcctgtg   4260
tattttttcc aggacgtggt aaaggtgact ctggatgttc agatacatgg gcataagccc   4320
gtctctgggg tggaggtagc accactgcag agcttcatgc tgcggggtgg tgttgtagat   4380
gatccagtcg tagcaggagc gctgggcgtg gtgcctaaaa atgtctttca gtagcaagct   4440
gattgccagg ggcaggccct tggtgtaagt gtttacaaag cggttaagct gggatgggtg   4500
catacgtggg gatatgagat gcatcttgga ctgtattttt aggttggcta tgttcccagc   4560
catatccctc cggggattca tgttgtgcag aaccaccagc acagtgtatc cggtgcactt   4620
gggaaatttg tcatgtagct tagaaggaaa tgcgtggaag aacttggaga cgcccttgtg   4680
acctccaaga ttttccatgc attcgtccat aatgatggca atgggcccac gggcggcggc   4740
ctgggcgaag atatttctgg gatcactaac gtcatagttg tgttccagga tgagatcgtc   4800
ataggccatt tttacaaagc gcgggcggag ggtgccagac tgcggtataa tggttccatc   4860
cggcccaggg gcgtagttac cctcacagat ttgcatttcc cacgctttga gttcagatgg   4920
ggggatcatg tctacctgcg gggcgatgaa gaaaacggtt tccggggtag gggagatcag   4980
ctgggaagaa agcaggttcc tgagcagctg cgacttaccg cagccggtgg gcccgtaaat   5040
cacacctatt accgggtgca actggtagtt aagagagctg cagctgccgt catccctgag   5100
caggggggcc acttcgttaa gcatgtccct gactcgcatg ttttccctga ccaaatccgc   5160
cagaaggcgc tcgccgccca gcgatagcag ttcttgcaag gaagcaaagt ttttcaacgg   5220
tttgagaccg tccgccgtag gcatgctttt gagcgtttga ccaagcagtt ccaggcggtc   5280
ccacagctcg gtcacctgct ctacggcatc tcgatccagc atatctcctc gtttcgcggg   5340
ttggggcggc tttcgctgta cggcagtagt cggtgctcgt ccagacgggc cagggtcatg   5400
tctttccacg ggcgcagggt cctcgtcagc gtagtctggg tcacggtgaa ggggtgcgct   5460
ccgggctgcg cgctggccag ggtgcgcttg aggctggtcc tgctggtgct gaagcgctgc   5520
cggtcttcgc cctgcgcgtc ggccaggtag catttgacca tggtgtcata gtccagcccc   5580
tccgcggcgt ggcccttggc gcgcagcttg cccttggagg aggcgccgca cgaggggcag   5640
tgcagacttt tgagggcgta gagcttgggc gcgagaaata ccgattccgg ggagtaggca   5700
tccgcgccgc aggccccgca gacggtctcg cattccacga gccaggtgag ctctggccgt   5760
tcggggtcaa aaaccaggtt tcccccatgc tttttgatgc gtttcttacc tctggtttcc   5820
atgagccggt gtccacgctc ggtgacgaaa aggctgtccg tgtccccgta tacagacttg   5880
agaggcctgt cctcgagcgg tgttccgcgg tcctcctcgt atagaaactc ggaccactct   5940
```

-continued

```
gagacaaagg ctcgcgtcca ggccagcacg aaggaggcta agtgggaggg gtagcggtcg   6000
ttgtccacta gggggtccac tcgctccagg gtgtgaagac acatgtcgcc ctcttcggca   6060
tcaaggaagg tgattggttt gtaggtgtag gccacgtgac cgggtgttcc tgaagggggg   6120
ctataaaagg gggtgggggc gcgttcgtcc tcactctctt ccgcatcgct gtctgcgagg   6180
gccagctgtt ggggtgagta ctccctctga aaagcgggca tgacttctgc gctaagattg   6240
tcagtttcca aaaacgagga ggatttgata ttcacctggc ccgcggtgat gcctttgagg   6300
gtggccgcat ccatctggtc agaaaagaca atctttttgt tgtcaagctt ggtggcaaac   6360
gacccgtaga gggcgttgga cagcaacttg gcgatggagc gcagggtttg gtttttgtcg   6420
cgatcggcgc gctccttggc cgcgatgttt agctgcacgt attcgcgcgc aacgcaccgc   6480
cattcgggaa agacggtggt gcgctcgtcg ggcaccaggt gcacgcgcca accgcggttg   6540
tgcagggtga caaggtcaac gctggtggct acctctccgc gtaggcgctc gttggtccag   6600
cagaggcggc cgcccttgcg cgagcagaat ggcggtaggg ggtctagctg cgtctcgtcc   6660
ggggggtctg cgtccacggt aaagaccccg ggcagcaggc gcgcgtcgaa gtagtctatc   6720
ttgcatcctt gcaagtctag cgcctgctgc catgcgcggg cggcaagcgc gcgctcgtat   6780
gggttgagtg gggaccccca tggcatgggg tgggtgagcg cggaggcgta catgccgcaa   6840
atgtcgtaaa cgtagagggg ctctctgagt attccaagat atgtagggta gcatcttcca   6900
ccgcggatgc tggcgcgcac gtaatcgtat agttcgtgcg agggagcgag gaggtcggga   6960
ccgaggttgc tacgggcggg ctgctctgct cggaagacta tctgcctgaa gatggcatgt   7020
gagttggatg atatggttgg acgctggaag acgttgaagc tggcgtctgt gagacctacc   7080
gcgtcacgca cgaaggaggc gtaggagtcg cgcagcttgt tgaccagctc ggcggtgacc   7140
tgcacgtcta gggcgcagta gtccagggtt tccttgatga tgtcatactt atcctgtccc   7200
ttttttttcc acagctcgcg gttgaggaca aactcttcgc ggtctttcca gtactcttgg   7260
atcggaaacc cgtcggcctc cgaacggtaa gagcctagca tgtagaactg gttgacggcc   7320
tggtaggcgc agcatccctt ttctacgggt agcgcgtatg cctgcgcggc cttccggagc   7380
gaggtgtggg tgagcgcaaa ggtgtccctg accatgactt tgaggtactg gtatttgaag   7440
tcagtgtcgt cgcatccgcc ctgctcccag agcaaaaagt ccgtgcgctt tttggaacgc   7500
ggatttggca gggcgaaggt gacatcgttg aagagtatct ttcccgcgcg aggcataaag   7560
ttgcgtgtga tgcggaaggg tcccggcacc tcggaacggt tgttaattac ctgggcggcg   7620
agcacgatct cgtcaaagcc gttgatgttg tggcccacaa tgtaaagttc caagaagcgc   7680
gggatgccct tgatggaagg caatttttta agttcctcgt aggtgagctc ttcaggggag   7740
ctgagcccgt gctctgaaag ggcccagtct gcaagatgag ggttggaagc gacgaatgag   7800
ctccacaggt cacgggccat tagcatttgc aggtggtcgc gaaaggtcct aaactggcga   7860
cctatggcca tttttctgg ggtgatgcag tagaaggtaa gcgggtcttg ttcccagcgg   7920
tcccatccaa ggttcgcggc taggtctcgc gcggcagtca ctagaggctc atctccgccg   7980
aacttcatga ccagcatgaa gggcacgagc tgcttcccaa aggcccccat ccaagtatag   8040
gtctctacat cgtaggtgac aaagagacgc tcggtgcgag gatgcgagcc gatcgggaag   8100
aactggatct cccgccacca attggaggag tggctattga tgtggtgaaa gtagaagtcc   8160
ctgcgacggg ccgaacactc gtgctggctt ttgtaaaaac gtgcgcagta ctggcagcgg   8220
tgcacgggct gtacatcctg cacgaggttg acctgacgac cgcgcacaag gaagcagagt   8280
gggaatttga gcccctcgcc tggcgggttt ggctggtggt cttctacttc ggctgcttgt   8340
```

```
ccttgaccgt ctggctgctc gaggggagtt acggtggatc ggaccaccac gccgcgcgag   8400
cccaaagtcc agatgtccgc gcgcggcggt cggagcttga tgacaacatc gcgcagatgg   8460
gagctgtcca tggtctggag ctcccgcggc gtcaggtcag gcgggagctc ctgcaggttt   8520
acctcgcata gacgggtcag ggcgcgggct agatccaggt gatacctaat ttccaggggc   8580
tggttggtgg cggcgtcgat ggcttgcaag aggccgcatc cccgcggcgc gactacggta   8640
ccgcgcggcg ggcggtgggc cgcgggggtg tccttggatg atgcatctaa aagcggtgac   8700
gcgggcgagc cccggaggt aggggggct ccggacccgc cgggagaggg ggcaggggca   8760
cgtcggcgcc gcgcgcgggc aggagctggt gctgcgcgcg taggttgctg gcgaacgcga   8820
cgacgcggcg gttgatctcc tgaatctggc gcctctgcgt gaagacgacg ggcccggtga   8880
gcttgagcct gaaagagagt tcgacagaat caatttcggt gtcgttgacg gcggcctggc   8940
gcaaaatctc ctgcacgtct cctgagttgt cttgataggc gatctcggcc atgaactgct   9000
cgatctcttc ctcctggaga tctccgcgtc cggctcgctc cacggtggcg gcgaggtcgt   9060
tggaaatgcg ggccatgagc tgcgagaagg cgttgaggcc tccctcgttc cagacgcggc   9120
tgtagaccac gcccccttcg gcatcgcggg cgcgcatgac cacctgcgcg agattgagct   9180
ccacgtgccg ggcgaagacg gcgtagtttc gcaggcgctg aaagaggtag ttgagggtgg   9240
tggcggtgtg ttctgccacg aagaagtaca taacccagcg tcgcaacgtg gattcgttga   9300
tatcccccaa ggcctcaagg cgctccatgg cctcgtagaa gtccacggcg aagttgaaaa   9360
actgggagtt gcgcgccgac acggttaact cctcctccag aagacggatg agctcggcga   9420
cagtgtcgcg cacctcgcgc tcaaaggcta caggggcctc ttcttcttct tcaatctcct   9480
cttccataag ggcctcccct tcttcttctt ctggcggcgg tgggggaggg gggacacggc   9540
ggcgacgacg gcgcaccggg aggcggtcga caaagcgctc gatcatctcc ccgcggcgac   9600
ggcgcatggt ctcggtgacg gcgcggccgt tctcgcgggg gcgcagttgg aagacgccgc   9660
ccgtcatgtc ccggttatgg gttggcgggg ggctgccatg cggcagggat acggcgctaa   9720
cgatgcatct caacaattgt tgtgtaggta ctccgccgcc gagggacctg agcgagtccg   9780
catcgaccgg atcggaaaac ctctcgagaa aggcgtctaa ccagtcacag tcgcaaggta   9840
ggctgagcac cgtggcgggc ggcagcgggc ggcggtcggg gttgtttctg gcggaggtgc   9900
tgctgatgat gtaattaaag taggcggtct tgagacggcg gatggtcgac agaagcacca   9960
tgtccttggg tccggcctgc tgaatgcgca ggcggtcggc catgccccag gcttcgtttt  10020
gacatcggcg caggtctttg tagtagtctt gcatgagcct ttctaccggc acttcttctt  10080
ctccttcctc ttgtcctgca tctcttgcat ctatcgctgc ggcggcggcg gagtttggcc  10140
gtaggtggcg ccctcttcct cccatgcgtg tgaccccgaa gcccctcatc ggctgaagca  10200
gggctaggtc ggcgacaacg cgctcggcta atatggcctg ctgcacctgc gtgagggtag  10260
actggaagtc atccatgtcc acaaagcggt ggtatgcgcc cgtgttgatg gtgtaagtgc  10320
agttggccat aacggaccag ttaacggtct ggtgacccgg ctgcgagagc tcggtgtacc  10380
tgagacgcga gtaagccctc gagtcaaata cgtagtcgtt gcaagtccgc accaggtact  10440
ggtatcccac caaaaagtgc ggcggcggct ggcggtagag gggccagcgt agggtggccg  10500
gggctccggg ggcgagatct tccaacataa ggcgatgata tccgtagatg tacctggaca  10560
tccaggtgat gccggcggcg gtggtggagg cgcgcggaaa gtcgcggacg cggttccaga  10620
tgttgcgcag cggcaaaaag tgctccatgg tcgggacgct ctggccggtc aggcgcgcgc  10680
aatcgttgac gctctagacc gtgcaaaagg agagcctgta agcgggcact cttccgtggt  10740
```

```
ctggtggata aattcgcaag ggtatcatgg cggacgaccg gggttcgagc cccgtatccg  10800
gccgtccgcc gtgatccatg cggttaccgc ccgcgtgtcg aacccaggtg tgcgacgtca  10860
gacaacgggg gagtgctcct tttggcttcc ttccaggcgc ggcggctgct gcgctagctt  10920
ttttggccac tggccgcgcg cagcgtaagc ggttaggctg gaaagcgaaa gcattaagtg  10980
gctcgctccc tgtagccgga gggttatttt ccaagggttg agtcgcggga cccccggttc  11040
gagtctcgga ccggccggac tgcggcgaac gggggtttgc ctccccgtca tgcaagaccc  11100
cgcttgcaaa ttcctccgga aacagggacg agcccctttt ttgcttttcc cagatgcatc  11160
cggtgctgcg gcagatgcgc ccccctcctc agcagcggca agagcaagag cagcggcaga  11220
catgcagggc accctcccct cctcctaccg cgtcaggagg ggcgacatcc gcggttgacg  11280
cggcagcaga tggtgattac gaacccccgc ggcgccgggc ccggcactac ctggacttgg  11340
aggagggcga gggcctggcg cggctaggag cgccctctcc tgagcggtac ccaagggtgc  11400
agctgaagcg tgatacgcgt gaggcgtacg tgccgcggca gaacctgttt cgcgaccgcg  11460
agggagagga gcccgaggag atgcgggatc gaaagttcca cgcagggcgc gagctgcggc  11520
atggcctgaa tcgcgagcgg ttgctgcgcg aggaggactt tgagcccgac gcgcgaaccg  11580
ggattagtcc cgcgcgcgca cacgtggcgg ccgccgacct ggtaaccgca tacgagcaga  11640
cggtgaacca ggagattaac tttcaaaaaa gctttaacaa ccacgtgcgt acgcttgtgg  11700
cgcgcgagga ggtggctata ggactgatgc atctgtggga ctttgtaagc gcgctggagc  11760
aaaacccaaa tagcaagccg ctcatggcgc agctgttcct tatagtgcag cacagcaggg  11820
acaacgaggc attcagggat gcgctgctaa acatagtaga gcccgagggc cgctggctgc  11880
tcgatttgat aaacatcctg cagagcatag tggtgcagga gcgcagcttg agcctggctg  11940
acaaggtggc cgccatcaac tattccatgc ttagcctggg caagttttac gcccgcaaga  12000
tataccatac cccttacgtt cccatagaca aggaggtaaa gatcgagggg ttctacatgc  12060
gcatggcgct gaaggtgctt accttgagcg acgacctggg cgtttatcgc aacgagcgca  12120
tccacaaggc cgtgagcgtg agccggcggc gcgagctcag cgaccgcgag ctgatgcaca  12180
gcctgcaaag ggccctggct ggcacgggca gcggcgatag agaggccgag tcctactttg  12240
acgcgggcgc tgacctgcgc tgggccccaa gccgacgcgc cctggaggca gctggggccg  12300
gacctgggct ggcggtggca cccgcgcgcg ctggcaacgt cggcggcgtg gaggaatatg  12360
acgaggacga tgagtacgag ccagaggacg gcgagtacta agcggtgatg tttctgatca  12420
gatgatgcaa gacgcaacgg acccggcggt gcgggcggcg ctgcagagcc agccgtccgg  12480
ccttaactcc acggacgact ggcgccaggt catggaccgc atcatgtcgc tgactgcgcg  12540
caatcctgac gcgttccggc agcagccgca ggccaaccgg ctctccgcaa ttctggaagc  12600
ggtggtcccg gcgcgcgcaa accccacgca cgagaaggtg ctggcgatcg taaacgcgct  12660
ggccgaaaac agggccatcc ggcccgacga ggccggcctg gtctacgacg cgctgcttca  12720
gcgcgtggct cgttacaaca gcggcaacgt gcagaccaac ctggaccggc tggtggggga  12780
tgtgcgcgag gccgtggcgc agcgtgagcg cgcgcagcag cagggcaacc tgggctccat  12840
ggttgcacta aacgccttcc tgagtacaca gcccgccaac gtgccgcggg gacaggagga  12900
ctacaccaac tttgtgagcg cactgcggct aatggtgact gagacaccgc aaagtgaggt  12960
gtaccagtct gggccagact atttttttcca gaccagtaga caaggcctgc agaccgtaaa  13020
cctgagccag gctttcaaaa acttgcaggg gctgtggggg gtgcgggctc ccacaggcga  13080
ccgcgcgacc gtgtctagct tgctgacgcc caactcgcgc ctgttgctgc tgctaatagc  13140
```

-continued

```
gcccttcacg gacagtggca gcgtgtcccg ggacacatac ctaggtcact tgctgacact  13200
gtaccgcgag gccataggtc aggcgcatgt ggacgagcat actttccagg agattacaag  13260
tgtcagccgc gcgctggggc aggaggacac gggcagcctg gaggcaaccc taaactacct  13320
gctgaccaac cggcggcaga agatcccctc gttgcacagt ttaaacagcg aggaggagcg  13380
cattttgcgc tacgtgcagc agagcgtgag ccttaacctg atgcgcgacg ggtaacgcc  13440
cagcgtggcg ctggacatga ccgcgcgcaa catggaaccg ggcatgtatg cctcaaaccg  13500
gccgtttatc aaccgcctaa tggactactt gcatcgcgcg gccgccgtga accccgagta  13560
tttcaccaat gccatcttga acccgcactg gctaccgccc cctggtttct acaccggggg  13620
attcgaggtg cccgagggta acgatggatt cctctgggac gacatagacg acagcgtgtt  13680
ttccccgcaa ccgcagaccc tgctagagtt gcaacagcgc gagcaggcag aggcggcgct  13740
gcgaaaggaa agcttccgca ggccaagcag cttgtccgat ctaggcgctg cggccccgcg  13800
gtcagatgct agtagcccat ttccaagctt gatagggtct cttaccagca ctcgcaccac  13860
ccgcccgcgc ctgctgggcg aggaggagta cctaaacaac tcgctgctgc agccgcagcg  13920
cgaaaaaaac ctgcctccgg catttcccaa caacgggata gagagcctag tggacaagat  13980
gagtagatgg aagacgtacg cgcaggagca cagggacgtg ccaggcccgc gcccgcccac  14040
ccgtcgtcaa aggcacgacc gtcagcgggg tctggtgtgg gaggacgatg actcggcaga  14100
cgacagcagc gtcctggatt tgggagggag tggcaacccg tttgcgcacc ttcgccccag  14160
gctggggaga atgttttaaa aaaaaaaaag catgatgcaa aataaaaaac tcaccaaggc  14220
catggcaccg agcgttggtt ttcttgtatt ccccttagta tgcggcgcgc ggcgatgtat  14280
gaggaaggtc ctcctccctc ctacgagagt gtggtgagcg cggcgccagt ggcggcggcg  14340
ctgggttctc ccttcgatgc tcccctggac ccgccgtttg tgcctccgcg gtacctgcgg  14400
cctaccgggg ggagaaacag catccgttac tctgagttgg cacccctatt cgacaccacc  14460
cgtgtgtacc tggtggacaa caagtcaacg gatgtggcat ccctgaacta ccagaacgac  14520
cacagcaact ttctgaccac ggtcattcaa aacaatgact acagcccggg ggaggcaagc  14580
acacagacca tcaatcttga cgaccggtcg cactggggcg gcgacctgaa aaccatcctg  14640
cataccaaca tgccaaatgt gaacgagttc atgtttacca ataagtttaa ggcgcgggtg  14700
atggtgtcgc gcttgcctac taaggacaat caggtggagc tgaaatacga gtgggtggag  14760
ttcacgctgc ccgagggcaa ctactccgag accatgacca tagaccttat gaacaacgcg  14820
atcgtggagc actacttgaa agtgggcaga cagaacgggg ttctggaaag cgacatcggg  14880
gtaaagtttg acacccgcaa cttcagactg ggtttgacc ccgtcactgg tcttgtcatg  14940
cctggggtat atacaaacga agccttccat ccagacatca ttttgctgcc aggatgcggg  15000
gtggacttca cccacagccg cctgagcaac ttgttgggca tccgcaagcg gcaacccttc  15060
caggagggct ttaggatcac ctacgatgat ctggagggtg gtaacattcc cgcactgttg  15120
gatgtggacg cctaccaggc gagcttgaaa gatgacaccg aacagggcgg gggtggcgca  15180
ggcggcagca acagcagtgg cagcggcgcg gaagagaact ccaacgcggc agccgcggca  15240
atgcagccgg tggaggacat gaacgatcat gccattcgcg gcgacacctt tgccacacgg  15300
gctgaggaga agcgcgctga ggccgaagca gcggccgaag ctgccgcccc cgctgcgcaa  15360
cccgaggtcg agaagcctca gaagaaaccg gtgatcaaac ccctgacaga ggacagcaag  15420
aaacgcagtt acaacctaat aagcaatgac agcaccttca cccagtaccg cagctggtac  15480
cttgcataca actacggcga ccctcagacc ggaatccgct catggaccct gctttgcact  15540
```

```
cctgacgtaa cctgcggctc ggagcaggtc tactggtcgt tgccagacat gatgcaagac  15600
cccgtgacct tccgctccac gcgccagatc agcaactttc cggtggtggg cgccgagctg  15660
ttgcccgtgc actccaagag cttctacaac gaccaggccg tctactccca actcatccgc  15720
cagtttacct ctctgaccca cgtgttcaat cgctttcccg agaaccagat tttggcgcgc  15780
ccgccagccc ccaccatcac caccgtcagt gaaaacgttc ctgctctcac agatcacggg  15840
acgctaccgc tgcgcaacag catcggagga gtccagcgag tgaccattac tgacgccaga  15900
cgccgcacct gcccctacgt ttacaaggcc ctgggcatag tctcgccgcg cgtcctatcg  15960
agccgcactt tttgagcaag catgtccatc cttatatcgc ccagcaataa cacaggctgg  16020
ggcctgcgct tcccaagcaa gatgtttggc ggggccaaga agcgctccga ccaacaccca  16080
gtgcgcgtgc gcgggcacta ccgcgcgccc tggggcgcgc acaaacgcgg ccgcactggg  16140
cgcaccaccg tcgatgacgc catcgacgcg gtggtggagg aggcgcgcaa ctacacgccc  16200
acgccgccac cagtgtccac agtggacgcg gccattcaga ccgtggtgcg cggagcccgg  16260
cgctatgcta aaatgaagag acggcggagg cgcgtagcac gtcgccaccg ccgccgaccc  16320
ggcactgccg cccaacgcgc ggcggcggcc ctgcttaacc gcgcacgtcg caccggccga  16380
cgggcggcca tgcgggccgc tcgaaggctg gccgcgggta ttgtcactgt gccccccagg  16440
tccaggcgac gagcggccgc cgcagcagcc gcggccatta gtgctatgac tcagggtcgc  16500
aggggcaacg tgtattgggt gcgcgactcg gttagcggcc tgcgcgtgcc cgtgcgcacc  16560
cgcccccgc gcaactagat tgcaagaaaa aactacttag actcgtactg ttgtatgtat  16620
ccagcggcgg cggcgcgcaa cgaagctatg tccaagcgca aaatcaaaga agagatgctc  16680
caggtcatcg cgccggagat ctatggcccc ccgaagaagg aagagcagga ttacaagccc  16740
cgaaagctaa agcgggtcaa aaagaaaaag aaagatgatg atgatgaact tgacgacgag  16800
gtggaactgc tgcacgctac cgcgcccagg cgacgggtac agtggaaagg tcgacgcgta  16860
aaacgtgttt tgcgacccgg caccaccgta gtctttacgc ccggtgagcg ctccacccgc  16920
acctacaagc gcgtgtatga tgaggtgtac ggcgacgagg acctgcttga gcaggccaac  16980
gagcgcctcg ggagtttgc ctacggaaag cggcataagg acatgctggc gttgccgctg  17040
gacgagggca acccaacacc tagcctaaag cccgtaacac tgcagcaggt gctgcccgcg  17100
cttgcaccgt ccgaagaaaa gcgcggccta aagcgcgagt ctggtgactt ggcacccacc  17160
gtgcagctga tggtacccaa gcgccagcga ctggaagatg tcttggaaaa aatgaccgtg  17220
gaacctgggc tggagcccga ggtccgcgtg cggccaatca agcaggtggc gccgggactg  17280
ggcgtgcaga ccgtggacgt tcagataccc actaccagta gcaccagtat tgccaccgcc  17340
acagagggca tggagacaca aacgtccccg gttgcctcag cggtggcgga tgccgcggtg  17400
caggcggtcg ctgcggccgc gtccaagacc tctacggagg tgcaaacgga cccgtggatg  17460
tttcgcgttt cagcccccg gcgcccgcgc ggttcgagga agtacggcgc cgccagcgcg  17520
ctactgcccg aatatgccct acatccttcc attgcgccta cccccggcta tcgtggctac  17580
acctaccgcc ccagaagacg agcaactacc cgacgccgaa ccaccactgg aacccgccgc  17640
cgccgtcgcc gtcgccagcc cgtgctggcc ccgatttccg tgcgcagggt ggctcgcgaa  17700
ggaggcagga ccctggtgct gccaacagcg cgctaccacc ccagcatcgt ttaaaagccg  17760
gtctttgtgg ttcttgcaga tatggccctc acctgccgcc tccgtttccc ggtgccggga  17820
ttccgaggaa gaatgcaccg taggaggggc atggccggcc acggcctgac gggcggcatg  17880
cgtcgtgcgc accaccggcg gcggcgcgcg tcgcaccgtc gcatgcgcgg cggtatcctg  17940
```

```
ccccctcctta ttccactgat cgccgcggcg attggcgccg tgcccggaat tgcatccgtg  18000
gccttgcagg cgcagagaca ctgattaaaa acaagttgca tgtggaaaaa tcaaaataaa  18060
aagtctggac tctcacgctc gcttggtcct gtaactattt tgtagaatgg aagacatcaa  18120
ctttgcgtct ctggccccgc gacacggctc gcgcccgttc atgggaaact ggcaagatat  18180
cggcaccagc aatatgagcg gtggcgcctt cagctggggc tcgctgtgga gcggcattaa  18240
aaatttcggt tccaccgtta agaactatgg cagcaaggcc tggaacagca gcacaggcca  18300
gatgctgagg gataagttga aagagcaaaa tttccaacaa aaggtggtag atggcctggc  18360
ctctggcatt agcggggtgg tggacctggc caaccaggca gtgcaaaata agattaacag  18420
taagcttgat ccccgccctc ccgtagagga gcctccaccg gccgtggaga cagtgtctcc  18480
agaggggcgt ggcgaaaagc gtccgcgccc cgacagggaa gaaactctgg tgacgcaaat  18540
agacgagcct ccctcgtacg aggaggcact aaagcaaggc ctgcccacca cccgtcccat  18600
cgcgcccatg gctaccggag tgctgggcca gcacacaccc gtaacgctgg acctgcctcc  18660
ccccgccgac acccagcaga aacctgtgct gccaggcccg accgccgttg ttgtaacccg  18720
tcctagccgc gcgtccctgc gccgcgccgc cagcggtccg cgatcgttgc ggcccgtagc  18780
cagtggcaac tggcaaagca cactgaacag catcgtgggt ctgggggtgc aatccctgaa  18840
gcgccgacga tgcttctgaa tagctaacgt gtcgtatgtg tgtcatgtat gcgtccatgt  18900
cgccgccaga ggagctgctg agccgccgcg cgcccgcttt ccaagatggc taccccttcg  18960
atgatgccgc agtggtctta catgcacatc tcgggccagg acgcctcgga gtacctgagc  19020
cccgggctgg tgcagtttgc ccgcgccacc gagacgtact tcagcctgaa taacaagttt  19080
agaaacccca cggtggcgcc tacgcacgac gtgaccacag accggtccca gcgtttgacg  19140
ctgcggttca tccctgtgga ccgtgaggat actgcgtact cgtacaaggc gcggttcacc  19200
ctagctgtgg gtgataaccg tgtgctggac atggcttcca cgtactttga catccgcggc  19260
gtgctggaca ggggccctac ttttaagccc tactctggca ctgcctacaa cgccctggct  19320
cccaagggtg ccccaaatcc ttgcgaatgg gatgaagctg ctactgctct tgaaataaac  19380
ctagaagaag aggacgatga caacgaagac gaagtagacg agcaagctga gcagcaaaaa  19440
actcacgtat ttgggcaggc gccttattct ggtataaata ttacaaagga gggtattcaa  19500
ataggtgtcg aaggtcaaac acctaaatat gccgataaaa catttcaacc tgaacctcaa  19560
ataggagaat ctcagtggta cgaaactgaa attaatcatg cagctgggag agtccttaaa  19620
aagactaccc caatgaaacc atgttacggt tcatatgcaa aacccacaaa tgaaaatgga  19680
gggcaaggca ttcttgtaaa gcaacaaaat ggaaagctag aaagtcaagt ggaaatgcaa  19740
tttttctcaa ctactgaggc gaccgcaggc aatggtgata acttgactcc taaagtggta  19800
ttgtacagtg aagatgtaga tatagaaacc ccagacactc atatttctta catgcccact  19860
attaaggaag gtaactcacg agaactaatg ggccaacaat ctatgcccaa caggcctaat  19920
tacattgctt ttagggacaa ttttattggt ctaatgtatt acaacagcac gggtaatatg  19980
ggtgttctgg cgggccaagc atcgcagttg aatgctgttg tagatttgca agacagaaac  20040
acagagcttt cataccagct tttgcttgat tccattggtg atagaaccag gtacttttct  20100
atgtggaatc aggctgttga cagctatgat ccagatgtta gaattattga aaatcatgga  20160
actgaagatg aacttccaaa ttactgcttt ccactgggag gtgtgattaa tacagagact  20220
cttaccaagg taaaacctaa aacaggtcag gaaaatggat gggaaaaaga tgctacagaa  20280
ttttcagata aaaatgaaat aagagttgga aataattttg ccatggaaat caatctaaat  20340
```

```
gccaacctgt ggagaaattt cctgtactcc aacatagcgc tgtatttgcc cgacaagcta  20400
aagtacagtc cttccaacgt aaaaatttct gataacccaa acacctacga ctacatgaac  20460
aagcgagtgg tggctcccgg gttagtggac tgctacatta accttggagc acgctggtcc  20520
cttgactata tggacaacgt caacccattt aaccaccacc gcaatgctgg cctgcgctac  20580
cgctcaatgt tgctgggcaa tggtcgctat gtgcccttcc acatccaggt gcctcagaag  20640
ttctttgcca ttaaaaacct ccttctcctg ccgggctcat acacctacga gtggaacttc  20700
aggaaggatg ttaacatggt tctgcagagc tccctaggaa atgacctaag ggttgacgga  20760
gccagcatta agtttgatag catttgcctt tacgccacct tcttccccat ggcccacaac  20820
accgcctcca cgcttgaggc catgcttaga aacgacacca acgaccagtc ctttaacgac  20880
tatctctccg ccgccaacat gctctaccct atacccgcca acgctaccaa cgtgcccata  20940
tccatcccct cccgcaactg ggcggctttc cgcggctggg ccttcacgcg ccttaagact  21000
aaggaaaccc catcactggg ctcgggctac gacccttatt acacctactc tggctctata  21060
ccctacctag atggaacctt ttacctcaac cacaccttta agaaggtggc cattaccttt  21120
gactcttctg tcagctggcc tggcaatgac cgcctgctta cccccaacga gtttgaaatt  21180
aagcgctcag ttgacgggga gggttacaac gttgcccagt gtaacatgac caaagactgg  21240
ttcctggtac aaatgctagc taactacaac attggctacc agggcttcta tatcccagag  21300
agctacaagg accgcatgta ctccttcttt agaaacttcc agcccatgag ccgtcaggtg  21360
gtggatgata ctaaatacaa ggactaccaa caggtgggca tcctacacca acacaacaac  21420
tctggatttg ttggctacct tgcccccacc atgcgcgaag gacaggccta ccctgctaac  21480
ttccccctatc cgcttatagg caagaccgca gttgacagca ttacccagaa aaagtttctt  21540
tgcgatcgca ccctttggcg catcccattc tccagtaact ttatgtccat gggcgcactc  21600
acagacctgg gccaaaacct tctctacgcc aactccgccc acgcgctaga catgactttt  21660
gaggtggatc ccatggacga gcccaccctt ctttatgttt tgtttgaagt ctttgacgtg  21720
gtccgtgtgc accggccgca ccgcggcgtc atcgaaaccg tgtacctgcg cacgcccttc  21780
tcggccggca acgccacaac ataaagaagc aagcaacatc aacaacagct gccgccatgg  21840
gctccagtga gcaggaactg aaagccattg tcaaagatct tggttgtggg ccatattttt  21900
tgggcaccta tgacaagcgc tttccaggct ttgtttctcc acacaagctc gcctgcgcca  21960
tagtcaatac ggccggtcgc gagactgggg gcgtacactg gatggccttt gcctggaacc  22020
cgcactcaaa aacatgctac ctctttgagc cctttggctt ttctgaccag cgactcaagc  22080
aggtttacca gtttgagtac gagtcactcc tgcgccgtag cgccattgct tcttcccccg  22140
accgctgtat aacgctggaa aagtccaccc aaagcgtaca ggggcccaac tcggccgcct  22200
gtggactatt ctgctgcatg tttctccacg cctttgccaa ctggccccaa actcccatgg  22260
atcacaaccc caccatgaac cttattaccg gggtacccaa ctccatgctc aacagtcccc  22320
aggtacagcc caccctgcgt cgcaaccagg aacagctcta cagcttcctg gagcgccact  22380
cgccctactt ccgcagccac agtgcgcaga ttaggagcgc cacttctttt tgtcacttga  22440
aaaacatgta aaaataatgt actagagaca ctttcaataa aggcaaatgc ttttatttgt  22500
acactctcgg gtgattattt acccccaccc ttgccgtctg cgccgtttaa aaatcaaagg  22560
ggttctgccg cgcatcgcta tgcgccactg gcagggacac gttgcgatac tggtgtttag  22620
tgctccactt aaactcaggc acaaccatcc gcggcagctc ggtgaagttt tcactccaca  22680
```

```
ggctgcgcac catcaccaac gcgtttagca ggtcgggcgc cgatatcttg aagtcgcagt  22740
tggggcctcc gccctgcgcg cgcgagttgc gatacacagg gttgcagcac tggaacacta  22800
tcagcgccgg gtggtgcacg ctggccagca cgctcttgtc ggagatcaga tccgcgtcca  22860
ggtcctccgc gttgctcagg gcgaacggag tcaactttgg tagctgcctt cccaaaaagg  22920
gcgcgtgccc aggctttgag ttgcactcgc accgtagtgg catcaaaagg tgaccgtgcc  22980
cggtctgggc gttaggatac agcgcctgca taaaagcctt gatctgctta aaagccacct  23040
gagcctttgc gccttcagag aagaacatgc cgcaagactt gccggaaaac tgattggccg  23100
gacaggccgc gtcgtgcacg cagcaccttg cgtcggtgtt ggagatctgc accacatttc  23160
ggccccaccg gttcttcacg atcttggcct tgctagactg ctccttcagc gcgcgctgcc  23220
cgttttcgct cgtcacatcc atttcaatca cgtgctcctt atttatcata atgcttccgt  23280
gtagacactt aagctcgcct tcgatctcag cgcagcggtg cagccacaac gcgcagcccg  23340
tgggctcgtg atgcttgtag gtcacctctg caaacgactg caggtacgcc tgcaggaatc  23400
gccccatcat cgtcacaaag gtcttgttgc tggtgaaggt cagctgcaac ccgcggtgct  23460
cctcgttcag ccaggtcttg catacggccg ccagagcttc cacttggtca ggcagtagtt  23520
tgaagttcgc ctttagatcg ttatccacgt ggtacttgtc catcagcgcg cgcgcagcct  23580
ccatgccctt ctcccacgca gacacgatcg gcacactcag cgggttcatc accgtaattt  23640
cactttccgc ttcgctgggc tcttcctctt cctcttgcgt ccgcatacca cgcgccactg  23700
ggtcgtcttc attcagccgc cgcactgtgc gcttacctcc tttgccatgc ttgattagca  23760
ccggtgggtt gctgaaaccc accatttgta gcgccacatc ttctctttct tcctcgctgt  23820
ccacgattac ctctggtgat ggcgggcgct cgggcttggg agaagggcgc ttctttttct  23880
tcttgggcgc aatggccaaa tccgccgccg aggtcgatgg ccgcgggctg ggtgtgcgcg  23940
gcaccagcgc gtcttgtgat gagtcttcct cgtcctcgga ctcgatacgc cgcctcatcc  24000
gctttttttgg gggcgcccgg ggaggcggcg gcgacgggga cggggacgac acgtcctcca  24060
tggttggggg acgtcgcgcc gcaccgcgtc cgcgctcggg ggtggtttcg cgctgctcct  24120
cttcccgact ggccatttcc ttctcctata ggcagaaaaa gatcatggag tcagtcgaga  24180
agaaggacag cctaaccgcc ccctctgagt tcgccaccac cgcctccacc gatgccgcca  24240
acgcgcctac caccttcccc gtcgaggcac ccccgcttga ggaggaggaa gtgattatcg  24300
agcaggaccc aggttttgta agcgaagacg acgaggaccg ctcagtacca acagaggata  24360
aaaagcaaga ccaggacaac gcagaggcaa acgaggaaca agtcgggcgg ggggacgaaa  24420
ggcatggcga ctacctagat gtgggagacg acgtgctgtt gaagcatctg cagcgccagt  24480
gcgccattat ctgcgacgcg ttgcaagagc gcagcgatgt gcccctcgcc atagcggatg  24540
tcagccttgc ctacgaacgc cacctattct caccgcgcgt acccccccaaa cgccaagaaa  24600
acggcacatg cgagcccaac ccgcgcctca acttctaccc cgtatttgcc gtgccagagg  24660
tgcttgccac ctatcacatc tttttccaaa actgcaagat acccctatcc tgccgtgcca  24720
accgcagccg agcggacaag cagctggcct tgcggcaggg cgctgtcata cctgatatcg  24780
cctcgctcaa cgaagtgcca aaaatctttg agggtcttgg acgcgacgag aagcgcgcgg  24840
caaacgctct gcaacaggaa aacagcgaaa atgaaagtca ctctggagtg ttggtggaac  24900
tcgagggtga caacgcgcgc ctagccgtac taaaacgcag catcgaggtc acccactttg  24960
cctacccggc acttaaccta ccccccaagg tcatgagcac agtcatgagt gagctgatcg  25020
tgcgccgtgc gcagcccctg gagagggatg caaatttgca agaacaaaca gaggagggcc  25080
```

```
taccgcagt tggcgacgag cagctagcgc gctggcttca aacgcgcgag cctgccgact  25140
tggaggagcg acgcaaacta atgatggccg cagtgctcgt taccgtggag cttgagtgca  25200
tgcagcggtt ctttgctgac ccggagatgc agcgcaagct agaggaaaca ttgcactaca  25260
cctttcgaca gggctacgta cgccaggcct gcaagatctc caacgtggag ctctgcaacc  25320
tggtctccta ccttggaatt ttgcacgaaa accgccttgg gcaaaacgtg cttcattcca  25380
cgctcaaggg cgaggcgcgc cgcgactacg tccgcgactg cgtttactta tttctatgct  25440
acacctggca gacggccatg ggcgtttggc agcagtgctt ggaggagtgc aacctcaagg  25500
agctgcagaa actgctaaag caaaacttga aggacctatg gacggccttc aacgagcgct  25560
ccgtggccgc gcacctggcg gacatcattt tccccgaacg cctgcttaaa accctgcaac  25620
agggtctgcc agacttcacc agtcaaagca tgttgcagaa ctttaggaac tttatcctag  25680
agcgctcagg aatcttgccc gccacctgct gtgcacttcc tagcgacttt gtgcccatta  25740
agtaccgcga atgccctccg ccgctttggg gccactgcta ccttctgcag ctagccaact  25800
accttgccta ccactctgac ataatggaag acgtgagcgg tgacggtcta ctggagtgtc  25860
actgtcgctg caacctatgc accccgcacc gctccctggt ttgcaattcg cagctgctta  25920
acgaaagtca aattatcggt acctttgagc tgcagggtcc ctcgcctgac gaaaagtccg  25980
cggctccggg gttgaaactc actccggggc tgtggacgtc ggcttacctt cgcaaatttg  26040
tacctgagga ctaccacgcc cacgagatta ggttctacga agaccaatcc cgcccgccaa  26100
atgcggagct taccgcctgc gtcattaccc agggccacat tcttggccaa ttgcaagcca  26160
tcaacaaagc ccgccaagag tttctgctac gaaagggacg gggggtttac ttggaccccc  26220
agtccggcga ggagctcaac ccaatccccc cgccgccgca gccctatcag cagcagccgc  26280
gggcccttgc ttcccaggat ggcacccaaa aagaagctgc agctgccgcc gccacccacg  26340
gacgaggagg aatactggga cagtcaggca gaggaggttt tggacgagga ggaggaggac  26400
atgatggaag actgggagag cctagacgag gaagcttccg aggtcgaaga ggtgtcagac  26460
gaaacaccgt caccctcggt cgcattcccc tcgccggcgc cccagaaatc ggcaaccggt  26520
tccagcatgg ctacaacctc cgctcctcag gcgccgccgg cactgcccgt tcgccgaccc  26580
aaccgtagat gggacaccac tggaaccagg gccggtaagt ccaagcagcc gccgccgtta  26640
gcccaagagc aacaacagcg ccaaggctac cgctcatggc gcgggcacaa gaacgccata  26700
gttgcttgct tgcaagactg tgggggcaac atctccttcg cccgccgctt tcttctctac  26760
catcacggcg tggccttccc ccgtaacatc ctgcattact accgtcatct ctacagccca  26820
tactgcaccg gcggcagcgg cagcggcagc aacagcagcg gccacacaga agcaaaggcg  26880
accggatagc aagactctga caaagcccaa gaaatccaca gcggcggcag cagcaggagg  26940
aggagcgctg cgtctggcgc ccaacgaacc cgtatcgacc cgcgagctta gaaacaggat  27000
ttttcccact ctgtatgcta tatttcaaca gagcaggggc caagaacaag agctgaaaat  27060
aaaaaacagg tctctgcgat ccctcacccg cagctgcctg tatcacaaaa gcgaagatca  27120
gcttcggcgc acgctggaag acgcggaggc tctcttcagt aaatactgcg cgctgactct  27180
taaggactag tttcgcgccc tttctcaaat ttaagcgcga aaactacgtc atctccagcg  27240
gccacacccg gcgccagcac ctgtcgtcag cgccattatg agcaaggaaa ttcccacgcc  27300
ctacatgtgg agttaccagc cacaaatggg acttgcggct ggagctgccc aagactactc  27360
aacccgaata aactacatga gcgcgggacc ccacatgata tcccgggtca acggaatccg  27420
```

```
cgcccaccga aaccgaattc tcttggaaca ggcggctatt accaccacac ctcgtaataa  27480
ccttaatccc cgtagttggc ccgctgccct ggtgtaccag gaaagtcccg ctcccaccac  27540
tgtggtactt cccagagacg cccaggccga agttcagatg actaactcag gggcgcagct  27600
tgcgggcggc tttcgtcaca gggtgcggtc gcccgggcag ggtataactc acctgacaat  27660
cagagggcga ggtattcagc tcaacgacga gtcggtgagc tcctcgcttg gtctccgtcc  27720
ggacgggaca tttcagatcg gcggcgccgg ccgctcttca ttcacgcctc gtcaggcaat  27780
cctaactctg cagacctcgt cctctgagcc gcgctctgga ggcattggaa ctctgcaatt  27840
tattgaggag tttgtgccat cggtctactt taaccccttc tcgggacctc ccggccacta  27900
tccggatcaa tttattccta actttgacgc ggtaaaggac tcggcggatg gctacgactg  27960
aatgttaagt ggagaggcag agcaactgcg cctgaaacac ctggtccact gtcgccgcca  28020
caagtgcttt gcccgcgact ccggtgagtt ttgctacttt gaattgcccg aggatcatat  28080
cgagggcccg gcgcacggcg tccggcttac cgcccaggga gagcttgccc gtagcctgat  28140
tcgggagttt acccagcgcc ccctgctagt tgagcgggac aggggaccct gtgttctcac  28200
tgtgatttgc aactgtccta accctggatt acatcaagat ctttgttgcc atctctgtgc  28260
tgagtataat aaatacagaa attaaaatat actggggctc ctatcgccat cctgtaaacg  28320
ccaccgtctt cacccgccca agcaaaccaa ggcgaacctt acctggtact tttaacatct  28380
ctccctctgt gatttacaac agtttcaacc cagacggagt gagtctacga gagaacctct  28440
ccgagctcag ctactccatc agaaaaaaca ccaccctcct tacctgccgg gaacgtacga  28500
tgtggctgca gagcctgctg ctcttgggca ctgtggcctg cagcatctct gcacccgccc  28560
gctcgcccag ccccagcacg cagccctggg agcatgtgaa tgccatccag gaggcccggc  28620
gtctcctgaa cctgagtaga gacactgctg ctgagatgaa tgaaacagta gaagtcatct  28680
cagaaatgtt tgacctccag gagccgacct gcctacagac ccgcctggag ctgtacaagc  28740
agggcctgcg gggcagcctc accaagctca agggcccctt gaccatgatg gccagccact  28800
acaagcagca ctgccctcca accccggaaa cttcctgtgc aacccagact atcacctttg  28860
aaagtttcaa agagaacctg aaggactttc tgcttgtcat cccctttgac tgctgggagc  28920
cagtccagga gtgacaattg actctatgtg ggatatgctc cagcgctaca accttgaagt  28980
caggcttcct ggatgtcagc atctgacttt ggccagcacc tgtcccgcgg atttgttcca  29040
gtccaactac agcgacccac cctaacagag atgaccaaca caaccaacgc ggccgccgct  29100
accggactta catctaccac aaatacaccc caagtttctg cctttgtcaa taactgggat  29160
aacttgggca tgtggtggtt ctccatagcg cttatgtttg tatgccttat tattatgtgg  29220
ctcatctgct gcctaaagcg caaacgcgcc cgaccaccca tctatagtcc catcattgtg  29280
ctacacccaa acaatgatgg aatccataga ttggacggac tgaaacacat gttcttttct  29340
cttacagtat gattaaatga gacatgattc ctcgagtttt tatattactg acccttgttg  29400
cgcttttttg tgcgtgctcc acattggctg cggtttctca catcgaagta gactgcattc  29460
cagccttcac agtctatttg ctttacggat ttgtcaccct cacgctcatc tgcagcctca  29520
tcactgtggt catcgccttt atccagtgca ttgactgggt ctgtgtgcgc tttgcatatc  29580
tcagacacca tccccagtac agggacagga ctatagctga gcttcttaga attctttaat  29640
tatgaaattt actgtgactt ttctgctgat tatttgcacc ctatctgcgt tttgttcccc  29700
gacctccaag cctcaaagac atatatcatg cagattcact cgtatatgga atattccaag  29760
ttgctacaat gaaaaaagcg atctttccga agcctggtta tatgcaatca tctctgttat  29820
```

```
ggtgttctgc agtaccatct tagccctagc tatatatccc taccttgaca ttggctggaa  29880
acgaatagat gccatgaacc acccaacttt ccccgcgccc gctatgcttc cactgcaaca  29940
agttgttgcc ggcggctttg tcccagccaa tcagcctcgc cccacttctc ccaccccccac  30000
tgaaatcagc tactttaatc taacaggagg agatgactga caccctagat ctagaaatgg  30060
acggaattat tacagagcag cgcctgctag aaagacgcag ggcagcggcc gagcaacagc  30120
gcatgaatca agagctccaa gacatggtta acttgcacca gtgcaaaagg ggtatctttt  30180
gtctggtaaa gcaggccaaa gtcacctacg acagtaatac caccggacac cgccttagct  30240
acaagttgcc aaccaagcgt cagaaattgg tggtcatggt gggagaaaag cccattacca  30300
taactcagca ctcggtagaa accgaaggct gcattcactc accttgtcaa ggacctgagg  30360
atctctgcac ccttattaag accctgtgcg gtctcaaaga tcttattccc tttaactaat  30420
aaaaaaaaat aataaagcat cacttactta aaatcagtta gcaaatttct gtccagttta  30480
ttcagcagca cctccttgcc ctcctcccag ctctggtatt gcagcttcct cctggctgca  30540
aactttctcc acaatctaaa tggaatgtca gtttcctcct gttcctgtcc atccgcaccc  30600
actatcttca tgttgttgca gatgaagcgc gcaagaccgt ctgaagatac cttcaacccc  30660
gtgtatccat atgacacgga aaccggtcct ccaactgtgc cttttcttac tcctcccttt  30720
gtatccccca atgggtttca agagagtccc cctggggtac tctctttgcg cctatccgaa  30780
cctctagtta cctccaatgg catgcttgcg ctcaaaatgg gcaacggcct ctctctggac  30840
gaggccggca accttacctc ccaaaatgta accactgtga gcccacctct caaaaaaacc  30900
aagtcaaaca taaacctgga aatatctgca cccctcacag ttacctcaga agccctaact  30960
gtggctgccg ccgcacctct aatggtcgcg ggcaacacac tcaccatgca atcacaggcc  31020
ccgctaaccg tgcacgactc caaacttagc attgccaccc aaggacccct cacagtgtca  31080
gaaggaaagc tagccctgca aacatcaggc cccctcacca ccaccgatag cagtaccctt  31140
actatcactg cctcaccccc tctaactact gccactggta gcttgggcat tgacttgaaa  31200
gagcccattt atacacaaaa tggaaaacta ggactaaagt acggggctcc tttgcatgta  31260
acagacgacc taaacacttt gaccgtagca actggtccag gtgtgactat taataatact  31320
tccttgcaaa ctaaagttac tggagccttg ggttttgatt cacaaggcaa tatgcaactt  31380
aatgtagcag gaggactaag gattgattct caaaacagac gccttatact tgatgttagt  31440
tatccgtttg atgctcaaaa ccaactaaat ctaagactag gacagggccc tctttttata  31500
aactcagccc acaacttgga tattaactac aacaaaggcc tttacttgtt tacagcttca  31560
aacaattcca aaaagcttga ggttaaccta agcactgcca aggggttgat gtttgacgct  31620
acagccatag ccattaatgc aggagatggg cttgaatttg gttcacctaa tgcaccaaac  31680
acaaatcccc tcaaaacaaa aattggccat ggcctagaat ttgattcaaa caaggctatg  31740
gttcctaaac taggaactgg ccttagtttt gacagcacag gtgccattac agtaggaaac  31800
aaaaataatg ataagctaac tttgtggacc acaccagctc catctcctaa ctgtagacta  31860
aatgcagaga aagatgctaa actcactttg gtcttaacaa aatgtggcag tcaaatactt  31920
gctacagttt cagttttggc tgttaaaggc agtttggctc caatatctgg aacagttcaa  31980
agtgctcatc ttattataag atttgacgaa aatggagtgc tactaaacaa ttccttcctg  32040
gacccagaat attggaactt tagaaatgga gatcttactg aaggcacagc ctatacaaac  32100
gctgttggat ttatgcctaa cctatcagct tatccaaaat ctcacggtaa aactgccaaa  32160
```

```
agtaacattg tcagtcaagt ttacttaaac ggagacaaaa ctaaacctgt aacactaacc  32220
attacactaa acggtacaca ggaaacagga gacacaactc caagtgcata ctctatgtca  32280
ttttcatggg actggtctgg ccacaactac attaatgaaa tatttgccac atcctcttac  32340
actttttcat acattgccca agaataaaga atcgtttgtg ttatgtttca acgtgtttat  32400
ttttcaattg cagaaaattt caagtcattt ttcattcagt agtatagccc caccaccaca  32460
tagcttatac agatcaccgt accttaatca aactcacaga accctagtat tcaacctgcc  32520
acctccctcc caacacacag agtacacagt cctttctccc cggctggcct taaaaagcat  32580
catatcatgg gtaacagaca tattcttagg tgttatattc cacacggttt cctgtcgagc  32640
caaacgctca tcagtgatat taataaactc cccgggcagc tcacttaagt tcatgtcgct  32700
gtccagctgc tgagccacag gctgctgtcc aacttgcggt tgcttaacgg gcggcgaagg  32760
agaagtccac gcctacatgg gggtagagtc ataatcgtgc atcaggatag ggcggtggtg  32820
ctgcagcagc gcgcgaataa actgctgccg ccgccgctcc gtcctgcagg aatacaacat  32880
ggcagtggtc tcctcagcga tgattcgcac cgcccgcagc ataaggcgcc ttgtcctccg  32940
ggcacagcag cgcaccctga tctcacttaa atcagcacag taactgcagc acagcaccac  33000
aatattgttc aaaatcccac agtgcaaggc gctgtatcca aagctcatgg cggggaccac  33060
agaacccacg tggccatcat accacaagcg caggtagatt aagtggcgac ccctcataaa  33120
cacgctggac ataaacatta cctcttttgg catgttgtaa ttcaccacct cccggtacca  33180
tataaacctc tgattaaaca tggcgccatc caccaccatc ctaaaccagc tggccaaaac  33240
ctgcccgccg gctatacact gcagggaacc gggactggaa caatgacagt ggagagccca  33300
ggactcgtaa ccatggatca tcatgctcgt catgatatca atgttggcac aacacaggca  33360
cacgtgcata cacttcctca ggattacaag ctcctcccgc gttagaacca tatcccaggg  33420
aacaacccat tcctgaatca gcgtaaatcc cacactgcag ggaagacctc gcacgtaact  33480
cacgttgtgc attgtcaaag tgttacattc gggcagcagc ggatgatcct ccagtatggt  33540
agcgcgggtt tctgtctcaa aaggaggtag acgatcccta ctgtacggag tgcgccgaga  33600
caaccgagat cgtgttggtc gtagtgtcat gccaaatgga acgccggacg tagtcatatt  33660
tcctgataaa ctctaaagaa tcgtttgtgt tatgtttcaa cgtgtttatt tttcaattgc  33720
agaaaatttc aagtcatttt tcattcagta gtatagcccc accaccacat agcttataca  33780
gatcaccgta ccttaatcaa actcacagaa ccctagtatt caacctgcca cctccctccc  33840
aacacacaga gtacacagtc ctttctcccc ggctggcctt aaaaagcatc atatcatggg  33900
taacagacat attcttaggt gttatattcc acacggtttc ctgtcgagcc aaacgctcat  33960
caagtgatat taataaactc cccgggcagc tcacttaagt tcatgtcgct gtccagctgc  34020
tgagccacag gctgctgtcc aacttgcggt tgcttaacgg gcggcgaagg agaagtccac  34080
gcctacatgg ggggagagtc ataatcgtgc atcaggatag ggcggtggtg ctgcagcagc  34140
gcgcgaataa actgctgccg ccgccgctcc gtcctgcagg aatacaacat ggcagtggtc  34200
tcctcagcga tgattcgcac cgcccgcagc ataaggcgcc ttgtcctccg ggcacagcag  34260
cgcaccctga tctcacttaa atcagcacag taactgcagc acagcaccac aatattgttc  34320
aaaatcccac agtgcaaggc gctgtatcca aagctcatgg cggggaccac agaacccacg  34380
tggccatcat accacaagcg caggtagatt aagtggcgac ccctcataaa cacgctggac  34440
ataaacatta cctcttttgg catgttgtaa ttcaccacct cccggtacca tataaacctc  34500
tgattaaaca tggcgccatc caccaccatc ctaaaccagc tggccaaaac ctgccccgcc  34560
```

```
gggntataca ctgcagggaa ccgggactgg aacaatgaca gtggagagcc caggactcgt  34620
aaccatggat catcatgctc gtcatgatat caatgttggc acaacacagg cacacgtgca  34680
tacacttcct caggattaca agctcctccc gcgttagaac catatcccag ggaacaaccc  34740
attcctgaat cagcgtaaat cccacactgc agggaagacc tcgcacgtaa ctcacgttgt  34800
gcattgtcaa agtgttacat tcgggcagca gcggatgatc ctccagtatg gtagcgcggg  34860
tttctgtctc aaaaggaggt agacgatccc tactgtacgg agtgcgccga gacaaccgag  34920
atcgtgttgg tcgtagtgtc atgccaaatg gaacgccgga cgtagtcata tttcctgaag  34980
caaaaccagg tgcgggcgtg acaaacagat ctgcgtctcc ggtctcgccg cttagatcgc  35040
tctgtgtagt agttgtagta tatccactct ctcaaagcat ccaggcgccc cctggcttcg  35100
ggttctatgt aaactccttc atgcgccgct gccctgataa catccaccac cgcagaataa  35160
gccacaccca gccaacctac acattcgttc tgcgagtcac acacgggagg agcgggaaga  35220
gctggaagaa ccatgttttt ttttttattc caaaagatta tccaaaacct caaaatgaag  35280
atctattaag tgaacgcgct cccctccggt ggcgtggtca aactctacag ccaaagaaca  35340
gataatggca tttgtaagat gttgcacaat ggcttccaaa aggcaaacgg ccctcacgtc  35400
caagtggacg taaaggctaa acccttcagg gtgaatctcc tctataaaca ttccagcacc  35460
ttcaaccatg cccaaataat tctcatctcg ccaccttctc aatatatctc taagcaaatc  35520
ccgaatatta agtccggcca ttgtaaaaat ttggctccag agcgccctcc accttcagcc  35580
tcaagcagcg aatcatgatt gcaaaaattc aggttcctca cagacctgta taagattcaa  35640
aagcggaaca ttaacaaaaa taccgcgatc ccgtaggtcc cttcgcaggg ccagctgaac  35700
ataatcgtgc aggtctgcac ggaccagcgc ggccacttcc ccgccaggaa ccatgacaaa  35760
agaacccaca ctgattatga cacgcatact cggagctatg ctaaccagcg tagccccgat  35820
gtaagcttgt tgcatgggcg gcgatataaa atgcaaggtg ctgctcaaaa aatcaggcaa  35880
agcctcgcgc aaaaaagaaa gcacatcgta gtcatgctca tgcagataaa ggcaggtaag  35940
ctccggaacc accacagaaa aagacaccat ttttctctca aacatgtctg cgggtttctg  36000
cataaacaca aaataaaata acaaaaaaac atttaaacat tagaagcctg tcttacaaca  36060
ggaaaaacaa cccttataag cataagacgg actacggcca tgccggcgtg accgtaaaaa  36120
aactggtcac cgtgattaaa aagcaccacc gacagctcct cggtcatgtc cggagtcata  36180
atgtaagact cggtaaacac atcaggttga ttcacatcgg tcagtgctaa aaagcgaccg  36240
aaatagcccg gggggaatac atacccgcagg cgtagagaca acattacagc ccccatagga  36300
ggtataacaa aattaatagg agagaaaaac acataaacac ctgaaaaacc ctcctgccta  36360
ggcaaaatag caccctcccg ctccagaaca acatacagcg cttccacagc ggcagccata  36420
acagtcagcc ttaccagtaa aaaagaaaac ctattaaaaa aacaccactc gacacggcac  36480
cagctcaatc agtcacagtg taaaaaaggg ccaagtgcag agcgagtata tataggacta  36540
aaaaatgacg taacggttaa agtccacaaa aaacacccag aaaaccgcac gcgaacctac  36600
gcccagaaac gaaagccaaa aaacccacaa cttcctcaaa tcgtcacttc cgttttccca  36660
cgttacgtca cttcccattt taagaaaact acaattccca acacatacaa gttactccgc  36720
cctaaaacct acgtcacccg ccccgttccc acgccccgcg ccacgtcaca aactccaccc  36780
cctcattatc atattggctt caatccaaaa taaggtatat tattgatgat gtta        36834
```

<210> SEQ ID NO 2

<211> LENGTH: 35553
<212> TYPE: DNA
<213> ORGANISM: Artificial Sequence
<220> FEATURE:
<223> OTHER INFORMATION: The nucleotide sequence encoding virus CGTG-602
<220> FEATURE:
<221> NAME/KEY: misc_feature
<222> LOCATION: (33283)..(33283)
<223> OTHER INFORMATION: n is a, c, g, or t

<400> SEQUENCE: 2

```
taacatcatc aataatatac cttattttgg attgaagcca atatgataat gaggggggtgg     60

agtttgtgac gtggcgcggg gcgtgggaac ggggcgggtg acgtagtagt gtggcggaag    120

tgtgatgttg caagtgtggc ggaacacatg taagcgacgg atgtggcaaa agtgacgttt    180

ttggtgtgcg ccggtgtaca caggaagtga caattttcgc gcggttttag gcggatgttg    240

tagtaaattt gggcgtaacc gagtaagatt tggccatttt cgcgggaaaa ctgaataaga    300

ggaagtgaaa tctgaataat tttgtgttac tcatagcgcg taatactggt accgcggccg    360

ctggtaccat ccggacaaag cctgcgcgcg ccccgccccg ccattggccg taccgccccg    420

cgccgccgcc ccatcccgcc cctcgccgcc gggtccggcg cgttaaagcc aataggaacc    480

gccgccgttg ttcccgtcac ggccggggca gccaattgtg gcggcgctcg gcggctcgtg    540

gctctttcgc ggcaaaaagg atttggcgcg taaaagtggc cgggactttg caggcagcgg    600

cggccggggg cggagcggga tcgagccctc gccctcgagc tagaagcttg ttttctcctc    660

cgagccgctc cgacaccggg actgaaaatg agacatatta tctgccacgg aggtgttatt    720

accgaagaaa tggccgccag tcttttggac cagctgatcg aagaggtact ggctgataat    780

cttccacctc ctagccattt tgaaccacct acccttcacg aactgtatga tttagacgtg    840

acggcccccg aagatcccaa cgaggaggcg gtttcgcaga tttttcccga ctctgtaatg    900

ttggcggtgc aggaagggat tgacttactc actttttccgc cggcgcccgg ttctccggag    960

ccgcctcacc tttcccggca gcccgagcag ccggagcaga gagccttggg tccggtttct   1020

atgccaaacc ttgtaccgga ggtgatcgat ccacccagtg acgacgagga tgaagagggt   1080

gaggagtttg tgttagatta tgtggagcac ccccgggcacg gttgcaggtc ttgtcattat   1140

caccggagga atacggggga cccagatatt atgtgttcgc tttgctatat gaggacctgt   1200

ggcatgtttg tctacagtaa gtgaaaatta tgggcagtgg gtgatagagt ggtgggtttg   1260

gtgtggtaat tttttttttta atttttacag ttttgtggtt taaagaattt tgtattgtga   1320

tttttttaaa aggtcctgtg tctgaacctg agcctgagcc cgagccagaa ccggagcctg   1380

caagacctac ccgccgtcct aaaatggcgc ctgctatcct gagacgcccg acatcacctg   1440

tgtctagaga atgcaatagt agtacggata gctgtgactc cggtccttct aacacacctc   1500

ctgagataca cccggtggtc ccgctgtgcc ccattaaacc agttgccgtg agagttggtg   1560

ggcgtcgcca ggctgtggaa tgtatcgagg acttgcttaa cgagcctggg caacctttgg   1620

acttgagctg taaacgcccc aggccataag gtgtaaacct gtgattgcgt gtgtggttaa   1680

cgcctttgtt tgctgaatga gttgatgtaa gtttaataaa gggtgagata atgtttaact   1740

tgcatggcgt gttaaatggg gcggggctta aagggtatat aatgcgccgt gggctaatct   1800

tggttacatc tgacctcatg gaggcttggg agtgtttgga agatttttct gctgtgcgta   1860

acttgctgga acagagctct aacagtacct cttggttttg gaggtttctg tggggctcat   1920

cccaggcaaa gttagtctgc agaattaagg aggattacaa gtgggaattt gaagagcttt   1980

tgaaatcctg tggtgagctg tttgattctt tgaatctggg tcaccaggcg cttttccaag   2040
```

```
agaaggtcat caagactttg gatttttcca caccggggcg cgctgcggct gctgttgctt   2100
ttttgagttt tataaaggat aaatggagcg aagaaaccca tctgagcggg ggtacctgc    2160
tggattttct ggccatgcat ctgtggagag cggttgtgag acacaagaat cgcctgctac   2220
tgttgtcttc cgtccgcccg gcgataatac cgacggagga gcagcagcag cagcaggagg   2280
aagccaggcg gcggcggcag gagcagagcc catggaaccc gagagccggc ctggaccctc   2340
gggaatgaat gttgtacagg tggctgaact gtatccagaa ctgagacgca ttttgacaat   2400
tacagaggat gggcaggggc taaagggggt aaagagggag cgggggggctt gtgaggctac  2460
agaggaggct aggaatctag cttttagctt aatgaccaga caccgtcctg agtgtattac   2520
ttttcaacag atcaaggata attgcgctaa tgagcttgat ctgctggcgc agaagtattc   2580
catagagcag ctgaccactt actggctgca gccaggggat gattttgagg aggctattag   2640
ggtatatgca aaggtggcac ttaggccaga ttgcaagtac aagatcagca aacttgtaaa   2700
tatcaggaat tgttgctaca tttctgggaa cggggccgag gtggagatag atacggagga   2760
tagggtggcc tttagatgta gcatgataaa tatgtggccg gggtgcttgg gcatggacgg   2820
ggtggttatt atgaatgtaa ggtttactgg ccccaatttt agcggtacgg ttttcctggc   2880
caataccaac cttatcctac acggtgtaag cttctatggg tttaacaata cctgtgtgga   2940
agcctggacc gatgtaaggg ttcggggctg tgccttttac tgctgctgga agggggtggt   3000
gtgtcgcccc aaaagcaggg cttcaattaa gaaatgcctc tttgaaaggt gtaccttggg   3060
tatcctgtct gagggtaact ccagggtgcg ccacaatgtg gcctccgact gtggttgctt   3120
catgctagtg aaaagcgtgg ctgtgattaa gcataacatg gtatgtggca actgcgagga   3180
cagggcctct cagatgctga cctgctcgga cggcaactgt cacctgctga agaccattca   3240
cgtagccagc cactctcgca aggcctggcc agtgtttgag cataacatac tgacccgctg   3300
ttccttgcat ttgggtaaca ggaggggggt gttcctacct taccaatgca atttgagtca   3360
cactaagata ttgcttgagc ccgagagcat gtccaaggtg aacctgaacg gggtgtttga   3420
catgaccatg aagatctgga aggtgctgag gtacgatgag acccgcacca ggtgcagacc   3480
ctgcgagtgt ggcggtaaac atattaggaa ccagcctgtg atgctggatg tgaccgagga   3540
gctgaggccc gatcacttgg tgctggcctg cacccgcgct gagtttggct ctagcgatga   3600
agatacagat tgaggtactg aaatgtgtgg gcgtggctta agggtgggaa agaatatata   3660
aggtgggggt cttatgtagt tttgtatctg ttttgcagca gccgccgccg ccatgagcac   3720
caactcgttt gatggaagca ttgtgagctc atatttgaca acgcgcatgc ccccatgggc   3780
cggggtgcgt cagaatgtga tgggctccag cattgatggt cgccccgtcc tgcccgcaaa   3840
ctctactacc ttgacctacg agaccgtgtc tggaacgccg ttggagactg cagcctccgc   3900
cgccgcttca gccgctgcag ccaccgcccg cgggattgtg actgactttg ctttcctgag   3960
cccgcttgca agcagtgcag cttcccgttc atccgcccgc gatgacaagt tgacggctct   4020
tttggcacaa ttggattctt tgacccggga acttaatgtc gtttctcagc agctgttgga   4080
tctgcgccag caggtttctg ccctgaaggc ttcctcccct cccaatgcgg tttaaaacat   4140
aaataaaaaa ccagactctg tttggatttg gatcaagcaa gtgtcttgct gtctttattt   4200
aggggttttg cgcgcgcggt aggcccggga ccagcggtct cggtcgttga gggtcctgtg   4260
tattttttcc aggacgtggt aaaggtgact ctggatgttc agatacatgg gcataagccc   4320
gtctctgggg tggaggtagc accactgcag agcttcatgc tgcggggtgg tgttgtagat   4380
```

```
gatccagtcg tagcaggagc gctgggcgtg gtgcctaaaa atgtctttca gtagcaagct   4440
gattgccagg ggcaggccct tggtgtaagt gtttacaaag cggttaagct gggatgggtg   4500
catacgtggg gatatgagat gcatcttgga ctgtattttt aggttggcta tgttcccagc   4560
catatccctc cggggattca tgttgtgcag aaccaccagc acagtgtatc cggtgcactt   4620
gggaaatttg tcatgtagct tagaaggaaa tgcgtggaag aacttggaga cgcccttgtg   4680
acctccaaga ttttccatgc attcgtccat aatgatggca atgggcccac gggcggcggc   4740
ctgggcgaag atatttctgg gatcactaac gtcatagttg tgttccagga tgagatcgtc   4800
ataggccatt tttacaaagc gcgggcggag ggtgccagac tgcggtataa tggttccatc   4860
cggcccaggg gcgtagttac cctcacagat ttgcatttcc cacgctttga gttcagatgg   4920
ggggatcatg tctacctgcg gggcgatgaa gaaaacggtt tccggggtag gggagatcag   4980
ctgggaagaa agcaggttcc tgagcagctg cgacttaccg cagccggtgg gcccgtaaat   5040
cacacctatt accgggtgca actggtagtt aagagagctg cagctgccgt catccctgag   5100
caggggggcc acttcgttaa gcatgtccct gactcgcatg ttttccctga ccaaatccgc   5160
cagaaggcgc tcgccgccca gcgatagcag ttcttgcaag gaagcaaagt ttttcaacgg   5220
tttgagaccg tccgccgtag gcatgctttt gagcgtttga ccaagcagtt ccaggcggtc   5280
ccacagctcg gtcacctgct ctacggcatc tcgatccagc atatctcctc gtttcgcggg   5340
ttggggcggc tttcgctgta cggcagtagt cggtgctcgt ccagacgggc cagggtcatg   5400
tctttccacg ggcgcagggt cctcgtcagc gtagtctggg tcacggtgaa ggggtgcgct   5460
ccgggctgcg cgctggccag ggtgcgcttg aggctggtcc tgctggtgct gaagcgctgc   5520
cggtcttcgc cctgcgcgtc ggccaggtag catttgacca tggtgtcata gtccagcccc   5580
tccgcggcgt ggcccttggc gcgcagcttg cccttggagg aggcgccgca cgaggggcag   5640
tgcagacttt tgagggcgta gagcttgggc gcgagaaata ccgattccgg ggagtaggca   5700
tccgcgccgc aggccccgca gacggtctcg cattccacga gccaggtgag ctctggccgt   5760
tcggggtcaa aaaccaggtt tcccccatgc tttttgatgc gtttcttacc tctggtttcc   5820
atgagccggt gtccacgctc ggtgacgaaa aggctgtccg tgtccccgta tacagacttg   5880
agaggcctgt cctcgagcgg tgttccgcgg tcctcctcgt atagaaactc ggaccactct   5940
gagacaaagg ctcgcgtcca ggccagcacg aaggaggcta agtgggaggg gtagcggtcg   6000
ttgtccacta gggggtccac tcgctccagg gtgtgaagac acatgtcgcc ctcttcggca   6060
tcaaggaagg tgattggttt gtaggtgtag gccacgtgac cgggtgttcc tgaagggggg   6120
ctataaaagg gggtgggggc gcgttcgtcc tcactctctt ccgcatcgct gtctgcgagg   6180
gccagctgtt ggggtgagta ctccctctga aaagcgggca tgacttctgc gctaagattg   6240
tcagtttcca aaaacgagga ggatttgata ttcacctggc ccgcggtgat gcctttgagg   6300
gtggccgcat ccatctggtc agaaaagaca atctttttgt tgtcaagctt ggtggcaaac   6360
gacccgtaga gggcgttgga cagcaacttg gcgatggagc gcagggtttg gtttttgtcg   6420
cgatcggcgc gctccttggc cgcgatgttt agctgcacgt attcgcgcgc aacgcaccgc   6480
cattcgggaa agacggtggt gcgctcgtcg ggcaccaggt gcacgcgcca accgcggttg   6540
tgcagggtga caaggtcaac gctggtggct acctctccgc gtaggcgctc gttggtccag   6600
cagaggcggc cgcccttgcg cgagcagaat ggcggtaggg ggtctagctg cgtctcgtcc   6660
ggggggtctg cgtccacggt aaagaccccg ggcagcaggc gcgcgtcgaa gtagtctatc   6720
ttgcatcctt gcaagtctag cgcctgctgc catgcgcggg cggcaagcgc gcgctcgtat   6780
```

```
gggttgagtg ggggacccca tggcatgggg tgggtgagcg cggaggcgta catgccgcaa   6840
atgtcgtaaa cgtagagggg ctctctgagt attccaagat atgtagggta gcatcttcca   6900
ccgcggatgc tggcgcgcac gtaatcgtat agttcgtgcg agggagcgag gaggtcggga   6960
ccgaggttgc tacgggcggg ctgctctgct cggaagacta tctgcctgaa gatggcatgt   7020
gagttggatg atatggttgg acgctggaag acgttgaagc tggcgtctgt gagacctacc   7080
gcgtcacgca cgaaggaggc gtaggagtcg cgcagcttgt tgaccagctc ggcggtgacc   7140
tgcacgtcta gggcgcagta gtccagggtt tccttgatga tgtcatactt atcctgtccc   7200
ttttttttcc acagctcgcg gttgaggaca aactcttcgc ggtctttcca gtactcttgg   7260
atcggaaacc cgtcggcctc cgaacggtaa gagcctagca tgtagaactg gttgacggcc   7320
tggtaggcgc agcatccctt ttctacgggt agcgcgtatg cctgcgcggc cttccggagc   7380
gaggtgtggg tgagcgcaaa ggtgtccctg accatgactt tgaggtactg gtatttgaag   7440
tcagtgtcgt cgcatccgcc ctgctcccag agcaaaaagt ccgtgcgctt tttggaacgc   7500
ggatttggca gggcgaaggt gacatcgttg aagagtatct ttcccgcgcg aggcataaag   7560
ttgcgtgtga tgcggaaggg tcccggcacc tcggaacggt tgttaattac ctgggcggcg   7620
agcacgatct cgtcaaagcc gttgatgttg tggcccacaa tgtaaagttc caagaagcgc   7680
gggatgccct tgatggaagg caatttttta agttcctcgt aggtgagctc ttcaggggag   7740
ctgagcccgt gctctgaaag ggcccagtct gcaagatgag ggttggaagc gacgaatgag   7800
ctccacaggt cacgggccat tagcatttgc aggtggtcgc gaaaggtcct aaactggcga   7860
cctatggcca tttttctggg ggtgatgcag tagaaggtaa gcgggtcttg ttcccagcgg   7920
tcccatccaa ggttcgcggc taggtctcgc gcggcagtca ctagaggctc atctccgccg   7980
aacttcatga ccagcatgaa gggcacgagc tgcttcccaa aggcccccat ccaagtatag   8040
gtctctacat cgtaggtgac aaagagacgc tcggtgcgag gatgcgagcc gatcgggaag   8100
aactggatct cccgccacca attggaggag tggctattga tgtggtgaaa gtagaagtcc   8160
ctgcgacggg ccgaacactc gtgctggctt ttgtaaaaac gtgcgcagta ctggcagcgg   8220
tgcacgggct gtacatcctg cacgaggttg acctgacgac cgcgcacaag gaagcagagt   8280
gggaatttga gcccctcgcc tggcgggttt ggctggtggt cttctacttc ggctgcttgt   8340
ccttgaccgt ctggctgctc gaggggagtt acggtggatc ggaccaccac gccgcgcgag   8400
cccaaagtcc agatgtccgc gcgcggcggt cggagcttga tgacaacatc gcgcagatgg   8460
gagctgtcca tggtctggag ctcccgcggc gtcaggtcag gcgggagctc ctgcaggttt   8520
acctcgcata gacgggtcag ggcgcgggct agatccaggt gatacctaat ttccaggggc   8580
tggttggtgg cggcgtcgat ggcttgcaag aggccgcatc cccgcggcgc gactacggta   8640
ccgcgcggcg ggcggtgggc cgcgggggtg tccttggatg atgcatctaa aagcggtgac   8700
gcgggcgagc ccccggaggt aggggggggct ccggacccgc cgggagaggg ggcaggggca   8760
cgtcggcgcc gcgcgcgggc aggagctggt gctgcgcgcg taggttgctg gcgaacgcga   8820
cgacgcggcg gttgatctcc tgaatctggc gcctctgcgt gaagacgacg ggcccggtga   8880
gcttgagcct gaaagagagt tcgacagaat caatttcggt gtcgttgacg gcggcctggc   8940
gcaaaatctc ctgcacgtct cctgagttgt cttgataggc gatctcggcc atgaactgct   9000
cgatctcttc ctcctggaga tctccgcgtc cggctcgctc cacggtggcg gcgaggtcgt   9060
tggaaatgcg ggccatgagc tgcgagaagg cgttgaggcc tccctcgttc cagacgcggc   9120
```

```
tgtagaccac gccccccttcg gcatcgcggg cgcgcatgac cacctgcgcg agattgagct   9180
ccacgtgccg ggcgaagacg gcgtagtttc gcaggcgctg aaagaggtag ttgagggtgg   9240
tggcggtgtg ttctgccacg aagaagtaca taacccagcg tcgcaacgtg gattcgttga   9300
tatcccccaa ggcctcaagg cgctccatgg cctcgtagaa gtccacggcg aagttgaaaa   9360
actgggagtt gcgcgccgac acggttaact cctcctccag aagacggatg agctcggcga   9420
cagtgtcgcg cacctcgcgc tcaaaggcta caggggcctc ttcttcttct tcaatctcct   9480
cttccataag ggcctcccct tcttcttctt ctggcggcgg tgggggaggg gggacacggc   9540
ggcgacgacg gcgcaccggg aggcggtcga caaagcgctc gatcatctcc ccgcggcgac   9600
ggcgcatggt ctcggtgacg gcgcggccgt tctcgcgggg gcgcagttgg aagacgccgc   9660
ccgtcatgtc ccggttatgg gttggcgggg ggctgccatg cggcagggat acggcgctaa   9720
cgatgcatct caacaattgt tgtgtaggta ctccgccgcc gagggacctg agcgagtccg   9780
catcgaccgg atcggaaaac ctctcgagaa aggcgtctaa ccagtcacag tcgcaaggta   9840
ggctgagcac cgtggcgggc ggcagcgggc ggcggtcggg gttgtttctg gcggaggtgc   9900
tgctgatgat gtaattaaag taggcggtct tgagacggcg gatggtcgac agaagcacca   9960
tgtccttggg tccggcctgc tgaatgcgca ggcggtcggc catgccccag gcttcgtttt  10020
gacatcggcg caggtctttg tagtagtctt gcatgagcct ttctaccggc acttcttctt  10080
ctccttcctc ttgtcctgca tctcttgcat ctatcgctgc ggcggcggcg gagtttggcc  10140
gtaggtggcg ccctcttcct cccatgcgtg tgaccccgaa gcccctcatc ggctgaagca  10200
gggctaggtc ggcgacaacg cgctcggcta atatggcctg ctgcacctgc gtgagggtag  10260
actggaagtc atccatgtcc acaaagcggt ggtatgcgcc cgtgttgatg gtgtaagtgc  10320
agttggccat aacggaccag ttaacggtct ggtgacccgg ctgcgagagc tcggtgtacc  10380
tgagacgcga gtaagccctc gagtcaaata cgtagtcgtt gcaagtccgc accaggtact  10440
ggtatcccac caaaaagtgc ggcggcggct ggcggtagag gggccagcgt agggtggccg  10500
gggctccggg ggcgagatct tccaacataa ggcgatgata tccgtagatg tacctggaca  10560
tccaggtgat gccggcggcg gtggtggagg cgcgcggaaa gtcgcggacg cggttccaga  10620
tgttgcgcag cggcaaaaag tgctccatgg tcgggacgct ctggccggtc aggcgcgcgc  10680
aatcgttgac gctctagacc gtgcaaaagg agagcctgta agcgggcact cttccgtggt  10740
ctggtggata aattcgcaag ggtatcatgg cggacgaccg gggttcgagc cccgtatccg  10800
gccgtccgcc gtgatccatg cggttaccgc ccgcgtgtcg aacccaggtg tgcgacgtca  10860
gacaacgggg gagtgctcct tttggcttcc ttccaggcgc ggcggctgct gcgctagctt  10920
ttttggccac tggccgcgcg cagcgtaagc ggttaggctg gaaagcgaaa gcattaagtg  10980
gctcgctccc tgtagccgga gggttatttt ccaagggttg agtcgcggga cccccggttc  11040
gagtctcgga ccggccggac tgcggcgaac gggggtttgc ctccccgtca tgcaagaccc  11100
cgcttgcaaa ttcctccgga aacagggacg agcccctttt ttgcttttcc cagatgcatc  11160
cggtgctgcg gcagatgcgc ccccctcctc agcagcggca agagcaagag cagcggcaga  11220
catgcagggc accctcccct cctcctaccg cgtcaggagg ggcgacatcc gcggttgacg  11280
cggcagcaga tggtgattac gaacccccgc ggcgccgggc ccggcactac ctggacttgg  11340
aggagggcga gggcctggcg cggctaggag cgccctctcc tgagcggtac ccaagggtgc  11400
agctgaagcg tgatacgcgt gaggcgtacg tgccgcggca gaacctgttt cgcgaccgcg  11460
agggagagga gcccgaggag atgcgggatc gaaagttcca cgcagggcgc gagctgcggc  11520
```

```
atggcctgaa tcgcgagcgg ttgctgcgcg aggaggactt tgagcccgac gcgcgaaccg  11580
ggattagtcc cgcgcgcgca cacgtggcgg ccgccgacct ggtaaccgca tacgagcaga  11640
cggtgaacca ggagattaac tttcaaaaaa gctttaacaa ccacgtgcgt acgcttgtgg  11700
cgcgcgagga ggtggctata ggactgatgc atctgtggga ctttgtaagc gcgctggagc  11760
aaaacccaaa tagcaagccg ctcatggcgc agctgttcct tatagtgcag cacagcaggg  11820
acaacgaggc attcagggat gcgctgctaa acatagtaga gcccgagggc cgctggctgc  11880
tcgatttgat aaacatcctg cagagcatag tggtgcagga gcgcagcttg agcctggctg  11940
acaaggtggc cgccatcaac tattccatgc ttagcctggg caagttttac gcccgcaaga  12000
tataccatac cccttacgtt cccatagaca aggaggtaaa gatcgagggg ttctacatgc  12060
gcatggcgct gaaggtgctt accttgagcg acgacctggg cgtttatcgc aacgagcgca  12120
tccacaaggc cgtgagcgtg agccggcggc gcgagctcag cgaccgcgag ctgatgcaca  12180
gcctgcaaag ggccctggct ggcacgggca gcggcgatag agaggccgag tcctactttg  12240
acgcgggcgc tgacctgcgc tgggccccaa gccgacgcgc cctggaggca gctggggccg  12300
gacctgggct ggcggtggca cccgcgcgcg ctggcaacgt cggcggcgtg gaggaatatg  12360
acgaggacga tgagtacgag ccagaggacg gcgagtacta agcggtgatg tttctgatca  12420
gatgatgcaa gacgcaacgg acccggcggt gcgggcggcg ctgcagagcc agccgtccgg  12480
ccttaactcc acggacgact ggcgccaggt catggaccgc atcatgtcgc tgactgcgcg  12540
caatcctgac gcgttccggc agcagccgca ggccaaccgg ctctccgcaa ttctggaagc  12600
ggtggtcccg gcgcgcgcaa accccacgca cgagaaggtg ctggcgatcg taaacgcgct  12660
ggccgaaaac agggccatcc ggcccgacga ggccggcctg gtctacgacg cgctgcttca  12720
gcgcgtggct cgttacaaca gcggcaacgt gcagaccaac ctggaccggc tggtggggga  12780
tgtgcgcgag gccgtggcgc agcgtgagcg cgcgcagcag cagggcaacc tgggctccat  12840
ggttgcacta aacgccttcc tgagtacaca gcccgccaac gtgccgcggg gacaggagga  12900
ctacaccaac tttgtgagcg cactgcggct aatggtgact gagacaccgc aaagtgaggt  12960
gtaccagtct gggccagact atttttttcca gaccagtaga caaggcctgc agaccgtaaa  13020
cctgagccag gctttcaaaa acttgcaggg gctgtggggg gtgcgggctc ccacaggcga  13080
ccgcgcgacc gtgtctagct tgctgacgcc caactcgcgc ctgttgctgc tgctaatagc  13140
gcccttcacg gacagtggca gcgtgtcccg ggacacatac ctaggtcact tgctgacact  13200
gtaccgcgag gccataggtc aggcgcatgt ggacgagcat actttccagg agattacaag  13260
tgtcagccgc gcgctggggc aggaggacac gggcagcctg gaggcaaccc taaactacct  13320
gctgaccaac cggcggcaga agatcccctc gttgcacagt ttaaacagcg aggaggagcg  13380
cattttgcgc tacgtgcagc agagcgtgag ccttaacctg atgcgcgacg gggtaacgcc  13440
cagcgtggcg ctggacatga ccgcgcgcaa catggaaccg ggcatgtatg cctcaaaccg  13500
gccgtttatc aaccgcctaa tggactactt gcatcgcgcg gccgccgtga accccgagta  13560
tttcaccaat gccatcttga acccgcactg gctaccgccc cctggtttct acaccggggg  13620
attcgaggtg cccgagggta acgatggatt cctctgggac gacatagacg acagcgtgtt  13680
ttccccgcaa ccgcagaccc tgctagagtt gcaacagcgc gagcaggcag aggcggcgct  13740
gcgaaaggaa agcttccgca ggccaagcag cttgtccgat ctaggcgctg cggccccgcg  13800
gtcagatgct agtagcccat ttccaagctt gatagggtct cttaccagca ctcgcaccac  13860
```

```
ccgcccgcgc ctgctgggcg aggaggagta cctaaacaac tcgctgctgc agccgcagcg  13920
cgaaaaaaac ctgcctccgg catttcccaa caacgggata gagagcctag tggacaagat  13980
gagtagatgg aagacgtacg cgcaggagca cagggacgtg ccaggcccgc gcccgcccac  14040
ccgtcgtcaa aggcacgacc gtcagcgggg tctggtgtgg gaggacgatg actcggcaga  14100
cgacagcagc gtcctggatt tgggagggag tggcaacccg tttgcgcacc ttcgccccag  14160
gctggggaga atgttttaaa aaaaaaaaag catgatgcaa aataaaaaac tcaccaaggc  14220
catggcaccg agcgttggtt ttcttgtatt ccccttagta tgcggcgcgc ggcgatgtat  14280
gaggaaggtc ctcctccctc ctacgagagt gtggtgagcg cggcgccagt ggcggcggcg  14340
ctgggttctc ccttcgatgc tcccctggac ccgccgtttg tgcctccgcg gtacctgcgg  14400
cctaccgggg ggagaaacag catccgttac tctgagttgg caccccta tt cgacaccacc  14460
cgtgtgtacc tggtggacaa caagtcaacg gatgtggcat ccctgaacta ccagaacgac  14520
cacagcaact ttctgaccac ggtcattcaa aacaatgact acagcccggg ggaggcaagc  14580
acacagacca tcaatcttga cgaccggtcg cactggggcg gcgacctgaa aaccatcctg  14640
cataccaaca tgccaaatgt gaacgagttc atgtttacca ataagtttaa ggcgcgggtg  14700
atggtgtcgc gcttgcctac taaggacaat caggtggagc tgaaatacga gtgggtggag  14760
ttcacgctgc ccgagggcaa ctactccgag accatgacca tagaccttat gaacaacgcg  14820
atcgtggagc actacttgaa agtgggcaga cagaacgggg ttctggaaag cgacatcggg  14880
gtaaagtttg acacccgcaa cttcagactg ggtttgacc ccgtcactgg tcttgtcatg  14940
cctggggtat atacaaacga agccttccat ccagacatca ttttgctgcc aggatgcggg  15000
gtggacttca cccacagccg cctgagcaac ttgttgggca tccgcaagcg gcaacccttc  15060
caggagggct ttaggatcac ctacgatgat ctggagggtg gtaacattcc cgcactgttg  15120
gatgtggacg cctaccaggc gagcttgaaa gatgacaccg aacagggcgg gggtggcgca  15180
ggcggcagca acagcagtgg cagcggcgcg gaagagaact ccaacgcggc agccgcggca  15240
atgcagccgg tggaggacat gaacgatcat gccattcgcg gcgacacctt tgccacacgg  15300
gctgaggaga agcgcgctga ggccgaagca gcggccgaag ctgccgcccc cgctgcgcaa  15360
cccgaggtcg agaagcctca gaagaaaccg gtgatcaaac ccctgacaga ggacagcaag  15420
aaacgcagtt acaacctaat aagcaatgac agcaccttca cccagtaccg cagctggtac  15480
cttgcataca actacggcga ccctcagacc ggaatccgct catggaccct gctttgcact  15540
cctgacgtaa cctgcggctc ggagcaggtc tactggtcgt tgccagacat gatgcaagac  15600
cccgtgacct tccgctccac gcgccagatc agcaactttc cggtggtggg cgccgagctg  15660
ttgcccgtgc actccaagag cttctacaac gaccaggccg tctactccca actcatccgc  15720
cagtttacct ctctgaccca cgtgttcaat cgctttcccg agaaccagat tttggcgcgc  15780
ccgccagccc ccaccatcac caccgtcagt gaaaacgttc ctgctctcac agatcacggg  15840
acgctaccgc tgcgcaacag catcggagga gtccagcgag tgaccattac tgacgccaga  15900
cgccgcacct gcccctacgt ttacaaggcc ctgggcatag tctcgccgcg cgtcctatcg  15960
agccgcactt tttgagcaag catgtccatc cttatatcgc ccagcaataa cacaggctgg  16020
ggcctgcgct tcccaagcaa gatgtttggc ggggccaaga agcgctccga ccaacaccca  16080
gtgcgcgtgc gcgggcacta ccgcgcgccc tggggcgcgc acaaacgcgg ccgcactggg  16140
cgcaccaccg tcgatgacgc catcgacgcg gtggtggagg aggcgcgcaa ctacacgccc  16200
acgccgccac cagtgtccac agtggacgcg gccattcaga ccgtggtgcg cggagcccgg  16260
```

```
cgctatgcta aaatgaagag acggcggagg cgcgtagcac gtcgccaccg ccgccgaccc  16320
ggcactgccg cccaacgcgc ggcggcggcc ctgcttaacc gcgcacgtcg caccggccga  16380
cgggcggcca tgcgggccgc tcgaaggctg gccgcgggta ttgtcactgt gccccccagg  16440
tccaggcgac gagcggccgc cgcagcagcc gcggccatta gtgctatgac tcagggtcgc  16500
aggggcaacg tgtattgggt gcgcgactcg gttagcggcc tgcgcgtgcc cgtgcgcacc  16560
cgccccccgc gcaactagat tgcaagaaaa aactacttag actcgtactg ttgtatgtat  16620
ccagcggcgg cggcgcgcaa cgaagctatg tccaagcgca aaatcaaaga agagatgctc  16680
caggtcatcg cgccggagat ctatggcccc ccgaagaagg aagagcagga ttacaagccc  16740
cgaaagctaa agcgggtcaa aaagaaaaag aaagatgatg atgatgaact tgacgacgag  16800
gtggaactgc tgcacgctac cgcgcccagg cgacgggtac agtggaaagg tcgacgcgta  16860
aaacgtgttt tgcgacccgg caccaccgta gtctttacgc ccggtgagcg ctccacccgc  16920
acctacaagc gcgtgtatga tgaggtgtac ggcgacgagg acctgcttga gcaggccaac  16980
gagcgcctcg gggagtttgc ctacggaaag cggcataagg acatgctggc gttgccgctg  17040
gacgagggca acccaacacc tagcctaaag cccgtaacac tgcagcaggt gctgcccgcg  17100
cttgcaccgt ccgaagaaaa gcgcggccta aagcgcgagt ctggtgactt ggcacccacc  17160
gtgcagctga tggtacccaa gcgccagcga ctggaagatg tcttggaaaa aatgaccgtg  17220
gaacctgggc tggagcccga ggtccgcgtg cggccaatca agcaggtggc gccgggactg  17280
ggcgtgcaga ccgtggacgt tcagataccc actaccagta gcaccagtat tgccaccgcc  17340
acagagggca tggagacaca aacgtccccg gttgcctcag cggtggcgga tgccgcggtg  17400
caggcggtcg ctgcggccgc gtccaagacc tctacggagg tgcaaacgga cccgtggatg  17460
tttcgcgttt cagcccccg gcgcccgcgc ggttcgagga agtacggcgc cgccagcgcg  17520
ctactgcccg aatatgccct acatccttcc attgcgccta cccccggcta tcgtggctac  17580
acctaccgcc ccagaagacg agcaactacc cgacgccgaa ccaccactgg aacccgccgc  17640
cgccgtcgcc gtcgccagcc cgtgctggcc ccgatttccg tgcgcagggt ggctcgcgaa  17700
ggaggcagga ccctggtgct gccaacagcg cgctaccacc ccagcatcgt ttaaaagccg  17760
gtctttgtgg ttcttgcaga tatggccctc acctgccgcc tccgtttccc ggtgccggga  17820
ttccgaggaa gaatgcaccg taggaggggc atggccggcc acggcctgac gggcggcatg  17880
cgtcgtgcgc accaccggcg gcggcgcgcg tcgcaccgtc gcatgcgcgg cggtatcctg  17940
cccctcctta ttccactgat cgccgcggcg attggcgccg tgcccggaat tgcatccgtg  18000
gccttgcagg cgcagagaca ctgattaaaa acaagttgca tgtggaaaaa tcaaaataaa  18060
aagtctggac tctcacgctc gcttggtcct gtaactattt tgtagaatgg aagacatcaa  18120
ctttgcgtct ctggccccgc gacacggctc gcgcccgttc atgggaaact ggcaagatat  18180
cggcaccagc aatatgagcg gtggcgcctt cagctggggc tcgctgtgga gcggcattaa  18240
aaatttcggt tccaccgtta agaactatgg cagcaaggcc tggaacagca gcacaggcca  18300
gatgctgagg gataagttga aagagcaaaa tttccaacaa aaggtggtag atggcctggc  18360
ctctggcatt agcggggtgg tggacctggc caaccaggca gtgcaaaata agattaacag  18420
taagcttgat ccccgccctc ccgtagagga gcctccaccg gccgtggaga cagtgtctcc  18480
agaggggcgt ggcgaaaagc gtccgcgccc cgacagggaa gaaactctgg tgacgcaaat  18540
agacgagcct ccctcgtacg aggaggcact aaagcaaggc ctgcccacca cccgtcccat  18600
```

```
cgcgcccatg gctaccggag tgctgggcca gcacacaccc gtaacgctgg acctgcctcc  18660
ccccgccgac acccagcaga aacctgtgct gccaggcccg accgccgttg ttgtaacccg  18720
tcctagccgc gcgtccctgc gccgcgccgc cagcggtccg cgatcgttgc ggcccgtagc  18780
cagtggcaac tggcaaagca cactgaacag catcgtgggt ctgggggtgc aatccctgaa  18840
gcgccgacga tgcttctgaa tagctaacgt gtcgtatgtg tgtcatgtat gcgtccatgt  18900
cgccgccaga ggagctgctg agccgccgcg cgcccgcttt ccaagatggc taccccttcg  18960
atgatgccgc agtggtctta catgcacatc tcgggccagg acgcctcgga gtacctgagc  19020
cccgggctgg tgcagtttgc ccgcgccacc gagacgtact tcagcctgaa taacaagttt  19080
agaaacccca cggtggcgcc tacgcacgac gtgaccacag accggtccca gcgtttgacg  19140
ctgcggttca tccctgtgga ccgtgaggat actgcgtact cgtacaaggc gcggttcacc  19200
ctagctgtgg gtgataaccg tgtgctggac atggcttcca cgtactttga catccgcggc  19260
gtgctggaca ggggccctac ttttaagccc tactctggca ctgcctacaa cgccctggct  19320
cccaagggtg ccccaaatcc ttgcgaatgg gatgaagctg ctactgctct tgaaataaac  19380
ctagaagaag aggacgatga caacgaagac gaagtagacg agcaagctga gcagcaaaaa  19440
actcacgtat ttgggcaggc gccttattct ggtataaata ttacaaagga gggtattcaa  19500
ataggtgtcg aaggtcaaac acctaaatat gccgataaaa catttcaacc tgaacctcaa  19560
ataggagaat ctcagtggta cgaaactgaa attaatcatg cagctgggag agtccttaaa  19620
aagactaccc caatgaaacc atgttacggt tcatatgcaa aacccacaaa tgaaaatgga  19680
gggcaaggca ttcttgtaaa gcaacaaaat ggaaagctag aaagtcaagt ggaaatgcaa  19740
tttttctcaa ctactgaggc gaccgcaggc aatggtgata acttgactcc taaagtggta  19800
ttgtacagtg aagatgtaga tatagaaacc ccagacactc atatttctta catgcccact  19860
attaaggaag gtaactcacg agaactaatg ggccaacaat ctatgcccaa caggcctaat  19920
tacattgctt ttagggacaa ttttattggt ctaatgtatt acaacagcac gggtaatatg  19980
ggtgttctgg cgggccaagc atcgcagttg aatgctgttg tagatttgca agacagaaac  20040
acagagcttt cataccagct tttgcttgat tccattggtg atagaaccag gtacttttct  20100
atgtggaatc aggctgttga cagctatgat ccagatgtta gaattattga aaatcatgga  20160
actgaagatg aacttccaaa ttactgcttt ccactgggag gtgtgattaa tacagagact  20220
cttaccaagg taaaacctaa aacaggtcag gaaaatggat gggaaaaaga tgctacagaa  20280
ttttcagata aaaatgaaat aagagttgga aataattttg ccatggaaat caatctaaat  20340
gccaacctgt ggagaaattt cctgtactcc aacatagcgc tgtatttgcc cgacaagcta  20400
aagtacagtc cttccaacgt aaaaatttct gataacccaa acacctacga ctacatgaac  20460
aagcgagtgg tggctcccgg gttagtggac tgctacatta accttggagc acgctggtcc  20520
cttgactata tggacaacgt caacccattt aaccaccacc gcaatgctgg cctgcgctac  20580
cgctcaatgt tgctgggcaa tggtcgctat gtgcccttcc acatccaggt gcctcagaag  20640
ttctttgcca ttaaaaacct ccttctcctg ccgggctcat acacctacga gtggaacttc  20700
aggaaggatg ttaacatggt tctgcagagc tccctaggaa atgacctaag ggttgacgga  20760
gccagcatta agtttgatag catttgcctt tacgccacct tcttccccat ggcccacaac  20820
accgcctcca cgcttgaggc catgcttaga aacgacacca acgaccagtc ctttaacgac  20880
tatctctccg ccgccaacat gctctaccct atacccgcca acgctaccaa cgtgcccata  20940
tccatcccct cccgcaactg ggcggctttc cgcggctggg ccttcacgcg ccttaagact  21000
```

```
aaggaaaccc catcactggg ctcgggctac gacccttatt acacctactc tggctctata  21060
ccctacctag atggaacctt ttacctcaac cacaccttta agaaggtggc cattaccttt  21120
gactcttctg tcagctggcc tggcaatgac cgcctgctta cccccaacga gtttgaaatt  21180
aagcgctcag ttgacgggga gggttacaac gttgcccagt gtaacatgac caaagactgg  21240
ttcctggtac aaatgctagc taactacaac attggctacc agggcttcta tatcccagag  21300
agctacaagg accgcatgta ctccttcttt agaaacttcc agcccatgag ccgtcaggtg  21360
gtggatgata ctaaatacaa ggactaccaa caggtgggca tcctacacca acacaacaac  21420
tctggatttg ttggctacct tgcccccacc atgcgcgaag gacaggccta ccctgctaac  21480
ttccccctatc cgcttatagg caagaccgca gttgacagca ttacccagaa aaagtttctt  21540
tgcgatcgca ccctttggcg catcccattc tccagtaact ttatgtccat gggcgcactc  21600
acagacctgg gccaaaacct tctctacgcc aactccgccc acgcgctaga catgactttt  21660
gaggtggatc ccatggacga gcccaccctt ctttatgttt tgtttgaagt ctttgacgtg  21720
gtccgtgtgc accggccgca ccgcggcgtc atcgaaaccg tgtacctgcg cacgcccttc  21780
tcggccggca acgccacaac ataaagaagc aagcaacatc aacaacagct gccgccatgg  21840
gctccagtga gcaggaactg aaagccattg tcaaagatct tggttgtggg ccatattttt  21900
tgggcaccta tgacaagcgc tttccaggct ttgtttctcc acacaagctc gcctgcgcca  21960
tagtcaatac ggccggtcgc gagactgggg gcgtacactg gatggccttt gcctggaacc  22020
cgcactcaaa aacatgctac ctctttgagc cctttggctt ttctgaccag cgactcaagc  22080
aggtttacca gtttgagtac gagtcactcc tgcgccgtag cgccattgct tcttcccccg  22140
accgctgtat aacgctggaa aagtccaccc aaagcgtaca ggggcccaac tcggccgcct  22200
gtggactatt ctgctgcatg tttctccacg cctttgccaa ctggccccaa actcccatgg  22260
atcacaaccc caccatgaac cttattaccg gggtacccaa ctccatgctc aacagtcccc  22320
aggtacagcc caccctgcgt cgcaaccagg aacagctcta cagcttcctg gagcgccact  22380
cgccctactt ccgcagccac agtgcgcaga ttaggagcgc cacttctttt tgtcacttga  22440
aaaacatgta aaaataatgt actagagaca ctttcaataa aggcaaatgc ttttatttgt  22500
acactctcgg gtgattattt acccccaccc ttgccgtctg cgccgtttaa aaatcaaagg  22560
ggttctgccg cgcatcgcta tgcgccactg gcagggacac gttgcgatac tggtgtttag  22620
tgctccactt aaactcaggc acaaccatcc gcggcagctc ggtgaagttt tcactccaca  22680
ggctgcgcac catcaccaac gcgtttagca ggtcgggcgc cgatatcttg aagtcgcagt  22740
tggggcctcc gccctgcgcg cgcgagttgc gatacacagg gttgcagcac tggaacacta  22800
tcagcgccgg gtggtgcacg ctggccagca cgctcttgtc ggagatcaga tccgcgtcca  22860
ggtcctccgc gttgctcagg gcgaacggag tcaactttgg tagctgcctt cccaaaaagg  22920
gcgcgtgccc aggctttgag ttgcactcgc accgtagtgg catcaaaagg tgaccgtgcc  22980
cggtctgggc gttaggatac agcgcctgca taaaagcctt gatctgctta aaagccacct  23040
gagcctttgc gccttcagag aagaacatgc cgcaagactt gccggaaaac tgattggccg  23100
gacaggccgc gtcgtgcacg cagcaccttg cgtcggtgtt ggagatctgc accacatttc  23160
ggccccaccg gttcttcacg atcttggcct tgctagactg ctccttcagc gcgcgctgcc  23220
cgttttcgct cgtcacatcc atttcaatca cgtgctcctt atttatcata atgcttccgt  23280
gtagacactt aagctcgcct tcgatctcag cgcagcggtg cagccacaac gcgcagcccg  23340
```

```
tgggctcgtg atgcttgtag gtcacctctg caaacgactg caggtacgcc tgcaggaatc  23400
gccccatcat cgtcacaaag gtcttgttgc tggtgaaggt cagctgcaac ccgcggtgct  23460
cctcgttcag ccaggtcttg catacggccg ccagagcttc cacttggtca ggcagtagtt  23520
tgaagttcgc ctttagatcg ttatccacgt ggtacttgtc catcagcgcg cgcgcagcct  23580
ccatgccctt ctcccacgca gacacgatcg gcacactcag cgggttcatc accgtaattt  23640
cactttccgc ttcgctgggc tcttcctctt cctcttgcgt ccgcatacca cgcgccactg  23700
ggtcgtcttc attcagccgc cgcactgtgc gcttacctcc tttgccatgc ttgattagca  23760
ccggtgggtt gctgaaaccc accatttgta gcgccacatc ttctctttct tcctcgctgt  23820
ccacgattac ctctggtgat ggcgggcgct cgggcttggg agaagggcgc ttcttttct  23880
tcttgggcgc aatggccaaa tccgccgccg aggtcgatgg ccgcgggctg ggtgtgcgcg  23940
gcaccagcgc gtcttgtgat gagtcttcct cgtcctcgga ctcgatacgc cgcctcatcc  24000
gctttttgg gggcgcccgg ggaggcggcg gcgacgggga cggggacgac acgtcctcca  24060
tggttggggg acgtcgcgcc gcaccgcgtc cgcgctcggg ggtggtttcg cgctgctcct  24120
cttcccgact ggccatttcc ttctcctata ggcagaaaaa gatcatggag tcagtcgaga  24180
agaaggacag cctaaccgcc ccctctgagt tcgccaccac cgcctccacc gatgccgcca  24240
acgcgcctac caccttcccc gtcgaggcac ccccgcttga ggaggaggaa gtgattatcg  24300
agcaggaccc aggttttgta agcgaagacg acgaggaccg ctcagtacca acagaggata  24360
aaaagcaaga ccaggacaac gcagaggcaa acgaggaaca agtcgggcgg ggggacgaaa  24420
ggcatggcga ctacctagat gtgggagacg acgtgctgtt gaagcatctg cagcgccagt  24480
gcgccattat ctgcgacgcg ttgcaagagc gcagcgatgt gcccctcgcc atagcggatg  24540
tcagccttgc ctacgaacgc cacctattct caccgcgcgt accccccaaa cgccaagaaa  24600
acggcacatg cgagcccaac ccgcgcctca acttctaccc cgtatttgcc gtgccagagg  24660
tgcttgccac ctatcacatc tttttccaaa actgcaagat acccctatcc tgccgtgcca  24720
accgcagccg agcggacaag cagctggcct tgcggcaggg cgctgtcata cctgatatcg  24780
cctcgctcaa cgaagtgcca aaaatctttg agggtcttgg acgcgacgag aagcgcgcgg  24840
caaacgctct gcaacaggaa aacagcgaaa atgaaagtca ctctggagtg ttggtggaac  24900
tcgagggtga caacgcgcgc ctagccgtac taaaacgcag catcgaggtc acccactttg  24960
cctacccggc acttaaccta ccccccaagg tcatgagcac agtcatgagt gagctgatcg  25020
tgcgccgtgc gcagcccctg gagagggatg caaatttgca agaacaaaca gaggagggcc  25080
tacccgcagt tggcgacgag cagctagcgc gctggcttca aacgcgcgag cctgccgact  25140
tggaggagcg acgcaaacta atgatggccg cagtgctcgt taccgtggag cttgagtgca  25200
tgcagcggtt ctttgctgac ccggagatgc agcgcaagct agaggaaaca ttgcactaca  25260
cctttcgaca gggctacgta cgccaggcct gcaagatctc caacgtggag ctctgcaacc  25320
tggtctccta ccttggaatt ttgcacgaaa accgccttgg gcaaaacgtg cttcattcca  25380
cgctcaaggg cgaggcgcgc cgcgactacg tccgcgactg cgtttactta tttctatgct  25440
acacctggca gacggccatg ggcgtttggc agcagtgctt ggaggagtgc aacctcaagg  25500
agctgcagaa actgctaaag caaaacttga aggacctatg gacggccttc aacgagcgct  25560
ccgtggccgc gcacctggcg gacatcattt tccccgaacg cctgcttaaa accctgcaac  25620
agggtctgcc agacttcacc agtcaaagca tgttgcagaa ctttaggaac tttatcctag  25680
agcgctcagg aatcttgccc gccacctgct gtgcacttcc tagcgacttt gtgcccatta  25740
```

```
agtaccgcga atgccctccg ccgctttggg gccactgcta ccttctgcag ctagccaact  25800
accttgccta ccactctgac ataatggaag acgtgagcgg tgacggtcta ctggagtgtc  25860
actgtcgctg caacctatgc accccgcacc gctccctggt ttgcaattcg cagctgctta  25920
acgaaagtca aattatcggt acctttgagc tgcagggtcc ctcgcctgac gaaaagtccg  25980
cggctccggg gttgaaactc actccggggc tgtggacgtc ggcttacctt cgcaaatttg  26040
tacctgagga ctaccacgcc cacgagatta ggttctacga agaccaatcc cgcccgccaa  26100
atgcggagct taccgcctgc gtcattaccc agggccacat tcttggccaa ttgcaagcca  26160
tcaacaaagc ccgccaagag tttctgctac gaaagggacg gggggtttac ttggaccccc  26220
agtccggcga ggagctcaac ccaatccccc cgccgccgca gccctatcag cagcagccgc  26280
gggcccttgc ttcccaggat ggcacccaaa aagaagctgc agctgccgcc gccacccacg  26340
gacgaggagg aatactggga cagtcaggca gaggaggttt tggacgagga ggaggaggac  26400
atgatggaag actgggagag cctagacgag gaagcttccg aggtcgaaga ggtgtcagac  26460
gaaacaccgt caccctcggt cgcattcccc tcgccggcgc cccagaaatc ggcaaccggt  26520
tccagcatgg ctacaacctc cgctcctcag gcgccgccgg cactgcccgt tcgccgaccc  26580
aaccgtagat gggacaccac tggaaccagg gccggtaagt ccaagcagcc gccgccgtta  26640
gcccaagagc aacaacagcg ccaaggctac cgctcatggc gcgggcacaa gaacgccata  26700
gttgcttgct tgcaagactg tgggggcaac atctccttcg cccgccgctt tcttctctac  26760
catcacggcg tggccttccc ccgtaacatc ctgcattact accgtcatct ctacagccca  26820
tactgcaccg gcggcagcgg cagcggcagc aacagcagcg gccacacaga agcaaaggcg  26880
accggatagc aagactctga caaagcccaa gaaatccaca gcggcggcag cagcaggagg  26940
aggagcgctg cgtctggcgc ccaacgaacc cgtatcgacc cgcgagctta gaaacaggat  27000
ttttcccact ctgtatgcta tatttcaaca gagcaggggc caagaacaag agctgaaaat  27060
aaaaaacagg tctctgcgat ccctcacccg cagctgcctg tatcacaaaa gcgaagatca  27120
gcttcggcgc acgctggaag acgcggaggc tctcttcagt aaatactgcg cgctgactct  27180
taaggactag tttcgcgccc tttctcaaat ttaagcgcga aaactacgtc atctccagcg  27240
gccacacccg gcgccagcac ctgtcgtcag cgccattatg agcaaggaaa ttcccacgcc  27300
ctacatgtgg agttaccagc cacaaatggg acttgcggct ggagctgccc aagactactc  27360
aacccgaata aactacatga gcgcgggacc ccacatgata tcccgggtca acggaatccg  27420
cgcccaccga aaccgaattc tcttggaaca ggcggctatt accaccacac ctcgtaataa  27480
ccttaatccc cgtagttggc ccgctgccct ggtgtaccag gaaagtcccg ctcccaccac  27540
tgtggtactt cccagagacg cccaggccga agttcagatg actaactcag ggcgcagct  27600
tgcgggcggc tttcgtcaca gggtgcggtc gcccgggcag ggtataactc acctgacaat  27660
cagagggcga ggtattcagc tcaacgacga gtcggtgagc tcctcgcttg gtctccgtcc  27720
ggacgggaca tttcagatcg gcggcgccgg ccgctcttca ttcacgcctc gtcaggcaat  27780
cctaactctg cagacctcgt cctctgagcc gcgctctgga ggcattggaa ctctgcaatt  27840
tattgaggag tttgtgccat cggtctactt taaccccttc tcgggacctc ccggccacta  27900
tccggatcaa tttattccta actttgacgc ggtaaaggac tcggcggatg gctacgactg  27960
aatgttaagt ggagaggcag agcaactgcg cctgaaacac ctggtccact gtcgccgcca  28020
caagtgcttt gcccgcgact ccggtgagtt ttgctacttt gaattgcccg aggatcatat  28080
```

```
cgagggcccg gcgcacggcg tccggcttac cgcccaggga gagcttgccc gtagcctgat  28140
tcgggagttt acccagcgcc ccctgctagt tgagcgggac aggggaccct gtgttctcac  28200
tgtgatttgc aactgtccta accctggatt acatcaagat ctttgttgcc atctctgtgc  28260
tgagtataat aaatacagaa attaaaatat actggggctc ctatcgccat cctgtaaacg  28320
ccaccgtctt cacccgccca agcaaaccaa ggcgaacctt acctggtact tttaacatct  28380
ctccctctgt gatttacaac agtttcaacc cagacggagt gagtctacga gagaacctct  28440
ccgagctcag ctactccatc agaaaaaaca ccaccctcct tacctgccgg gaacgtacga  28500
tgtggctgca gagcctgctg ctcttgggca ctgtggcctg cagcatctct gcacccgccc  28560
gctcgcccag ccccagcacg cagccctggg agcatgtgaa tgccatccag gaggcccggc  28620
gtctcctgaa cctgagtaga gacactgctg ctgagatgaa tgaaacagta gaagtcatct  28680
cagaaatgtt tgacctccag gagccgacct gcctacagac ccgcctggag ctgtacaagc  28740
agggcctgcg gggcagcctc accaagctca agggcccctt gaccatgatg gccagccact  28800
acaagcagca ctgccctcca accccggaaa cttcctgtgc aacccagact atcacctttg  28860
aaagtttcaa agagaacctg aaggactttc tgcttgtcat cccctttgac tgctgggagc  28920
cagtccagga gtgacaattg actctatgtg ggatatgctc cagcgctaca accttgaagt  28980
caggcttcct ggatgtcagc atctgacttt ggccagcacc tgtcccgcgg atttgttcca  29040
gtccaactac agcgacccac cctaacagag atgaccaaca caaccaacgc ggccgccgct  29100
accggactta catctaccac aaatacaccc caagtttctg cctttgtcaa taactgggat  29160
aacttgggca tgtggtggtt ctccatagcg cttatgtttg tatgccttat tattatgtgg  29220
ctcatctgct gcctaaagcg caaacgcgcc cgaccaccca tctatagtcc catcattgtg  29280
ctacacccaa acaatgatgg aatccataga ttggacggac tgaaacacat gttcttttct  29340
cttacagtat gattaaatga gacatgattc ctcgagtttt tatattactg acccttgttg  29400
cgcttttttg tgcgtgctcc acattggctg cggtttctca catcgaagta gactgcattc  29460
cagccttcac agtctatttg ctttacggat ttgtcaccct cacgctcatc tgcagcctca  29520
tcactgtggt catcgccttt atccagtgca ttgactgggt ctgtgtgcgc tttgcatatc  29580
tcagacacca tccccagtac agggacagga ctatagctga gcttcttaga attctttaat  29640
tatgaaattt actgtgactt ttctgctgat tatttgcacc ctatctgcgt tttgttcccc  29700
gacctccaag cctcaaagac atatatcatg cagattcact cgtatatgga atattccaag  29760
ttgctacaat gaaaaaagcg atctttccga agcctggtta tatgcaatca tctctgttat  29820
ggtgttctgc agtaccatct tagccctagc tatatatccc taccttgaca ttggctggaa  29880
acgaatagat gccatgaacc acccaacttt ccccgcgccc gctatgcttc cactgcaaca  29940
agttgttgcc ggcggctttg tcccagccaa tcagcctcgc cccacttctc ccaccccccac  30000
tgaaatcagc tactttaatc taacaggagg agatgactga caccctagat ctagaaatgg  30060
acggaattat tacagagcag cgcctgctag aaagacgcag ggcagcggcc gagcaacagc  30120
gcatgaatca agagctccaa gacatggtta acttgcacca gtgcaaaagg ggtatctttt  30180
gtctggtaaa gcaggccaaa gtcacctacg acagtaatac caccggacac cgccttagct  30240
acaagttgcc aaccaagcgt cagaaattgg tggtcatggt gggagaaaag cccattacca  30300
taactcagca ctcggtagaa accgaaggct gcattcactc accttgtcaa ggacctgagg  30360
atctctgcac ccttattaag accctgtgcg gtctcaaaga tcttattccc tttaactaat  30420
aaaaaaaaat aataaagcat cacttactta aaatcagtta gcaaatttct gtccagttta  30480
```

```
ttcagcagca cctccttgcc ctcctcccag ctctggtatt gcagcttcct cctggctgca  30540
aactttctcc acaatctaaa tggaatgtca gtttcctcct gttcctgtcc atccgcaccc  30600
actatcttca tgttgttgca gatgaagcgc gcaagaccgt ctgaagatac cttcaacccc  30660
gtgtatccat atgacacgga aaccggtcct ccaactgtgc cttttcttac tcctcccttt  30720
gtatccccca atgggtttca agagagtccc cctggggtac tctctttgcg cctatccgaa  30780
cctctagtta cctccaatgg catgcttgcg ctcaaaatgg gcaacggcct ctctctggac  30840
gaggccggca accttacctc ccaaaatgta accactgtga gcccacctct caaaaaaacc  30900
aagtcaaaca taaacctgga aatatctgca cccctcacag ttacctcaga agccctaact  30960
gtggctgccg ccgcacctct aatggtcgcg ggcaacacac tcaccatgca atcacaggcc  31020
ccgctaaccg tgcacgactc caaacttagc attgccaccc aaggacccct cacagtgtca  31080
gaaggaaagc tagccctgca aacatcaggc cccctcacca ccaccgatag cagtaccctt  31140
actatcactg cctcaccccc tctaactact gccactggta gcttgggcat tgacttgaaa  31200
gagcccattt atacacaaaa tggaaaacta ggactaaagt acggggctcc tttgcatgta  31260
acagacgacc taaacacttt gaccgtagca actggtccag gtgtgactat taataatact  31320
tccttgcaaa ctaaagttac tggagccttg ggttttgatt cacaaggcaa tatgcaactt  31380
aatgtagcag gaggactaag gattgattct caaaacagac gccttatact tgatgttagt  31440
tatccgtttg atgctcaaaa ccaactaaat ctaagactag gacagggccc tctttttata  31500
aactcagccc acaacttgga tattaactac aacaaaggcc tttacttgtt tacagcttca  31560
aacaattcca aaaagcttga ggttaaccta agcactgcca aggggttgat gtttgacgct  31620
acagccatag ccattaatgc aggagatggg cttgaatttg gttcacctaa tgcaccaaac  31680
acaaatcccc tcaaaacaaa aattggccat ggcctagaat ttgattcaaa caaggctatg  31740
gttcctaaac taggaactgg ccttagtttt gacagcacag gtgccattac agtaggaaac  31800
aaaaataatg ataagctaac cctatggaca ggtccaaaac cagaagccaa ctgcataatt  31860
gaatacggga aacaaaaccc agatagcaaa ctaactttaa tccttgtaaa aaatggagga  31920
attgttaatg gatatgtaac gctaatggga gcctcagact acgttaacac cttatttaaa  31980
aacaaaaatg tctccattaa tgtagaacta tactttgatg ccactggtca tatattacca  32040
gactcatctt ctcttaaaac agatctagaa ctaaaataca agcaaaccgc tgactttagt  32100
gcaagaggtt ttatgccaag tactacagcg tatccatttg tccttcctaa tgcgggaaca  32160
cataatgaaa attatatttt tggtcaatgc tactacaaag caagcgatgg tgcccttttt  32220
ccgttggaag ttactgttat gcttaataaa cgcctgccag atagtcgcac atcctatgtt  32280
atgactttttt tatggtcctt gaatgctggt ctagctccag aaactactca ggcaaccctc  32340
ataacctccc catttacctt ttcctatatt agagaagatg actaataaac tctaaagaat  32400
cgtttgtgtt atgtttcaac gtgtttattt ttcaattgca gaaaatttca agtcattttt  32460
cattcagtag tatagcccca ccaccacata gcttatacag atcaccgtac cttaatcaaa  32520
ctcacagaac cctagtattc aacctgccac ctccctccca acacacagag tacacagtcc  32580
tttctccccg gctggcctta aaaagcatca tatcatgggt aacagacata ttcttaggtg  32640
ttatattcca cacggtttcc tgtcgagcca aacgctcatc aagtgatatt aataaactcc  32700
ccgggcagct cacttaagtt catgtcgctg tccagctgct gagccacagg ctgctgtcca  32760
acttgcggtt gcttaacggg cggcgaagga gaagtccacg cctacatggg ggagagtca  32820
```

```
taatcgtgca tcaggatagg gcggtggtgc tgcagcagcg cgcgaataaa ctgctgccgc  32880
cgccgctccg tcctgcagga atacaacatg gcagtggtct cctcagcgat gattcgcacc  32940
gcccgcagca taaggcgcct tgtcctccgg gcacagcagc gcaccctgat ctcacttaaa  33000
tcagcacagt aactgcagca cagcaccaca atattgttca aaatcccaca gtgcaaggcg  33060
ctgtatccaa agctcatggc ggggaccaca gaacccacgt ggccatcata ccacaagcgc  33120
aggtagatta agtggcgacc cctcataaac acgctggaca taaacattac ctcttttggc  33180
atgttgtaat tcaccacctc ccggtaccat ataaacctct gattaaacat ggcgccatcc  33240
accaccatcc taaaccagct ggccaaaacc tgccccgccg ggntatacac tgcagggaac  33300
cgggactgga acaatgacag tggagagccc aggactcgta accatggatc atcatgctcg  33360
tcatgatatc aatgttggca caacacaggc acacgtgcat acacttcctc aggattacaa  33420
gctcctcccg cgttagaacc atatcccagg gaacaaccca ttcctgaatc agcgtaaatc  33480
ccacactgca gggaagacct cgcacgtaac tcacgttgtg cattgtcaaa gtgttacatt  33540
cgggcagcag cggatgatcc tccagtatgg tagcgcgggt ttctgtctca aaaggaggta  33600
gacgatccct actgtacgga gtgcgccgag acaaccgaga tcgtgttggt cgtagtgtca  33660
tgccaaatgg aacgccggac gtagtcatat ttcctgaagc aaaaccaggt gcgggcgtga  33720
caaacagatc tgcgtctccg gtctcgccgc ttagatcgct ctgtgtagta gttgtagtat  33780
atccactctc tcaaagcatc caggcgcccc ctggcttcgg gttctatgta aactccttca  33840
tgcgccgctg ccctgataac atccaccacc gcagaataag ccacacccag ccaacctaca  33900
cattcgttct gcgagtcaca cacgggagga gcgggaagag ctggaagaac catgtttttt  33960
tttttattcc aaaagattat ccaaaacctc aaaatgaaga tctattaagt gaacgcgctc  34020
ccctccggtg gcgtggtcaa actctacagc caaagaacag ataatggcat ttgtaagatg  34080
ttgcacaatg gcttccaaaa ggcaaacggc cctcacgtcc aagtggacgt aaaggctaaa  34140
cccttcaggg tgaatctcct ctataaacat tccagcacct tcaaccatgc ccaaataatt  34200
ctcatctcgc caccttctca atatatctct aagcaaatcc cgaatattaa gtccggccat  34260
tgtaaaaatt tggctccaga gcgccctcca ccttcagcct caagcagcga atcatgattg  34320
caaaaattca ggttcctcac agacctgtat aagattcaaa agcggaacat taacaaaaat  34380
accgcgatcc cgtaggtccc ttcgcagggc cagctgaaca taatcgtgca ggtctgcacg  34440
gaccagcgcg gccacttccc cgccaggaac catgacaaaa gaacccacac tgattatgac  34500
acgcatactc ggagctatgc taaccagcgt agccccgatg taagcttgtt gcatgggcgg  34560
cgatataaaa tgcaaggtgc tgctcaaaaa atcaggcaaa gcctcgcgca aaaaagaaag  34620
cacatcgtag tcatgctcat gcagataaag gcaggtaagc tccggaacca ccacagaaaa  34680
agacaccatt tttctctcaa acatgtctgc gggtttctgc ataaacacaa aataaaataa  34740
caaaaaaaca tttaaacatt agaagcctgt cttacaacag gaaaaacaac ccttataagc  34800
ataagacgga ctacggccat gccggcgtga ccgtaaaaaa actggtcacc gtgattaaaa  34860
agcaccaccg acagctcctc ggtcatgtcc ggagtcataa tgtaagactc ggtaaacaca  34920
tcaggttgat tcacatcggt cagtgctaaa aagcgaccga aatagcccgg gggaatacat  34980
acccgcaggc gtagagacaa cattacagcc cccataggag gtataacaaa attaatagga  35040
gagaaaaaca cataaacacc tgaaaaaccc tcctgcctag gcaaaatagc accctcccgc  35100
tccagaacaa catacagcgc ttccacagcg gcagccataa cagtcagcct taccagtaaa  35160
aaagaaaacc tattaaaaaa acaccactcg acacggcacc agctcaatca gtcacagtgt  35220
```

aaaaaagggc caagtgcaga gcgagtatat ataggactaa aaaatgacgt aacggttaaa 35280
gtccacaaaa aacacccaga aaaccgcacg cgaacctacg cccagaaacg aaagccaaaa 35340
aacccacaac ttcctcaaat cgtcacttcc gttttcccac gttacgtcac ttcccatttt 35400
aagaaaacta caattcccaa cacatacaag ttactccgcc ctaaaaccta cgtcacccgc 35460
cccgttccca cgccccgcgc cacgtcacaa actccacccc ctcattatca tattggcttc 35520
aatccaaaat aaggtatatt attgatgatg tta 35553

<210> SEQ ID NO 3
<211> LENGTH: 36861
<212> TYPE: DNA
<213> ORGANISM: Artificial Sequence
<220> FEATURE:
<223> OTHER INFORMATION: The nucleotide sequence encoding virus CGTG-603
<220> FEATURE:
<221> NAME/KEY: misc_feature
<222> LOCATION: (34591)..(34591)
<223> OTHER INFORMATION: n is a, c, g, or t

<400> SEQUENCE: 3
taacatcatc aataatatac cttattttgg attgaagcca atatgataat gaggggggtgg 60 agtttgtgac gtggcgcggg gcgtgggaac ggggcgggtg acgtagtagt gtggcggaag 120
tgtgatgttg caagtgtggc ggaacacatg taagcgacgg atgtggcaaa agtgacgttt 180
ttggtgtgcg ccggtgtaca caggaagtga caattttcgc gcggttttag gcggatgttg 240
tagtaaattt gggcgtaacc gagtaagatt tggccatttt cgcgggaaaa ctgaataaga 300
ggaagtgaaa tctgaataat tttgtgttac tcatagcgcg taatactggt accgcggccg 360
ctggtaccat ccggacaaag cctgcgcgcg ccccgccccg ccattggccg taccgccccg 420
cgccgccgcc ccatcccgcc cctcgccgcc gggtccggcg cgttaaagcc aataggaacc 480
gccgccgttg ttcccgtcac ggccggggca gccaattgtg gcggcgctcg gcggctcgtg 540
gctctttcgc ggcaaaaagg atttggcgcg taaaagtggc cgggactttg caggcagcgg 600
cggccggggg cggagcggga tcgagccctc gccctcgagc tagaagcttg ttttctcctc 660
cgagccgctc cgacaccggg actgaaaatg agacatatta tctgccacgg aggtgttatt 720
accgaagaaa tggccgccag tcttttggac cagctgatcg aagaggtact ggctgataat 780
cttccacctc ctagccattt tgaaccacct acccttcacg aactgtatga tttagacgtg 840
acggcccccg aagatcccaa cgaggaggcg gtttcgcaga tttttcccga ctctgtaatg 900
ttggcggtgc aggaagggat tgacttactc acttttccgc cggcgcccgg ttctccggag 960
ccgcctcacc tttcccggca gcccgagcag ccggagcaga gagccttggg tccggtttct 1020
atgccaaacc ttgtaccgga ggtgatcgat ccacccagtg acgacgagga tgaagagggt 1080
gaggagtttg tgttagatta tgtggagcac cccgggcacg gttgcaggtc ttgtcattat 1140
caccggagga atacgggggga cccagatatt atgtgttcgc tttgctatat gaggacctgt 1200
ggcatgtttg tctacagtaa gtgaaaatta tgggcagtgg gtgatagagt ggtgggtttg 1260
gtgtggtaat tttttttta atttttacag ttttgtggtt taaagaattt tgtattgtga 1320
tttttttaaa aggtcctgtg tctgaacctg agcctgagcc cgagccagaa ccggagcctg 1380
caagacctac ccgccgtcct aaaatggcgc ctgctatcct gagacgcccg acatcacctg 1440
tgtctagaga atgcaatagt agtacggata gctgtgactc cggtccttct aacacacctc 1500
ctgagataca cccggtggtc ccgctgtgcc ccattaaacc agttgccgtg agagttggtg 1560

-continued

```
ggcgtcgcca ggctgtggaa tgtatcgagg acttgcttaa cgagcctggg caacctttgg   1620
acttgagctg taaacgcccc aggccataag gtgtaaacct gtgattgcgt gtgtggttaa   1680
cgcctttgtt tgctgaatga gttgatgtaa gtttaataaa gggtgagata atgtttaact   1740
tgcatggcgt gttaaatggg gcggggctta aagggtatat aatgcgccgt gggctaatct   1800
tggttacatc tgacctcatg gaggcttggg agtgtttgga agatttttct gctgtgcgta   1860
acttgctgga acagagctct aacagtacct cttggttttg gaggtttctg tggggctcat   1920
cccaggcaaa gttagtctgc agaattaagg aggattacaa gtgggaattt gaagagcttt   1980
tgaaatcctg tggtgagctg tttgattctt tgaatctggg tcaccaggcg cttttccaag   2040
agaaggtcat caagactttg gatttttcca caccggggcg cgctgcggct gctgttgctt   2100
ttttgagttt tataaaggat aaatggagcg aagaaaccca tctgagcggg gggtacctgc   2160
tggattttct ggccatgcat ctgtggagag cggttgtgag acacaagaat cgcctgctac   2220
tgttgtcttc cgtccgcccg gcgataatac cgacggagga gcagcagcag cagcaggagg   2280
aagccaggcg gcggcggcag gagcagagcc catggaaccc gagagccggc ctggaccctc   2340
gggaatgaat gttgtacagg tggctgaact gtatccagaa ctgagacgca ttttgacaat   2400
tacagaggat gggcaggggc taaagggggt aaagagggag cggggggctt gtgaggctac   2460
agaggaggct aggaatctag cttttagctt aatgaccaga caccgtcctg agtgtattac   2520
ttttcaacag atcaaggata attgcgctaa tgagcttgat ctgctggcgc agaagtattc   2580
catagagcag ctgaccactt actggctgca gccaggggat gattttgagg aggctattag   2640
ggtatatgca aaggtggcac ttaggccaga ttgcaagtac aagatcagca aacttgtaaa   2700
tatcaggaat tgttgctaca tttctgggaa cggggccgag gtggagatag atacggagga   2760
tagggtggcc tttagatgta gcatgataaa tatgtggccg gggtgcttg gcatggacgg   2820
ggtggttatt atgaatgtaa ggtttactgg ccccaatttt agcggtacgg ttttcctggc   2880
caataccaac cttatcctac acggtgtaag cttctatggg tttaacaata cctgtgtgga   2940
agcctggacc gatgtaaggg ttcggggctg tgccttttac tgctgctgga agggggtggt   3000
gtgtcgcccc aaaagcaggg cttcaattaa gaaatgcctc tttgaaaggt gtaccttggg   3060
tatcctgtct gagggtaact ccagggtgcg ccacaatgtg gcctccgact gtggttgctt   3120
catgctagtg aaaagcgtgg ctgtgattaa gcataacatg gtatgtggca actgcgagga   3180
cagggcctct cagatgctga cctgctcgga cggcaactgt cacctgctga agaccattca   3240
cgtagccagc cactctcgca aggcctggcc agtgtttgag cataacatac tgacccgctg   3300
ttccttgcat ttgggtaaca ggagggggt gttcctacct taccaatgca atttgagtca   3360
cactaagata ttgcttgagc ccgagagcat gtccaaggtg aacctgaacg gggtgtttga   3420
catgaccatg aagatctgga aggtgctgag gtacgatgag acccgcacca ggtgcagacc   3480
ctgcgagtgt ggcggtaaac atattaggaa ccagcctgtg atgctggatg tgaccgagga   3540
gctgaggccc gatcacttgg tgctggcctg cacccgcgct gagtttggct ctagcgatga   3600
agatacagat tgaggtactg aaatgtgtgg gcgtggctta agggtgggaa agaatatata   3660
aggtgggggt cttatgtagt tttgtatctg ttttgcagca gccgccgccg ccatgagcac   3720
caactcgttt gatggaagca ttgtgagctc atatttgaca acgcgcatgc ccccatgggc   3780
cggggtgcgt cagaatgtga tgggctccag cattgatggt cgccccgtcc tgcccgcaaa   3840
ctctactacc ttgacctacg agaccgtgtc tggaacgccg ttggagactg cagcctccgc   3900
cgccgcttca gccgctgcag ccaccgcccg cgggattgtg actgactttg ctttcctgag   3960
```

```
cccgcttgca agcagtgcag cttcccgttc atccgcccgc gatgacaagt tgacggctct   4020
tttggcacaa ttggattctt tgacccggga acttaatgtc gtttctcagc agctgttgga   4080
tctgcgccag caggtttctg ccctgaaggc ttcctcccct cccaatgcgg tttaaaacat   4140
aaataaaaaa ccagactctg tttggatttg gatcaagcaa gtgtcttgct gtctttattt   4200
aggggttttg cgcgcgcggt aggcccggga ccagcggtct cggtcgttga gggtcctgtg   4260
tatttttcc aggacgtggt aaaggtgact ctggatgttc agatacatgg gcataagccc    4320
gtctctgggg tggaggtagc accactgcag agcttcatgc tgcggggtgg tgttgtagat   4380
gatccagtcg tagcaggagc gctgggcgtg gtgcctaaaa atgtctttca gtagcaagct   4440
gattgccagg ggcaggccct tggtgtaagt gtttacaaag cggttaagct gggatgggtg   4500
catacgtggg gatatgagat gcatcttgga ctgtattttt aggttggcta tgttcccagc   4560
catatccctc cggggattca tgttgtgcag aaccaccagc acagtgtatc cggtgcactt   4620
gggaaatttg tcatgtagct tagaaggaaa tgcgtggaag aacttggaga cgcccttgtg   4680
acctccaaga ttttccatgc attcgtccat aatgatggca atgggcccac gggcggcggc   4740
ctgggcgaag atatttctgg gatcactaac gtcatagttg tgttccagga tgagatcgtc   4800
ataggccatt tttacaaagc gcgggcggag ggtgccagac tgcggtataa tggttccatc   4860
cggcccaggg gcgtagttac cctcacagat ttgcatttcc cacgctttga gttcagatgg   4920
ggggatcatg tctacctgcg gggcgatgaa gaaaacggtt tccggggtag gggagatcag   4980
ctgggaagaa agcaggttcc tgagcagctg cgacttaccg cagccggtgg gcccgtaaat   5040
cacacctatt accgggtgca actggtagtt aagagagctg cagctgccgt catccctgag   5100
caggggggcc acttcgttaa gcatgtccct gactcgcatg ttttccctga ccaaatccgc   5160
cagaaggcgc tcgccgccca gcgatagcag ttcttgcaag gaagcaaagt ttttcaacgg   5220
tttgagaccg tccgccgtag gcatgctttt gagcgtttga ccaagcagtt ccaggcggtc   5280
ccacagctcg gtcacctgct ctacggcatc tcgatccagc atatctcctc gtttcgcggg   5340
ttggggcggc tttcgctgta cggcagtagt cggtgctcgt ccagacgggc cagggtcatg   5400
tctttccacg ggcgcagggt cctcgtcagc gtagtctggg tcacggtgaa ggggtgcgct   5460
ccgggctgcg cgctggccag ggtgcgcttg aggctggtcc tgctggtgct gaagcgctgc   5520
cggtcttcgc cctgcgcgtc ggccaggtag catttgacca tggtgtcata gtccagcccc   5580
tccgcggcgt ggcccttggc gcgcagcttg cccttggagg aggcgccgca cgaggggcag   5640
tgcagacttt tgagggcgta gagcttgggc gcgagaaata ccgattccgg ggagtaggca   5700
tccgcgccgc aggccccgca gacggtctcg cattccacga gccaggtgag ctctggccgt   5760
tcggggtcaa aaaccaggtt tcccccatgc tttttgatgc gtttcttacc tctggtttcc   5820
atgagccggt gtccacgctc ggtgacgaaa aggctgtccg tgtccccgta tacagacttg   5880
agaggcctgt cctcgagcgg tgttccgcgg tcctcctcgt atagaaactc ggaccactct   5940
gagacaaagg ctcgcgtcca ggccagcacg aaggaggcta agtgggaggg gtagcggtcg   6000
ttgtccacta gggggtccac tcgctccagg gtgtgaagac acatgtcgcc ctcttcggca   6060
tcaaggaagg tgattggttt gtaggtgtag gccacgtgac cgggtgttcc tgaagggggg   6120
ctataaaagg gggtgggggc gcgttcgtcc tcactctctt ccgcatcgct gtctgcgagg   6180
gccagctgtt ggggtgagta ctccctctga aaagcgggca tgacttctgc gctaagattg   6240
tcagtttcca aaaacgagga ggatttgata ttcacctggc ccgcggtgat gcctttgagg   6300
```

-continued

```
gtggccgcat ccatctggtc agaaaagaca atctttttgt tgtcaagctt ggtggcaaac   6360
gacccgtaga gggcgttgga cagcaacttg gcgatggagc gcagggtttg gtttttgtcg   6420
cgatcggcgc gctccttggc cgcgatgttt agctgcacgt attcgcgcgc aacgcaccgc   6480
cattcgggaa agacggtggt gcgctcgtcg ggcaccaggt gcacgcgcca accgcggttg   6540
tgcagggtga caaggtcaac gctggtggct acctctccgc gtaggcgctc gttggtccag   6600
cagaggcggc cgcccttgcg cgagcagaat ggcggtaggg ggtctagctg cgtctcgtcc   6660
ggggggtctg cgtccacggt aaagaccccg ggcagcaggc gcgcgtcgaa gtagtctatc   6720
ttgcatcctt gcaagtctag cgcctgctgc catgcgcggg cggcaagcgc gcgctcgtat   6780
gggttgagtg ggggacccca tggcatgggg tgggtgagcg cggaggcgta catgccgcaa   6840
atgtcgtaaa cgtagagggg ctctctgagt attccaagat atgtagggta gcatcttcca   6900
ccgcggatgc tggcgcgcac gtaatcgtat agttcgtgcg agggagcgag gaggtcggga   6960
ccgaggttgc tacgggcggg ctgctctgct cggaagacta tctgcctgaa gatggcatgt   7020
gagttggatg atatggttgg acgctggaag acgttgaagc tggcgtctgt gagacctacc   7080
gcgtcacgca cgaaggaggc gtaggagtcg cgcagcttgt tgaccagctc ggcggtgacc   7140
tgcacgtcta gggcgcagta gtccagggtt tccttgatga tgtcatactt atcctgtccc   7200
ttttttttcc acagctcgcg gttgaggaca aactcttcgc ggtctttcca gtactcttgg   7260
atcggaaacc cgtcggcctc cgaacggtaa gagcctagca tgtagaactg gttgacggcc   7320
tggtaggcgc agcatccctt ttctacgggt agcgcgtatg cctgcgcggc cttccggagc   7380
gaggtgtggg tgagcgcaaa ggtgtccctg accatgactt tgaggtactg gtatttgaag   7440
tcagtgtcgt cgcatccgcc ctgctcccag agcaaaaagt ccgtgcgctt tttggaacgc   7500
ggatttggca gggcgaaggt gacatcgttg aagagtatct ttcccgcgcg aggcataaag   7560
ttgcgtgtga tgcggaaggg tcccggcacc tcggaacggt tgttaattac ctgggcggcg   7620
agcacgatct cgtcaaagcc gttgatgttg tggcccacaa tgtaaagttc caagaagcgc   7680
gggatgccct tgatggaagg caattttta agttcctcgt aggtgagctc ttcaggggag    7740
ctgagcccgt gctctgaaag ggcccagtct gcaagatgag ggttggaagc gacgaatgag   7800
ctccacaggt cacgggccat tagcatttgc aggtggtcgc gaaaggtcct aaactggcga   7860
cctatggcca tttttctgg ggtgatgcag tagaaggtaa gcgggtcttg ttcccagcgg    7920
tcccatccaa ggttcgcggc taggtctcgc gcggcagtca ctagaggctc atctccgccg   7980
aacttcatga ccagcatgaa gggcacgagc tgcttcccaa aggcccccat ccaagtatag   8040
gtctctacat cgtaggtgac aaagagacgc tcggtgcgag gatgcgagcc gatcgggaag   8100
aactggatct cccgccacca attggaggag tggctattga tgtggtgaaa gtagaagtcc   8160
ctgcgacggg ccgaacactc gtgctggctt ttgtaaaaac gtgcgcagta ctggcagcgg   8220
tgcacgggct gtacatcctg cacgaggttg acctgacgac cgcgcacaag gaagcagagt   8280
gggaatttga gcccctcgcc tggcgggttt ggctggtggt cttctacttc ggctgcttgt   8340
ccttgaccgt ctggctgctc gaggggagtt acggtggatc ggaccaccac gccgcgcgag   8400
cccaaagtcc agatgtccgc gcgcggcggt cggagcttga tgacaacatc gcgcagatgg   8460
gagctgtcca tggtctggag ctcccgcggc gtcaggtcag gcgggagctc ctgcaggttt   8520
acctcgcata gacgggtcag ggcgcgggct agatccaggt gatacctaat ttccaggggc   8580
tggttggtgg cggcgtcgat ggcttgcaag aggccgcatc cccgcggcgc gactacggta   8640
ccgcgcggcg ggcggtgggc cgcgggggtg tccttggatg atgcatctaa aagcggtgac   8700
```

```
gcgggcgagc ccccggaggt aggggggggct ccggacccgc cgggagaggg ggcaggggca   8760
cgtcggcgcc gcgcgcgggc aggagctggt gctgcgcgcg taggttgctg gcgaacgcga   8820
cgacgcggcg gttgatctcc tgaatctggc gcctctgcgt gaagacgacg ggcccggtga   8880
gcttgagcct gaaagagagt tcgacagaat caatttcggt gtcgttgacg gcggcctggc   8940
gcaaaatctc ctgcacgtct cctgagttgt cttgataggc gatctcggcc atgaactgct   9000
cgatctcttc ctcctggaga tctccgcgtc cggctcgctc cacggtggcg gcgaggtcgt   9060
tggaaatgcg ggccatgagc tgcgagaagg cgttgaggcc tccctcgttc cagacgcggc   9120
tgtagaccac gccccccttcg gcatcgcggg cgcgcatgac cacctgcgcg agattgagct   9180
ccacgtgccg ggcgaagacg gcgtagtttc gcaggcgctg aaagaggtag ttgagggtgg   9240
tggcggtgtg ttctgccacg aagaagtaca taacccagcg tcgcaacgtg gattcgttga   9300
tatcccccaa ggcctcaagg cgctccatgg cctcgtagaa gtccacggcg aagttgaaaa   9360
actgggagtt gcgcgccgac acggttaact cctcctccag aagacggatg agctcggcga   9420
cagtgtcgcg cacctcgcgc tcaaaggcta caggggcctc ttcttcttct tcaatctcct   9480
cttccataag ggcctcccct tcttcttctt ctggcggcgg tgggggaggg gggacacggc   9540
ggcgacgacg gcgcaccggg aggcggtcga caaagcgctc gatcatctcc ccgcggcgac   9600
ggcgcatggt ctcggtgacg gcgcggccgt tctcgcgggg gcgcagttgg aagacgccgc   9660
ccgtcatgtc ccggttatgg gttggcgggg ggctgccatg cggcagggat acggcgctaa   9720
cgatgcatct caacaattgt tgtgtaggta ctccgccgcc gagggacctg agcgagtccg   9780
catcgaccgg atcggaaaac ctctcgagaa aggcgtctaa ccagtcacag tcgcaaggta   9840
ggctgagcac cgtggcgggc ggcagcgggc ggcggtcggg gttgtttctg gcggaggtgc   9900
tgctgatgat gtaattaaag taggcggtct tgagacggcg gatggtcgac agaagcacca   9960
tgtccttggg tccggcctgc tgaatgcgca ggcggtcggc catgccccag gcttcgtttt  10020
gacatcggcg caggtctttg tagtagtctt gcatgagcct ttctaccggc acttcttctt  10080
ctccttcctc ttgtcctgca tctcttgcat ctatcgctgc ggcggcggcg gagtttggcc  10140
gtaggtggcg ccctcttcct cccatgcgtg tgaccccgaa gcccctcatc ggctgaagca  10200
gggctaggtc ggcgacaacg cgctcggcta atatggcctg ctgcacctgc gtgagggtag  10260
actggaagtc atccatgtcc acaaagcggt ggtatgcgcc cgtgttgatg gtgtaagtgc  10320
agttggccat aacggaccag ttaacggtct ggtgacccgg ctgcgagagc tcggtgtacc  10380
tgagacgcga gtaagccctc gagtcaaata cgtagtcgtt gcaagtccgc accaggtact  10440
ggtatcccac caaaaagtgc ggcggcggct ggcggtagag gggccagcgt agggtggccg  10500
gggctccggg ggcgagatct tccaacataa ggcgatgata tccgtagatg tacctggaca  10560
tccaggtgat gccggcggcg gtggtggagg cgcgcggaaa gtcgcggacg cggttccaga  10620
tgttgcgcag cggcaaaaag tgctccatgg tcgggacgct ctggccggtc aggcgcgcgc  10680
aatcgttgac gctctagacc gtgcaaaagg agagcctgta agcgggcact cttccgtggt  10740
ctggtggata aattcgcaag ggtatcatgg cggacgaccg gggttcgagc cccgtatccg  10800
gccgtccgcc gtgatccatg cggttaccgc ccgcgtgtcg aacccaggtg tgcgacgtca  10860
gacaacgggg gagtgctcct tttggcttcc ttccaggcgc ggcggctgct gcgctagctt  10920
ttttggccac tggccgcgcg cagcgtaagc ggttaggctg gaaagcgaaa gcattaagtg  10980
gctcgctccc tgtagccgga gggttatttt ccaagggttg agtcgcggga cccccggttc  11040
```

-continued

```
gagtctcgga ccggccggac tgcggcgaac gggggtttgc ctccccgtca tgcaagaccc  11100
cgcttgcaaa ttcctccgga aacagggacg agcccctttt ttgcttttcc cagatgcatc  11160
cggtgctgcg gcagatgcgc ccccctcctc agcagcggca agagcaagag cagcggcaga  11220
catgcagggc accctcccct cctcctaccg cgtcaggagg ggcgacatcc gcggttgacg  11280
cggcagcaga tggtgattac gaacccccgc ggcgccgggc ccggcactac ctggacttgg  11340
aggagggcga gggcctggcg cggctaggag cgccctctcc tgagcggtac ccaagggtgc  11400
agctgaagcg tgatacgcgt gaggcgtacg tgccgcggca gaacctgttt cgcgaccgcg  11460
agggagagga gcccgaggag atgcgggatc gaaagttcca cgcagggcgc gagctgcggc  11520
atggcctgaa tcgcgagcgg ttgctgcgcg aggaggactt tgagcccgac gcgcgaaccg  11580
ggattagtcc cgcgcgcgca cacgtggcgg ccgccgacct ggtaaccgca tacgagcaga  11640
cggtgaacca ggagattaac tttcaaaaaa gctttaacaa ccacgtgcgt acgcttgtgg  11700
cgcgcgagga ggtggctata ggactgatgc atctgtggga ctttgtaagc gcgctggagc  11760
aaaacccaaa tagcaagccg ctcatggcgc agctgttcct tatagtgcag cacagcaggg  11820
acaacgaggc attcagggat gcgctgctaa acatagtaga gcccgagggc cgctggctgc  11880
tcgatttgat aaacatcctg cagagcatag tggtgcagga gcgcagcttg agcctggctg  11940
acaaggtggc cgccatcaac tattccatgc ttagcctggg caagttttac gcccgcaaga  12000
tataccatac cccttacgtt cccatagaca aggaggtaaa gatcgagggg ttctacatgc  12060
gcatggcgct gaaggtgctt accttgagcg acgacctggg cgtttatcgc aacgagcgca  12120
tccacaaggc cgtgagcgtg agccggcggc gcgagctcag cgaccgcgag ctgatgcaca  12180
gcctgcaaag ggccctggct ggcacgggca gcggcgatag agaggccgag tcctactttg  12240
acgcgggcgc tgacctgcgc tgggccccaa gccgacgcgc cctggaggca gctggggccg  12300
gacctgggct ggcggtggca cccgcgcgcg ctggcaacgt cggcggcgtg gaggaatatg  12360
acgaggacga tgagtacgag ccagaggacg gcgagtacta agcggtgatg tttctgatca  12420
gatgatgcaa gacgcaacgg acccggcggt gcgggcggcg ctgcagagcc agccgtccgg  12480
ccttaactcc acggacgact ggcgccaggt catggaccgc atcatgtcgc tgactgcgcg  12540
caatcctgac gcgttccggc agcagccgca ggccaaccgg ctctccgcaa ttctggaagc  12600
ggtggtcccg gcgcgcgcaa accccacgca cgagaaggtg ctggcgatcg taaacgcgct  12660
ggccgaaaac agggccatcc ggcccgacga ggccggcctg gtctacgacg cgctgcttca  12720
gcgcgtggct cgttacaaca gcggcaacgt gcagaccaac ctggaccggc tggtgggga  12780
tgtgcgcgag gccgtggcgc agcgtgagcg cgcgcagcag cagggcaacc tgggctccat  12840
ggttgcacta aacgccttcc tgagtacaca gcccgccaac gtgccgcggg gacaggagga  12900
ctacaccaac tttgtgagcg cactgcggct aatggtgact gagacaccgc aaagtgaggt  12960
gtaccagtct gggccagact attttttcca gaccagtaga caaggcctgc agaccgtaaa  13020
cctgagccag gctttcaaaa acttgcaggg gctgtggggg gtgcgggctc ccacaggcga  13080
ccgcgcgacc gtgtctagct tgctgacgcc caactcgcgc ctgttgctgc tgctaatagc  13140
gcccttcacg gacagtggca gcgtgtcccg ggacacatac ctaggtcact tgctgacact  13200
gtaccgcgag gccataggtc aggcgcatgt ggacgagcat actttccagg agattacaag  13260
tgtcagccgc gcgctggggc aggaggacac gggcagcctg gaggcaaccc taaactacct  13320
gctgaccaac cggcggcaga agatcccctc gttgcacagt ttaaacagcg aggaggagcg  13380
cattttgcgc tacgtgcagc agagcgtgag ccttaacctg atgcgcgacg ggtaacgcc  13440
```

```
cagcgtggcg ctggacatga ccgcgcgcaa catggaaccg ggcatgtatg cctcaaaccg  13500
gccgtttatc aaccgcctaa tggactactt gcatcgcgcg gccgccgtga accccgagta  13560
tttcaccaat gccatcttga acccgcactg gctaccgccc cctggtttct acaccggggg  13620
attcgaggtg cccgagggta acgatggatt cctctgggac gacatagacg acagcgtgtt  13680
ttccccgcaa ccgcagaccc tgctagagtt gcaacagcgc gagcaggcag aggcggcgct  13740
gcgaaaggaa agcttccgca ggccaagcag cttgtccgat ctaggcgctg cggccccgcg  13800
gtcagatgct agtagcccat ttccaagctt gatagggtct cttaccagca ctcgcaccac  13860
ccgcccgcgc ctgctgggcg aggaggagta cctaaacaac tcgctgctgc agccgcagcg  13920
cgaaaaaaac ctgcctccgg catttcccaa caacgggata gagagcctag tggacaagat  13980
gagtagatgg aagacgtacg cgcaggagca cagggacgtg ccaggcccgc gcccgcccac  14040
ccgtcgtcaa aggcacgacc gtcagcgggg tctggtgtgg gaggacgatg actcggcaga  14100
cgacagcagc gtcctggatt tgggagggag tggcaacccg tttgcgcacc ttcgccccag  14160
gctggggaga atgttttaaa aaaaaaaaag catgatgcaa aataaaaaac tcaccaaggc  14220
catggcaccg agcgttggtt ttcttgtatt ccccttagta tgcggcgcgc ggcgatgtat  14280
gaggaaggtc ctcctccctc ctacgagagt gtggtgagcg cggcgccagt ggcggcggcg  14340
ctgggttctc ccttcgatgc tcccctggac ccgccgtttg tgcctccgcg gtacctgcgg  14400
cctaccgggg ggagaaacag catccgttac tctgagttgg caccccctatt cgacaccacc  14460
cgtgtgtacc tggtggacaa caagtcaacg gatgtggcat ccctgaacta ccagaacgac  14520
cacagcaact ttctgaccac ggtcattcaa aacaatgact acagcccggg ggaggcaagc  14580
acacagacca tcaatcttga cgaccggtcg cactggggcg gcgacctgaa aaccatcctg  14640
cataccaaca tgccaaatgt gaacgagttc atgtttacca ataagtttaa ggcgcgggtg  14700
atggtgtcgc gcttgcctac taaggacaat caggtggagc tgaaatacga gtgggtggag  14760
ttcacgctgc ccgagggcaa ctactccgag accatgacca tagaccttat gaacaacgcg  14820
atcgtggagc actacttgaa agtgggcaga cagaacgggg ttctggaaag cgacatcggg  14880
gtaaagtttg acacccgcaa cttcagactg ggtttgaccc ccgtcactgg tcttgtcatg  14940
cctggggtat atacaaacga agccttccat ccagacatca ttttgctgcc aggatgcggg  15000
gtggacttca cccacagccg cctgagcaac ttgttgggca tccgcaagcg gcaacccttc  15060
caggagggct ttaggatcac ctacgatgat ctggagggtg gtaacattcc cgcactgttg  15120
gatgtggacg cctaccaggc gagcttgaaa gatgacaccg aacagggcgg gggtggcgca  15180
ggcggcagca acagcagtgg cagcggcgcg gaagagaact ccaacgcggc agccgcggca  15240
atgcagccgg tggaggacat gaacgatcat gccattcgcg gcgacacctt tgccacacgg  15300
gctgaggaga agcgcgctga ggccgaagca gcggccgaag ctgccgcccc cgctgcgcaa  15360
cccgaggtcg agaagcctca gaagaaaccg gtgatcaaac ccctgacaga ggacagcaag  15420
aaacgcagtt acaacctaat aagcaatgac agcaccttca cccagtaccg cagctggtac  15480
cttgcataca actacggcga ccctcagacc ggaatccgct catggaccct gctttgcact  15540
cctgacgtaa cctgcggctc ggagcaggtc tactggtcgt tgccagacat gatgcaagac  15600
cccgtgacct tccgctccac gcgccagatc agcaactttc cggtggtggg cgccgagctg  15660
ttgcccgtgc actccaagag cttctacaac gaccaggccg tctactccca actcatccgc  15720
cagtttacct ctctgaccca cgtgttcaat cgctttcccg agaaccagat tttggcgcgc  15780
```

```
ccgccagccc ccaccatcac caccgtcagt gaaaacgttc ctgctctcac agatcacggg  15840
acgctaccgc tgcgcaacag catcggagga gtccagcgag tgaccattac tgacgccaga  15900
cgccgcacct gcccctacgt ttacaaggcc ctgggcatag tctcgccgcg cgtcctatcg  15960
agccgcactt tttgagcaag catgtccatc cttatatcgc ccagcaataa cacaggctgg  16020
ggcctgcgct tcccaagcaa gatgtttggc ggggccaaga agcgctccga ccaacaccca  16080
gtgcgcgtgc gcgggcacta ccgcgcgccc tggggcgcgc acaaacgcgg ccgcactggg  16140
cgcaccaccg tcgatgacgc catcgacgcg gtggtggagg aggcgcgcaa ctacacgccc  16200
acgccgccac cagtgtccac agtggacgcg gccattcaga ccgtggtgcg cggagcccgg  16260
cgctatgcta aaatgaagag acggcggagg cgcgtagcac gtcgccaccg ccgccgaccc  16320
ggcactgccg cccaacgcgc ggcggcggcc ctgcttaacc gcgcacgtcg caccggccga  16380
cgggcggcca tgcgggccgc tcgaaggctg gccgcgggta ttgtcactgt gccccccagg  16440
tccaggcgac gagcggccgc cgcagcagcc gcggccatta gtgctatgac tcagggtcgc  16500
aggggcaacg tgtattgggt gcgcgactcg gttagcggcc tgcgcgtgcc cgtgcgcacc  16560
cgccccccgc gcaactagat tgcaagaaaa aactacttag actcgtactg ttgtatgtat  16620
ccagcggcgg cggcgcgcaa cgaagctatg tccaagcgca aaatcaaaga agagatgctc  16680
caggtcatcg cgccggagat ctatggcccc ccgaagaagg aagagcagga ttacaagccc  16740
cgaaagctaa agcgggtcaa aaagaaaaag aaagatgatg atgatgaact tgacgacgag  16800
gtggaactgc tgcacgctac cgcgcccagg cgacgggtac agtggaaagg tcgacgcgta  16860
aaacgtgttt tgcgacccgg caccaccgta gtctttacgc ccggtgagcg ctccacccgc  16920
acctacaagc gcgtgtatga tgaggtgtac ggcgacgagg acctgcttga gcaggccaac  16980
gagcgcctcg gggagtttgc ctacggaaag cggcataagg acatgctggc gttgccgctg  17040
gacgagggca acccaacacc tagcctaaag cccgtaacac tgcagcaggt gctgcccgcg  17100
cttgcaccgt ccgaagaaaa gcgcggccta aagcgcgagt ctggtgactt ggcacccacc  17160
gtgcagctga tggtacccaa gcgccagcga ctggaagatg tcttggaaaa aatgaccgtg  17220
gaacctgggc tggagcccga ggtccgcgtg cggccaatca agcaggtggc gccgggactg  17280
ggcgtgcaga ccgtggacgt tcagataccc actaccagta gcaccagtat tgccaccgcc  17340
acagagggca tggagacaca aacgtccccg gttgcctcag cggtggcgga tgccgcggtg  17400
caggcggtcg ctgcggccgc gtccaagacc tctacggagg tgcaaacgga cccgtggatg  17460
tttcgcgttt cagcccccg gcgcccgcgc ggttcgagga agtacggcgc cgccagcgcg  17520
ctactgcccg aatatgccct acatccttcc attgcgccta cccccggcta tcgtggctac  17580
acctaccgcc ccagaagacg agcaactacc cgacgccgaa ccaccactgg aacccgccgc  17640
cgccgtcgcc gtcgccagcc cgtgctggcc ccgatttccg tgcgcagggt ggctcgcgaa  17700
ggaggcagga ccctggtgct gccaacagcg cgctaccacc ccagcatcgt ttaaaagccg  17760
gtctttgtgg ttcttgcaga tatggccctc acctgccgcc tccgtttccc ggtgccggga  17820
ttccgaggaa gaatgcaccg taggaggggc atggccggcc acggcctgac gggcggcatg  17880
cgtcgtgcgc accaccggcg gcggcgcgcg tcgcaccgtc gcatgcgcgg cggtatcctg  17940
cccctcctta ttccactgat cgccgcggcg attggcgccg tgcccggaat tgcatccgtg  18000
gccttgcagg cgcagagaca ctgattaaaa acaagttgca tgtggaaaaa tcaaaataaa  18060
aagtctggac tctcacgctc gcttggtcct gtaactattt tgtagaatgg aagacatcaa  18120
ctttgcgtct ctggccccgc gacacggctc gcgcccgttc atgggaaact ggcaagatat  18180
```

```
cggcaccagc aatatgagcg gtggcgcctt cagctggggc tcgctgtgga gcggcattaa  18240
aaatttcggt tccaccgtta agaactatgg cagcaaggcc tggaacagca gcacaggcca  18300
gatgctgagg gataagttga aagagcaaaa tttccaacaa aaggtggtag atggcctggc  18360
ctctggcatt agcggggtgg tggacctggc caaccaggca gtgcaaaata agattaacag  18420
taagcttgat ccccgccctc ccgtagagga gcctccaccg gccgtggaga cagtgtctcc  18480
agaggggcgt ggcgaaaagc gtccgcgccc cgacagggaa gaaactctgg tgacgcaaat  18540
agacgagcct ccctcgtacg aggaggcact aaagcaaggc ctgcccacca cccgtcccat  18600
cgcgcccatg gctaccggag tgctgggcca gcacacaccc gtaacgctgg acctgcctcc  18660
ccccgccgac acccagcaga aacctgtgct gccaggcccg accgccgttg ttgtaacccg  18720
tcctagccgc gcgtccctgc gccgcgccgc cagcggtccg cgatcgttgc ggcccgtagc  18780
cagtggcaac tggcaaagca cactgaacag catcgtgggt ctgggggtgc aatccctgaa  18840
gcgccgacga tgcttctgaa tagctaacgt gtcgtatgtg tgtcatgtat gcgtccatgt  18900
cgccgccaga ggagctgctg agccgccgcg cgcccgcttt ccaagatggc taccccttcg  18960
atgatgccgc agtggtctta catgcacatc tcgggccagg acgcctcgga gtacctgagc  19020
cccgggctgg tgcagtttgc ccgcgccacc gagacgtact tcagcctgaa taacaagttt  19080
agaaacccca cggtggcgcc tacgcacgac gtgaccacag accggtccca gcgtttgacg  19140
ctgcggttca tccctgtgga ccgtgaggat actgcgtact cgtacaaggc gcggttcacc  19200
ctagctgtgg gtgataaccg tgtgctggac atggcttcca cgtactttga catccgcggc  19260
gtgctggaca ggggccctac ttttaagccc tactctggca ctgcctacaa cgccctggct  19320
cccaagggtg ccccaaatcc ttgcgaatgg gatgaagctg ctactgctct tgaaataaac  19380
ctagaagaag aggacgatga caacgaagac gaagtagacg agcaagctga gcagcaaaaa  19440
actcacgtat ttgggcaggc gccttattct ggtataaata ttacaaagga gggtattcaa  19500
ataggtgtcg aaggtcaaac acctaaatat gccgataaaa catttcaacc tgaacctcaa  19560
ataggagaat ctcagtggta cgaaactgaa attaatcatg cagctgggag agtccttaaa  19620
aagactaccc caatgaaacc atgttacggt tcatatgcaa aacccacaaa tgaaaatgga  19680
gggcaaggca ttcttgtaaa gcaacaaaat ggaaagctag aaagtcaagt ggaaatgcaa  19740
tttttctcaa ctactgaggc gaccgcaggc aatggtgata acttgactcc taaagtggta  19800
ttgtacagtg aagatgtaga tatagaaacc ccagacactc atatttctta catgcccact  19860
attaaggaag gtaactcacg agaactaatg ggccaacaat ctatgcccaa caggcctaat  19920
tacattgctt ttagggacaa ttttattggt ctaatgtatt acaacagcac gggtaatatg  19980
ggtgttctgg cgggccaagc atcgcagttg aatgctgttg tagatttgca agacagaaac  20040
acagagcttt cataccagct tttgcttgat tccattggtg atagaaccag gtacttttct  20100
atgtggaatc aggctgttga cagctatgat ccagatgtta gaattattga aaatcatgga  20160
actgaagatg aacttccaaa ttactgcttt ccactgggag gtgtgattaa tacagagact  20220
cttaccaagg taaaacctaa aacaggtcag gaaaatggat gggaaaaaga tgctacagaa  20280
ttttcagata aaaatgaaat aagagttgga aataattttg ccatggaaat caatctaaat  20340
gccaacctgt ggagaaattt cctgtactcc aacatagcgc tgtatttgcc cgacaagcta  20400
aagtacagtc cttccaacgt aaaaatttct gataacccaa acacctacga ctacatgaac  20460
aagcgagtgg tggctcccgg gttagtggac tgctacatta accttggagc acgctggtcc  20520
```

-continued

```
cttgactata tggacaacgt caacccattt aaccaccacc gcaatgctgg cctgcgctac  20580
cgctcaatgt tgctgggcaa tggtcgctat gtgcccttcc acatccaggt gcctcagaag  20640
ttctttgcca ttaaaaacct ccttctcctg ccgggctcat acacctacga gtggaacttc  20700
aggaaggatg ttaacatggt tctgcagagc tccctaggaa atgacctaag ggttgacgga  20760
gccagcatta agtttgatag catttgcctt tacgccacct tcttccccat ggcccacaac  20820
accgcctcca cgcttgaggc catgcttaga aacgacacca acgaccagtc ctttaacgac  20880
tatctctccg ccgccaacat gctctaccct atacccgcca acgctaccaa cgtgcccata  20940
tccatcccct cccgcaactg ggcggctttc cgcggctggg ccttcacgcg ccttaagact  21000
aaggaaaccc catcactggg ctcgggctac gacccttatt acacctactc tggctctata  21060
ccctacctag atggaacctt ttacctcaac cacaccttta agaaggtggc cattaccttt  21120
gactcttctg tcagctggcc tggcaatgac cgcctgctta cccccaacga gtttgaaatt  21180
aagcgctcag ttgacgggga gggttacaac gttgcccagt gtaacatgac caaagactgg  21240
ttcctggtac aaatgctagc taactacaac attggctacc agggcttcta tatcccagag  21300
agctacaagg accgcatgta ctccttcttt agaaacttcc agcccatgag ccgtcaggtg  21360
gtggatgata ctaaatacaa ggactaccaa caggtgggca tcctacacca acacaacaac  21420
tctggatttg ttggctacct tgcccccacc atgcgcgaag gacaggccta ccctgctaac  21480
ttcccctatc cgcttatagg caagaccgca gttgacagca ttacccagaa aaagtttctt  21540
tgcgatcgca ccctttggcg catcccattc tccagtaact ttatgtccat gggcgcactc  21600
acagacctgg gccaaaacct tctctacgcc aactccgccc acgcgctaga catgactttt  21660
gaggtggatc ccatggacga gcccaccctt ctttatgttt tgtttgaagt ctttgacgtg  21720
gtccgtgtgc accggccgca ccgcggcgtc atcgaaaccg tgtacctgcg cacgcccttc  21780
tcggccggca acgccacaac ataaagaagc aagcaacatc aacaacagct gccgccatgg  21840
gctccagtga gcaggaactg aaagccattg tcaaagatct tggttgtggg ccatattttt  21900
tgggcaccta tgacaagcgc tttccaggct ttgtttctcc acacaagctc gcctgcgcca  21960
tagtcaatac ggccggtcgc gagactgggg gcgtacactg gatggccttt gcctggaacc  22020
cgcactcaaa aacatgctac ctctttgagc cctttggctt ttctgaccag cgactcaagc  22080
aggtttacca gtttgagtac gagtcactcc tgcgccgtag cgccattgct tcttcccccg  22140
accgctgtat aacgctggaa aagtccaccc aaagcgtaca ggggcccaac tcggccgcct  22200
gtggactatt ctgctgcatg tttctccacg cctttgccaa ctggccccaa actcccatgg  22260
atcacaaccc caccatgaac cttattaccg gggtacccaa ctccatgctc aacagtcccc  22320
aggtacagcc caccctgcgt cgcaaccagg aacagctcta cagcttcctg gagcgccact  22380
cgccctactt ccgcagccac agtgcgcaga ttaggagcgc cacttctttt tgtcacttga  22440
aaaacatgta aaaataatgt actagagaca ctttcaataa aggcaaatgc ttttatttgt  22500
acactctcgg gtgattattt acccccaccc ttgccgtctg cgccgtttaa aaatcaaagg  22560
ggttctgccg cgcatcgcta tgcgccactg gcagggacac gttgcgatac tggtgtttag  22620
tgctccactt aaactcaggc acaaccatcc gcggcagctc ggtgaagttt tcactccaca  22680
ggctgcgcac catcaccaac gcgtttagca ggtcgggcgc cgatatcttg aagtcgcagt  22740
tggggcctcc gccctgcgcg cgcgagttgc gatacacagg gttgcagcac tggaacacta  22800
tcagcgccgg gtggtgcacg ctggccagca cgctcttgtc ggagatcaga tccgcgtcca  22860
ggtcctccgc gttgctcagg gcgaacggag tcaactttgg tagctgcctt cccaaaaagg  22920
```

```
gcgcgtgccc aggctttgag ttgcactcgc accgtagtgg catcaaaagg tgaccgtgcc  22980
cggtctgggc gttaggatac agcgcctgca taaaagcctt gatctgctta aaagccacct  23040
gagcctttgc gccttcagag aagaacatgc cgcaagactt gccggaaaac tgattggccg  23100
gacaggccgc gtcgtgcacg cagcaccttg cgtcggtgtt ggagatctgc accacatttc  23160
ggccccaccg gttcttcacg atcttggcct tgctagactg ctccttcagc gcgcgctgcc  23220
cgttttcgct cgtcacatcc atttcaatca cgtgctcctt atttatcata atgcttccgt  23280
gtagacactt aagctcgcct tcgatctcag cgcagcggtg cagccacaac gcgcagcccg  23340
tgggctcgtg atgcttgtag gtcacctctg caaacgactg caggtacgcc tgcaggaatc  23400
gccccatcat cgtcacaaag gtcttgttgc tggtgaaggt cagctgcaac ccgcggtgct  23460
cctcgttcag ccaggtcttg catacggccg ccagagcttc cacttggtca ggcagtagtt  23520
tgaagttcgc ctttagatcg ttatccacgt ggtacttgtc catcagcgcg cgcgcagcct  23580
ccatgccctt ctcccacgca gacacgatcg gcacactcag cgggttcatc accgtaattt  23640
cactttccgc ttcgctgggc tcttcctctt cctcttgcgt ccgcatacca cgcgccactg  23700
ggtcgtcttc attcagccgc cgcactgtgc gcttacctcc tttgccatgc ttgattagca  23760
ccggtgggtt gctgaaaccc accatttgta gcgccacatc ttctctttct tcctcgctgt  23820
ccacgattac ctctggtgat ggcgggcgct cgggcttggg agaagggcgc ttcttttttct  23880
tcttgggcgc aatggccaaa tccgccgccg aggtcgatgg ccgcgggctg ggtgtgcgcg  23940
gcaccagcgc gtcttgtgat gagtcttcct cgtcctcgga ctcgatacgc cgcctcatcc  24000
gcttttttgg gggcgcccgg ggaggcggcg gcgacgggga cggggacgac acgtcctcca  24060
tggttggggg acgtcgcgcc gcaccgcgtc cgcgctcggg ggtggtttcg cgctgctcct  24120
cttcccgact ggccatttcc ttctcctata ggcagaaaaa gatcatggag tcagtcgaga  24180
agaaggacag cctaaccgcc ccctctgagt tcgccaccac cgcctccacc gatgccgcca  24240
acgcgcctac caccttcccc gtcgaggcac cccgcttgga ggaggaggaa gtgattatcg  24300
agcaggaccc aggttttgta agcgaagacg acgaggaccg ctcagtacca acagaggata  24360
aaaagcaaga ccaggacaac gcagaggcaa acgaggaaca agtcgggcgg ggggacgaaa  24420
ggcatggcga ctacctagat gtgggagacg acgtgctgtt gaagcatctg cagcgccagt  24480
gcgccattat ctgcgacgcg ttgcaagagc gcagcgatgt gcccctcgcc atagcggatg  24540
tcagccttgc ctacgaacgc cacctattct caccgcgcgt accccccaaa cgccaagaaa  24600
acggcacatg cgagcccaac ccgcgcctca acttctaccc cgtatttgcc gtgccagagg  24660
tgcttgccac ctatcacatc tttttccaaa actgcaagat acccctatcc tgccgtgcca  24720
accgcagccg agcggacaag cagctggcct tgcggcaggg cgctgtcata cctgatatcg  24780
cctcgctcaa cgaagtgcca aaaatctttg agggtcttgg acgcgacgag aagcgcgcgg  24840
caaacgctct gcaacaggaa aacagcgaaa atgaaagtca ctctggagtg ttggtggaac  24900
tcgagggtga caacgcgcgc ctagccgtac taaaacgcag catcgaggtc acccactttg  24960
cctacccggc acttaaccta ccccccaagg tcatgagcac agtcatgagt gagctgatcg  25020
tgcgccgtgc gcagcccctg gagagggatg caaatttgca agaacaaaca gaggagggcc  25080
tacccgcagt tggcgacgag cagctagcgc gctggcttca aacgcgcgag cctgccgact  25140
tggaggagcg acgcaaacta atgatggccg cagtgctcgt taccgtggag cttgagtgca  25200
tgcagcggtt ctttgctgac ccggagatgc agcgcaagct agaggaaaca ttgcactaca  25260
```

-continued

```
cctttcgaca gggctacgta cgccaggcct gcaagatctc caacgtggag ctctgcaacc  25320
tggtctccta ccttggaatt ttgcacgaaa accgccttgg gcaaaacgtg cttcattcca  25380
cgctcaaggg cgaggcgcgc cgcgactacg tccgcgactg cgtttactta tttctatgct  25440
acacctggca gacggccatg ggcgtttggc agcagtgctt ggaggagtgc aacctcaagg  25500
agctgcagaa actgctaaag caaaacttga aggacctatg gacggccttc aacgagcgct  25560
ccgtggccgc gcacctggcg gacatcattt tccccgaacg cctgcttaaa accctgcaac  25620
agggtctgcc agacttcacc agtcaaagca tgttgcagaa ctttaggaac tttatcctag  25680
agcgctcagg aatcttgccc gccacctgct gtgcacttcc tagcgacttt gtgcccatta  25740
agtaccgcga atgccctccg ccgctttggg gccactgcta ccttctgcag ctagccaact  25800
accttgccta ccactctgac ataatggaag acgtgagcgg tgacggtcta ctggagtgtc  25860
actgtcgctg caacctatgc accccgcacc gctccctggt ttgcaattcg cagctgctta  25920
acgaaagtca aattatcggt acctttgagc tgcagggtcc ctcgcctgac gaaaagtccg  25980
cggctccggg gttgaaactc actccggggc tgtggacgtc ggcttacctt cgcaaatttg  26040
tacctgagga ctaccacgcc cacgagatta ggttctacga agaccaatcc cgcccgccaa  26100
atgcggagct taccgcctgc gtcattaccc agggccacat tcttggccaa ttgcaagcca  26160
tcaacaaagc ccgccaagag tttctgctac gaaagggacg gggggtttac ttggaccccc  26220
agtccggcga ggagctcaac ccaatccccc cgccgccgca gccctatcag cagcagccgc  26280
gggcccttgc ttcccaggat ggcacccaaa aagaagctgc agctgccgcc gccacccacg  26340
gacgaggagg aatactggga cagtcaggca gaggaggttt tggacgagga ggaggaggac  26400
atgatggaag actgggagag cctagacgag gaagcttccg aggtcgaaga ggtgtcagac  26460
gaaacaccgt caccctcggt cgcattcccc tcgccggcgc cccagaaatc ggcaaccggt  26520
tccagcatgg ctacaacctc cgctcctcag gcgccgccgg cactgcccgt tcgccgaccc  26580
aaccgtagat gggacaccac tggaaccagg gccggtaagt ccaagcagcc gccgccgtta  26640
gcccaagagc aacaacagcg ccaaggctac cgctcatggc gcgggcacaa gaacgccata  26700
gttgcttgct tgcaagactg tgggggcaac atctccttcg cccgccgctt tcttctctac  26760
catcacggcg tggccttccc ccgtaacatc ctgcattact accgtcatct ctacagccca  26820
tactgcaccg gcggcagcgg cagcggcagc aacagcagcg gccacacaga agcaaaggcg  26880
accggatagc aagactctga caaagcccaa gaaatccaca gcggcggcag cagcaggagg  26940
aggagcgctg cgtctggcgc ccaacgaacc cgtatcgacc cgcgagctta gaaacaggat  27000
ttttcccact ctgtatgcta tatttcaaca gagcaggggc caagaacaag agctgaaaat  27060
aaaaaacagg tctctgcgat ccctcacccg cagctgcctg tatcacaaaa gcgaagatca  27120
gcttcggcgc acgctggaag acgcggaggc tctcttcagt aaatactgcg cgctgactct  27180
taaggactag tttcgcgccc tttctcaaat ttaagcgcga aaactacgtc atctccagcg  27240
gccacacccg gcgccagcac ctgtcgtcag cgccattatg agcaaggaaa ttcccacgcc  27300
ctacatgtgg agttaccagc cacaaatggg acttgcggct ggagctgccc aagactactc  27360
aacccgaata aactacatga gcgcgggacc ccacatgata tcccgggtca acggaatccg  27420
cgcccaccga aaccgaattc tcttggaaca ggcggctatt accaccacac ctcgtaataa  27480
ccttaatccc cgtagttggc ccgctgccct ggtgtaccag gaaagtcccg ctcccaccac  27540
tgtggtactt cccagagacg cccaggccga agttcagatg actaactcag gggcgcagct  27600
tgcgggcggc tttcgtcaca gggtgcggtc gcccgggcag ggtataactc acctgacaat  27660
```

```
cagagggcga ggtattcagc tcaacgacga gtcggtgagc tcctcgcttg gtctccgtcc  27720
ggacgggaca tttcagatcg gcggcgccgg ccgctcttca ttcacgcctc gtcaggcaat  27780
cctaactctg cagacctcgt cctctgagcc gcgctctgga ggcattggaa ctctgcaatt  27840
tattgaggag tttgtgccat cggtctactt taacccottc tcgggacctc ccggccacta  27900
tccggatcaa tttattccta actttgacgc ggtaaaggac tcggcggatg gctacgactg  27960
aatgttaagt ggagaggcag agcaactgcg cctgaaacac ctggtccact gtcgccgcca  28020
caagtgcttt gcccgcgact ccggtgagtt ttgctacttt gaattgcccg aggatcatat  28080
cgagggcccg gcgcacggcg tccggcttac cgcccaggga gagcttgccc gtagcctgat  28140
tcgggagttt acccagcgcc ccctgctagt tgagcgggac aggggaccct gtgttctcac  28200
tgtgatttgc aactgtccta accctggatt acatcaagat ctttgttgcc atctctgtgc  28260
tgagtataat aaatacagaa attaaaatat actggggctc ctatcgccat cctgtaaacg  28320
ccaccgtctt cacccgccca agcaaaccaa ggcgaacctt acctggtact tttaacatct  28380
ctccctctgt gatttacaac agtttcaacc cagacggagt gagtctacga gagaacctct  28440
ccgagctcag ctactccatc agaaaaaaca ccaccctcct tacctgccgg gaacgtacga  28500
tgtggctgca gagcctgctg ctcttgggca ctgtggcctg cagcatctct gcacccgccc  28560
gctcgcccag ccccagcacg cagccctggg agcatgtgaa tgccatccag gaggcccggc  28620
gtctcctgaa cctgagtaga gacactgctg ctgagatgaa tgaaacagta gaagtcatct  28680
cagaaatgtt tgacctccag gagccgacct gcctacagac ccgcctggag ctgtacaagc  28740
agggcctgcg gggcagcctc accaagctca agggcccctt gaccatgatg gccagccact  28800
acaagcagca ctgccctcca accccggaaa cttcctgtgc aacccagact atcacctttg  28860
aaagtttcaa agagaacctg aaggactttc tgcttgtcat cccctttgac tgctgggagc  28920
cagtccagga gtgacaattg actctatgtg ggatatgctc cagcgctaca accttgaagt  28980
caggcttcct ggatgtcagc atctgacttt ggccagcacc tgtcccgcgg atttgttcca  29040
gtccaactac agcgacccac cctaacagag atgaccaaca caaccaacgc ggccgccgct  29100
accggactta catctaccac aaatacaccc caagtttctg cctttgtcaa taactgggat  29160
aacttgggca tgtggtggtt ctccatagcg cttatgtttg tatgccttat tattatgtgg  29220
ctcatctgct gcctaaagcg caaacgcgcc cgaccaccca tctatagtcc catcattgtg  29280
ctacacccaa acaatgatgg aatccataga ttggacggac tgaaacacat gttcttttct  29340
cttacagtat gattaaatga gacatgattc ctcgagtttt tatattactg acccttgttg  29400
cgcttttttg tgcgtgctcc acattggctg cggtttctca catcgaagta gactgcattc  29460
cagccttcac agtctatttg ctttacggat ttgtcaccct cacgctcatc tgcagcctca  29520
tcactgtggt catcgccttt atccagtgca ttgactgggt ctgtgtgcgc tttgcatatc  29580
tcagacacca tccccagtac agggacagga ctatagctga gcttcttaga attctttaat  29640
tatgaaattt actgtgactt ttctgctgat tatttgcacc ctatctgcgt tttgttcccc  29700
gacctccaag cctcaaagac atatatcatg cagattcact cgtatatgga atattccaag  29760
ttgctacaat gaaaaaagcg atctttccga agcctggtta tatgcaatca tctctgttat  29820
ggtgttctgc agtaccatct tagccctagc tatatatccc taccttgaca ttggctggaa  29880
acgaatagat gccatgaacc acccaacttt ccccgcgccc gctatgcttc cactgcaaca  29940
agttgttgcc ggcggctttg tcccagccaa tcagcctcgc cccacttctc ccaccccac  30000
```

```
tgaaatcagc tactttaatc taacaggagg agatgactga caccctagat ctagaaatgg  30060
acggaattat tacagagcag cgcctgctag aaagacgcag ggcagcggcc gagcaacagc  30120
gcatgaatca agagctccaa gacatggtta acttgcacca gtgcaaaagg ggtatctttt  30180
gtctggtaaa gcaggccaaa gtcacctacg acagtaatac caccggacac cgccttagct  30240
acaagttgcc aaccaagcgt cagaaattgg tggtcatggt gggagaaaag cccattacca  30300
taactcagca ctcggtagaa accgaaggct gcattcactc accttgtcaa ggacctgagg  30360
atctctgcac ccttattaag accctgtgcg gtctcaaaga tcttattccc tttaactaat  30420
aaaaaaaaat aataaagcat cacttactta aaatcagtta gcaaatttct gtccagttta  30480
ttcagcagca cctccttgcc ctcctcccag ctctggtatt gcagcttcct cctggctgca  30540
aactttctcc acaatctaaa tggaatgtca gtttcctcct gttcctgtcc atccgcaccc  30600
actatcttca tgttgttgca gatgaagcgc gcaagaccgt ctgaagatac cttcaacccc  30660
gtgtatccat atgacacgga aaccggtcct ccaactgtgc cttttcttac tcctcccttt  30720
gtatccccca atgggtttca agagagtccc cctggggtac tctctttgcg cctatccgaa  30780
cctctagtta cctccaatgg catgcttgcg ctcaaaatgg gcaacggcct ctctctggac  30840
gaggccggca accttacctc ccaaaatgta accactgtga gcccacctct caaaaaaacc  30900
aagtcaaaca taaacctgga aatatctgca cccctcacag ttacctcaga agccctaact  30960
gtggctgccg ccgcacctct aatggtcgcg ggcaacacac tcaccatgca atcacaggcc  31020
ccgctaaccg tgcacgactc caaacttagc attgccaccc aaggacccct cacagtgtca  31080
gaaggaaagc tagccctgca aacatcaggc cccctcacca ccaccgatag cagtaccctt  31140
actatcactg cctcaccccc tctaactact gccactggta gcttgggcat tgacttgaaa  31200
gagcccattt atacacaaaa tggaaaacta ggactaaagt acggggctcc tttgcatgta  31260
acagacgacc taaacacttt gaccgtagca actggtccag gtgtgactat taataatact  31320
tccttgcaaa ctaaagttac tggagccttg ggttttgatt cacaaggcaa tatgcaactt  31380
aatgtagcag gaggactaag gattgattct caaaacagac gccttatact tgatgttagt  31440
tatccgtttg atgctcaaaa ccaactaaat ctaagactag gacagggccc tctttttata  31500
aactcagccc acaacttgga tattaactac aacaaaggcc tttacttgtt tacagcttca  31560
aacaattcca aaaagcttga ggttaaccta agcactgcca aggggttgat gtttgacgct  31620
acagccatag ccattaatgc aggagatggg cttgaatttg gttcacctaa tgcaccaaac  31680
acaaatcccc tcaaaacaaa aattggccat ggcctagaat ttgattcaaa caaggctatg  31740
gttcctaaac taggaactgg ccttagtttt gacagcacag gtgccattac agtaggaaac  31800
aaaaataatg ataagctaac tttgtggacc acaccagctc catctcctaa ctgtagacta  31860
aatgcagaga aagatgctaa actcactttg gtcttaacaa aatgtggcag tcaaatactt  31920
gctacagttt cagttttggc tgttaaaggc agtttggctc caatatctgg aacagttcaa  31980
agtgctcatc ttattataag atttgacgaa aatggagtgc tactaaacaa ttccttcctg  32040
gacccagaat attggaactt tagaaatgga gatcttactg aaggcacagc ctatacaaac  32100
gctgttggat ttatgcctaa cctatcagct tatccaaaat ctcacggtaa aactgccaaa  32160
agtaacattg tcagtcaagt ttacttaaac ggagacaaaa ctaaacctgt aacactaacc  32220
attacactaa acggtacaca ggaaacagga gacacaactt gtgactgccg cggagactgt  32280
ttctgcccaa gtgcatactc tatgtcattt tcatgggact ggtctggcca caactacatt  32340
aatgaaatat ttgccacatc ctcttacact ttttcataca ttgcccaaga ataaagaatc  32400
```

```
gtttgtgtta tgtttcaacg tgtttatttt tcaattgcag aaaatttcaa gtcatttttc  32460
attcagtagt atagccccac caccacatag cttatacaga tcaccgtacc ttaatcaaac  32520
tcacagaacc ctagtattca acctgccacc tccctcccaa cacacagagt acacagtcct  32580
ttctccccgg ctggccttaa aaagcatcat atcatgggta acagacatat tcttaggtgt  32640
tatattccac acggtttcct gtcgagccaa acgctcatca gtgatattaa taaactcccc  32700
gggcagctca cttaagttca tgtcgctgtc cagctgctga gccacaggct gctgtccaac  32760
ttgcggttgc ttaacgggcg gcgaaggaga agtccacgcc tacatggggg tagagtcata  32820
atcgtgcatc aggatagggc ggtggtgctg cagcagcgcg cgaataaact gctgccgccg  32880
ccgctccgtc ctgcaggaat acaacatggc agtggtctcc tcagcgatga ttcgcaccgc  32940
ccgcagcata aggcgccttg tcctccgggc acagcagcgc accctgatct cacttaaatc  33000
agcacagtaa ctgcagcaca gcaccacaat attgttcaaa atcccacagt gcaaggcgct  33060
gtatccaaag ctcatggcgg ggaccacaga acccacgtgg ccatcatacc acaagcgcag  33120
gtagattaag tggcgacccc tcataaacac gctggacata aacattacct cttttggcat  33180
gttgtaattc accacctccc ggtaccatat aaacctctga ttaaacatgg cgccatccac  33240
caccatccta aaccagctgg ccaaaacctg cccgccggct atacactgca gggaaccggg  33300
actggaacaa tgacagtgga gagcccagga ctcgtaacca tggatcatca tgctcgtcat  33360
gatatcaatg ttggcacaac acaggcacac gtgcatacac ttcctcagga ttacaagctc  33420
ctcccgcgtt agaaccatat cccagggaac aacccattcc tgaatcagcg taaatcccac  33480
actgcaggga agacctcgca cgtaactcac gttgtgcatt gtcaaagtgt tacattcggg  33540
cagcagcgga tgatcctcca gtatggtagc gcgggtttct gtctcaaaag gaggtagacg  33600
atccctactg tacggagtgc gccgagacaa ccgagatcgt gttggtcgta gtgtcatgcc  33660
aaatggaacg ccggacgtag tcatatttcc tgataaactc taaagaatcg tttgtgttat  33720
gtttcaacgt gtttattttt caattgcaga aaatttcaag tcatttttca ttcagtagta  33780
tagccccacc accacatagc ttatacagat caccgtacct taatcaaact cacagaaccc  33840
tagtattcaa cctgccacct ccctcccaac acacagagta cacagtcctt tctccccggc  33900
tggccttaaa aagcatcata tcatgggtaa cagacatatt cttaggtgtt atattccaca  33960
cggtttcctg tcgagccaaa cgctcatcaa gtgatattaa taaactcccc gggcagctca  34020
cttaagttca tgtcgctgtc cagctgctga gccacaggct gctgtccaac ttgcggttgc  34080
ttaacgggcg gcgaaggaga agtccacgcc tacatggggg gagagtcata atcgtgcatc  34140
aggatagggc ggtggtgctg cagcagcgcg cgaataaact gctgccgccg ccgctccgtc  34200
ctgcaggaat acaacatggc agtggtctcc tcagcgatga ttcgcaccgc ccgcagcata  34260
aggcgccttg tcctccgggc acagcagcgc accctgatct cacttaaatc agcacagtaa  34320
ctgcagcaca gcaccacaat attgttcaaa atcccacagt gcaaggcgct gtatccaaag  34380
ctcatggcgg ggaccacaga acccacgtgg ccatcatacc acaagcgcag gtagattaag  34440
tggcgacccc tcataaacac gctggacata aacattacct cttttggcat gttgtaattc  34500
accacctccc ggtaccatat aaacctctga ttaaacatgg cgccatccac caccatccta  34560
aaccagctgg ccaaaacctg ccccgccggg ntatacactg cagggaaccg ggactggaac  34620
aatgacagtg gagagcccag gactcgtaac catggatcat catgctcgtc atgatatcaa  34680
tgttggcaca acacaggcac acgtgcatac acttcctcag gattacaagc tcctcccgcg  34740
```

```
ttagaaccat atcccaggga acaacccatt cctgaatcag cgtaaatccc acactgcagg  34800
gaagacctcg cacgtaactc acgttgtgca ttgtcaaagt gttacattcg ggcagcagcg  34860
gatgatcctc cagtatggta gcgcgggttt ctgtctcaaa aggaggtaga cgatccctac  34920
tgtacggagt gcgccgagac aaccgagatc gtgttggtcg tagtgtcatg ccaaatggaa  34980
cgccggacgt agtcatattt cctgaagcaa aaccaggtgc gggcgtgaca aacagatctg  35040
cgtctccggt ctcgccgctt agatcgctct gtgtagtagt tgtagtatat ccactctctc  35100
aaagcatcca ggcgcccct ggcttcgggt tctatgtaaa ctccttcatg cgccgctgcc  35160
ctgataacat ccaccaccgc agaataagcc acacccagcc aacctacaca ttcgttctgc  35220
gagtcacaca cgggaggagc gggaagagct ggaagaacca tgtttttttt tttattccaa  35280
aagattatcc aaaacctcaa aatgaagatc tattaagtga acgcgctccc ctccggtggc  35340
gtggtcaaac tctacagcca aagaacagat aatggcattt gtaagatgtt gcacaatggc  35400
ttccaaaagg caaacggccc tcacgtccaa gtggacgtaa aggctaaacc cttcagggtg  35460
aatctcctct ataaacattc cagcaccttc aaccatgccc aaataattct catctcgcca  35520
ccttctcaat atatctctaa gcaaatcccg aatattaagt ccggccattg taaaaatttg  35580
gctccagagc gccctccacc ttcagcctca agcagcgaat catgattgca aaaattcagg  35640
ttcctcacag acctgtataa gattcaaaag cggaacatta acaaaaatac cgcgatcccg  35700
taggtccctt cgcagggcca gctgaacata atcgtgcagg tctgcacgga ccagcgcggc  35760
cacttccccg ccaggaacca tgacaaaaga acccacactg attatgacac gcatactcgg  35820
agctatgcta accagcgtag ccccgatgta agcttgttgc atgggcggcg atataaaatg  35880
caaggtgctg ctcaaaaaat caggcaaagc ctcgcgcaaa aaagaaagca catcgtagtc  35940
atgctcatgc agataaaggc aggtaagctc cggaaccacc acagaaaaag acaccatttt  36000
tctctcaaac atgtctgcgg gtttctgcat aaacacaaaa taaaataaca aaaaaacatt  36060
taaacattag aagcctgtct tacaacagga aaaacaaccc ttataagcat aagacggact  36120
acggccatgc cggcgtgacc gtaaaaaaac tggtcaccgt gattaaaaag caccaccgac  36180
agctcctcgg tcatgtccgg agtcataatg taagactcgg taaacacatc aggttgattc  36240
acatcggtca gtgctaaaaa gcgaccgaaa tagcccgggg gaatacatac ccgcaggcgt  36300
agagacaaca ttacagcccc cataggaggt ataacaaaat taataggaga gaaaaacaca  36360
taaacacctg aaaaaccctc ctgcctaggc aaaatagcac cctcccgctc cagaacaaca  36420
tacagcgctt ccacagcggc agccataaca gtcagcctta ccagtaaaaa agaaaaccta  36480
ttaaaaaaac accactcgac acggcaccag ctcaatcagt cacagtgtaa aaaagggcca  36540
agtgcagagc gagtatatat aggactaaaa aatgacgtaa cggttaaagt ccacaaaaaa  36600
cacccagaaa accgcacgcg aacctacgcc cagaaacgaa agccaaaaaa cccacaactt  36660
cctcaaatcg tcacttccgt tttcccacgt tacgtcactt cccattttaa gaaaactaca  36720
attcccaaca catacaagtt actccgccct aaaacctacg tcacccgccc cgttcccacg  36780
ccccgcgcca cgtcacaaac tccacccct cattatcata ttggcttcaa tccaaaataa  36840
ggtatattat tgatgatgtt a                                             36861
```

<210> SEQ ID NO 4
<211> LENGTH: 36885
<212> TYPE: DNA
<213> ORGANISM: Artificial Sequence
<220> FEATURE:
<223> OTHER INFORMATION: The nucleotide sequence encoding virus CGTG-604

<220> FEATURE:
<221> NAME/KEY: misc_feature
<222> LOCATION: (34615)..(34615)
<223> OTHER INFORMATION: n is a, c, g, or t

<400> SEQUENCE: 4

```
taacatcatc aataatatac cttattttgg attgaagcca atatgataat gaggggtgg      60
agtttgtgac gtggcgcggg gcgtgggaac ggggcgggtg acgtagtagt gtggcggaag    120
tgtgatgttg caagtgtggc ggaacacatg taagcgacgg atgtggcaaa agtgacgttt    180
ttggtgtgcg ccggtgtaca caggaagtga caattttcgc gcggttttag gcggatgttg    240
tagtaaattt gggcgtaacc gagtaagatt tggccatttt cgcgggaaaa ctgaataaga    300
ggaagtgaaa tctgaataat tttgtgttac tcatagcgcg taatactggt accgcggccg    360
ctggtaccat ccggacaaag cctgcgcgcg ccccgccccg ccattggccg taccgccccg    420
cgccgccgcc ccatcccgcc cctcgccgcc gggtccggcg cgttaaagcc aataggaacc    480
gccgccgttg ttcccgtcac ggccggggca gccaattgtg gcggcgctcg gcggctcgtg    540
gctctttcgc ggcaaaaagg atttggcgcg taaaagtggc cgggactttg caggcagcgg    600
cggccggggg cggagcggga tcgagccctc gccctcgagc tagaagcttg ttttctcctc    660
cgagccgctc cgacaccggg actgaaaatg agacatatta tctgccacgg aggtgttatt    720
accgaagaaa tggccgccag tcttttggac cagctgatcg aagaggtact ggctgataat    780
cttccacctc ctagccattt tgaaccacct acccttcacg aactgtatga tttagacgtg    840
acggcccccg aagatcccaa cgaggaggcg gtttcgcaga tttttcccga ctctgtaatg    900
ttggcggtgc aggaagggat tgacttactc acttttccgc cggcgcccgg ttctccggag    960
ccgcctcacc tttcccggca gcccgagcag ccggagcaga gagccttggg tccggtttct   1020
atgccaaacc ttgtaccgga ggtgatcgat ccacccagtg acgacgagga tgaagagggt   1080
gaggagtttg tgttagatta tgtggagcac ccccgggcacg gttgcaggtc ttgtcattat  1140
caccggagga atacggggga cccagatatt atgtgttcgc tttgctatat gaggacctgt   1200
ggcatgtttg tctacagtaa gtgaaaatta tgggcagtgg gtgatagagt ggtgggtttg   1260
gtgtggtaat tttttttta atttttacag ttttgtggtt taaagaattt tgtattgtga    1320
ttttttaaa aggtcctgtg tctgaacctg agcctgagcc cgagccagaa ccggagcctg    1380
caagacctac ccgccgtcct aaaatggcgc ctgctatcct gagacgcccg acatcacctg   1440
tgtctagaga atgcaatagt agtacggata gctgtgactc cggtccttct aacacacctc   1500
ctgagataca cccggtggtc ccgctgtgcc ccattaaacc agttgccgtg agagttggtg   1560
ggcgtcgcca ggctgtggaa tgtatcgagg acttgcttaa cgagcctggg caacctttgg   1620
acttgagctg taaacgcccc aggccataag gtgtaaacct gtgattgcgt gtgtggttaa   1680
cgcctttgtt tgctgaatga gttgatgtaa gtttaataaa gggtgagata atgtttaact   1740
tgcatggcgt gttaaatggg gcggggctta aagggtatat aatgcgccgt gggctaatct   1800
tggttacatc tgacctcatg gaggcttggg agtgtttgga agatttttct gctgtgcgta   1860
acttgctgga acagagctct aacagtacct cttggttttg gaggtttctg tggggctcat   1920
cccaggcaaa gttagtctgc agaattaagg aggattacaa gtgggaattt gaagagcttt   1980
tgaaatcctg tggtgagctg tttgattctt tgaatctggg tcaccaggcg cttttccaag   2040
agaaggtcat caagactttg gatttttcca caccggggcg cgctgcggct gctgttgctt   2100
ttttgagttt tataaaggat aaatggagcg aagaaaccca tctgagcggg gggtacctgc   2160
```

-continued

```
tggattttct ggccatgcat ctgtggagag cggttgtgag acacaagaat cgcctgctac   2220
tgttgtcttc cgtccgcccg gcgataatac cgacggagga gcagcagcag cagcaggagg   2280
aagccaggcg gcggcggcag gagcagagcc catggaaccc gagagccggc ctggaccctc   2340
gggaatgaat gttgtacagg tggctgaact gtatccagaa ctgagacgca ttttgacaat   2400
tacagaggat gggcaggggc taaagggggt aaagagggag cggggggctt gtgaggctac   2460
agaggaggct aggaatctag cttttagctt aatgaccaga caccgtcctg agtgtattac   2520
ttttcaacag atcaaggata attgcgctaa tgagcttgat ctgctggcgc agaagtattc   2580
catagagcag ctgaccactt actggctgca gccaggggat gattttgagg aggctattag   2640
ggtatatgca aaggtggcac ttaggccaga ttgcaagtac aagatcagca aacttgtaaa   2700
tatcaggaat tgttgctaca tttctgggaa cggggccgag gtggagatag atacggagga   2760
tagggtggcc tttagatgta gcatgataaa tatgtggccg gggtgcttg gcatggacgg   2820
ggtggttatt atgaatgtaa ggtttactgg ccccaatttt agcggtacgg ttttcctggc   2880
caataccaac cttatcctac acggtgtaag cttctatggg tttaacaata cctgtgtgga   2940
agcctggacc gatgtaaggg ttcggggctg tgccttttac tgctgctgga agggggtggt   3000
gtgtcgcccc aaaagcaggg cttcaattaa gaaatgcctc tttgaaaggt gtaccttggg   3060
tatcctgtct gagggtaact ccagggtgcg ccacaatgtg gcctccgact gtggttgctt   3120
catgctagtg aaaagcgtgg ctgtgattaa gcataacatg gtatgtggca actgcgagga   3180
cagggcctct cagatgctga cctgctcgga cggcaactgt cacctgctga agaccattca   3240
cgtagccagc cactctcgca aggcctggcc agtgtttgag cataacatac tgacccgctg   3300
ttccttgcat ttgggtaaca ggaggggggt gttcctacct taccaatgca atttgagtca   3360
cactaagata ttgcttgagc ccgagagcat gtccaaggtg aacctgaacg ggtgtttga   3420
catgaccatg aagatctgga aggtgctgag gtacgatgag acccgcacca ggtgcagacc   3480
ctgcgagtgt ggcggtaaac atattaggaa ccagcctgtg atgctggatg tgaccgagga   3540
gctgaggccc gatcacttgg tgctggcctg cacccgcgct gagtttggct ctagcgatga   3600
agatacagat tgaggtactg aaatgtgtgg gcgtggctta agggtgggaa agaatatata   3660
aggtgggggt cttatgtagt tttgtatctg ttttgcagca gccgccgccg ccatgagcac   3720
caactcgttt gatggaagca ttgtgagctc atatttgaca acgcgcatgc ccccatgggc   3780
cggggtgcgt cagaatgtga tgggctccag cattgatggt cgccccgtcc tgcccgcaaa   3840
ctctactacc ttgacctacg agaccgtgtc tggaacgccg ttggagactg cagcctccgc   3900
cgccgcttca gccgctgcag ccaccgcccg cgggattgtg actgactttg ctttcctgag   3960
cccgcttgca agcagtgcag cttcccgttc atccgcccgc gatgacaagt tgacggctct   4020
tttggcacaa ttggattctt tgacccggga acttaatgtc gtttctcagc agctgttgga   4080
tctgcgccag caggtttctg ccctgaaggc ttcctcccct cccaatgcgg tttaaaacat   4140
aaataaaaaa ccagactctg tttggatttg gatcaagcaa gtgtcttgct gtctttattt   4200
aggggttttg cgcgcgcggt aggcccggga ccagcggtct cggtcgttga gggtcctgtg   4260
tattttttcc aggacgtggt aaaggtgact ctggatgttc agatacatgg gcataagccc   4320
gtctctgggg tggaggtagc accactgcag agcttcatgc tgcggggtgg tgttgtagat   4380
gatccagtcg tagcaggagc gctgggcgtg gtgcctaaaa atgtctttca gtagcaagct   4440
gattgccagg ggcaggccct tggtgtaagt gtttacaaag cggttaagct gggatgggtg   4500
catacgtggg gatatgagat gcatcttgga ctgtattttt aggttggcta tgttcccagc   4560
```

```
catatccctc cggggattca tgttgtgcag aaccaccagc acagtgtatc cggtgcactt   4620
gggaaatttg tcatgtagct tagaaggaaa tgcgtggaag aacttggaga cgcccttgtg   4680
acctccaaga ttttccatgc attcgtccat aatgatggca atgggcccac gggcggcggc   4740
ctgggcgaag atatttctgg gatcactaac gtcatagttg tgttccagga tgagatcgtc   4800
ataggccatt tttacaaagc gcgggcggag ggtgccagac tgcggtataa tggttccatc   4860
cggcccaggg gcgtagttac cctcacagat ttgcatttcc cacgctttga gttcagatgg   4920
ggggatcatg tctacctgcg gggcgatgaa gaaaacggtt tccggggtag gggagatcag   4980
ctgggaagaa agcaggttcc tgagcagctg cgacttaccg cagccggtgg gcccgtaaat   5040
cacacctatt accgggtgca actggtagtt aagagagctg cagctgccgt catccctgag   5100
caggggggcc acttcgttaa gcatgtccct gactcgcatg ttttccctga ccaaatccgc   5160
cagaaggcgc tcgccgccca gcgatagcag ttcttgcaag gaagcaaagt ttttcaacgg   5220
tttgagaccg tccgccgtag gcatgctttt gagcgtttga ccaagcagtt ccaggcggtc   5280
ccacagctcg gtcacctgct ctacggcatc tcgatccagc atatctcctc gtttcgcggg   5340
ttggggcggc tttcgctgta cggcagtagt cggtgctcgt ccagacgggc cagggtcatg   5400
tctttccacg ggcgcagggt cctcgtcagc gtagtctggg tcacggtgaa ggggtgcgct   5460
ccgggctgcg cgctggccag ggtgcgcttg aggctggtcc tgctggtgct gaagcgctgc   5520
cggtcttcgc cctgcgcgtc ggccaggtag catttgacca tggtgtcata gtccagcccc   5580
tccgcggcgt ggcccttggc gcgcagcttg cccttggagg aggcgccgca cgaggggcag   5640
tgcagacttt tgagggcgta gagcttgggc gcgagaaata ccgattccgg ggagtaggca   5700
tccgcgccgc aggccccgca gacggtctcg cattccacga gccaggtgag ctctggccgt   5760
tcggggtcaa aaaccaggtt tcccccatgc tttttgatgc gtttcttacc tctggtttcc   5820
atgagccggt gtccacgctc ggtgacgaaa aggctgtccg tgtccccgta tacagacttg   5880
agaggcctgt cctcgagcgg tgttccgcgg tcctcctcgt atagaaactc ggaccactct   5940
gagacaaagg ctcgcgtcca ggccagcacg aaggaggcta agtgggaggg gtagcggtcg   6000
ttgtccacta gggggtccac tcgctccagg gtgtgaagac acatgtcgcc ctcttcggca   6060
tcaaggaagg tgattggttt gtaggtgtag gccacgtgac cgggtgttcc tgaagggggg   6120
ctataaaagg gggtgggggc gcgttcgtcc tcactctctt ccgcatcgct gtctgcgagg   6180
gccagctgtt ggggtgagta ctccctctga aaagcgggca tgacttctgc gctaagattg   6240
tcagtttcca aaaacgagga ggatttgata ttcacctggc ccgcggtgat gcctttgagg   6300
gtggccgcat ccatctggtc agaaaagaca atctttttgt tgtcaagctt ggtggcaaac   6360
gacccgtaga gggcgttgga cagcaacttg gcgatggagc gcagggtttg gtttttgtcg   6420
cgatcggcgc gctccttggc cgcgatgttt agctgcacgt attcgcgcgc aacgcaccgc   6480
cattcgggaa agacggtggt gcgctcgtcg ggcaccaggt gcacgcgcca accgcggttg   6540
tgcagggtga caaggtcaac gctggtggct acctctccgc gtaggcgctc gttggtccag   6600
cagaggcggc cgcccttgcg cgagcagaat ggcggtaggg ggtctagctg cgtctcgtcc   6660
ggggggtctg cgtccacggt aaagaccccg ggcagcaggc gcgcgtcgaa gtagtctatc   6720
ttgcatcctt gcaagtctag cgcctgctgc catgcgcggg cggcaagcgc gcgctcgtat   6780
gggttgagtg ggggacccca tggcatgggg tgggtgagcg cggaggcgta catgccgcaa   6840
atgtcgtaaa cgtagagggg ctctctgagt attccaagat atgtagggta gcatcttcca   6900
```

```
ccgcggatgc tggcgcgcac gtaatcgtat agttcgtgcg agggagcgag gaggtcggga   6960
ccgaggttgc tacgggcggg ctgctctgct cggaagacta tctgcctgaa gatggcatgt   7020
gagttggatg atatggttgg acgctggaag acgttgaagc tggcgtctgt gagacctacc   7080
gcgtcacgca cgaaggaggc gtaggagtcg cgcagcttgt tgaccagctc ggcggtgacc   7140
tgcacgtcta gggcgcagta gtccagggtt tccttgatga tgtcatactt atcctgtccc   7200
ttttttttcc acagctcgcg gttgaggaca aactcttcgc ggtctttcca gtactcttgg   7260
atcggaaacc cgtcggcctc cgaacggtaa gagcctagca tgtagaactg gttgacggcc   7320
tggtaggcgc agcatccctt ttctacgggt agcgcgtatg cctgcgcggc cttccggagc   7380
gaggtgtggg tgagcgcaaa ggtgtccctg accatgactt tgaggtactg gtatttgaag   7440
tcagtgtcgt cgcatccgcc ctgctcccag agcaaaaagt ccgtgcgctt tttggaacgc   7500
ggatttggca gggcgaaggt gacatcgttg aagagtatct ttcccgcgcg aggcataaag   7560
ttgcgtgtga tgcggaaggg tcccggcacc tcggaacggt tgttaattac ctgggcggcg   7620
agcacgatct cgtcaaagcc gttgatgttg tggcccacaa tgtaaagttc caagaagcgc   7680
gggatgccct tgatggaagg caatttttta agttcctcgt aggtgagctc ttcaggggag   7740
ctgagcccgt gctctgaaag ggcccagtct gcaagatgag ggttggaagc gacgaatgag   7800
ctccacaggt cacgggccat tagcatttgc aggtggtcgc gaaaggtcct aaactggcga   7860
cctatggcca tttttctgg ggtgatgcag tagaaggtaa gcgggtcttg ttcccagcgg   7920
tcccatccaa ggttcgcggc taggtctcgc gcggcagtca ctagaggctc atctccgccg   7980
aacttcatga ccagcatgaa gggcacgagc tgcttcccaa aggcccccat ccaagtatag   8040
gtctctacat cgtaggtgac aaagagacgc tcggtgcgag gatgcgagcc gatcgggaag   8100
aactggatct cccgccacca attggaggag tggctattga tgtggtgaaa gtagaagtcc   8160
ctgcgacggg ccgaacactc gtgctggctt ttgtaaaaac gtgcgcagta ctggcagcgg   8220
tgcacgggct gtacatcctg cacgaggttg acctgacgac cgcgcacaag gaagcagagt   8280
gggaatttga gcccctcgcc tggcgggttt ggctggtggt cttctacttc ggctgcttgt   8340
ccttgaccgt ctggctgctc gaggggagtt acggtggatc ggaccaccac gccgcgcgag   8400
cccaaagtcc agatgtccgc gcgcggcggt cggagcttga tgacaacatc gcgcagatgg   8460
gagctgtcca tggtctggag ctcccgcggc gtcaggtcag gcgggagctc ctgcaggttt   8520
acctcgcata gacgggtcag ggcgcgggct agatccaggt gatacctaat ttccaggggc   8580
tggttggtgg cggcgtcgat ggcttgcaag aggccgcatc cccgcggcgc gactacggta   8640
ccgcgcggcg ggcggtgggc cgcgggggtg tccttggatg atgcatctaa aagcggtgac   8700
gcgggcgagc cccggaggt aggggggct ccggacccgc cgggagaggg ggcaggggca   8760
cgtcggcgcc gcgcgcgggc aggagctggt gctgcgcgcg taggttgctg gcgaacgcga   8820
cgacgcggcg gttgatctcc tgaatctggc gcctctgcgt gaagacgacg ggcccggtga   8880
gcttgagcct gaaagagagt tcgacagaat caatttcggt gtcgttgacg gcggcctggc   8940
gcaaaatctc ctgcacgtct cctgagttgt cttgataggc gatctcggcc atgaactgct   9000
cgatctcttc ctcctggaga tctccgcgtc cggctcgctc cacggtggcg gcgaggtcgt   9060
tggaaatgcg ggccatgagc tgcgagaagg cgttgaggcc tccctcgttc cagacgcggc   9120
tgtagaccac gccccttcg gcatcgcggg cgcgcatgac cacctgcgcg agattgagct   9180
ccacgtgccg ggcgaagacg gcgtagtttc gcaggcgctg aaagaggtag ttgagggtgg   9240
tggcggtgtg ttctgccacg aagaagtaca taacccagcg tcgcaacgtg gattcgttga   9300
```

```
tatcccccaa ggcctcaagg cgctccatgg cctcgtagaa gtccacggcg aagttgaaaa   9360
actgggagtt gcgcgccgac acggttaact cctcctccag aagacggatg agctcggcga   9420
cagtgtcgcg cacctcgcgc tcaaaggcta caggggcctc ttcttcttct tcaatctcct   9480
cttccataag ggcctcccct tcttcttctt ctggcggcgg tgggggaggg gggacacggc   9540
ggcgacgacg gcgcaccggg aggcggtcga caaagcgctc gatcatctcc ccgcggcgac   9600
ggcgcatggt ctcggtgacg gcgcggccgt tctcgcgggg gcgcagttgg aagacgccgc   9660
ccgtcatgtc ccggttatgg gttggcgggg ggctgccatg cggcagggat acggcgctaa   9720
cgatgcatct caacaattgt tgtgtaggta ctccgccgcc gagggacctg agcgagtccg   9780
catcgaccgg atcggaaaac ctctcgagaa aggcgtctaa ccagtcacag tcgcaaggta   9840
ggctgagcac cgtggcgggc ggcagcgggc ggcggtcggg gttgtttctg gcggaggtgc   9900
tgctgatgat gtaattaaag taggcggtct tgagacggcg gatggtcgac agaagcacca   9960
tgtccttggg tccggcctgc tgaatgcgca ggcggtcggc catgccccag gcttcgtttt  10020
gacatcggcg caggtctttg tagtagtctt gcatgagcct ttctaccggc acttcttctt  10080
ctccttcctc ttgtcctgca tctcttgcat ctatcgctgc ggcggcggcg gagtttggcc  10140
gtaggtggcg ccctcttcct cccatgcgtg tgaccccgaa gcccctcatc ggctgaagca  10200
gggctaggtc ggcgacaacg cgctcggcta atatggcctg ctgcacctgc gtgagggtag  10260
actggaagtc atccatgtcc acaaagcggt ggtatgcgcc cgtgttgatg gtgtaagtgc  10320
agttggccat aacggaccag ttaacggtct ggtgacccgg ctgcgagagc tcggtgtacc  10380
tgagacgcga gtaagccctc gagtcaaata cgtagtcgtt gcaagtccgc accaggtact  10440
ggtatcccac caaaaagtgc ggcggcggct ggcggtagag gggccagcgt agggtggccg  10500
gggctccggg ggcgagatct tccaacataa ggcgatgata tccgtagatg tacctggaca  10560
tccaggtgat gccggcggcg gtggtggagg cgcgcggaaa gtcgcggacg cggttccaga  10620
tgttgcgcag cggcaaaaag tgctccatgg tcgggacgct ctggccggtc aggcgcgcgc  10680
aatcgttgac gctctagacc gtgcaaaagg agagcctgta agcgggcact cttccgtggt  10740
ctggtggata aattcgcaag ggtatcatgg cggacgaccg gggttcgagc cccgtatccg  10800
gccgtccgcc gtgatccatg cggttaccgc ccgcgtgtcg aacccaggtg tgcgacgtca  10860
gacaacgggg gagtgctcct tttggcttcc ttccaggcgc ggcggctgct gcgctagctt  10920
ttttggccac tggccgcgcg cagcgtaagc ggttaggctg gaaagcgaaa gcattaagtg  10980
gctcgctccc tgtagccgga gggttatttt ccaagggttg agtcgcggga cccccggttc  11040
gagtctcgga ccggccggac tgcggcgaac gggggtttgc ctccccgtca tgcaagaccc  11100
cgcttgcaaa ttcctccgga aacagggacg agcccctttt ttgcttttcc cagatgcatc  11160
cggtgctgcg gcagatgcgc ccccctcctc agcagcggca agagcaagag cagcggcaga  11220
catgcagggc accctcccct cctcctaccg cgtcaggagg ggcgacatcc gcggttgacg  11280
cggcagcaga tggtgattac gaacccccgc ggcgccgggc ccggcactac ctggacttgg  11340
aggagggcga gggcctggcg cggctaggag cgccctctcc tgagcggtac ccaagggtgc  11400
agctgaagcg tgatacgcgt gaggcgtacg tgccgcggca gaacctgttt cgcgaccgcg  11460
agggagagga gcccgaggag atgcgggatc gaaagttcca cgcagggcgc gagctgcggc  11520
atggcctgaa tcgcgagcgg ttgctgcgcg aggaggactt tgagcccgac gcgcgaaccg  11580
ggattagtcc cgcgcgcgca cacgtggcgg ccgccgacct ggtaaccgca tacgagcaga  11640
```

```
cggtgaacca ggagattaac tttcaaaaaa gctttaacaa ccacgtgcgt acgcttgtgg  11700
cgcgcgagga ggtggctata ggactgatgc atctgtggga ctttgtaagc gcgctggagc  11760
aaaacccaaa tagcaagccg ctcatggcgc agctgttcct tatagtgcag cacagcaggg  11820
acaacgaggc attcagggat gcgctgctaa acatagtaga gcccgagggc cgctggctgc  11880
tcgatttgat aaacatcctg cagagcatag tggtgcagga gcgcagcttg agcctggctg  11940
acaaggtggc cgccatcaac tattccatgc ttagcctggg caagttttac gcccgcaaga  12000
tataccatac cccttacgtt cccatagaca aggaggtaaa gatcgagggg ttctacatgc  12060
gcatggcgct gaaggtgctt accttgagcg acgacctggg cgtttatcgc aacgagcgca  12120
tccacaaggc cgtgagcgtg agccggcggc gcgagctcag cgaccgcgag ctgatgcaca  12180
gcctgcaaag ggccctggct ggcacgggca gcggcgatag agaggccgag tcctactttg  12240
acgcgggcgc tgacctgcgc tgggccccaa gccgacgcgc cctggaggca gctggggccg  12300
gacctgggct ggcggtggca cccgcgcgcg ctggcaacgt cggcggcgtg gaggaatatg  12360
acgaggacga tgagtacgag ccagaggacg gcgagtacta agcggtgatg tttctgatca  12420
gatgatgcaa gacgcaacgg acccggcggt gcgggcggcg ctgcagagcc agccgtccgg  12480
ccttaactcc acggacgact ggcgccaggt catggaccgc atcatgtcgc tgactgcgcg  12540
caatcctgac gcgttccggc agcagccgca ggccaaccgg ctctccgcaa ttctggaagc  12600
ggtggtcccg gcgcgcgcaa accccacgca cgagaaggtg ctggcgatcg taaacgcgct  12660
ggccgaaaac agggccatcc ggcccgacga ggccggcctg gtctacgacg cgctgcttca  12720
gcgcgtggct cgttacaaca gcggcaacgt gcagaccaac ctggaccggc tggtggggga  12780
tgtgcgcgag gccgtggcgc agcgtgagcg cgcgcagcag cagggcaacc tgggctccat  12840
ggttgcacta aacgccttcc tgagtacaca gcccgccaac gtgccgcggg gacaggagga  12900
ctacaccaac tttgtgagcg cactgcggct aatggtgact gagacaccgc aaagtgaggt  12960
gtaccagtct gggccagact attttttcca gaccagtaga caaggcctgc agaccgtaaa  13020
cctgagccag gctttcaaaa acttgcaggg gctgtggggg gtgcgggctc ccacaggcga  13080
ccgcgcgacc gtgtctagct tgctgacgcc caactcgcgc ctgttgctgc tgctaatagc  13140
gcccttcacg gacagtggca gcgtgtcccg ggacacatac ctaggtcact tgctgacact  13200
gtaccgcgag gccataggtc aggcgcatgt ggacgagcat actttccagg agattacaag  13260
tgtcagccgc gcgctggggc aggaggacac gggcagcctg gaggcaaccc taaactacct  13320
gctgaccaac cggcggcaga agatcccctc gttgcacagt ttaaacagcg aggaggagcg  13380
cattttgcgc tacgtgcagc agagcgtgag ccttaacctg atgcgcgacg gggtaacgcc  13440
cagcgtggcg ctggacatga ccgcgcgcaa catggaaccg ggcatgtatg cctcaaaccg  13500
gccgtttatc aaccgcctaa tggactactt gcatcgcgcg gccgccgtga accccgagta  13560
tttcaccaat gccatcttga acccgcactg gctaccgccc cctggtttct acaccggggg  13620
attcgaggtg cccgagggta acgatggatt cctctgggac gacatagacg acagcgtgtt  13680
ttccccgcaa ccgcagaccc tgctagagtt gcaacagcgc gagcaggcag aggcggcgct  13740
gcgaaaggaa agcttccgca ggccaagcag cttgtccgat ctaggcgctg cggccccgcg  13800
gtcagatgct agtagcccat ttccaagctt gatagggtct cttaccagca ctcgcaccac  13860
ccgcccgcgc ctgctgggcg aggaggagta cctaaacaac tcgctgctgc agccgcagcg  13920
cgaaaaaaac ctgcctccgg catttcccaa caacgggata gagagcctag tggacaagat  13980
gagtagatgg aagacgtacg cgcaggagca cagggacgtg ccaggcccgc gcccgcccac  14040
```

```
ccgtcgtcaa aggcacgacc gtcagcgggg tctggtgtgg gaggacgatg actcggcaga  14100
cgacagcagc gtcctggatt tgggagggag tggcaacccg tttgcgcacc ttcgccccag  14160
gctggggaga atgttttaaa aaaaaaaaag catgatgcaa aataaaaaac tcaccaaggc  14220
catggcaccg agcgttggtt ttcttgtatt ccccttagta tgcggcgcgc ggcgatgtat  14280
gaggaaggtc ctcctccctc ctacgagagt gtggtgagcg cggcgccagt ggcggcggcg  14340
ctgggttctc ccttcgatgc tcccctggac ccgccgtttg tgcctccgcg gtacctgcgg  14400
cctaccgggg ggagaaacag catccgttac tctgagttgg cacccctatt cgacaccacc  14460
cgtgtgtacc tggtggacaa caagtcaacg gatgtggcat ccctgaacta ccagaacgac  14520
cacagcaact ttctgaccac ggtcattcaa aacaatgact acagcccggg ggaggcaagc  14580
acacagacca tcaatcttga cgaccggtcg cactggggcg gcgacctgaa aaccatcctg  14640
cataccaaca tgccaaatgt gaacgagttc atgtttacca ataagtttaa ggcgcgggtg  14700
atggtgtcgc gcttgcctac taaggacaat caggtggagc tgaaatacga gtgggtggag  14760
ttcacgctgc ccgagggcaa ctactccgag accatgacca tagaccttat gaacaacgcg  14820
atcgtggagc actacttgaa agtgggcaga cagaacgggg ttctggaaag cgacatcggg  14880
gtaaagtttg acacccgcaa cttcagactg gggtttgacc ccgtcactgg tcttgtcatg  14940
cctggggtat atacaaacga agccttccat ccagacatca ttttgctgcc aggatgcggg  15000
gtggacttca cccacagccg cctgagcaac ttgttgggca tccgcaagcg gcaacccttc  15060
caggagggct ttaggatcac ctacgatgat ctggagggtg gtaacattcc cgcactgttg  15120
gatgtggacg cctaccaggc gagcttgaaa gatgacaccg aacagggcgg gggtggcgca  15180
ggcggcagca acagcagtgg cagcggcgcg gaagagaact ccaacgcggc agccgcggca  15240
atgcagccgg tggaggacat gaacgatcat gccattcgcg gcgacacctt tgccacacgg  15300
gctgaggaga agcgcgctga ggccgaagca gcggccgaag ctgccgcccc cgctgcgcaa  15360
cccgaggtcg agaagcctca gaagaaaccg gtgatcaaac ccctgacaga ggacagcaag  15420
aaacgcagtt acaacctaat aagcaatgac agcaccttca cccagtaccg cagctggtac  15480
cttgcataca actacggcga ccctcagacc ggaatccgct catggaccct gctttgcact  15540
cctgacgtaa cctgcggctc ggagcaggtc tactggtcgt tgccagacat gatgcaagac  15600
cccgtgacct tccgctccac gcgccagatc agcaactttc cggtggtggg cgccgagctg  15660
ttgcccgtgc actccaagag cttctacaac gaccaggccg tctactccca actcatccgc  15720
cagtttacct ctctgaccca cgtgttcaat cgctttcccg agaaccagat tttggcgcgc  15780
ccgccagccc ccaccatcac caccgtcagt gaaaacgttc ctgctctcac agatcacggg  15840
acgctaccgc tgcgcaacag catcggagga gtccagcgag tgaccattac tgacgccaga  15900
cgccgcacct gcccctacgt ttacaaggcc ctgggcatag tctcgccgcg cgtcctatcg  15960
agccgcactt tttgagcaag catgtccatc cttatatcgc ccagcaataa cacaggctgg  16020
ggcctgcgct tcccaagcaa gatgtttggc ggggccaaga agcgctccga ccaacaccca  16080
gtgcgcgtgc gcgggcacta ccgcgcgccc tggggcgcgc acaaacgcgg ccgcactggg  16140
cgcaccaccg tcgatgacgc catcgacgcg gtggtggagg aggcgcgcaa ctacacgccc  16200
acgccgccac cagtgtccac agtggacgcg gccattcaga ccgtggtgcg cggagcccgg  16260
cgctatgcta aaatgaagag acggcggagg cgcgtagcac gtcgccaccg ccgccgaccc  16320
ggcactgccg cccaacgcgc ggcggcggcc ctgcttaacc gcgcacgtcg caccggccga  16380
```

```
cgggcggcca tgcgggccgc tcgaaggctg gccgcgggta ttgtcactgt gccccccagg  16440
tccaggcgac gagcggccgc cgcagcagcc gcggccatta gtgctatgac tcagggtcgc  16500
aggggcaacg tgtattgggt gcgcgactcg gttagcggcc tgcgcgtgcc cgtgcgcacc  16560
cgcccccgc gcaactagat tgcaagaaaa aactacttag actcgtactg ttgtatgtat  16620
ccagcggcgg cggcgcgcaa cgaagctatg tccaagcgca aaatcaaaga agagatgctc  16680
caggtcatcg cgccggagat ctatggcccc ccgaagaagg aagagcagga ttacaagccc  16740
cgaaagctaa agcgggtcaa aaagaaaaag aaagatgatg atgatgaact tgacgacgag  16800
gtggaactgc tgcacgctac cgcgcccagg cgacgggtac agtggaaagg tcgacgcgta  16860
aaacgtgttt tgcgacccgg caccaccgta gtctttacgc ccggtgagcg ctccacccgc  16920
acctacaagc gcgtgtatga tgaggtgtac ggcgacgagg acctgcttga gcaggccaac  16980
gagcgcctcg gggagtttgc ctacggaaag cggcataagg acatgctggc gttgccgctg  17040
gacgagggca acccaacacc tagcctaaag cccgtaacac tgcagcaggt gctgcccgcg  17100
cttgcaccgt ccgaagaaaa gcgcggccta aagcgcgagt ctggtgactt ggcacccacc  17160
gtgcagctga tggtacccaa gcgccagcga ctggaagatg tcttggaaaa aatgaccgtg  17220
gaacctgggc tggagcccga ggtccgcgtg cggccaatca agcaggtggc gccgggactg  17280
ggcgtgcaga ccgtggacgt tcagataccc actaccagta gcaccagtat tgccaccgcc  17340
acagagggca tggagacaca aacgtccccg gttgcctcag cggtggcgga tgccgcggtg  17400
caggcggtcg ctgcggccgc gtccaagacc tctacggagg tgcaaacgga cccgtggatg  17460
tttcgcgttt cagccccccg gcgcccgcgc ggttcgagga agtacggcgc cgccagcgcg  17520
ctactgcccg aatatgccct acatccttcc attgcgccta cccccggcta tcgtggctac  17580
acctaccgcc ccagaagacg agcaactacc cgacgccgaa ccaccactgg aacccgccgc  17640
cgccgtcgcc gtcgccagcc cgtgctggcc ccgatttccg tgcgcagggt ggctcgcgaa  17700
ggaggcagga ccctggtgct gccaacagcg cgctaccacc ccagcatcgt ttaaaagccg  17760
gtctttgtgg ttcttgcaga tatggccctc acctgccgcc tccgtttccc ggtgccggga  17820
ttccgaggaa gaatgcaccg taggaggggc atggccggcc acggcctgac gggcggcatg  17880
cgtcgtgcgc accaccggcg gcggcgcgcg tcgcaccgtc gcatgcgcgg cggtatcctg  17940
cccctcctta ttccactgat cgccgcggcg attggcgccg tgcccggaat tgcatccgtg  18000
gccttgcagg cgcagagaca ctgattaaaa acaagttgca tgtggaaaaa tcaaaataaa  18060
aagtctggac tctcacgctc gcttggtcct gtaactattt tgtagaatgg aagacatcaa  18120
ctttgcgtct ctggccccgc gacacggctc gcgcccgttc atgggaaact ggcaagatat  18180
cggcaccagc aatatgagcg gtggcgcctt cagctggggc tcgctgtgga gcggcattaa  18240
aaatttcggt tccaccgtta agaactatgg cagcaaggcc tggaacagca gcacaggcca  18300
gatgctgagg gataagttga aagagcaaaa tttccaacaa aaggtggtag atggcctggc  18360
ctctggcatt agcggggtgg tggacctggc caaccaggca gtgcaaaata agattaacag  18420
taagcttgat ccccgccctc ccgtagagga gcctccaccg gccgtggaga cagtgtctcc  18480
agaggggcgt ggcgaaaagc gtccgcgccc cgacagggaa gaaactctgg tgacgcaaat  18540
agacgagcct ccctcgtacg aggaggcact aaagcaaggc ctgcccacca cccgtcccat  18600
cgcgcccatg gctaccggag tgctgggcca gcacacaccc gtaacgctgg acctgcctcc  18660
ccccgccgac acccagcaga aacctgtgct gccaggcccg accgccgttg ttgtaacccg  18720
tcctagccgc gcgtccctgc gccgcgccgc cagcggtccg cgatcgttgc ggcccgtagc  18780
```

```
cagtggcaac tggcaaagca cactgaacag catcgtgggt ctgggggtgc aatccctgaa  18840
gcgccgacga tgcttctgaa tagctaacgt gtcgtatgtg tgtcatgtat gcgtccatgt  18900
cgccgccaga ggagctgctg agccgccgcg cgcccgcttt ccaagatggc taccccttcg  18960
atgatgccgc agtggtctta catgcacatc tcgggccagg acgcctcgga gtacctgagc  19020
cccgggctgg tgcagtttgc ccgcgccacc gagacgtact tcagcctgaa taacaagttt  19080
agaaacccca cggtggcgcc tacgcacgac gtgaccacag accggtccca gcgtttgacg  19140
ctgcggttca tccctgtgga ccgtgaggat actgcgtact cgtacaaggc gcggttcacc  19200
ctagctgtgg gtgataaccg tgtgctggac atggcttcca cgtactttga catccgcggc  19260
gtgctggaca ggggccctac ttttaagccc tactctggca ctgcctacaa cgccctggct  19320
cccaagggtg ccccaaatcc ttgcgaatgg gatgaagctg ctactgctct tgaaataaac  19380
ctagaagaag aggacgatga caacgaagac gaagtagacg agcaagctga gcagcaaaaa  19440
actcacgtat ttgggcaggc gccttattct ggtataaata ttacaaagga gggtattcaa  19500
ataggtgtcg aaggtcaaac acctaaatat gccgataaaa catttcaacc tgaacctcaa  19560
ataggagaat ctcagtggta cgaaactgaa attaatcatg cagctgggag agtccttaaa  19620
aagactaccc caatgaaacc atgttacggt tcatatgcaa aacccacaaa tgaaaatgga  19680
gggcaaggca ttcttgtaaa gcaacaaaat ggaaagctag aaagtcaagt ggaaatgcaa  19740
tttttctcaa ctactgaggc gaccgcaggc aatggtgata acttgactcc taaagtggta  19800
ttgtacagtg aagatgtaga tatagaaacc ccagacactc atatttctta catgcccact  19860
attaaggaag gtaactcacg agaactaatg ggccaacaat ctatgcccaa caggcctaat  19920
tacattgctt ttagggacaa ttttattggt ctaatgtatt acaacagcac gggtaatatg  19980
ggtgttctgg cgggccaagc atcgcagttg aatgctgttg tagatttgca agacagaaac  20040
acagagcttt cataccagct tttgcttgat tccattggtg atagaaccag gtacttttct  20100
atgtggaatc aggctgttga cagctatgat ccagatgtta gaattattga aaatcatgga  20160
actgaagatg aacttccaaa ttactgcttt ccactgggag gtgtgattaa tacagagact  20220
cttaccaagg taaaacctaa aacaggtcag gaaaatggat gggaaaaaga tgctacagaa  20280
ttttcagata aaaatgaaat aagagttgga aataattttg ccatggaaat caatctaaat  20340
gccaacctgt ggagaaattt cctgtactcc aacatagcgc tgtatttgcc cgacaagcta  20400
aagtacagtc cttccaacgt aaaaatttct gataacccaa acacctacga ctacatgaac  20460
aagcgagtgg tggctcccgg gttagtggac tgctacatta accttggagc acgctggtcc  20520
cttgactata tggacaacgt caacccattt aaccaccacc gcaatgctgg cctgcgctac  20580
cgctcaatgt tgctgggcaa tggtcgctat gtgcccttcc acatccaggt gcctcagaag  20640
ttctttgcca ttaaaaacct ccttctcctg ccgggctcat acacctacga gtggaacttc  20700
aggaaggatg ttaacatggt tctgcagagc tccctaggaa atgacctaag ggttgacgga  20760
gccagcatta agtttgatag catttgcctt tacgccacct tcttccccat ggcccacaac  20820
accgcctcca cgcttgaggc catgcttaga aacgacacca acgaccagtc ctttaacgac  20880
tatctctccg ccgccaacat gctctaccct atacccgcca acgctaccaa cgtgcccata  20940
tccatcccct cccgcaactg ggcggctttc cgcggctggg ccttcacgcg ccttaagact  21000
aaggaaaccc catcactggg ctcgggctac gacccttatt acacctactc tggctctata  21060
ccctacctag atggaacctt ttacctcaac cacaccttta agaaggtggc cattaccttt  21120
```

```
gactcttctg tcagctggcc tggcaatgac cgcctgctta cccccaacga gtttgaaatt  21180
aagcgctcag ttgacgggga gggttacaac gttgcccagt gtaacatgac caaagactgg  21240
ttcctggtac aaatgctagc taactacaac attggctacc agggcttcta tatcccagag  21300
agctacaagg accgcatgta ctccttcttt agaaacttcc agcccatgag ccgtcaggtg  21360
gtggatgata ctaaatacaa ggactaccaa caggtgggca tcctacacca acacaacaac  21420
tctggatttg ttggctacct tgcccccacc atgcgcgaag gacaggccta ccctgctaac  21480
ttcccctatc cgcttatagg caagaccgca gttgacagca ttacccagaa aaagtttctt  21540
tgcgatcgca ccctttggcg catcccattc tccagtaact ttatgtccat gggcgcactc  21600
acagacctgg gccaaaacct tctctacgcc aactccgccc acgcgctaga catgactttt  21660
gaggtggatc ccatggacga gcccaccctt ctttatgttt tgtttgaagt ctttgacgtg  21720
gtccgtgtgc accggccgca ccgcggcgtc atcgaaaccg tgtacctgcg cacgcccttc  21780
tcggccggca acgccacaac ataaagaagc aagcaacatc aacaacagct gccgccatgg  21840
gctccagtga gcaggaactg aaagccattg tcaaagatct tggttgtggg ccatattttt  21900
tgggcaccta tgacaagcgc tttccaggct ttgtttctcc acacaagctc gcctgcgcca  21960
tagtcaatac ggccggtcgc gagactgggg gcgtacactg gatggccttt gcctggaacc  22020
cgcactcaaa aacatgctac ctctttgagc cctttggctt ttctgaccag cgactcaagc  22080
aggtttacca gtttgagtac gagtcactcc tgcgccgtag cgccattgct tcttcccccg  22140
accgctgtat aacgctggaa aagtccaccc aaagcgtaca ggggcccaac tcggccgcct  22200
gtggactatt ctgctgcatg tttctccacg cctttgccaa ctggccccaa actcccatgg  22260
atcacaaccc caccatgaac cttattaccg gggtacccaa ctccatgctc aacagtcccc  22320
aggtacagcc caccctgcgt cgcaaccagg aacagctcta cagcttcctg gagcgccact  22380
cgccctactt ccgcagccac agtgcgcaga ttaggagcgc cacttctttt tgtcacttga  22440
aaaacatgta aaaataatgt actagagaca ctttcaataa aggcaaatgc ttttatttgt  22500
acactctcgg gtgattattt acccccaccc ttgccgtctg cgccgtttaa aaatcaaagg  22560
ggttctgccg cgcatcgcta tgcgccactg gcagggacac gttgcgatac tggtgtttag  22620
tgctccactt aaactcaggc acaaccatcc gcggcagctc ggtgaagttt tcactccaca  22680
ggctgcgcac catcaccaac gcgtttagca ggtcgggcgc cgatatcttg aagtcgcagt  22740
tggggcctcc gccctgcgcg cgcgagttgc gatacacagg gttgcagcac tggaacacta  22800
tcagcgccgg gtggtgcacg ctggccagca cgctcttgtc ggagatcaga tccgcgtcca  22860
ggtcctccgc gttgctcagg gcgaacggag tcaactttgg tagctgcctt cccaaaaagg  22920
gcgcgtgccc aggctttgag ttgcactcgc accgtagtgg catcaaaagg tgaccgtgcc  22980
cggtctgggc gttaggatac agcgcctgca taaaagcctt gatctgctta aaagccacct  23040
gagcctttgc gccttcagag aagaacatgc cgcaagactt gccggaaaac tgattggccg  23100
gacaggccgc gtcgtgcacg cagcaccttg cgtcggtgtt ggagatctgc accacatttc  23160
ggccccaccg gttcttcacg atcttggcct tgctagactg ctccttcagc gcgcgctgcc  23220
cgttttcgct cgtcacatcc atttcaatca cgtgctcctt atttatcata atgcttccgt  23280
gtagacactt aagctcgcct tcgatctcag cgcagcggtg cagccacaac gcgcagcccg  23340
tgggctcgtg atgcttgtag gtcacctctg caaacgactg caggtacgcc tgcaggaatc  23400
gccccatcat cgtcacaaag gtcttgttgc tggtgaaggt cagctgcaac ccgcggtgct  23460
cctcgttcag ccaggtcttg catacggccg ccagagcttc cacttggtca ggcagtagtt  23520
```

```
tgaagttcgc ctttagatcg ttatccacgt ggtacttgtc catcagcgcg cgcgcagcct  23580
ccatgccctt ctcccacgca gacacgatcg gcacactcag cgggttcatc accgtaattt  23640
cactttccgc ttcgctgggc tcttcctctt cctcttgcgt ccgcatacca cgcgccactg  23700
ggtcgtcttc attcagccgc cgcactgtgc gcttacctcc tttgccatgc ttgattagca  23760
ccggtgggtt gctgaaaccc accatttgta gcgccacatc ttctctttct tcctcgctgt  23820
ccacgattac ctctggtgat ggcgggcgct cgggcttggg agaagggcgc ttcttttct  23880
tcttgggcgc aatggccaaa tccgccgccg aggtcgatgg ccgcgggctg ggtgtgcgcg  23940
gcaccagcgc gtcttgtgat gagtcttcct cgtcctcgga ctcgatacgc cgcctcatcc  24000
gctttttgg gggcgcccgg ggaggcggcg gcgacgggga cggggacgac acgtcctcca  24060
tggttggggg acgtcgcgcc gcaccgcgtc cgcgctcggg ggtggtttcg cgctgctcct  24120
cttcccgact ggccatttcc ttctcctata ggcagaaaaa gatcatggag tcagtcgaga  24180
agaaggacag cctaaccgcc ccctctgagt tcgccaccac cgcctccacc gatgccgcca  24240
acgcgcctac caccttcccc gtcgaggcac ccccgcttga ggaggaggaa gtgattatcg  24300
agcaggaccc aggttttgta agcgaagacg acgaggaccg ctcagtacca acagaggata  24360
aaaagcaaga ccaggacaac gcagaggcaa acgaggaaca agtcgggcgg ggggacgaaa  24420
ggcatggcga ctacctagat gtgggagacg acgtgctgtt gaagcatctg cagcgccagt  24480
gcgccattat ctgcgacgcg ttgcaagagc gcagcgatgt gcccctcgcc atagcggatg  24540
tcagccttgc ctacgaacgc cacctattct caccgcgcgt accccccaaa cgccaagaaa  24600
acggcacatg cgagcccaac ccgcgcctca acttctaccc cgtatttgcc gtgccagagg  24660
tgcttgccac ctatcacatc tttttccaaa actgcaagat acccctatcc tgccgtgcca  24720
accgcagccg agcggacaag cagctggcct tgcggcaggg cgctgtcata cctgatatcg  24780
cctcgctcaa cgaagtgcca aaaatctttg agggtcttgg acgcgacgag aagcgcgcgg  24840
caaacgctct gcaacaggaa aacagcgaaa atgaaagtca ctctggagtg ttggtggaac  24900
tcgagggtga caacgcgcgc ctagccgtac taaaacgcag catcgaggtc acccactttg  24960
cctacccggc acttaaccta ccccccaagg tcatgagcac agtcatgagt gagctgatcg  25020
tgcgccgtgc gcagcccctg gagagggatg caaatttgca agaacaaaca gaggagggcc  25080
tacccgcagt tggcgacgag cagctagcgc gctggcttca aacgcgcgag cctgccgact  25140
tggaggagcg acgcaaacta atgatggccg cagtgctcgt taccgtggag cttgagtgca  25200
tgcagcggtt ctttgctgac ccggagatgc agcgcaagct agaggaaaca ttgcactaca  25260
cctttcgaca gggctacgta cgccaggcct gcaagatctc caacgtggag ctctgcaacc  25320
tggtctccta ccttggaatt ttgcacgaaa accgccttgg gcaaaacgtg cttcattcca  25380
cgctcaaggg cgaggcgcgc cgcgactacg tccgcgactg cgtttactta tttctatgct  25440
acacctggca gacggccatg ggcgtttggc agcagtgctt ggaggagtgc aacctcaagg  25500
agctgcagaa actgctaaag caaaacttga aggacctatg gacggccttc aacgagcgct  25560
ccgtggccgc gcacctggcg gacatcattt tccccgaacg cctgcttaaa accctgcaac  25620
agggtctgcc agacttcacc agtcaaagca tgttgcagaa ctttaggaac tttatcctag  25680
agcgctcagg aatcttgccc gccacctgct gtgcacttcc tagcgacttt gtgcccatta  25740
agtaccgcga atgccctccg ccgctttggg gccactgcta ccttctgcag ctagccaact  25800
accttgccta ccactctgac ataatggaag acgtgagcgg tgacggtcta ctggagtgtc  25860
```

```
actgtcgctg caacctatgc accccgcacc gctccctggt ttgcaattcg cagctgctta  25920
acgaaagtca aattatcggt acctttgagc tgcagggtcc ctcgcctgac gaaaagtccg  25980
cggctccggg gttgaaactc actccggggc tgtggacgtc ggcttacctt cgcaaatttg  26040
tacctgagga ctaccacgcc cacgagatta ggttctacga agaccaatcc cgcccgccaa  26100
atgcggagct taccgcctgc gtcattaccc agggccacat tcttggccaa ttgcaagcca  26160
tcaacaaagc ccgccaagag tttctgctac gaaagggacg gggggtttac ttggaccccc  26220
agtccggcga ggagctcaac ccaatccccc cgccgccgca gccctatcag cagcagccgc  26280
gggcccttgc ttcccaggat ggcacccaaa aagaagctgc agctgccgcc gccacccacg  26340
gacgaggagg aatactggga cagtcaggca gaggaggttt tggacgagga ggaggaggac  26400
atgatggaag actgggagag cctagacgag gaagcttccg aggtcgaaga ggtgtcagac  26460
gaaacaccgt caccctcggt cgcattcccc tcgccggcgc cccagaaatc ggcaaccggt  26520
tccagcatgg ctacaacctc cgctcctcag gcgccgccgg cactgcccgt tcgccgaccc  26580
aaccgtagat gggacaccac tggaaccagg gccggtaagt ccaagcagcc gccgccgtta  26640
gcccaagagc aacaacagcg ccaaggctac cgctcatggc gcgggcacaa gaacgccata  26700
gttgcttgct tgcaagactg tgggggcaac atctccttcg cccgccgctt tcttctctac  26760
catcacggcg tggccttccc ccgtaacatc ctgcattact accgtcatct ctacagccca  26820
tactgcaccg gcggcagcgg cagcggcagc aacagcagcg gccacacaga agcaaaggcg  26880
accggatagc aagactctga caaagcccaa gaaatccaca gcggcggcag cagcaggagg  26940
aggagcgctg cgtctggcgc ccaacgaacc cgtatcgacc cgcgagctta gaaacaggat  27000
ttttcccact ctgtatgcta tatttcaaca gagcaggggc caagaacaag agctgaaaat  27060
aaaaaacagg tctctgcgat ccctcacccg cagctgcctg tatcacaaaa gcgaagatca  27120
gcttcggcgc acgctggaag acgcggaggc tctcttcagt aaatactgcg cgctgactct  27180
taaggactag tttcgcgccc tttctcaaat ttaagcgcga aaactacgtc atctccagcg  27240
gccacacccg gcgccagcac ctgtcgtcag cgccattatg agcaaggaaa ttcccacgcc  27300
ctacatgtgg agttaccagc cacaaatggg acttgcggct ggagctgccc aagactactc  27360
aacccgaata aactacatga gcgcgggacc ccacatgata tcccgggtca acggaatccg  27420
cgcccaccga aaccgaattc tcttggaaca ggcggctatt accaccacac ctcgtaataa  27480
ccttaatccc cgtagttggc ccgctgccct ggtgtaccag gaaagtcccg ctcccaccac  27540
tgtggtactt cccagagacg cccaggccga agttcagatg actaactcag ggcgcagct  27600
tgcgggcggc tttcgtcaca gggtgcggtc gcccgggcag ggtataactc acctgacaat  27660
cagagggcga ggtattcagc tcaacgacga gtcggtgagc tcctcgcttg gtctccgtcc  27720
ggacgggaca tttcagatcg gcggcgccgg ccgctcttca ttcacgcctc gtcaggcaat  27780
cctaactctg cagacctcgt cctctgagcc gcgctctgga ggcattggaa ctctgcaatt  27840
tattgaggag tttgtgccat cggtctactt taaccccttc tcgggacctc ccggccacta  27900
tccggatcaa tttattccta actttgacgc ggtaaaggac tcggcggatg gctacgactg  27960
aatgttaagt ggagaggcag agcaactgcg cctgaaacac ctggtccact gtcgccgcca  28020
caagtgcttt gcccgcgact ccggtgagtt ttgctacttt gaattgcccg aggatcatat  28080
cgagggcccg gcgcacggcg tccggcttac cgcccaggga gagcttgccc gtagcctgat  28140
tcgggagttt acccagcgcc ccctgctagt tgagcgggac aggggaccct gtgttctcac  28200
tgtgatttgc aactgtccta accctggatt acatcaagat ctttgttgcc atctctgtgc  28260
```

```
tgagtataat aaatacagaa attaaaatat actggggctc ctatcgccat cctgtaaacg  28320
ccaccgtctt cacccgccca agcaaaccaa ggcgaacctt acctggtact tttaacatct  28380
ctccctctgt gatttacaac agtttcaacc cagacggagt gagtctacga gagaacctct  28440
ccgagctcag ctactccatc agaaaaaaca ccaccctcct tacctgccgg gaacgtacga  28500
tgtggctgca gagcctgctg ctcttgggca ctgtggcctg cagcatctct gcacccgccc  28560
gctcgcccag ccccagcacg cagccctggg agcatgtgaa tgccatccag gaggcccggc  28620
gtctcctgaa cctgagtaga gacactgctg ctgagatgaa tgaaacagta gaagtcatct  28680
cagaaatgtt tgacctccag gagccgacct gcctacagac ccgcctggag ctgtacaagc  28740
agggcctgcg gggcagcctc accaagctca agggcccctt gaccatgatg gccagccact  28800
acaagcagca ctgccctcca accccggaaa cttcctgtgc aacccagact atcacctttg  28860
aaagtttcaa agagaacctg aaggactttc tgcttgtcat cccctttgac tgctgggagc  28920
cagtccagga gtgacaattg actctatgtg ggatatgctc cagcgctaca accttgaagt  28980
caggcttcct ggatgtcagc atctgacttt ggccagcacc tgtcccgcgg atttgttcca  29040
gtccaactac agcgacccac cctaacagag atgaccaaca caaccaacgc ggccgccgct  29100
accggactta catctaccac aaatacaccc caagtttctg cctttgtcaa taactgggat  29160
aacttgggca tgtggtggtt ctccatagcg cttatgtttg tatgccttat tattatgtgg  29220
ctcatctgct gcctaaagcg caaacgcgcc cgaccaccca tctatagtcc catcattgtg  29280
ctacacccaa acaatgatgg aatccataga ttggacggac tgaaacacat gttcttttct  29340
cttacagtat gattaaatga gacatgattc ctcgagtttt tatattactg acccttgttg  29400
cgcttttttg tgcgtgctcc acattggctg cggtttctca catcgaagta gactgcattc  29460
cagccttcac agtctatttg ctttacggat ttgtcaccct cacgctcatc tgcagcctca  29520
tcactgtggt catcgccttt atccagtgca ttgactgggt ctgtgtgcgc tttgcatatc  29580
tcagacacca tccccagtac agggacagga ctatagctga gcttcttaga attctttaat  29640
tatgaaattt actgtgactt ttctgctgat tatttgcacc ctatctgcgt tttgttcccc  29700
gacctccaag cctcaaagac atatatcatg cagattcact cgtatatgga atattccaag  29760
ttgctacaat gaaaaaagcg atctttccga agcctggtta tatgcaatca tctctgttat  29820
ggtgttctgc agtaccatct tagccctagc tatatatccc taccttgaca ttggctggaa  29880
acgaatagat gccatgaacc acccaacttt ccccgcgccc gctatgcttc cactgcaaca  29940
agttgttgcc ggcggctttg tcccagccaa tcagcctcgc cccacttctc ccacccccac  30000
tgaaatcagc tactttaatc taacaggagg agatgactga caccctagat ctagaaatgg  30060
acggaattat tacagagcag cgcctgctag aaagacgcag ggcagcggcc gagcaacagc  30120
gcatgaatca agagctccaa gacatggtta acttgcacca gtgcaaaagg ggtatctttt  30180
gtctggtaaa gcaggccaaa gtcacctacg acagtaatac caccggacac cgccttagct  30240
acaagttgcc aaccaagcgt cagaaattgg tggtcatggt gggagaaaag cccattacca  30300
taactcagca ctcggtagaa accgaaggct gcattcactc accttgtcaa ggacctgagg  30360
atctctgcac ccttattaag accctgtgcg gtctcaaaga tcttattccc tttaactaat  30420
aaaaaaaaat aataaagcat cacttactta aaatcagtta gcaaatttct gtccagttta  30480
ttcagcagca cctccttgcc ctcctcccag ctctggtatt gcagcttcct cctggctgca  30540
aactttctcc acaatctaaa tggaatgtca gtttcctcct gttcctgtcc atccgcaccc  30600
```

```
actatcttca tgttgttgca gatgaagcgc gcaagaccgt ctgaagatac cttcaacccc 30660
gtgtatccat atgacacgga aaccggtcct ccaactgtgc cttttcttac tcctcccttt 30720
gtatccccca atgggtttca agagagtccc cctggggtac tctctttgcg cctatccgaa 30780
cctctagtta cctccaatgg catgcttgcg ctcaaaatgg gcaacggcct ctctctggac 30840
gaggccggca accttacctc ccaaaatgta accactgtga gcccacctct caaaaaaacc 30900
aagtcaaaca taaacctgga aatatctgca cccctcacag ttacctcaga agccctaact 30960
gtggctgccg ccgcacctct aatggtcgcg ggcaacacac tcaccatgca atcacaggcc 31020
ccgctaaccg tgcacgactc caaacttagc attgccaccc aaggacccct cacagtgtca 31080
gaaggaaagc tagccctgca aacatcaggc cccctcacca ccaccgatag cagtaccctt 31140
actatcactg cctcaccccc tctaactact gccactggta gcttgggcat tgacttgaaa 31200
gagcccattt atacacaaaa tggaaaacta ggactaaagt acggggctcc tttgcatgta 31260
acagacgacc taaacacttt gaccgtagca actggtccag gtgtgactat taataatact 31320
tccttgcaaa ctaaagttac tggagccttg ggttttgatt cacaaggcaa tatgcaactt 31380
aatgtagcag gaggactaag gattgattct caaaacagac gccttatact tgatgttagt 31440
tatccgtttg atgctcaaaa ccaactaaat ctaagactag gacagggccc tctttttata 31500
aactcagccc acaacttgga tattaactac aacaaaggcc tttacttgtt tacagcttca 31560
aacaattcca aaaagcttga ggttaaccta agcactgcca aggggttgat gtttgacgct 31620
acagccatag ccattaatgc aggagatggg cttgaatttg gttcacctaa tgcaccaaac 31680
acaaatcccc tcaaaacaaa aattggccat ggcctagaat ttgattcaaa caaggctatg 31740
gttcctaaac taggaactgg ccttagtttt gacagcacag gtgccattac agtaggaaac 31800
aaaaataatg ataagctaac tttgtggacc acaccagctc catctcctaa ctgtagacta 31860
aatgcagaga aagatgctaa actcactttg gtcttaacaa aatgtggcag tcaaatactt 31920
gctacagttt cagttttggc tgttaaaggc agtttggctc caatatctgg aacagttcaa 31980
agtgctcatc ttattataag atttgacgaa aatggagtgc tactaaacaa ttccttcctg 32040
gacccagaat attggaactt tagaaatgga gatcttactg aaggcacagc ctatacaaac 32100
gctgttggat ttatgcctaa cctatcagct tatccaaaat ctcacggtaa aactgccaaa 32160
agtaacattg tcagtcaagt ttacttaaac ggagacaaaa ctaaacctgt aacactaacc 32220
attacactaa acggtacaca ggaaacagga gacacaactc caagtgcata ctctatgtca 32280
ttttcatggg actggtctgg ccacaactac attaatgaaa tatttgccac atcctcttac 32340
actttttcat acattgccca agaaggatca ggatcaggtt cagggagtgg ctctaaaaag 32400
aagaaaaaga agaagtaaag aatcgtttgt gttatgtttc aacgtgttta tttttcaatt 32460
gcagaaaatt tcaagtcatt tttcattcag tagtatagcc ccaccaccac atagcttata 32520
cagatcaccg taccttaatc aaactcacag aaccctagta ttcaacctgc cacctccctc 32580
ccaacacaca gagtacacag tcctttctcc ccggctggcc ttaaaaagca tcatatcatg 32640
ggtaacagac atattcttag gtgttatatt ccacacggtt tcctgtcgag ccaaacgctc 32700
atcagtgata ttaataaact ccccgggcag ctcacttaag ttcatgtcgc tgtccagctg 32760
ctgagccaca ggctgctgtc caacttgcgg ttgcttaacg ggcggcgaag gagaagtcca 32820
cgcctacatg ggggtagagt cataatcgtg catcaggata gggcggtggt gctgcagcag 32880
cgcgcgaata aactgctgcc gccgccgctc cgtcctgcag gaatacaaca tggcagtggt 32940
ctcctcagcg atgattcgca ccgcccgcag cataaggcgc cttgtcctcc gggcacagca 33000
```

```
gcgcaccctg atctcactta aatcagcaca gtaactgcag cacagcacca caatattgtt  33060
caaaatccca cagtgcaagg cgctgtatcc aaagctcatg gcggggacca cagaacccac  33120
gtggccatca taccacaagc gcaggtagat taagtggcga cccctcataa acacgctgga  33180
cataaacatt acctcttttg gcatgttgta attcaccacc tcccggtacc atataaacct  33240
ctgattaaac atggcgccat ccaccaccat cctaaaccag ctggccaaaa cctgcccgcc  33300
ggctatacac tgcagggaac cgggactgga acaatgacag tggagagccc aggactcgta  33360
accatggatc atcatgctcg tcatgatatc aatgttggca caacacaggc acacgtgcat  33420
acacttcctc aggattacaa gctcctcccg cgttagaacc atatcccagg gaacaaccca  33480
ttcctgaatc agcgtaaatc ccacactgca gggaagacct cgcacgtaac tcacgttgtg  33540
cattgtcaaa gtgttacatt cgggcagcag cggatgatcc tccagtatgg tagcgcgggt  33600
ttctgtctca aaaggaggta gacgatccct actgtacgga gtgcgccgag acaaccgaga  33660
tcgtgttggt cgtagtgtca tgccaaatgg aacgccggac gtagtcatat ttcctgataa  33720
actctaaaga atcgtttgtg ttatgtttca acgtgtttat ttttcaattg cagaaaattt  33780
caagtcattt ttcattcagt agtatagccc caccaccaca tagcttatac agatcaccgt  33840
accttaatca aactcacaga accctagtat tcaacctgcc acctccctcc caacacacag  33900
agtacacagt cctttctccc cggctggcct taaaaagcat catatcatgg gtaacagaca  33960
tattcttagg tgttatattc cacacggttt cctgtcgagc caaacgctca tcaagtgata  34020
ttaataaact ccccgggcag ctcacttaag ttcatgtcgc tgtccagctg ctgagccaca  34080
ggctgctgtc caacttgcgg ttgcttaacg ggcggcgaag gagaagtcca cgcctacatg  34140
gggggagagt cataatcgtg catcaggata gggcggtggt gctgcagcag cgcgcgaata  34200
aactgctgcc gccgccgctc cgtcctgcag gaatacaaca tggcagtggt ctcctcagcg  34260
atgattcgca ccgcccgcag cataaggcgc cttgtcctcc gggcacagca gcgcaccctg  34320
atctcactta aatcagcaca gtaactgcag cacagcacca caatattgtt caaaatccca  34380
cagtgcaagg cgctgtatcc aaagctcatg gcggggacca cagaacccac gtggccatca  34440
taccacaagc gcaggtagat taagtggcga cccctcataa acacgctgga cataaacatt  34500
acctcttttg gcatgttgta attcaccacc tcccggtacc atataaacct ctgattaaac  34560
atggcgccat ccaccaccat cctaaaccag ctggccaaaa cctgccccgc cgggntatac  34620
actgcaggga accgggactg gaacaatgac agtggagagc ccaggactcg taaccatgga  34680
tcatcatgct cgtcatgata tcaatgttgg cacaacacag gcacacgtgc atacacttcc  34740
tcaggattac aagctcctcc cgcgttagaa ccatatccca gggaacaacc cattcctgaa  34800
tcagcgtaaa tcccacactg cagggaagac ctcgcacgta actcacgttg tgcattgtca  34860
aagtgttaca ttcgggcagc agcggatgat cctccagtat ggtagcgcgg gtttctgtct  34920
caaaaggagg tagacgatcc ctactgtacg gagtgcgccg agacaaccga gatcgtgttg  34980
gtcgtagtgt catgccaaat ggaacgccgg acgtagtcat atttcctgaa gcaaaaccag  35040
gtgcgggcgt gacaaacaga tctgcgtctc cggtctcgcc gcttagatcg ctctgtgtag  35100
tagttgtagt atatccactc tctcaaagca tccaggcgcc ccctggcttc gggttctatg  35160
taaactcctt catgcgccgc tgccctgata acatccacca ccgcagaata agccacaccc  35220
agccaaccta cacattcgtt ctgcgagtca cacacgggag gagcgggaag agctggaaga  35280
accatgtttt tttttttatt ccaaaagatt atccaaaacc tcaaaatgaa gatctattaa  35340
```

```
gtgaacgcgc tcccctccgg tggcgtggtc aaactctaca gccaaagaac agataatggc  35400
atttgtaaga tgttgcacaa tggcttccaa aaggcaaacg gccctcacgt ccaagtggac  35460
gtaaaggcta aacccttcag ggtgaatctc ctctataaac attccagcac cttcaaccat  35520
gcccaaataa ttctcatctc gccaccttct caatatatct ctaagcaaat cccgaatatt  35580
aagtccggcc attgtaaaaa tttggctcca gagcgccctc caccttcagc ctcaagcagc  35640
gaatcatgat tgcaaaaatt caggttcctc acagacctgt ataagattca aaagcggaac  35700
attaacaaaa ataccgcgat cccgtaggtc ccttcgcagg gccagctgaa cataatcgtg  35760
caggtctgca cggaccagcg cggccacttc cccgccagga accatgacaa aagaacccac  35820
actgattatg acacgcatac tcggagctat gctaaccagc gtagccccga tgtaagcttg  35880
ttgcatgggc ggcgatataa aatgcaaggt gctgctcaaa aaatcaggca aagcctcgcg  35940
caaaaaagaa agcacatcgt agtcatgctc atgcagataa aggcaggtaa gctccggaac  36000
caccacagaa aaagacacca tttttctctc aaacatgtct gcgggtttct gcataaacac  36060
aaaataaaat aacaaaaaaa catttaaaca ttagaagcct gtcttacaac aggaaaaaca  36120
acccttataa gcataagacg gactacggcc atgccggcgt gaccgtaaaa aaactggtca  36180
ccgtgattaa aaagcaccac cgacagctcc tcggtcatgt ccggagtcat aatgtaagac  36240
tcggtaaaca catcaggttg attcacatcg gtcagtgcta aaaagcgacc gaaatagccc  36300
gggggaatac atacccgcag gcgtagagac aacattacag cccccatagg aggtataaca  36360
aaattaatag gagagaaaaa cacataaaca cctgaaaaac cctcctgcct aggcaaaata  36420
gcaccctccc gctccagaac aacatacagc gcttccacag cggcagccat aacagtcagc  36480
cttaccagta aaaaagaaaa cctattaaaa aaacaccact cgacacggca ccagctcaat  36540
cagtcacagt gtaaaaaagg gccaagtgca gagcgagtat atataggact aaaaaatgac  36600
gtaacggtta aagtccacaa aaaacaccca gaaaaccgca cgcgaaccta cgcccagaaa  36660
cgaaagccaa aaaacccaca acttcctcaa atcgtcactt ccgttttccc acgttacgtc  36720
acttcccatt ttaagaaaac tacaattccc aacacataca agttactccg ccctaaaacc  36780
tacgtcaccc gccccgttcc cacgccccgc gccacgtcac aaactccacc ccctcattat  36840
catattggct tcaatccaaa ataaggtata ttattgatga tgtta                  36885
```

<210> SEQ ID NO 5
<211> LENGTH: 35745
<212> TYPE: DNA
<213> ORGANISM: Artificial Sequence
<220> FEATURE:
<223> OTHER INFORMATION: The nucleotide sequence encoding virus CGTG-605
<220> FEATURE:
<221> NAME/KEY: misc_feature
<222> LOCATION: (33475)..(33475)
<223> OTHER INFORMATION: n is a, c, g, or t

<400> SEQUENCE: 5

```
taacatcatc aataatatac cttattttgg attgaagcca atatgataat gagggggtgg     60
agtttgtgac gtggcgcggg gcgtgggaac ggggcgggtg acgtagtagt gtggcggaag    120
tgtgatgttg caagtgtggc ggaacacatg taagcgacgg atgtggcaaa agtgacgttt    180
ttggtgtgcg ccggtgtaca caggaagtga caattttcgc gcggttttag gcggatgttg    240
tagtaaattt gggcgtaacc gagtaagatt tggccatttt cgcgggaaaa ctgaataaga    300
ggaagtgaaa tctgaataat tttgtgttac tcatagcgcg taatactggt accgcggccg    360
ctggtaccat ccggacaaag cctgcgcgcg ccccgccccg ccattggccg taccgccccg    420
```

```
cgccgccgcc ccatcccgcc cctcgccgcc gggtccggcg cgttaaagcc aataggaacc    480
gccgccgttg ttcccgtcac ggccggggca gccaattgtg gcggcgctcg gcggctcgtg    540
gctctttcgc ggcaaaaagg atttggcgcg taaaagtggc cgggactttg caggcagcgg    600
cggccggggg cggagcggga tcgagccctc gccctcgagc tagaagcttg ttttctcctc    660
cgagccgctc cgacaccggg actgaaaatg agacatatta tctgccacgg aggtgttatt    720
accgaagaaa tggccgccag tcttttggac cagctgatcg aagaggtact ggctgataat    780
cttccacctc ctagccattt tgaaccacct acccttcacg aactgtatga tttagacgtg    840
acggcccccg aagatcccaa cgaggaggcg gtttcgcaga tttttcccga ctctgtaatg    900
ttggcggtgc aggaagggat tgacttactc acttttccgc cggcgcccgg ttctccggag    960
ccgcctcacc tttcccggca gcccgagcag ccggagcaga gagccttggg tccggtttct   1020
atgccaaacc ttgtaccgga ggtgatcgat ccacccagtg acgacgagga tgaagagggt   1080
gaggagtttg tgttagatta tgtggagcac ccccgggcacg gttgcaggtc ttgtcattat   1140
caccggagga atacggggga cccagatatt atgtgttcgc tttgctatat gaggacctgt   1200
ggcatgtttg tctacagtaa gtgaaaatta tgggcagtgg gtgatagagt ggtgggtttg   1260
gtgtggtaat ttttttttta atttttacag ttttgtggtt taaagaattt tgtattgtga   1320
tttttttaaa aggtcctgtg tctgaacctg agcctgagcc cgagccagaa ccggagcctg   1380
caagacctac ccgccgtcct aaaatggcgc ctgctatcct gagacgcccg acatcacctg   1440
tgtctagaga atgcaatagt agtacggata gctgtgactc cggtccttct aacacacctc   1500
ctgagataca cccggtggtc ccgctgtgcc ccattaaacc agttgccgtg agagttggtg   1560
ggcgtcgcca ggctgtggaa tgtatcgagg acttgcttaa cgagcctggg caacctttgg   1620
acttgagctg taaacgcccc aggccataag gtgtaaacct gtgattgcgt gtgtggttaa   1680
cgcctttgtt tgctgaatga gttgatgtaa gtttaataaa gggtgagata atgtttaact   1740
tgcatggcgt gttaaatggg gcggggctta aagggtatat aatgcgccgt gggctaatct   1800
tggttacatc tgacctcatg gaggcttggg agtgtttgga agatttttct gctgtgcgta   1860
acttgctgga acagagctct aacagtacct cttggttttg gaggtttctg tggggctcat   1920
cccaggcaaa gttagtctgc agaattaagg aggattacaa gtgggaattt gaagagcttt   1980
tgaaatcctg tggtgagctg tttgattctt tgaatctggg tcaccaggcg cttttccaag   2040
agaaggtcat caagactttg gatttttcca caccggggcg cgctgcggct gctgttgctt   2100
ttttgagttt tataaaggat aaatggagcg aagaaaccca tctgagcggg gggtacctgc   2160
tggattttct ggccatgcat ctgtggagag cggttgtgag acacaagaat cgcctgctac   2220
tgttgtcttc cgtccgcccg gcgataatac cgacggagga gcagcagcag cagcaggagg   2280
aagccaggcg gcggcggcag gagcagagcc catggaaccc gagagccggc ctggaccctc   2340
gggaatgaat gttgtacagg tggctgaact gtatccagaa ctgagacgca ttttgacaat   2400
tacagaggat gggcaggggc taaagggggt aaagagggag cgggggctt gtgaggctac   2460
agaggaggct aggaatctag cttttagctt aatgaccaga caccgtcctg agtgtattac   2520
ttttcaacag atcaaggata attgcgctaa tgagcttgat ctgctggcgc agaagtattc   2580
catagagcag ctgaccactt actggctgca gccaggggat gattttgagg aggctattag   2640
ggtatatgca aaggtggcac ttaggccaga ttgcaagtac aagatcagca aacttgtaaa   2700
tatcaggaat tgttgctaca tttctgggaa cggggccgag gtggagatag atacggagga   2760
```

```
tagggtggcc tttagatgta gcatgataaa tatgtggccg ggggtgcttg gcatggacgg   2820
ggtggttatt atgaatgtaa ggtttactgg ccccaatttt agcggtacgg ttttcctggc   2880
caataccaac cttatcctac acggtgtaag cttctatggg tttaacaata cctgtgtgga   2940
agcctggacc gatgtaaggg ttcggggctg tgccttttac tgctgctgga agggggtggt   3000
gtgtcgcccc aaaagcaggg cttcaattaa gaaatgcctc tttgaaaggt gtaccttggg   3060
tatcctgtct gagggtaact ccagggtgcg ccacaatgtg gcctccgact gtggttgctt   3120
catgctagtg aaaagcgtgg ctgtgattaa gcataacatg gtatgtggca actgcgagga   3180
cagggcctct cagatgctga cctgctcgga cggcaactgt cacctgctga agaccattca   3240
cgtagccagc cactctcgca aggcctggcc agtgtttgag cataacatac tgacccgctg   3300
ttccttgcat ttgggtaaca ggaggggggt gttcctacct taccaatgca atttgagtca   3360
cactaagata ttgcttgagc ccgagagcat gtccaaggtg aacctgaacg gggtgtttga   3420
catgaccatg aagatctgga aggtgctgag gtacgatgag acccgcacca ggtgcagacc   3480
ctgcgagtgt ggcggtaaac atattaggaa ccagcctgtg atgctggatg tgaccgagga   3540
gctgaggccc gatcacttgg tgctggcctg cacccgcgct gagtttggct ctagcgatga   3600
agatacagat tgaggtactg aaatgtgtgg gcgtggctta agggtgggaa agaatatata   3660
aggtgggggt cttatgtagt tttgtatctg ttttgcagca gccgccgccg ccatgagcac   3720
caactcgttt gatggaagca ttgtgagctc atatttgaca acgcgcatgc ccccatgggc   3780
cggggtgcgt cagaatgtga tgggctccag cattgatggt cgccccgtcc tgcccgcaaa   3840
ctctactacc ttgacctacg agaccgtgtc tggaacgccg ttggagactg cagcctccgc   3900
cgccgcttca gccgctgcag ccaccgcccg cgggattgtg actgactttg ctttcctgag   3960
cccgcttgca agcagtgcag cttcccgttc atccgcccgc gatgacaagt tgacggctct   4020
tttggcacaa ttggattctt tgacccggga acttaatgtc gtttctcagc agctgttgga   4080
tctgcgccag caggtttctg ccctgaaggc ttcctcccct cccaatgcgg tttaaaacat   4140
aaataaaaaa ccagactctg tttggatttg gatcaagcaa gtgtcttgct gtctttattt   4200
aggggttttg cgcgcgcggt aggcccggga ccagcggtct cggtcgttga gggtcctgtg   4260
tatttttcc aggacgtggt aaaggtgact ctggatgttc agatacatgg gcataagccc   4320
gtctctgggg tggaggtagc accactgcag agcttcatgc tgcggggtgg tgttgtagat   4380
gatccagtcg tagcaggagc gctgggcgtg gtgcctaaaa atgtctttca gtagcaagct   4440
gattgccagg ggcaggccct tggtgtaagt gtttacaaag cggttaagct gggatgggtg   4500
catacgtggg gatatgagat gcatcttgga ctgtattttt aggttggcta tgttcccagc   4560
catatccctc cggggattca tgttgtgcag aaccaccagc acagtgtatc cggtgcactt   4620
gggaaatttg tcatgtagct tagaaggaaa tgcgtggaag aacttggaga cgcccttgtg   4680
acctccaaga ttttccatgc attcgtccat aatgatggca atgggcccac gggcggcggc   4740
ctgggcgaag atatttctgg gatcactaac gtcatagttg tgttccagga tgagatcgtc   4800
ataggccatt tttacaaagc gcgggcggag ggtgccagac tgcggtataa tggttccatc   4860
cggcccaggg gcgtagttac cctcacagat ttgcatttcc cacgctttga gttcagatgg   4920
ggggatcatg tctacctgcg gggcgatgaa gaaaacggtt tccggggtag gggagatcag   4980
ctgggaagaa agcaggttcc tgagcagctg cgacttaccg cagccggtgg gcccgtaaat   5040
cacacctatt accgggtgca actggtagtt aagagagctg cagctgccgt catccctgag   5100
caggggggcc acttcgttaa gcatgtccct gactcgcatg ttttccctga ccaaatccgc   5160
```

```
cagaaggcgc tcgccgccca gcgatagcag ttcttgcaag gaagcaaagt ttttcaacgg   5220
tttgagaccg tccgccgtag gcatgctttt gagcgtttga ccaagcagtt ccaggcggtc   5280
ccacagctcg gtcacctgct ctacggcatc tcgatccagc atatctcctc gtttcgcggg   5340
ttggggcggc tttcgctgta cggcagtagt cggtgctcgt ccagacgggc cagggtcatg   5400
tctttccacg ggcgcagggt cctcgtcagc gtagtctggg tcacggtgaa ggggtgcgct   5460
ccgggctgcg cgctggccag ggtgcgcttg aggctggtcc tgctggtgct gaagcgctgc   5520
cggtcttcgc cctgcgcgtc ggccaggtag catttgacca tggtgtcata gtccagcccc   5580
tccgcggcgt ggcccttggc gcgcagcttg cccttggagg aggcgccgca cgaggggcag   5640
tgcagacttt tgagggcgta gagcttgggc gcgagaaata ccgattccgg ggagtaggca   5700
tccgcgccgc aggccccgca gacggtctcg cattccacga gccaggtgag ctctggccgt   5760
tcggggtcaa aaaccaggtt tcccccatgc tttttgatgc gtttcttacc tctggtttcc   5820
atgagccggt gtccacgctc ggtgacgaaa aggctgtccg tgtccccgta tacagacttg   5880
agaggcctgt cctcgagcgg tgttccgcgg tcctcctcgt atagaaactc ggaccactct   5940
gagacaaagg ctcgcgtcca ggccagcacg aaggaggcta agtgggaggg gtagcggtcg   6000
ttgtccacta gggggtccac tcgctccagg gtgtgaagac acatgtcgcc ctcttcggca   6060
tcaaggaagg tgattggttt gtaggtgtag gccacgtgac cgggtgttcc tgaagggggg   6120
ctataaaagg gggtgggggc gcgttcgtcc tcactctctt ccgcatcgct gtctgcgagg   6180
gccagctgtt ggggtgagta ctccctctga aaagcgggca tgacttctgc gctaagattg   6240
tcagtttcca aaaacgagga ggatttgata ttcacctggc ccgcggtgat gcctttgagg   6300
gtggccgcat ccatctggtc agaaaagaca atctttttgt tgtcaagctt ggtggcaaac   6360
gacccgtaga gggcgttgga cagcaacttg gcgatggagc gcagggtttg gtttttgtcg   6420
cgatcggcgc gctccttggc cgcgatgttt agctgcacgt attcgcgcgc aacgcaccgc   6480
cattcgggaa agacggtggt gcgctcgtcg ggcaccaggt gcacgcgcca accgcggttg   6540
tgcagggtga caaggtcaac gctggtggct acctctccgc gtaggcgctc gttggtccag   6600
cagaggcggc cgcccttgcg cgagcagaat ggcggtaggg ggtctagctg cgtctcgtcc   6660
ggggggtctg cgtccacggt aaagaccccg ggcagcaggc gcgcgtcgaa gtagtctatc   6720
ttgcatcctt gcaagtctag cgcctgctgc catgcgcggg cggcaagcgc gcgctcgtat   6780
gggttgagtg gggaccccca tggcatgggg tgggtgagcg cggaggcgta catgccgcaa   6840
atgtcgtaaa cgtagagggg ctctctgagt attccaagat atgtagggta gcatcttcca   6900
ccgcggatgc tggcgcgcac gtaatcgtat agttcgtgcg agggagcgag gaggtcggga   6960
ccgaggttgc tacgggcggg ctgctctgct cggaagacta tctgcctgaa gatggcatgt   7020
gagttggatg atatggttgg acgctggaag acgttgaagc tggcgtctgt gagacctacc   7080
gcgtcacgca cgaaggaggc gtaggagtcg cgcagcttgt tgaccagctc ggcggtgacc   7140
tgcacgtcta gggcgcagta gtccagggtt tccttgatga tgtcatactt atcctgtccc   7200
ttttttttcc acagctcgcg gttgaggaca aactcttcgc ggtctttcca gtactcttgg   7260
atcggaaacc cgtcggcctc cgaacggtaa gagcctagca tgtagaactg gttgacggcc   7320
tggtaggcgc agcatccctt ttctacgggt agcgcgtatg cctgcgcggc cttccggagc   7380
gaggtgtggg tgagcgcaaa ggtgtccctg accatgactt tgaggtactg gtatttgaag   7440
tcagtgtcgt cgcatccgcc ctgctcccag agcaaaaagt ccgtgcgctt tttggaacgc   7500
```

```
ggatttggca gggcgaaggt gacatcgttg aagagtatct ttcccgcgcg aggcataaag   7560
ttgcgtgtga tgcggaaggg tcccggcacc tcggaacggt tgttaattac ctgggcggcg   7620
agcacgatct cgtcaaagcc gttgatgttg tggcccacaa tgtaaagttc caagaagcgc   7680
gggatgccct tgatggaagg caattttttta agttcctcgt aggtgagctc ttcaggggag   7740
ctgagcccgt gctctgaaag ggcccagtct gcaagatgag ggttggaagc gacgaatgag   7800
ctccacaggt cacgggccat tagcatttgc aggtggtcgc gaaaggtcct aaactggcga   7860
cctatggcca tttttctgg ggtgatgcag tagaaggtaa gcgggtcttg ttcccagcgg   7920
tcccatccaa ggttcgcggc taggtctcgc gcggcagtca ctagaggctc atctccgccg   7980
aacttcatga ccagcatgaa gggcacgagc tgcttcccaa aggcccccat ccaagtatag   8040
gtctctacat cgtaggtgac aaagagacgc tcggtgcgag gatgcgagcc gatcgggaag   8100
aactggatct cccgccacca attggaggag tggctattga tgtggtgaaa gtagaagtcc   8160
ctgcgacggg ccgaacactc gtgctggctt ttgtaaaaac gtgcgcagta ctggcagcgg   8220
tgcacgggct gtacatcctg cacgaggttg acctgacgac cgcgcacaag gaagcagagt   8280
gggaatttga gcccctcgcc tggcgggttt ggctggtggt cttctacttc ggctgcttgt   8340
ccttgaccgt ctggctgctc gaggggagtt acggtggatc ggaccaccac gccgcgcgag   8400
cccaaagtcc agatgtccgc gcgcggcggt cggagcttga tgacaacatc gcgcagatgg   8460
gagctgtcca tggtctggag ctcccgcggc gtcaggtcag gcgggagctc ctgcaggttt   8520
acctcgcata gacgggtcag ggcgcgggct agatccaggt gatacctaat ttccaggggc   8580
tggttggtgg cggcgtcgat ggcttgcaag aggccgcatc cccgcggcgc gactacggta   8640
ccgcgcggcg ggcggtgggc cgcgggggtg tccttggatg atgcatctaa aagcggtgac   8700
gcgggcgagc ccccggaggt agggggggct ccggacccgc cgggagaggg ggcaggggca   8760
cgtcggcgcc gcgcgcgggc aggagctggt gctgcgcgcg taggttgctg gcgaacgcga   8820
cgacgcggcg gttgatctcc tgaatctggc gcctctgcgt gaagacgacg ggcccggtga   8880
gcttgagcct gaaagagagt tcgacagaat caatttcggt gtcgttgacg gcggcctggc   8940
gcaaaatctc ctgcacgtct cctgagttgt cttgataggc gatctcggcc atgaactgct   9000
cgatctcttc ctcctggaga tctccgcgtc cggctcgctc cacggtggcg gcgaggtcgt   9060
tggaaatgcg ggccatgagc tgcgagaagg cgttgaggcc tccctcgttc cagacgcggc   9120
tgtagaccac gccccccttcg gcatcgcggg cgcgcatgac cacctgcgcg agattgagct   9180
ccacgtgccg ggcgaagacg gcgtagtttc gcaggcgctg aaagaggtag ttgagggtgg   9240
tggcggtgtg ttctgccacg aagaagtaca taacccagcg tcgcaacgtg gattcgttga   9300
tatcccccaa ggcctcaagg cgctccatgg cctcgtagaa gtccacggcg aagttgaaaa   9360
actgggagtt gcgcgccgac acggttaact cctcctccag aagacggatg agctcggcga   9420
cagtgtcgcg cacctcgcgc tcaaaggcta caggggcctc ttcttcttct tcaatctcct   9480
cttccataag ggcctcccct tcttcttctt ctggcggcgg tgggggaggg gggacacggc   9540
ggcgacgacg gcgcaccggg aggcggtcga caaagcgctc gatcatctcc ccgcggcgac   9600
ggcgcatggt ctcggtgacg gcgcggccgt tctcgcgggg gcgcagttgg aagacgccgc   9660
ccgtcatgtc ccggttatgg gttggcgggg ggctgccatg cggcagggat acggcgctaa   9720
cgatgcatct caacaattgt tgtgtaggta ctccgccgcc gagggacctg agcgagtccg   9780
catcgaccgg atcggaaaac ctctcgagaa aggcgtctaa ccagtcacag tcgcaaggta   9840
ggctgagcac cgtggcgggc ggcagcgggc ggcggtcggg gttgtttctg gcggaggtgc   9900
```

```
tgctgatgat gtaattaaag taggcggtct tgagacggcg gatggtcgac agaagcacca   9960
tgtccttggg tccggcctgc tgaatgcgca ggcggtcggc catgccccag gcttcgtttt  10020
gacatcggcg caggtctttg tagtagtctt gcatgagcct ttctaccggc acttcttctt  10080
ctccttcctc ttgtcctgca tctcttgcat ctatcgctgc ggcggcggcg gagtttggcc  10140
gtaggtggcg ccctcttcct cccatgcgtg tgaccccgaa gcccctcatc ggctgaagca  10200
gggctaggtc ggcgacaacg cgctcggcta atatggcctg ctgcacctgc gtgagggtag  10260
actggaagtc atccatgtcc acaaagcggt ggtatgcgcc cgtgttgatg gtgtaagtgc  10320
agttggccat aacggaccag ttaacggtct ggtgacccgg ctgcgagagc tcggtgtacc  10380
tgagacgcga gtaagccctc gagtcaaata cgtagtcgtt gcaagtccgc accaggtact  10440
ggtatcccac caaaaagtgc ggcggcggct ggcggtagag gggccagcgt agggtggccg  10500
gggctccggg ggcgagatct tccaacataa ggcgatgata tccgtagatg tacctggaca  10560
tccaggtgat gccggcggcg gtggtggagg cgcgcggaaa gtcgcggacg cggttccaga  10620
tgttgcgcag cggcaaaaag tgctccatgg tcgggacgct ctggccggtc aggcgcgcgc  10680
aatcgttgac gctctagacc gtgcaaaagg agagcctgta agcgggcact cttccgtggt  10740
ctggtggata aattcgcaag ggtatcatgg cggacgaccg gggttcgagc cccgtatccg  10800
gccgtccgcc gtgatccatg cggttaccgc ccgcgtgtcg aacccaggtg tgcgacgtca  10860
gacaacgggg gagtgctcct tttggcttcc ttccaggcgc ggcggctgct gcgctagctt  10920
ttttggccac tggccgcgcg cagcgtaagc ggttaggctg gaaagcgaaa gcattaagtg  10980
gctcgctccc tgtagccgga gggttatttt ccaagggttg agtcgcggga cccccggttc  11040
gagtctcgga ccggccggac tgcggcgaac gggggtttgc ctccccgtca tgcaagaccc  11100
cgcttgcaaa ttcctccgga aacagggacg agcccctttt ttgcttttcc cagatgcatc  11160
cggtgctgcg gcagatgcgc ccccctcctc agcagcggca agagcaagag cagcggcaga  11220
catgcagggc accctcccct cctcctaccg cgtcaggagg ggcgacatcc gcggttgacg  11280
cggcagcaga tggtgattac gaacccccgc ggcgccgggc ccggcactac ctggacttgg  11340
aggagggcga gggcctggcg cggctaggag cgccctctcc tgagcggtac ccaagggtgc  11400
agctgaagcg tgatacgcgt gaggcgtacg tgccgcggca gaacctgttt cgcgaccgcg  11460
agggagagga gcccgaggag atgcgggatc gaaagttcca cgcagggcgc gagctgcggc  11520
atggcctgaa tcgcgagcgg ttgctgcgcg aggaggactt tgagcccgac gcgcgaaccg  11580
ggattagtcc cgcgcgcgca cacgtggcgg ccgccgacct ggtaaccgca tacgagcaga  11640
cggtgaacca ggagattaac tttcaaaaaa gctttaacaa ccacgtgcgt acgcttgtgg  11700
cgcgcgagga ggtggctata ggactgatgc atctgtggga ctttgtaagc gcgctggagc  11760
aaaacccaaa tagcaagccg ctcatggcgc agctgttcct tatagtgcag cacagcaggg  11820
acaacgaggc attcagggat gcgctgctaa acatagtaga gcccgagggc cgctggctgc  11880
tcgatttgat aaacatcctg cagagcatag tggtgcagga gcgcagcttg agcctggctg  11940
acaaggtggc cgccatcaac tattccatgc ttagcctggg caagttttac gcccgcaaga  12000
tataccatac cccttacgtt cccatagaca aggaggtaaa gatcgagggg ttctacatgc  12060
gcatggcgct gaaggtgctt accttgagcg acgacctggg cgtttatcgc aacgagcgca  12120
tccacaaggc cgtgagcgtg agccggcggc gcgagctcag cgaccgcgag ctgatgcaca  12180
gcctgcaaag ggccctggct ggcacgggca gcggcgatag agaggccgag tcctactttg  12240
```

```
acgcgggcgc tgacctgcgc tgggccccaa gccgacgcgc cctggaggca gctggggccg  12300
gacctgggct ggcggtggca cccgcgcgcg ctggcaacgt cggcggcgtg gaggaatatg  12360
acgaggacga tgagtacgag ccagaggacg gcgagtacta agcggtgatg tttctgatca  12420
gatgatgcaa gacgcaacgg acccggcggt gcgggcggcg ctgcagagcc agccgtccgg  12480
ccttaactcc acggacgact ggcgccaggt catggaccgc atcatgtcgc tgactgcgcg  12540
caatcctgac gcgttccggc agcagccgca ggccaaccgg ctctccgcaa ttctggaagc  12600
ggtggtcccg gcgcgcgcaa accccacgca cgagaaggtg ctggcgatcg taaacgcgct  12660
ggccgaaaac agggccatcc ggcccgacga ggccggcctg gtctacgacg cgctgcttca  12720
gcgcgtggct cgttacaaca gcggcaacgt gcagaccaac ctggaccggc tggtgggga  12780
tgtgcgcgag gccgtggcgc agcgtgagcg cgcgcagcag cagggcaacc tgggctccat  12840
ggttgcacta aacgccttcc tgagtacaca gcccgccaac gtgccgcggg gacaggagga  12900
ctacaccaac tttgtgagcg cactgcggct aatggtgact gagacaccgc aaagtgaggt  12960
gtaccagtct gggccagact attttttcca gaccagtaga caaggcctgc agaccgtaaa  13020
cctgagccag gctttcaaaa acttgcaggg gctgtggggg gtgcgggctc ccacaggcga  13080
ccgcgcgacc gtgtctagct tgctgacgcc caactcgcgc ctgttgctgc tgctaatagc  13140
gcccttcacg gacagtggca gcgtgtcccg ggacacatac ctaggtcact tgctgacact  13200
gtaccgcgag gccataggtc aggcgcatgt ggacgagcat actttccagg agattacaag  13260
tgtcagccgc gcgctggggc aggaggacac gggcagcctg gaggcaaccc taaactacct  13320
gctgaccaac cggcggcaga agatcccctc gttgcacagt ttaaacagcg aggaggagcg  13380
cattttgcgc tacgtgcagc agagcgtgag ccttaacctg atgcgcgacg gggtaacgcc  13440
cagcgtggcg ctggacatga ccgcgcgcaa catggaaccg ggcatgtatg cctcaaaccg  13500
gccgtttatc aaccgcctaa tggactactt gcatcgcgcg gccgccgtga accccgagta  13560
tttcaccaat gccatcttga acccgcactg gctaccgccc cctggtttct acaccggggg  13620
attcgaggtg cccgagggta acgatggatt cctctgggac gacatagacg acagcgtgtt  13680
ttccccgcaa ccgcagaccc tgctagagtt gcaacagcgc gagcaggcag aggcggcgct  13740
gcgaaaggaa agcttccgca ggccaagcag cttgtccgat ctaggcgctg cggccccgcg  13800
gtcagatgct agtagcccat ttccaagctt gatagggtct cttaccagca ctcgcaccac  13860
ccgcccgcgc ctgctgggcg aggaggagta cctaaacaac tcgctgctgc agccgcagcg  13920
cgaaaaaaac ctgcctccgg catttcccaa caacgggata gagagcctag tggacaagat  13980
gagtagatgg aagacgtacg cgcaggagca cagggacgtg ccaggcccgc gcccgcccac  14040
ccgtcgtcaa aggcacgacc gtcagcgggg tctggtgtgg gaggacgatg actcggcaga  14100
cgacagcagc gtcctggatt tgggagggag tggcaacccg tttgcgcacc ttcgccccag  14160
gctggggaga atgttttaaa aaaaaaaaag catgatgcaa aataaaaaac tcaccaaggc  14220
catggcaccg agcgttggtt ttcttgtatt ccccttagta tgcggcgcgc ggcgatgtat  14280
gaggaaggtc ctcctccctc ctacgagagt gtggtgagcg cggcgccagt ggcggcggcg  14340
ctgggttctc ccttcgatgc tcccctggac ccgccgtttg tgcctccgcg gtacctgcgg  14400
cctaccgggg ggagaaacag catccgttac tctgagttgg caccccctatt cgacaccacc  14460
cgtgtgtacc tggtggacaa caagtcaacg gatgtggcat ccctgaacta ccagaacgac  14520
cacagcaact ttctgaccac ggtcattcaa aacaatgact acagcccggg ggaggcaagc  14580
acacagacca tcaatcttga cgaccggtcg cactggggcg gcgacctgaa aaccatcctg  14640
```

```
cataccaaca tgccaaatgt gaacgagttc atgtttacca ataagtttaa ggcgcgggtg  14700
atggtgtcgc gcttgcctac taaggacaat caggtggagc tgaaatacga gtgggtggag  14760
ttcacgctgc ccgagggcaa ctactccgag accatgacca tagaccttat gaacaacgcg  14820
atcgtggagc actacttgaa agtgggcaga cagaacgggg ttctggaaag cgacatcggg  14880
gtaaagtttg acacccgcaa cttcagactg gggtttgacc ccgtcactgg tcttgtcatg  14940
cctggggtat atacaaacga agccttccat ccagacatca ttttgctgcc aggatgcggg  15000
gtggacttca cccacagccg cctgagcaac ttgttgggca tccgcaagcg gcaacccttc  15060
caggagggct ttaggatcac ctacgatgat ctggagggtg gtaacattcc cgcactgttg  15120
gatgtggacg cctaccaggc gagcttgaaa gatgacaccg aacagggcgg gggtggcgca  15180
ggcggcagca acagcagtgg cagcggcgcg gaagagaact ccaacgcggc agccgcggca  15240
atgcagccgg tggaggacat gaacgatcat gccattcgcg gcgacacctt tgccacacgg  15300
gctgaggaga agcgcgctga ggccgaagca gcggccgaag ctgccgcccc cgctgcgcaa  15360
cccgaggtcg agaagcctca gaagaaaccg gtgatcaaac ccctgacaga ggacagcaag  15420
aaacgcagtt acaacctaat aagcaatgac agcaccttca cccagtaccg cagctggtac  15480
cttgcataca actacggcga ccctcagacc ggaatccgct catggaccct gctttgcact  15540
cctgacgtaa cctgcggctc ggagcaggtc tactggtcgt tgccagacat gatgcaagac  15600
cccgtgacct tccgctccac gcgccagatc agcaactttc cggtggtggg cgccgagctg  15660
ttgcccgtgc actccaagag cttctacaac gaccaggccg tctactccca actcatccgc  15720
cagtttacct ctctgaccca cgtgttcaat cgctttcccg agaaccagat tttggcgcgc  15780
ccgccagccc ccaccatcac caccgtcagt gaaaacgttc ctgctctcac agatcacggg  15840
acgctaccgc tgcgcaacag catcggagga gtccagcgag tgaccattac tgacgccaga  15900
cgccgcacct gcccctacgt ttacaaggcc ctgggcatag tctcgccgcg cgtcctatcg  15960
agccgcactt tttgagcaag catgtccatc cttatatcgc ccagcaataa cacaggctgg  16020
ggcctgcgct tcccaagcaa gatgtttggc ggggccaaga agcgctccga ccaacaccca  16080
gtgcgcgtgc gcgggcacta ccgcgcgccc tggggcgcgc acaaacgcgg ccgcactggg  16140
cgcaccaccg tcgatgacgc catcgacgcg gtggtggagg aggcgcgcaa ctacacgccc  16200
acgccgccac cagtgtccac agtggacgcg gccattcaga ccgtggtgcg cggagcccgg  16260
cgctatgcta aaatgaagag acggcggagg cgcgtagcac gtcgccaccg ccgccgaccc  16320
ggcactgccg cccaacgcgc ggcggcggcc ctgcttaacc gcgcacgtcg caccggccga  16380
cgggcggcca tgcgggccgc tcgaaggctg gccgcgggta ttgtcactgt gccccccagg  16440
tccaggcgac gagcggccgc cgcagcagcc gcggccatta gtgctatgac tcagggtcgc  16500
aggggcaacg tgtattgggt gcgcgactcg gttagcggcc tgcgcgtgcc cgtgcgcacc  16560
cgcccccgc gcaactagat tgcaagaaaa aactacttag actcgtactg ttgtatgtat  16620
ccagcggcgg cggcgcgcaa cgaagctatg tccaagcgca aaatcaaaga agagatgctc  16680
caggtcatcg cgccggagat ctatggcccc ccgaagaagg aagagcagga ttacaagccc  16740
cgaaagctaa agcgggtcaa aaagaaaaag aaagatgatg atgatgaact tgacgacgag  16800
gtggaactgc tgcacgctac cgcgcccagg cgacgggtac agtggaaagg tcgacgcgta  16860
aaacgtgttt tgcgacccgg caccaccgta gtctttacgc ccggtgagcg ctccacccgc  16920
acctacaagc gcgtgtatga tgaggtgtac ggcgacgagg acctgcttga gcaggccaac  16980
```

```
gagcgcctcg gggagtttgc ctacggaaag cggcataagg acatgctggc gttgccgctg  17040
gacgagggca acccaacacc tagcctaaag cccgtaacac tgcagcaggt gctgcccgcg  17100
cttgcaccgt ccgaagaaaa gcgcggccta aagcgcgagt ctggtgactt ggcacccacc  17160
gtgcagctga tggtacccaa gcgccagcga ctggaagatg tcttggaaaa aatgaccgtg  17220
gaacctgggc tggagcccga ggtccgcgtg cggccaatca agcaggtggc gccgggactg  17280
ggcgtgcaga ccgtggacgt tcagataccc actaccagta gcaccagtat tgccaccgcc  17340
acagagggca tggagacaca aacgtccccg gttgcctcag cggtggcgga tgccgcggtg  17400
caggcggtcg ctgcggccgc gtccaagacc tctacggagg tgcaaacgga cccgtggatg  17460
tttcgcgttt cagcccccccg gcgcccgcgc ggttcgagga agtacggcgc cgccagcgcg  17520
ctactgcccg aatatgccct acatccttcc attgcgccta cccccggcta tcgtggctac  17580
acctaccgcc ccagaagacg agcaactacc cgacgccgaa ccaccactgg aacccgccgc  17640
cgccgtcgcc gtcgccagcc cgtgctggcc ccgatttccg tgcgcagggt ggctcgcgaa  17700
ggaggcagga ccctggtgct gccaacagcg cgctaccacc ccagcatcgt ttaaaagccg  17760
gtctttgtgg ttcttgcaga tatggccctc acctgccgcc tccgtttccc ggtgccggga  17820
ttccgaggaa gaatgcaccg taggaggggc atggccggcc acggcctgac gggcggcatg  17880
cgtcgtgcgc accaccggcg gcggcgcgcg tcgcaccgtc gcatgcgcgg cggtatcctg  17940
cccctcctta ttccactgat cgccgcggcg attggcgccg tgcccggaat tgcatccgtg  18000
gccttgcagg cgcagagaca ctgattaaaa acaagttgca tgtggaaaaa tcaaaataaa  18060
aagtctggac tctcacgctc gcttggtcct gtaactattt tgtagaatgg aagacatcaa  18120
ctttgcgtct ctggccccgc gacacggctc gcgcccgttc atgggaaact ggcaagatat  18180
cggcaccagc aatatgagcg gtggcgcctt cagctggggc tcgctgtgga gcggcattaa  18240
aaatttcggt tccaccgtta agaactatgg cagcaaggcc tggaacagca gcacaggcca  18300
gatgctgagg gataagttga aagagcaaaa tttccaacaa aaggtggtag atggcctggc  18360
ctctggcatt agcggggtgg tggacctggc caaccaggca gtgcaaaata agattaacag  18420
taagcttgat ccccgccctc ccgtagagga gcctccaccg gccgtggaga cagtgtctcc  18480
agaggggcgt ggcgaaaagc gtccgcgccc cgacagggaa gaaactctgg tgacgcaaat  18540
agacgagcct ccctcgtacg aggaggcact aaagcaaggc ctgcccacca cccgtcccat  18600
cgcgcccatg gctaccggag tgctgggcca gcacacaccc gtaacgctgg acctgcctcc  18660
ccccgccgac acccagcaga aacctgtgct gccaggcccg accgccgttg ttgtaacccg  18720
tcctagccgc gcgtccctgc gccgcgccgc cagcggtccg cgatcgttgc ggcccgtagc  18780
cagtggcaac tggcaaagca cactgaacag catcgtgggt ctgggggtgc aatccctgaa  18840
gcgccgacga tgcttctgaa tagctaacgt gtcgtatgtg tgtcatgtat gcgtccatgt  18900
cgccgccaga ggagctgctg agccgccgcg cgcccgcttt ccaagatggc taccccttcg  18960
atgatgccgc agtggtctta catgcacatc tcgggccagg acgcctcgga gtacctgagc  19020
cccgggctgg tgcagtttgc ccgcgccacc gagacgtact tcagcctgaa taacaagttt  19080
agaaacccca cggtggcgcc tacgcacgac gtgaccacag accggtccca gcgtttgacg  19140
ctgcggttca tccctgtgga ccgtgaggat actgcgtact cgtacaaggc gcggttcacc  19200
ctagctgtgg gtgataaccg tgtgctggac atggcttcca cgtactttga catccgcggc  19260
gtgctggaca ggggccctac ttttaagccc tactctggca ctgcctacaa cgccctggct  19320
cccaagggtg ccccaaatcc ttgcgaatgg gatgaagctg ctactgctct tgaaataaac  19380
```

```
ctagaagaag aggacgatga caacgaagac gaagtagacg agcaagctga gcagcaaaaa  19440
actcacgtat ttgggcaggc gccttattct ggtataaata ttacaaagga gggtattcaa  19500
ataggtgtcg aaggtcaaac acctaaatat gccgataaaa catttcaacc tgaacctcaa  19560
ataggagaat ctcagtggta cgaaactgaa attaatcatg cagctgggag agtccttaaa  19620
aagactaccc caatgaaacc atgttacggt tcatatgcaa aacccacaaa tgaaaatgga  19680
gggcaaggca ttcttgtaaa gcaacaaaat ggaaagctag aaagtcaagt ggaaatgcaa  19740
tttttctcaa ctactgaggc gaccgcaggc aatggtgata acttgactcc taaagtggta  19800
ttgtacagtg aagatgtaga tatagaaacc ccagacactc atatttctta catgcccact  19860
attaaggaag gtaactcacg agaactaatg ggccaacaat ctatgcccaa caggcctaat  19920
tacattgctt ttagggacaa ttttattggt ctaatgtatt acaacagcac gggtaatatg  19980
ggtgttctgg cgggccaagc atcgcagttg aatgctgttg tagatttgca agacagaaac  20040
acagagcttt cataccagct tttgcttgat tccattggtg atagaaccag gtacttttct  20100
atgtggaatc aggctgttga cagctatgat ccagatgtta gaattattga aaatcatgga  20160
actgaagatg aacttccaaa ttactgcttt ccactgggag gtgtgattaa tacagagact  20220
cttaccaagg taaaacctaa aacaggtcag gaaaatggat gggaaaaaga tgctacagaa  20280
ttttcagata aaaatgaaat aagagttgga aataattttg ccatggaaat caatctaaat  20340
gccaacctgt ggagaaattt cctgtactcc aacatagcgc tgtatttgcc cgacaagcta  20400
aagtacagtc cttccaacgt aaaaatttct gataacccaa acacctacga ctacatgaac  20460
aagcgagtgg tggctcccgg gttagtggac tgctacatta accttggagc acgctggtcc  20520
cttgactata tggacaacgt caacccattt aaccaccacc gcaatgctgg cctgcgctac  20580
cgctcaatgt tgctgggcaa tggtcgctat gtgcccttcc acatccaggt gcctcagaag  20640
ttctttgcca ttaaaaacct ccttctcctg ccgggctcat acacctacga gtggaacttc  20700
aggaaggatg ttaacatggt tctgcagagc tccctaggaa atgacctaag ggttgacgga  20760
gccagcatta agtttgatag catttgcctt tacgccacct tcttccccat ggcccacaac  20820
accgcctcca cgcttgaggc catgcttaga aacgacacca acgaccagtc ctttaacgac  20880
tatctctccg ccgccaacat gctctaccct atacccgcca acgctaccaa cgtgcccata  20940
tccatcccct cccgcaactg ggcggctttc cgcggctggg ccttcacgcg ccttaagact  21000
aaggaaaccc catcactggg ctcgggctac gacccttatt acacctactc tggctctata  21060
ccctacctag atggaacctt ttacctcaac cacaccttta agaaggtggc cattaccttt  21120
gactcttctg tcagctggcc tggcaatgac cgcctgctta cccccaacga gtttgaaatt  21180
aagcgctcag ttgacgggga gggttacaac gttgcccagt gtaacatgac caaagactgg  21240
ttcctggtac aaatgctagc taactacaac attggctacc agggcttcta tatcccagag  21300
agctacaagg accgcatgta ctccttcttt agaaacttcc agcccatgag ccgtcaggtg  21360
gtggatgata ctaaatacaa ggactaccaa caggtgggca tcctacacca acacaacaac  21420
tctggatttg ttggctacct tgcccccacc atgcgcgaag gacaggccta ccctgctaac  21480
ttcccctatc cgcttatagg caagaccgca gttgacagca ttacccagaa aaagtttctt  21540
tgcgatcgca ccctttggcg catcccattc tccagtaact ttatgtccat gggcgcactc  21600
acagacctgg gccaaaacct tctctacgcc aactccgccc acgcgctaga catgactttt  21660
gaggtggatc ccatggacga gcccaccctt ctttatgttt tgtttgaagt ctttgacgtg  21720
```

-continued

```
gtccgtgtgc accggccgca ccgcggcgtc atcgaaaccg tgtacctgcg cacgcccttc  21780
tcggccggca acgccacaac ataaagaagc aagcaacatc aacaacagct gccgccatgg  21840
gctccagtga gcaggaactg aaagccattg tcaaagatct tggttgtggg ccatattttt  21900
tgggcaccta tgacaagcgc tttccaggct ttgtttctcc acacaagctc gcctgcgcca  21960
tagtcaatac ggccggtcgc gagactgggg gcgtacactg gatggccttt gcctggaacc  22020
cgcactcaaa aacatgctac ctctttgagc cctttggctt ttctgaccag cgactcaagc  22080
aggtttacca gtttgagtac gagtcactcc tgcgccgtag cgccattgct tcttcccccg  22140
accgctgtat aacgctggaa aagtccaccc aaagcgtaca ggggcccaac tcggccgcct  22200
gtggactatt ctgctgcatg tttctccacg cctttgccaa ctggccccaa actcccatgg  22260
atcacaaccc caccatgaac cttattaccg gggtacccaa ctccatgctc aacagtcccc  22320
aggtacagcc caccctgcgt cgcaaccagg aacagctcta cagcttcctg gagcgccact  22380
cgccctactt ccgcagccac agtgcgcaga ttaggagcgc cacttctttt tgtcacttga  22440
aaaacatgta aaaataatgt actagagaca ctttcaataa aggcaaatgc ttttatttgt  22500
acactctcgg gtgattattt acccccaccc ttgccgtctg cgccgtttaa aaatcaaagg  22560
ggttctgccg cgcatcgcta tgcgccactg gcagggacac gttgcgatac tggtgtttag  22620
tgctccactt aaactcaggc acaaccatcc gcggcagctc ggtgaagttt tcactccaca  22680
ggctgcgcac catcaccaac gcgtttagca ggtcgggcgc cgatatcttg aagtcgcagt  22740
tggggcctcc gccctgcgcg cgcgagttgc gatacacagg gttgcagcac tggaacacta  22800
tcagcgccgg gtggtgcacg ctggccagca cgctcttgtc ggagatcaga tccgcgtcca  22860
ggtcctccgc gttgctcagg gcgaacggag tcaactttgg tagctgcctt cccaaaaagg  22920
gcgcgtgccc aggctttgag ttgcactcgc accgtagtgg catcaaaagg tgaccgtgcc  22980
cggtctgggc gttaggatac agcgcctgca taaaagcctt gatctgctta aaagccacct  23040
gagcctttgc gccttcagag aagaacatgc cgcaagactt gccggaaaac tgattggccg  23100
gacaggccgc gtcgtgcacg cagcaccttg cgtcggtgtt ggagatctgc accacatttc  23160
ggccccaccg gttcttcacg atcttggcct tgctagactg ctccttcagc gcgcgctgcc  23220
cgttttcgct cgtcacatcc atttcaatca cgtgctcctt atttatcata atgcttccgt  23280
gtagacactt aagctcgcct tcgatctcag cgcagcggtg cagccacaac gcgcagcccg  23340
tgggctcgtg atgcttgtag gtcacctctg caaacgactg caggtacgcc tgcaggaatc  23400
gccccatcat cgtcacaaag gtcttgttgc tggtgaaggt cagctgcaac ccgcggtgct  23460
cctcgttcag ccaggtcttg catacggccg ccagagcttc cacttggtca ggcagtagtt  23520
tgaagttcgc ctttagatcg ttatccacgt ggtacttgtc catcagcgcg cgcgcagcct  23580
ccatgccctt ctcccacgca gacacgatcg gcacactcag cgggttcatc accgtaattt  23640
cactttccgc ttcgctgggc tcttcctctt cctcttgcgt ccgcatacca cgcgccactg  23700
ggtcgtcttc attcagccgc cgcactgtgc gcttacctcc tttgccatgc ttgattagca  23760
ccggtgggtt gctgaaaccc accatttgta gcgccacatc ttctctttct tcctcgctgt  23820
ccacgattac ctctggtgat ggcgggcgct cgggcttggg agaagggcgc ttcttttttct  23880
tcttgggcgc aatggccaaa tccgccgccg aggtcgatgg ccgcgggctg ggtgtgcgcg  23940
gcaccagcgc gtcttgtgat gagtcttcct cgtcctcgga ctcgatacgc cgcctcatcc  24000
gctttttttgg gggcgcccgg ggaggcggcg gcgacgggga cggggacgac acgtcctcca  24060
tggttggggg acgtcgcgcc gcaccgcgtc cgcgctcggg ggtggtttcg cgctgctcct  24120
```

```
cttcccgact ggccatttcc ttctcctata ggcagaaaaa gatcatggag tcagtcgaga  24180
agaaggacag cctaaccgcc ccctctgagt tcgccaccac cgcctccacc gatgccgcca  24240
acgcgcctac caccttcccc gtcgaggcac ccccgcttga ggaggaggaa gtgattatcg  24300
agcaggaccc aggttttgta agcgaagacg acgaggaccg ctcagtacca acagaggata  24360
aaaagcaaga ccaggacaac gcagaggcaa acgaggaaca agtcgggcgg ggggacgaaa  24420
ggcatggcga ctacctagat gtgggagacg acgtgctgtt gaagcatctg cagcgccagt  24480
gcgccattat ctgcgacgcg ttgcaagagc gcagcgatgt gcccctcgcc atagcggatg  24540
tcagccttgc ctacgaacgc cacctattct caccgcgcgt accccccaaa cgccaagaaa  24600
acggcacatg cgagcccaac ccgcgcctca acttctaccc cgtatttgcc gtgccagagg  24660
tgcttgccac ctatcacatc tttttccaaa actgcaagat acccctatcc tgccgtgcca  24720
accgcagccg agcggacaag cagctggcct tgcggcaggg cgctgtcata cctgatatcg  24780
cctcgctcaa cgaagtgcca aaaatctttg agggtcttgg acgcgacgag aagcgcgcgg  24840
caaacgctct gcaacaggaa aacagcgaaa atgaaagtca ctctggagtg ttggtggaac  24900
tcgagggtga caacgcgcgc ctagccgtac taaaacgcag catcgaggtc acccactttg  24960
cctacccggc acttaaccta ccccccaagg tcatgagcac agtcatgagt gagctgatcg  25020
tgcgccgtgc gcagcccctg gagagggatg caaatttgca agaacaaaca gaggagggcc  25080
tacccgcagt tggcgacgag cagctagcgc gctggcttca aacgcgcgag cctgccgact  25140
tggaggagcg acgcaaacta atgatggccg cagtgctcgt taccgtggag cttgagtgca  25200
tgcagcggtt ctttgctgac ccggagatgc agcgcaagct agaggaaaca ttgcactaca  25260
cctttcgaca gggctacgta cgccaggcct gcaagatctc caacgtggag ctctgcaacc  25320
tggtctccta ccttggaatt ttgcacgaaa accgccttgg gcaaaacgtg cttcattcca  25380
cgctcaaggg cgaggcgcgc cgcgactacg tccgcgactg cgtttactta tttctatgct  25440
acacctggca gacggccatg ggcgtttggc agcagtgctt ggaggagtgc aacctcaagg  25500
agctgcagaa actgctaaag caaaacttga aggacctatg gacggccttc aacgagcgct  25560
ccgtggccgc gcacctggcg gacatcattt tccccgaacg cctgcttaaa accctgcaac  25620
agggtctgcc agacttcacc agtcaaagca tgttgcagaa ctttaggaac tttatcctag  25680
agcgctcagg aatcttgccc gccacctgct gtgcacttcc tagcgacttt gtgcccatta  25740
agtaccgcga atgccctccg ccgctttggg gccactgcta ccttctgcag ctagccaact  25800
accttgccta ccactctgac ataatggaag acgtgagcgg tgacggtcta ctggagtgtc  25860
actgtcgctg caacctatgc accccgcacc gctccctggt ttgcaattcg cagctgctta  25920
acgaaagtca aattatcggt acctttgagc tgcagggtcc ctcgcctgac gaaaagtccg  25980
cggctccggg gttgaaactc actccggggc tgtggacgtc ggcttacctt cgcaaatttg  26040
tacctgagga ctaccacgcc cacgagatta ggttctacga agaccaatcc cgcccgccaa  26100
atgcggagct taccgcctgc gtcattaccc agggccacat tcttggccaa ttgcaagcca  26160
tcaacaaagc ccgccaagag tttctgctac gaaagggacg gggggtttac ttggaccccc  26220
agtccggcga ggagctcaac ccaatccccc cgccgccgca gccctatcag cagcagccgc  26280
gggcccttgc ttcccaggat ggcacccaaa aagaagctgc agctgccgcc gccacccacg  26340
gacgaggagg aatactggga cagtcaggca gaggaggttt tggacgagga ggaggaggac  26400
atgatggaag actgggagag cctagacgag gaagcttccg aggtcgaaga ggtgtcagac  26460
```

```
gaaacaccgt caccctcggt cgcattcccc tcgccggcgc cccagaaatc ggcaaccggt  26520
tccagcatgg ctacaacctc cgctcctcag gcgccgccgg cactgcccgt tcgccgaccc  26580
aaccgtagat gggacaccac tggaaccagg gccggtaagt ccaagcagcc gccgccgtta  26640
gcccaagagc aacaacagcg ccaaggctac cgctcatggc gcgggcacaa gaacgccata  26700
gttgcttgct tgcaagactg tgggggcaac atctccttcg cccgccgctt tcttctctac  26760
catcacggcg tggccttccc ccgtaacatc ctgcattact accgtcatct ctacagccca  26820
tactgcaccg gcggcagcgg cagcggcagc aacagcagcg gccacacaga agcaaaggcg  26880
accggatagc aagactctga caaagcccaa gaaatccaca gcggcggcag cagcaggagg  26940
aggagcgctg cgtctggcgc ccaacgaacc cgtatcgacc cgcgagctta gaaacaggat  27000
ttttcccact ctgtatgcta tatttcaaca gagcaggggc caagaacaag agctgaaaat  27060
aaaaaacagg tctctgcgat ccctcacccg cagctgcctg tatcacaaaa gcgaagatca  27120
gcttcggcgc acgctggaag acgcggaggc tctcttcagt aaatactgcg cgctgactct  27180
taaggactag tttcgcgccc tttctcaaat ttaagcgcga aaactacgtc atctccagcg  27240
gccacacccg gcgccagcac ctgtcgtcag cgccattatg agcaaggaaa ttcccacgcc  27300
ctacatgtgg agttaccagc cacaaatggg acttgcggct ggagctgccc aagactactc  27360
aacccgaata aactacatga gcgcgggacc ccacatgata tcccgggtca acggaatccg  27420
cgcccaccga aaccgaattc tcttggaaca ggcggctatt accaccacac ctcgtaataa  27480
ccttaatccc cgtagttggc ccgctgccct ggtgtaccag gaaagtcccg ctcccaccac  27540
tgtggtactt cccagagacg cccaggccga agttcagatg actaactcag gggcgcagct  27600
tgcgggcggc tttcgtcaca gggtgcggtc gcccgggcag ggtataactc acctgacaat  27660
cagagggcga ggtattcagc tcaacgacga gtcggtgagc tcctcgcttg gtctccgtcc  27720
ggacgggaca tttcagatcg gcggcgccgg ccgctcttca ttcacgcctc gtcaggcaat  27780
cctaactctg cagacctcgt cctctgagcc gcgctctgga ggcattggaa ctctgcaatt  27840
tattgaggag tttgtgccat cggtctactt taacccctte tcgggacctc ccggccacta  27900
tccggatcaa tttattccta actttgacgc ggtaaaggac tcggcggatg gctacgactg  27960
aatgttaagt ggagaggcag agcaactgcg cctgaaacac ctggtccact gtcgccgcca  28020
caagtgcttt gcccgcgact ccggtgagtt ttgctacttt gaattgcccg aggatcatat  28080
cgagggcccg gcgcacggcg tccggcttac cgcccaggga gagcttgccc gtagcctgat  28140
tcgggagttt acccagcgcc ccctgctagt tgagcgggac aggggaccct gtgttctcac  28200
tgtgatttgc aactgtccta accctggatt acatcaagat ctttgttgcc atctctgtgc  28260
tgagtataat aaatacagaa attaaaatat actggggctc ctatcgccat cctgtaaacg  28320
ccaccgtctt cacccgccca agcaaaccaa ggcgaacctt acctggtact tttaacatct  28380
ctccctctgt gatttacaac agtttcaacc cagacggagt gagtctacga gagaacctct  28440
ccgagctcag ctactccatc agaaaaaaca ccaccctcct tacctgccgg gaacgtacga  28500
tgtggctgca gagcctgctg ctcttgggca ctgtggcctg cagcatctct gcacccgccc  28560
gctcgcccag ccccagcacg cagccctggg agcatgtgaa tgccatccag gaggcccggc  28620
gtctcctgaa cctgagtaga gacactgctg ctgagatgaa tgaaacagta gaagtcatct  28680
cagaaatgtt tgacctccag gagccgacct gcctacagac ccgcctggag ctgtacaagc  28740
agggcctgcg gggcagcctc accaagctca agggcccctt gaccatgatg gccagccact  28800
acaagcagca ctgccctcca accccggaaa cttcctgtgc aacccagact atcacctttg  28860
```

```
aaagtttcaa agagaacctg aaggactttc tgcttgtcat cccctttgac tgctgggagc  28920
cagtccagga gtgacaattg actctatgtg ggatatgctc cagcgctaca accttgaagt  28980
caggcttcct ggatgtcagc atctgacttt ggccatgaat tccatatgtc gtcgttttcg  29040
gcgcgcgccg aaattcgtcg ttttcggcgc gcgccgaaat tcgtcgtttt cggcgcgcgc  29100
cgaaatttcg tcgtcgttcg aacgacgttg ataaatttcg tcgtcgttcg aacgacgttg  29160
ataaatttcg tcgtcgttcg aacgacgttg atcatatgaa gtggccagca cctgtcccgc  29220
ggatttgttc cagtccaact acagcgaccc accctaacag agatgaccaa cacaaccaac  29280
gcggccgccg ctaccggact tacatctacc acaaatacac cccaagtttc tgcctttgtc  29340
aataactggg ataacttggg catgtggtgg ttctccatag cgcttatgtt tgtatgcctt  29400
attattatgt ggctcatctg ctgcctaaag cgcaaacgcg cccgaccacc catctatagt  29460
cccatcattg tgctacaccc aaacaatgat ggaatccata gattggacgg actgaaacac  29520
atgttctttt ctcttacagt atgattaaat gagacatgat tcctcgagtt tttatattac  29580
tgacccttgt tgcgcttttt tgtgcgtgct ccacattggc tgcggtttct cacatcgaag  29640
tagactgcat tccagccttc acagtctatt tgctttacgg atttgtcacc ctcacgctca  29700
tctgcagcct catcactgtg gtcatcgcct ttatccagtg cattgactgg gtctgtgtgc  29760
gctttgcata tctcagacac catccccagt acagggacag gactatagct gagcttctta  29820
gaattcttta attatgaaat ttactgtgac ttttctgctg attatttgca ccctatctgc  29880
gttttgttcc ccgacctcca agcctcaaag acatatatca tgcagattca ctcgtatatg  29940
gaatattcca agttgctaca atgaaaaaag cgatctttcc gaagcctggt tatatgcaat  30000
catctctgtt atggtgttct gcagtaccat cttagcccta gctatatatc cctaccttga  30060
cattggctgg aaacgaatag atgccatgaa ccacccaact ttccccgcgc ccgctatgct  30120
tccactgcaa caagttgttg ccggcggctt tgtcccagcc aatcagcctc gccccacttc  30180
tcccaccccc actgaaatca gctactttaa tctaacagga ggagatgact gacaccctag  30240
atctagaaat ggacggaatt attacagagc agcgcctgct agaaagacgc agggcagcgg  30300
ccgagcaaca gcgcatgaat caagagctcc aagacatggt taacttgcac cagtgcaaaa  30360
ggggtatctt ttgtctggta aagcaggcca aagtcaccta cgacagtaat accaccggac  30420
accgccttag ctacaagttg ccaaccaagc gtcagaaatt ggtggtcatg gtgggagaaa  30480
agcccattac cataactcag cactcggtag aaaccgaagg ctgcattcac tcaccttgtc  30540
aaggacctga ggatctctgc acccttatta agaccctgtg cggtctcaaa gatcttattc  30600
cctttaacta ataaaaaaaa ataataaagc atcacttact taaaatcagt tagcaaattt  30660
ctgtccagtt tattcagcag cacctccttg ccctcctccc agctctggta ttgcagcttc  30720
ctcctggctg caaactttct ccacaatcta aatggaatgt cagtttcctc ctgttcctgt  30780
ccatccgcac ccactatctt catgttgttg cagatgaagc gcgcaagacc gtctgaagat  30840
accttcaacc ccgtgtatcc atatgacacg gaaaccggtc ctccaactgt gccttttctt  30900
actcctccct ttgtatcccc caatgggttt caagagagtc cccctggggt actctctttg  30960
cgcctatccg aacctctagt tacctccaat ggcatgcttg cgctcaaaat gggcaacggc  31020
ctctctctgg acgaggccgg caaccttacc tcccaaaatg taaccactgt gagcccacct  31080
ctcaaaaaaa ccaagtcaaa cataaacctg gaaatatctg cacccctcac agttacctca  31140
gaagccctaa ctgtggctgc cgccgcacct ctaatggtcg cgggcaacac actcaccatg  31200
```

```
caatcacagg ccccgctaac cgtgcacgac tccaaactta gcattgccac ccaaggaccc  31260
ctcacagtgt cagaaggaaa gctagccctg caaacatcag gcccccctcac caccaccgat  31320
agcagtaccc ttactatcac tgcctcaccc cctctaacta ctgccactgg tagcttgggc  31380
attgacttga aagagcccat ttatacacaa aatggaaaac taggactaaa gtacggggct  31440
cctttgcatg taacagacga cctaaacact ttgaccgtag caactggtcc aggtgtgact  31500
attaataata cttccttgca aactaaagtt actggagcct tgggttttga ttcacaaggc  31560
aatatgcaac ttaatgtagc aggaggacta aggattgatt ctcaaaacag acgccttata  31620
cttgatgtta gttatccgtt tgatgctcaa aaccaactaa atctaagact aggacagggc  31680
cctcttttta taaactcagc ccacaacttg gatattaact acaacaaagg cctttacttg  31740
tttacagctt caaacaattc caaaaagctt gaggttaacc taagcactgc caaggggttg  31800
atgtttgacg ctacagccat agccattaat gcaggagatg ggcttgaatt tggttcacct  31860
aatgcaccaa acacaaatcc cctcaaaaca aaaattggcc atggcctaga atttgattca  31920
aacaaggcta tggttcctaa actaggaact ggccttagtt ttgacagcac aggtgccatt  31980
acagtaggaa acaaaaataa tgataagcta accctatgga caggtccaaa accagaagcc  32040
aactgcataa ttgaatacgg gaaacaaaac ccagatagca aactaacttt aatccttgta  32100
aaaaatggag gaattgttaa tggatatgta acgctaatgg gagcctcaga ctacgttaac  32160
accttattta aaaacaaaaa tgtctccatt aatgtagaac tatactttga tgccactggt  32220
catatattac cagactcatc ttctcttaaa acagatctag aactaaaata caagcaaacc  32280
gctgacttta gtgcaagagg ttttatgcca agtactacag cgtatccatt tgtccttcct  32340
aatgcgggaa cacataatga aaattatatt tttggtcaat gctactacaa agcaagcgat  32400
ggtgcccttt ttccgttgga agttactgtt atgcttaata aacgcctgcc agatagtcgc  32460
acatcctatg ttatgacttt tttatggtcc ttgaatgctg gtctagctcc agaaactact  32520
caggcaaccc tcataacctc cccatttacc ttttcctata ttagagaaga tgactaataa  32580
actctaaaga atcgtttgtg ttatgtttca acgtgtttat ttttcaattg cagaaaattt  32640
caagtcattt ttcattcagt agtatagccc caccaccaca tagcttatac agatcaccgt  32700
accttaatca aactcacaga accctagtat tcaacctgcc acctccctcc caacacacag  32760
agtacacagt cctttctccc cggctggcct taaaaagcat catatcatgg gtaacagaca  32820
tattcttagg tgttatattc cacacggttt cctgtcgagc caaacgctca tcaagtgata  32880
ttaataaact ccccgggcag ctcacttaag ttcatgtcgc tgtccagctg ctgagccaca  32940
ggctgctgtc caacttgcgg ttgcttaacg ggcggcgaag gagaagtcca cgcctacatg  33000
gggggagagt cataatcgtg catcaggata gggcggtggt gctgcagcag cgcgcgaata  33060
aactgctgcc gccgccgctc cgtcctgcag gaatacaaca tggcagtggt ctcctcagcg  33120
atgattcgca ccgcccgcag cataaggcgc cttgtcctcc gggcacagca gcgcaccctg  33180
atctcactta aatcagcaca gtaactgcag cacagcacca caatattgtt caaaatccca  33240
cagtgcaagg cgctgtatcc aaagctcatg gcggggacca cagaacccac gtggccatca  33300
taccacaagc gcaggtagat taagtggcga cccctcataa acacgctgga cataaacatt  33360
acctcttttg gcatgttgta attcaccacc tcccggtacc atataaacct ctgattaaac  33420
atggcgccat ccaccaccat cctaaaccag ctggccaaaa cctgccccgc cgggntatac  33480
actgcaggga accgggactg gaacaatgac agtggagagc ccaggactcg taaccatgga  33540
tcatcatgct cgtcatgata tcaatgttgg cacaacacag gcacacgtgc atacacttcc  33600
```

```
tcaggattac aagctcctcc cgcgttagaa ccatatccca gggaacaacc cattcctgaa  33660
tcagcgtaaa tcccacactg cagggaagac ctcgcacgta actcacgttg tgcattgtca  33720
aagtgttaca ttcgggcagc agcggatgat cctccagtat ggtagcgcgg gtttctgtct  33780
caaaaggagg tagacgatcc ctactgtacg gagtgcgccg agacaaccga gatcgtgttg  33840
gtcgtagtgt catgccaaat ggaacgccgg acgtagtcat atttcctgaa gcaaaaccag  33900
gtgcgggcgt gacaaacaga tctgcgtctc cggtctcgcc gcttagatcg ctctgtgtag  33960
tagttgtagt atatccactc tctcaaagca tccaggcgcc ccctggcttc gggttctatg  34020
taaactcctt catgcgccgc tgccctgata acatccacca ccgcagaata agccacaccc  34080
agccaaccta cacattcgtt ctgcgagtca cacacgggag gagcgggaag agctggaaga  34140
accatgtttt ttttttattt ccaaaagatt atccaaaacc tcaaaatgaa gatctattaa  34200
gtgaacgcgc tcccctccgg tggcgtggtc aaactctaca gccaaagaac agataatggc  34260
atttgtaaga tgttgcacaa tggcttccaa aaggcaaacg gccctcacgt ccaagtggac  34320
gtaaaggcta aacccttcag ggtgaatctc ctctataaac attccagcac cttcaaccat  34380
gcccaaataa ttctcatctc gccaccttct caatatatct ctaagcaaat cccgaatatt  34440
aagtccggcc attgtaaaaa tttggctcca gagcgccctc caccttcagc ctcaagcagc  34500
gaatcatgat tgcaaaaatt caggttcctc acagacctgt ataagattca aaagcggaac  34560
attaacaaaa ataccgcgat cccgtaggtc ccttcgcagg gccagctgaa cataatcgtg  34620
caggtctgca cggaccagcg cggccacttc cccgccagga accatgacaa aagaacccac  34680
actgattatg acacgcatac tcggagctat gctaaccagc gtagccccga tgtaagcttg  34740
ttgcatgggc ggcgatataa aatgcaaggt gctgctcaaa aaatcaggca aagcctcgcg  34800
caaaaaagaa agcacatcgt agtcatgctc atgcagataa aggcaggtaa gctccggaac  34860
caccacagaa aaagacacca tttttctctc aaacatgtct gcgggtttct gcataaacac  34920
aaaataaaat aacaaaaaaa catttaaaca ttagaagcct gtcttacaac aggaaaaaca  34980
acccttataa gcataagacg gactacggcc atgccggcgt gaccgtaaaa aaactggtca  35040
ccgtgattaa aaagcaccac cgacagctcc tcggtcatgt ccggagtcat aatgtaagac  35100
tcggtaaaca catcaggttg attcacatcg gtcagtgcta aaaagcgacc gaaatagccc  35160
gggggaatac atacccgcag gcgtagagac aacattacag cccccatagg aggtataaca  35220
aaattaatag gagagaaaaa cacataaaca cctgaaaaac cctcctgcct aggcaaaata  35280
gcaccctccc gctccagaac aacatacagc gcttccacag cggcagccat aacagtcagc  35340
cttaccagta aaaaagaaaa cctattaaaa aaacaccact cgacacggca ccagctcaat  35400
cagtcacagt gtaaaaaagg gccaagtgca gagcgagtat atataggact aaaaaatgac  35460
gtaacggtta aagtccacaa aaaacaccca gaaaaccgca cgcgaaccta cgcccagaaa  35520
cgaaagccaa aaaacccaca acttcctcaa atcgtcactt ccgttttccc acgttacgtc  35580
acttcccatt ttaagaaaac tacaattccc aacacataca agttactccg ccctaaaacc  35640
tacgtcaccc gccccgttcc cacgccccgc gccacgtcac aaactccacc ccctcattat  35700
catattggct tcaatccaaa ataaggtata ttattgatga tgtta                 35745
```

<210> SEQ ID NO 6
<211> LENGTH: 35553
<212> TYPE: DNA
<213> ORGANISM: Artificial Sequence
<220> FEATURE:

<223> OTHER INFORMATION: The nucleotide sequence encoding virus CGTG-606
<220> FEATURE:
<221> NAME/KEY: misc_feature
<222> LOCATION: (33283)..(33283)
<223> OTHER INFORMATION: n is a, c, g, or t

<400> SEQUENCE: 6

```
taacatcatc aataatatac cttattttgg attgaagcca atatgataat gaggggtgg      60
agtttgtgac gtggcgcggg gcgtgggaac ggggcgggtg acgtagtagt gtggcggaag    120
tgtgatgttg caagtgtggc ggaacacatg taagcgacgg atgtggcaaa agtgacgttt    180
ttggtgtgcg ccggtgtaca caggaagtga caattttcgc gcggttttag gcggatgttg    240
tagtaaattt gggcgtaacc gagtaagatt tggccatttt cgcgggaaaa ctgaataaga    300
ggaagtgaaa tctgaataat tttgtgttac tcatagcgcg taatactggt accgcggccg    360
ctggtaccat ccggacaaag cctgcgcgcg ccccgccccg ccattggccg taccgccccg    420
cgccgccgcc ccatcccgcc cctcgccgcc gggtccggcg cgttaaagcc aataggaacc    480
gccgccgttg ttcccgtcac ggccggggca gccaattgtg gcggcgctcg gcggctcgtg    540
gctctttcgc ggcaaaaagg atttggcgcg taaaagtggc cgggactttg caggcagcgg    600
cggccggggg cggagcggga tcgagccctc gccctcgagc tagaagcttg ttttctcctc    660
cgagccgctc cgacaccggg actgaaaatg agacatatta tctgccacgg aggtgttatt    720
accgaagaaa tggccgccag tcttttggac cagctgatcg aagaggtact ggctgataat    780
cttccacctc ctagccattt tgaaccacct acccttcacg aactgtatga tttagacgtg    840
acggcccccg aagatcccaa cgaggaggcg gtttcgcaga tttttcccga ctctgtaatg    900
ttggcggtgc aggaagggat tgacttactc acttttccgc cggcgcccgg ttctccggag    960
ccgcctcacc tttcccggca gcccgagcag ccggagcaga gagccttggg tccggtttct   1020
atgccaaacc ttgtaccgga ggtgatcgat ccacccagtg acgacgagga tgaagagggt   1080
gaggagtttg tgttagatta tgtggagcac cccgggcacg gttgcaggtc ttgtcattat   1140
caccggagga atacgggggga cccagatatt atgtgttcgc tttgctatat gaggacctgt   1200
ggcatgtttg tctacagtaa gtgaaaatta tgggcagtgg gtgatagagt ggtgggtttg   1260
gtgtggtaat ttttttttta atttttacag ttttgtggtt taaagaattt tgtattgtga   1320
tttttttaaa aggtcctgtg tctgaacctg agcctgagcc cgagccagaa ccggagcctg   1380
caagacctac ccgccgtcct aaaatggcgc ctgctatcct gagacgcccg acatcacctg   1440
tgtctagaga atgcaatagt agtacggata gctgtgactc cggtccttct aacacacctc   1500
ctgagataca cccggtggtc ccgctgtgcc ccattaaacc agttgccgtg agagttggtg   1560
ggcgtcgcca ggctgtggaa tgtatcgagg acttgcttaa cgagcctggg caacctttgg   1620
acttgagctg taaacgcccc aggccataag gtgtaaacct gtgattgcgt gtgtggttaa   1680
cgcctttgtt tgctgaatga gttgatgtaa gtttaataaa gggtgagata atgtttaact   1740
tgcatggcgt gttaaatggg gcggggctta aagggtatat aatgcgccgt gggctaatct   1800
tggttacatc tgacctcatg gaggcttggg agtgtttgga agatttttct gctgtgcgta   1860
acttgctgga acagagctct aacagtacct cttggttttg gaggtttctg tggggctcat   1920
cccaggcaaa gttagtctgc agaattaagg aggattacaa gtgggaattt gaagagcttt   1980
tgaaatcctg tggtgagctg tttgattctt tgaatctggg tcaccaggcg cttttccaag   2040
agaaggtcat caagactttg gatttttcca caccggggcg cgctgcggct gctgttgctt   2100
ttttgagttt tataaaggat aaatggagcg aagaaaccca tctgagcggg gggtacctgc   2160
```

```
tggattttct ggccatgcat ctgtggagag cggttgtgag acacaagaat cgcctgctac   2220
tgttgtcttc cgtccgcccg gcgataatac cgacggagga gcagcagcag cagcaggagg   2280
aagccaggcg gcggcggcag gagcagagcc catggaaccc gagagccggc ctggaccctc   2340
gggaatgaat gttgtacagg tggctgaact gtatccagaa ctgagacgca ttttgacaat   2400
tacagaggat gggcaggggc taaagggggt aaagagggag cggggggctt gtgaggctac   2460
agaggaggct aggaatctag cttttagctt aatgaccaga caccgtcctg agtgtattac   2520
ttttcaacag atcaaggata attgcgctaa tgagcttgat ctgctggcgc agaagtattc   2580
catagagcag ctgaccactt actggctgca gccaggggat gattttgagg aggctattag   2640
ggtatatgca aaggtggcac ttaggccaga ttgcaagtac aagatcagca aacttgtaaa   2700
tatcaggaat tgttgctaca tttctgggaa cggggccgag gtggagatag atacggagga   2760
tagggtggcc tttagatgta gcatgataaa tatgtggccg gggtgcttg gcatggacgg   2820
ggtggttatt atgaatgtaa ggtttactgg ccccaatttt agcggtacgg ttttcctggc   2880
caataccaac cttatcctac acggtgtaag cttctatggg tttaacaata cctgtgtgga   2940
agcctggacc gatgtaaggg ttcggggctg tgccttttac tgctgctgga agggggtggt   3000
gtgtcgcccc aaaagcaggg cttcaattaa gaaatgcctc tttgaaaggt gtaccttggg   3060
tatcctgtct gagggtaact ccagggtgcg ccacaatgtg gcctccgact gtggttgctt   3120
catgctagtg aaaagcgtgg ctgtgattaa gcataacatg gtatgtggca actgcgagga   3180
cagggcctct cagatgctga cctgctcgga cggcaactgt cacctgctga agaccattca   3240
cgtagccagc cactctcgca aggcctggcc agtgtttgag cataacatac tgacccgctg   3300
ttccttgcat ttgggtaaca ggagggggt gttcctacct taccaatgca atttgagtca   3360
cactaagata ttgcttgagc ccgagagcat gtccaaggtg aacctgaacg gggtgtttga   3420
catgaccatg aagatctgga aggtgctgag gtacgatgag acccgcacca ggtgcagacc   3480
ctgcgagtgt ggcggtaaac atattaggaa ccagcctgtg atgctggatg tgaccgagga   3540
gctgaggccc gatcacttgg tgctggcctg cacccgcgct gagtttggct ctagcgatga   3600
agatacagat tgaggtactg aaatgtgtgg gcgtggctta agggtgggaa agaatatata   3660
aggtgggggt cttatgtagt tttgtatctg ttttgcagca gccgccgccg ccatgagcac   3720
caactcgttt gatggaagca ttgtgagctc atatttgaca acgcgcatgc ccccatgggc   3780
cggggtgcgt cagaatgtga tgggctccag cattgatggt cgccccgtcc tgcccgcaaa   3840
ctctactacc ttgacctacg agaccgtgtc tggaacgccg ttggagactg cagcctccgc   3900
cgccgcttca gccgctgcag ccaccgcccg cgggattgtg actgactttg ctttcctgag   3960
cccgcttgca agcagtgcag cttcccgttc atccgcccgc gatgacaagt tgacggctct   4020
tttggcacaa ttggattctt tgacccggga acttaatgtc gtttctcagc agctgttgga   4080
tctgcgccag caggtttctg ccctgaaggc ttcctcccct cccaatgcgg tttaaaacat   4140
aaataaaaaa ccagactctg tttggatttg gatcaagcaa gtgtcttgct gtctttattt   4200
aggggttttg cgcgcgcggt aggcccggga ccagcggtct cggtcgttga gggtcctgtg   4260
tatttttcc aggacgtggt aaaggtgact ctggatgttc agatacatgg gcataagccc   4320
gtctctgggg tggaggtagc accactgcag agcttcatgc tgcggggtgg tgttgtagat   4380
gatccagtcg tagcaggagc gctgggcgtg gtgcctaaaa atgtctttca gtagcaagct   4440
gattgccagg ggcaggccct tggtgtaagt gtttacaaag cggttaagct gggatgggtg   4500
```

```
catacgtggg gatatgagat gcatcttgga ctgtattttt aggttggcta tgttcccagc   4560
catatccctc cggggattca tgttgtgcag aaccaccagc acagtgtatc cggtgcactt   4620
gggaaatttg tcatgtagct tagaaggaaa tgcgtggaag aacttggaga cgcccttgtg   4680
acctccaaga ttttccatgc attcgtccat aatgatggca atgggcccac gggcggcggc   4740
ctgggcgaag atatttctgg gatcactaac gtcatagttg tgttccagga tgagatcgtc   4800
ataggccatt tttacaaagc gcgggcggag ggtgccagac tgcggtataa tggttccatc   4860
cggcccaggg gcgtagttac cctcacagat ttgcatttcc cacgctttga gttcagatgg   4920
ggggatcatg tctacctgcg gggcgatgaa gaaaacggtt tccggggtag gggagatcag   4980
ctgggaagaa agcaggttcc tgagcagctg cgacttaccg cagccggtgg gcccgtaaat   5040
cacacctatt accgggtgca actggtagtt aagagagctg cagctgccgt catccctgag   5100
caggggggcc acttcgttaa gcatgtccct gactcgcatg ttttccctga ccaaatccgc   5160
cagaaggcgc tcgccgccca gcgatagcag ttcttgcaag gaagcaaagt ttttcaacgg   5220
tttgagaccg tccgccgtag gcatgctttt gagcgtttga ccaagcagtt ccaggcggtc   5280
ccacagctcg gtcacctgct ctacggcatc tcgatccagc atatctcctc gtttcgcggg   5340
ttggggcggc tttcgctgta cggcagtagt cggtgctcgt ccagacgggc cagggtcatg   5400
tctttccacg ggcgcagggt cctcgtcagc gtagtctggg tcacggtgaa ggggtgcgct   5460
ccgggctgcg cgctggccag ggtgcgcttg aggctggtcc tgctggtgct gaagcgctgc   5520
cggtcttcgc cctgcgcgtc ggccaggtag catttgacca tggtgtcata gtccagcccc   5580
tccgcggcgt ggcccttggc gcgcagcttg cccttggagg aggcgccgca cgaggggcag   5640
tgcagacttt tgagggcgta gagcttgggc gcgagaaata ccgattccgg ggagtaggca   5700
tccgcgccgc aggccccgca gacggtctcg cattccacga gccaggtgag ctctggccgt   5760
tcggggtcaa aaaccaggtt tcccccatgc tttttgatgc gtttcttacc tctggtttcc   5820
atgagccggt gtccacgctc ggtgacgaaa aggctgtccg tgtccccgta tacagacttg   5880
agaggcctgt cctcgagcgg tgttccgcgg tcctcctcgt atagaaactc ggaccactct   5940
gagacaaagg ctcgcgtcca ggccagcacg aaggaggcta agtgggaggg gtagcggtcg   6000
ttgtccacta gggggtccac tcgctccagg gtgtgaagac acatgtcgcc ctcttcggca   6060
tcaaggaagg tgattggttt gtaggtgtag gccacgtgac cgggtgttcc tgaagggggg   6120
ctataaaagg gggtgggggc gcgttcgtcc tcactctctt ccgcatcgct gtctgcgagg   6180
gccagctgtt ggggtgagta ctccctctga aaagcgggca tgacttctgc gctaagattg   6240
tcagtttcca aaaacgagga ggatttgata ttcacctggc ccgcggtgat gcctttgagg   6300
gtggccgcat ccatctggtc agaaaagaca atctttttgt tgtcaagctt ggtggcaaac   6360
gacccgtaga gggcgttgga cagcaacttg gcgatggagc gcagggtttg gtttttgtcg   6420
cgatcggcgc gctccttggc cgcgatgttt agctgcacgt attcgcgcgc aacgcaccgc   6480
cattcgggaa agacggtggt gcgctcgtcg ggcaccaggt gcacgcgcca accgcggttg   6540
tgcagggtga caaggtcaac gctggtggct acctctccgc gtaggcgctc gttggtccag   6600
cagaggcggc cgcccttgcg cgagcagaat ggcggtaggg ggtctagctg cgtctcgtcc   6660
ggggggtctg cgtccacggt aaagaccccg ggcagcaggc gcgcgtcgaa gtagtctatc   6720
ttgcatcctt gcaagtctag cgcctgctgc catgcgcggg cggcaagcgc gcgctcgtat   6780
gggttgagtg ggggacccca tggcatgggg tgggtgagcg cggaggcgta catgccgcaa   6840
atgtcgtaaa cgtagagggg ctctctgagt attccaagat atgtagggta gcatcttcca   6900
```

```
ccgcggatgc tggcgcgcac gtaatcgtat agttcgtgcg agggagcgag gaggtcggga   6960
ccgaggttgc tacgggcggg ctgctctgct cggaagacta tctgcctgaa gatggcatgt   7020
gagttggatg atatggttgg acgctggaag acgttgaagc tggcgtctgt gagacctacc   7080
gcgtcacgca cgaaggaggc gtaggagtcg cgcagcttgt tgaccagctc ggcggtgacc   7140
tgcacgtcta gggcgcagta gtccagggtt tccttgatga tgtcatactt atcctgtccc   7200
ttttttttcc acagctcgcg gttgaggaca aactcttcgc ggtctttcca gtactcttgg   7260
atcggaaacc cgtcggcctc cgaacggtaa gagcctagca tgtagaactg gttgacggcc   7320
tggtaggcgc agcatccctt ttctacgggt agcgcgtatg cctgcgcggc cttccggagc   7380
gaggtgtggg tgagcgcaaa ggtgtccctg accatgactt tgaggtactg gtatttgaag   7440
tcagtgtcgt cgcatccgcc ctgctcccag agcaaaaagt ccgtgcgctt tttggaacgc   7500
ggatttggca gggcgaaggt gacatcgttg aagagtatct ttcccgcgcg aggcataaag   7560
ttgcgtgtga tgcggaaggg tcccggcacc tcggaacggt tgttaattac ctgggcggcg   7620
agcacgatct cgtcaaagcc gttgatgttg tggcccacaa tgtaaagttc caagaagcgc   7680
gggatgccct tgatggaagg caatttttta agttcctcgt aggtgagctc ttcaggggag   7740
ctgagcccgt gctctgaaag ggcccagtct gcaagatgag ggttggaagc gacgaatgag   7800
ctccacaggt cacgggccat tagcatttgc aggtggtcgc gaaaggtcct aaactggcga   7860
cctatggcca tttttctgg ggtgatgcag tagaaggtaa gcgggtcttg ttcccagcgg   7920
tcccatccaa ggttcgcggc taggtctcgc gcggcagtca ctagaggctc atctccgccg   7980
aacttcatga ccagcatgaa gggcacgagc tgcttcccaa aggcccccat ccaagtatag   8040
gtctctacat cgtaggtgac aaagagacgc tcggtgcgag gatgcgagcc gatcgggaag   8100
aactggatct cccgccacca attggaggag tggctattga tgtggtgaaa gtagaagtcc   8160
ctgcgacggg ccgaacactc gtgctggctt ttgtaaaaac gtgcgcagta ctggcagcgg   8220
tgcacgggct gtacatcctg cacgaggttg acctgacgac cgcgcacaag gaagcagagt   8280
gggaatttga gcccctcgcc tggcgggttt ggctggtggt cttctacttc ggctgcttgt   8340
ccttgaccgt ctggctgctc gaggggagtt acggtggatc ggaccaccac gccgcgcgag   8400
cccaaagtcc agatgtccgc gcgcggcggt cggagcttga tgacaacatc gcgcagatgg   8460
gagctgtcca tggtctggag ctcccgcggc gtcaggtcag gcgggagctc ctgcaggttt   8520
acctcgcata gacgggtcag ggcgcgggct agatccaggt gatacctaat ttccaggggc   8580
tggttggtgg cggcgtcgat ggcttgcaag aggccgcatc cccgcggcgc gactacggta   8640
ccgcgcggcg ggcggtgggc cgcgggggtg tccttggatg atgcatctaa aagcggtgac   8700
gcgggcgagc ccccggaggt agggggggct ccggacccgc cgggagaggg ggcaggggca   8760
cgtcggcgcc gcgcgcgggc aggagctggt gctgcgcgcg taggttgctg gcgaacgcga   8820
cgacgcggcg gttgatctcc tgaatctggc gcctctgcgt gaagacgacg ggcccggtga   8880
gcttgagcct gaaagagagt tcgacagaat caatttcggt gtcgttgacg gcggcctggc   8940
gcaaaatctc ctgcacgtct cctgagttgt cttgataggc gatctcggcc atgaactgct   9000
cgatctcttc ctcctggaga tctccgcgtc cggctcgctc cacggtggcg gcgaggtcgt   9060
tggaaatgcg ggccatgagc tgcgagaagg cgttgaggcc tccctcgttc cagacgcggc   9120
tgtagaccac gcccccttcg gcatcgcggg cgcgcatgac cacctgcgcg agattgagct   9180
ccacgtgccg ggcgaagacg gcgtagtttc gcaggcgctg aaagaggtag ttgagggtgg   9240
```

-continued

```
tggcggtgtg ttctgccacg aagaagtaca taacccagcg tcgcaacgtg gattcgttga   9300
tatcccccaa ggcctcaagg cgctccatgg cctcgtagaa gtccacggcg aagttgaaaa   9360
actgggagtt gcgcgccgac acggttaact cctcctccag aagacggatg agctcggcga   9420
cagtgtcgcg cacctcgcgc tcaaaggcta caggggcctc ttcttcttct tcaatctcct   9480
cttccataag ggcctcccct tcttcttctt ctggcggcgg tgggggaggg gggacacggc   9540
ggcgacgacg gcgcaccggg aggcggtcga caaagcgctc gatcatctcc ccgcggcgac   9600
ggcgcatggt ctcggtgacg gcgcggccgt tctcgcgggg gcgcagttgg aagacgccgc   9660
ccgtcatgtc ccggttatgg gttggcgggg ggctgccatg cggcagggat acggcgctaa   9720
cgatgcatct caacaattgt tgtgtaggta ctccgccgcc gagggacctg agcgagtccg   9780
catcgaccgg atcggaaaac ctctcgagaa aggcgtctaa ccagtcacag tcgcaaggta   9840
ggctgagcac cgtggcgggc ggcagcgggc ggcggtcggg gttgtttctg gcggaggtgc   9900
tgctgatgat gtaattaaag taggcggtct tgagacggcg gatggtcgac agaagcacca   9960
tgtccttggg tccggcctgc tgaatgcgca ggcggtcggc catgccccag gcttcgtttt  10020
gacatcggcg caggtctttg tagtagtctt gcatgagcct ttctaccggc acttcttctt  10080
ctccttcctc ttgtcctgca tctcttgcat ctatcgctgc ggcggcggcg gagtttggcc  10140
gtaggtggcg ccctcttcct cccatgcgtg tgaccccgaa gcccctcatc ggctgaagca  10200
gggctaggtc ggcgacaacg cgctcggcta atatggcctg ctgcacctgc gtgagggtag  10260
actggaagtc atccatgtcc acaaagcggt ggtatgcgcc cgtgttgatg gtgtaagtgc  10320
agttggccat aacggaccag ttaacggtct ggtgacccgg ctgcgagagc tcggtgtacc  10380
tgagacgcga gtaagccctc gagtcaaata cgtagtcgtt gcaagtccgc accaggtact  10440
ggtatcccac caaaaagtgc ggcggcggct ggcggtagag gggccagcgt agggtggccg  10500
gggctccggg ggcgagatct tccaacataa ggcgatgata tccgtagatg tacctggaca  10560
tccaggtgat gccggcggcg gtggtggagg cgcgcggaaa gtcgcggacg cggttccaga  10620
tgttgcgcag cggcaaaaag tgctccatgg tcgggacgct ctggccggtc aggcgcgcgc  10680
aatcgttgac gctctagacc gtgcaaaagg agagcctgta agcgggcact cttccgtggt  10740
ctggtggata aattcgcaag ggtatcatgg cggacgaccg gggttcgagc cccgtatccg  10800
gccgtccgcc gtgatccatg cggttaccgc ccgcgtgtcg aacccaggtg tgcgacgtca  10860
gacaacgggg gagtgctcct tttggcttcc ttccaggcgc ggcggctgct gcgctagctt  10920
ttttggccac tggccgcgcg cagcgtaagc ggttaggctg gaaagcgaaa gcattaagtg  10980
gctcgctccc tgtagccgga gggttatttt ccaagggttg agtcgcggga cccccggttc  11040
gagtctcgga ccggccggac tgcggcgaac gggggtttgc ctccccgtca tgcaagaccc  11100
cgcttgcaaa ttcctccgga aacagggacg agcccctttt ttgcttttcc cagatgcatc  11160
cggtgctgcg gcagatgcgc ccccctcctc agcagcggca agagcaagag cagcggcaga  11220
catgcagggc accctcccct cctcctaccg cgtcaggagg ggcgacatcc gcggttgacg  11280
cggcagcaga tggtgattac gaacccccgc ggcgccgggc ccggcactac ctggacttgg  11340
aggagggcga gggcctggcg cggctaggag cgccctctcc tgagcggtac ccaagggtgc  11400
agctgaagcg tgatacgcgt gaggcgtacg tgccgcggca gaacctgttt cgcgaccgcg  11460
agggagagga gcccgaggag atgcgggatc gaaagttcca cgcagggcgc gagctgcggc  11520
atggcctgaa tcgcgagcgg ttgctgcgcg aggaggactt tgagcccgac gcgcgaaccg  11580
ggattagtcc cgcgcgcgca cacgtggcgg ccgccgacct ggtaaccgca tacgagcaga  11640
```

```
cggtgaacca ggagattaac tttcaaaaaa gctttaacaa ccacgtgcgt acgcttgtgg  11700
cgcgcgagga ggtggctata ggactgatgc atctgtggga ctttgtaagc gcgctggagc  11760
aaaacccaaa tagcaagccg ctcatggcgc agctgttcct tatagtgcag cacagcaggg  11820
acaacgaggc attcagggat gcgctgctaa acatagtaga gcccgagggc cgctggctgc  11880
tcgatttgat aaacatcctg cagagcatag tggtgcagga gcgcagcttg agcctggctg  11940
acaaggtggc cgccatcaac tattccatgc ttagcctggg caagttttac gcccgcaaga  12000
tataccatac cccttacgtt cccatagaca aggaggtaaa gatcgagggg ttctacatgc  12060
gcatggcgct gaaggtgctt accttgagcg acgacctggg cgtttatcgc aacgagcgca  12120
tccacaaggc cgtgagcgtg agccggcggc gcgagctcag cgaccgcgag ctgatgcaca  12180
gcctgcaaag ggccctggct ggcacgggca gcggcgatag agaggccgag tcctactttg  12240
acgcgggcgc tgacctgcgc tgggccccaa gccgacgcgc cctggaggca gctggggccg  12300
gacctgggct ggcggtggca cccgcgcgcg ctggcaacgt cggcggcgtg gaggaatatg  12360
acgaggacga tgagtacgag ccagaggacg gcgagtacta agcggtgatg tttctgatca  12420
gatgatgcaa gacgcaacgg acccggcggt gcgggcggcg ctgcagagcc agccgtccgg  12480
ccttaactcc acggacgact ggcgccaggt catggaccgc atcatgtcgc tgactgcgcg  12540
caatcctgac gcgttccggc agcagccgca ggccaaccgg ctctccgcaa ttctggaagc  12600
ggtggtcccg gcgcgcgcaa accccacgca cgagaaggtg ctggcgatcg taaacgcgct  12660
ggccgaaaac agggccatcc ggcccgacga ggccggcctg gtctacgacg cgctgcttca  12720
gcgcgtggct cgttacaaca gcggcaacgt gcagaccaac ctggaccggc tggtggggga  12780
tgtgcgcgag gccgtggcgc agcgtgagcg cgcgcagcag cagggcaacc tgggctccat  12840
ggttgcacta aacgccttcc tgagtacaca gcccgccaac gtgccgcggg gacaggagga  12900
ctacaccaac tttgtgagcg cactgcggct aatggtgact gagacaccgc aaagtgaggt  12960
gtaccagtct gggccagact attttttcca gaccagtaga caaggcctgc agaccgtaaa  13020
cctgagccag gctttcaaaa acttgcaggg gctgtggggg gtgcgggctc ccacaggcga  13080
ccgcgcgacc gtgtctagct tgctgacgcc caactcgcgc ctgttgctgc tgctaatagc  13140
gcccttcacg gacagtggca gcgtgtcccg ggacacatac ctaggtcact tgctgacact  13200
gtaccgcgag gccataggtc aggcgcatgt ggacgagcat actttccagg agattacaag  13260
tgtcagccgc gcgctggggc aggaggacac gggcagcctg gaggcaaccc taaactacct  13320
gctgaccaac cggcggcaga agatccccctc gttgcacagt ttaaacagcg aggaggagcg  13380
cattttgcgc tacgtgcagc agagcgtgag ccttaacctg atgcgcgacg ggtaacgcc  13440
cagcgtggcg ctggacatga ccgcgcgcaa catggaaccg ggcatgtatg cctcaaaccg  13500
gccgtttatc aaccgcctaa tggactactt gcatcgcgcg gccgccgtga accccgagta  13560
tttcaccaat gccatcttga acccgcactg gctaccgccc cctggtttct acaccggggg  13620
attcgaggtg cccgagggta acgatggatt cctctgggac gacatagacg acagcgtgtt  13680
ttccccgcaa ccgcagaccc tgctagagtt gcaacagcgc gagcaggcag aggcggcgct  13740
gcgaaaggaa agcttccgca ggccaagcag cttgtccgat ctaggcgctg cggccccgcg  13800
gtcagatgct agtagcccat ttccaagctt gatagggtct cttaccagca ctcgcaccac  13860
ccgcccgcgc ctgctgggcg aggaggagta cctaaacaac tcgctgctgc agccgcagcg  13920
cgaaaaaaac ctgcctccgg catttcccaa caacgggata gagagcctag tggacaagat  13980
```

-continued

```
gagtagatgg aagacgtacg cgcaggagca cagggacgtg ccaggcccgc gcccgcccac  14040
ccgtcgtcaa aggcacgacc gtcagcgggg tctggtgtgg gaggacgatg actcggcaga  14100
cgacagcagc gtcctggatt tgggagggag tggcaacccg tttgcgcacc ttcgccccag  14160
gctggggaga atgttttaaa aaaaaaaaag catgatgcaa aataaaaaac tcaccaaggc  14220
catggcaccg agcgttggtt ttcttgtatt ccccttagta tgcggcgcgc ggcgatgtat  14280
gaggaaggtc ctcctccctc ctacgagagt gtggtgagcg cggcgccagt ggcggcggcg  14340
ctgggttctc ccttcgatgc tcccctggac ccgccgtttg tgcctccgcg gtacctgcgg  14400
cctaccgggg ggagaaacag catccgttac tctgagttgg caccccctatt cgacaccacc  14460
cgtgtgtacc tggtggacaa caagtcaacg gatgtggcat ccctgaacta ccagaacgac  14520
cacagcaact ttctgaccac ggtcattcaa aacaatgact acagcccggg ggaggcaagc  14580
acacagacca tcaatcttga cgaccggtcg cactggggcg gcgacctgaa aaccatcctg  14640
cataccaaca tgccaaatgt gaacgagttc atgtttacca ataagtttaa ggcgcgggtg  14700
atggtgtcgc gcttgcctac taaggacaat caggtggagc tgaaatacga gtgggtggag  14760
ttcacgctgc ccgagggcaa ctactccgag accatgacca tagaccttat gaacaacgcg  14820
atcgtggagc actacttgaa agtgggcaga cagaacgggg ttctggaaag cgacatcggg  14880
gtaaagtttg acacccgcaa cttcagactg ggtttgacc ccgtcactgg tcttgtcatg  14940
cctggggtat atacaaacga agccttccat ccagacatca ttttgctgcc aggatgcggg  15000
gtggacttca cccacagccg cctgagcaac ttgttgggca tccgcaagcg gcaacccttc  15060
caggagggct ttaggatcac ctacgatgat ctggagggtg gtaacattcc cgcactgttg  15120
gatgtggacg cctaccaggc gagcttgaaa gatgacaccg aacagggcgg gggtggcgca  15180
ggcggcagca acagcagtgg cagcggcgcg gaagagaact ccaacgcggc agccgcggca  15240
atgcagccgg tggaggacat gaacgatcat gccattcgcg gcgacacctt tgccacacgg  15300
gctgaggaga agcgcgctga ggccgaagca gcggccgaag ctgccgcccc cgctgcgcaa  15360
cccgaggtcg agaagcctca gaagaaaccg gtgatcaaac ccctgacaga ggacagcaag  15420
aaacgcagtt acaacctaat aagcaatgac agcaccttca cccagtaccg cagctggtac  15480
cttgcataca actacggcga ccctcagacc ggaatccgct catggaccct gctttgcact  15540
cctgacgtaa cctgcggctc ggagcaggtc tactggtcgt tgccagacat gatgcaagac  15600
cccgtgacct tccgctccac gcgccagatc agcaactttc cggtggtggg cgccgagctg  15660
ttgcccgtgc actccaagag cttctacaac gaccaggccg tctactccca actcatccgc  15720
cagtttacct ctctgaccca cgtgttcaat cgctttcccg agaaccagat tttggcgcgc  15780
ccgccagccc ccaccatcac caccgtcagt gaaaacgttc ctgctctcac agatcacggg  15840
acgctaccgc tgcgcaacag catcggagga gtccagcgag tgaccattac tgacgccaga  15900
cgccgcacct gcccctacgt ttacaaggcc ctgggcatag tctcgccgcg cgtcctatcg  15960
agccgcactt tttgagcaag catgtccatc cttatatcgc ccagcaataa cacaggctgg  16020
ggcctgcgct tcccaagcaa gatgtttggc ggggccaaga agcgctccga ccaacaccca  16080
gtgcgcgtgc gcgggcacta ccgcgcgccc tggggcgcgc acaaacgcgg ccgcactggg  16140
cgcaccaccg tcgatgacgc catcgacgcg gtggtggagg aggcgcgcaa ctacacgccc  16200
acgccgccac cagtgtccac agtggacgcg gccattcaga ccgtggtgcg cggagcccgg  16260
cgctatgcta aaatgaagag acggcggagg cgcgtagcac gtcgccaccg ccgccgaccc  16320
ggcactgccg cccaacgcgc ggcggcggcc ctgcttaacc gcgcacgtcg caccggccga  16380
```

```
cgggcggcca tgcgggccgc tcgaaggctg gccgcgggta ttgtcactgt gccccccagg  16440
tccaggcgac gagcggccgc cgcagcagcc gcggccatta gtgctatgac tcagggtcgc  16500
aggggcaacg tgtattgggt gcgcgactcg gttagcggcc tgcgcgtgcc cgtgcgcacc  16560
cgcccccccgc gcaactagat tgcaagaaaa aactacttag actcgtactg ttgtatgtat  16620
ccagcggcgg cggcgcgcaa cgaagctatg tccaagcgca aaatcaaaga agagatgctc  16680
caggtcatcg cgccggagat ctatggcccc ccgaagaagg aagagcagga ttacaagccc  16740
cgaaagctaa agcgggtcaa aaagaaaaag aaagatgatg atgatgaact tgacgacgag  16800
gtggaactgc tgcacgctac cgcgcccagg cgacgggtac agtggaaagg tcgacgcgta  16860
aaacgtgttt tgcgacccgg caccaccgta gtctttacgc ccggtgagcg ctccacccgc  16920
acctacaagc gcgtgtatga tgaggtgtac ggcgacgagg acctgcttga gcaggccaac  16980
gagcgcctcg gggagtttgc ctacggaaag cggcataagg acatgctggc gttgccgctg  17040
gacgagggca acccaacacc tagcctaaag cccgtaacac tgcagcaggt gctgcccgcg  17100
cttgcaccgt ccgaagaaaa gcgcggccta aagcgcgagt ctggtgactt ggcacccacc  17160
gtgcagctga tggtacccaa gcgccagcga ctggaagatg tcttggaaaa aatgaccgtg  17220
gaacctgggc tggagcccga ggtccgcgtg cggccaatca agcaggtggc gccgggactg  17280
ggcgtgcaga ccgtggacgt tcagataccc actaccagta gcaccagtat tgccaccgcc  17340
acagagggca tggagacaca aacgtccccg gttgcctcag cggtggcgga tgccgcggtg  17400
caggcggtcg ctgcggccgc gtccaagacc tctacggagg tgcaaacgga cccgtggatg  17460
tttcgcgttt cagcccccccg gcgcccgcgc ggttcgagga agtacggcgc cgccagcgcg  17520
ctactgcccg aatatgccct acatccttcc attgcgccta cccccggcta tcgtggctac  17580
acctaccgcc ccagaagacg agcaactacc cgacgccgaa ccaccactgg aacccgccgc  17640
cgccgtcgcc gtcgccagcc cgtgctggcc ccgatttccg tgcgcagggt ggctcgcgaa  17700
ggaggcagga ccctggtgct gccaacagcg cgctaccacc ccagcatcgt ttaaaagccg  17760
gtctttgtgg ttcttgcaga tatggccctc acctgccgcc tccgtttccc ggtgccggga  17820
ttccgaggaa gaatgcaccg taggaggggc atggccggcc acggcctgac gggcggcatg  17880
cgtcgtgcgc accaccggcg gcggcgcgcg tcgcaccgtc gcatgcgcgg cggtatcctg  17940
cccctcctta ttccactgat cgccgcggcg attggcgccg tgcccggaat tgcatccgtg  18000
gccttgcagg cgcagagaca ctgattaaaa acaagttgca tgtggaaaaa tcaaaataaa  18060
aagtctggac tctcacgctc gcttggtcct gtaactattt tgtagaatgg aagacatcaa  18120
ctttgcgtct ctggccccgc gacacggctc gcgcccgttc atgggaaact ggcaagatat  18180
cggcaccagc aatatgagcg gtggcgcctt cagctggggc tcgctgtgga gcggcattaa  18240
aaatttcggt tccaccgtta agaactatgg cagcaaggcc tggaacagca gcacaggcca  18300
gatgctgagg gataagttga aagagcaaaa tttccaacaa aaggtggtag atggcctggc  18360
ctctggcatt agcggggtgg tggacctggc caaccaggca gtgcaaaata agattaacag  18420
taagcttgat ccccgccctc ccgtagagga gcctccaccg gccgtggaga cagtgtctcc  18480
agaggggcgt ggcgaaaagc gtccgcgccc cgacagggaa gaaactctgg tgacgcaaat  18540
agacgagcct ccctcgtacg aggaggcact aaagcaaggc ctgcccacca cccgtcccat  18600
cgcgcccatg gctaccggag tgctgggcca gcacacaccc gtaacgctgg acctgcctcc  18660
ccccgccgac acccagcaga aacctgtgct gccaggcccg accgccgttg ttgtaacccg  18720
```

```
tcctagccgc gcgtccctgc gccgcgccgc cagcggtccg cgatcgttgc ggcccgtagc  18780
cagtggcaac tggcaaagca cactgaacag catcgtgggt ctgggggtgc aatccctgaa  18840
gcgccgacga tgcttctgaa tagctaacgt gtcgtatgtg tgtcatgtat gcgtccatgt  18900
cgccgccaga ggagctgctg agccgccgcg cgcccgcttt ccaagatggc taccccttcg  18960
atgatgccgc agtggtctta catgcacatc tcgggccagg acgcctcgga gtacctgagc  19020
cccgggctgg tgcagtttgc ccgcgccacc gagacgtact tcagcctgaa taacaagttt  19080
agaaacccca cggtggcgcc tacgcacgac gtgaccacag accggtccca gcgtttgacg  19140
ctgcggttca tccctgtgga ccgtgaggat actgcgtact cgtacaaggc gcggttcacc  19200
ctagctgtgg gtgataaccg tgtgctggac atggcttcca cgtactttga catccgcggc  19260
gtgctggaca ggggccctac ttttaagccc tactctggca ctgcctacaa cgccctggct  19320
cccaagggtg ccccaaatcc ttgcgaatgg gatgaagctg ctactgctct tgaaataaac  19380
ctagaagaag aggacgatga caacgaagac gaagtagacg agcaagctga gcagcaaaaa  19440
actcacgtat ttgggcaggc gccttattct ggtataaata ttacaaagga gggtattcaa  19500
ataggtgtcg aaggtcaaac acctaaatat gccgataaaa catttcaacc tgaacctcaa  19560
ataggagaat ctcagtggta cgaaactgaa attaatcatg cagctgggag agtccttaaa  19620
aagactaccc caatgaaacc atgttacggt tcatatgcaa aacccacaaa tgaaaatgga  19680
gggcaaggca ttcttgtaaa gcaacaaaat ggaaagctag aaagtcaagt ggaaatgcaa  19740
tttttctcaa ctactgaggc gaccgcaggc aatggtgata acttgactcc taaagtggta  19800
ttgtacagtg aagatgtaga tatagaaacc ccagacactc atatttctta catgcccact  19860
attaaggaag gtaactcacg agaactaatg ggccaacaat ctatgcccaa caggcctaat  19920
tacattgctt ttagggacaa ttttattggt ctaatgtatt acaacagcac gggtaatatg  19980
ggtgttctgg cgggccaagc atcgcagttg aatgctgttg tagatttgca agacagaaac  20040
acagagcttt cataccagct tttgcttgat tccattggtg atagaaccag gtacttttct  20100
atgtggaatc aggctgttga cagctatgat ccagatgtta gaattattga aaatcatgga  20160
actgaagatg aacttccaaa ttactgcttt ccactgggag gtgtgattaa tacagagact  20220
cttaccaagg taaaacctaa aacaggtcag gaaaatggat gggaaaaaga tgctacagaa  20280
ttttcagata aaaatgaaat aagagttgga aataattttg ccatggaaat caatctaaat  20340
gccaacctgt ggagaaattt cctgtactcc aacatagcgc tgtatttgcc cgacaagcta  20400
aagtacagtc cttccaacgt aaaaatttct gataacccaa acacctacga ctacatgaac  20460
aagcgagtgg tggctcccgg gttagtggac tgctacatta accttggagc acgctggtcc  20520
cttgactata tggacaacgt caacccattt aaccaccacc gcaatgctgg cctgcgctac  20580
cgctcaatgt tgctgggcaa tggtcgctat gtgcccttcc acatccaggt gcctcagaag  20640
ttctttgcca ttaaaaacct ccttctcctg ccgggctcat acacctacga gtggaacttc  20700
aggaaggatg ttaacatggt tctgcagagc tccctaggaa atgacctaag ggttgacgga  20760
gccagcatta agtttgatag catttgcctt tacgccacct tcttccccat ggcccacaac  20820
accgcctcca cgcttgaggc catgcttaga aacgacacca acgaccagtc ctttaacgac  20880
tatctctccg ccgccaacat gctctaccct atacccgcca acgctaccaa cgtgcccata  20940
tccatcccct cccgcaactg ggcggctttc cgcggctggg ccttcacgcg ccttaagact  21000
aaggaaaccc catcactggg ctcgggctac gacccttatt acacctactc tggctctata  21060
ccctacctag atggaacctt ttacctcaac cacaccttta agaaggtggc cattaccttt  21120
```

```
gactcttctg tcagctggcc tggcaatgac cgcctgctta cccccaacga gtttgaaatt  21180
aagcgctcag ttgacgggga gggttacaac gttgcccagt gtaacatgac caaagactgg  21240
ttcctggtac aaatgctagc taactacaac attggctacc agggcttcta tatcccagag  21300
agctacaagg accgcatgta ctccttcttt agaaacttcc agcccatgag ccgtcaggtg  21360
gtggatgata ctaaatacaa ggactaccaa caggtgggca tcctacacca acacaacaac  21420
tctggatttg ttggctacct tgcccccacc atgcgcgaag gacaggccta ccctgctaac  21480
ttcccctatc cgcttatagg caagaccgca gttgacagca ttacccagaa aaagtttctt  21540
tgcgatcgca ccctttggcg catcccattc tccagtaact ttatgtccat gggcgcactc  21600
acagacctgg gccaaaacct tctctacgcc aactccgccc acgcgctaga catgactttt  21660
gaggtggatc ccatggacga gcccaccctt ctttatgttt tgtttgaagt ctttgacgtg  21720
gtccgtgtgc accggccgca ccgcggcgtc atcgaaaccg tgtacctgcg cacgcccttc  21780
tcggccggca acgccacaac ataaagaagc aagcaacatc aacaacagct gccgccatgg  21840
gctccagtga gcaggaactg aaagccattg tcaaagatct tggttgtggg ccatattttt  21900
tgggcaccta tgacaagcgc tttccaggct ttgtttctcc acacaagctc gcctgcgcca  21960
tagtcaatac ggccggtcgc gagactgggg gcgtacactg gatggccttt gcctggaacc  22020
cgcactcaaa aacatgctac ctctttgagc cctttggctt ttctgaccag cgactcaagc  22080
aggtttacca gtttgagtac gagtcactcc tgcgccgtag cgccattgct tcttcccccg  22140
accgctgtat aacgctggaa aagtccaccc aaagcgtaca ggggcccaac tcggccgcct  22200
gtggactatt ctgctgcatg tttctccacg cctttgccaa ctggccccaa actcccatgg  22260
atcacaaccc caccatgaac cttattaccg gggtacccaa ctccatgctc aacagtcccc  22320
aggtacagcc caccctgcgt cgcaaccagg aacagctcta cagcttcctg gagcgccact  22380
cgccctactt ccgcagccac agtgcgcaga ttaggagcgc cacttctttt tgtcacttga  22440
aaaacatgta aaaataatgt actagagaca ctttcaataa aggcaaatgc ttttatttgt  22500
acactctcgg gtgattattt acccccaccc ttgccgtctg cgccgtttaa aaatcaaagg  22560
ggttctgccg cgcatcgcta tgcgccactg gcagggacac gttgcgatac tggtgtttag  22620
tgctccactt aaactcaggc acaaccatcc gcggcagctc ggtgaagttt tcactccaca  22680
ggctgcgcac catcaccaac gcgtttagca ggtcgggcgc cgatatcttg aagtcgcagt  22740
tggggcctcc gccctgcgcg cgcgagttgc gatacacagg gttgcagcac tggaacacta  22800
tcagcgccgg gtggtgcacg ctggccagca cgctcttgtc ggagatcaga tccgcgtcca  22860
ggtcctccgc gttgctcagg gcgaacggag tcaactttgg tagctgcctt cccaaaaagg  22920
gcgcgtgccc aggctttgag ttgcactcgc accgtagtgg catcaaaagg tgaccgtgcc  22980
cggtctgggc gttaggatac agcgcctgca taaaagcctt gatctgctta aaagccacct  23040
gagcctttgc gccttcagag aagaacatgc cgcaagactt gccggaaaac tgattggccg  23100
gacaggccgc gtcgtgcacg cagcaccttg cgtcggtgtt ggagatctgc accacatttc  23160
ggccccaccg gttcttcacg atcttggcct tgctagactg ctccttcagc gcgcgctgcc  23220
cgttttcgct cgtcacatcc atttcaatca cgtgctcctt atttatcata atgcttccgt  23280
gtagacactt aagctcgcct tcgatctcag cgcagcggtg cagccacaac gcgcagcccg  23340
tgggctcgtg atgcttgtag gtcacctctg caaacgactg caggtacgcc tgcaggaatc  23400
gccccatcat cgtcacaaag gtcttgttgc tggtgaaggt cagctgcaac ccgcggtgct  23460
```

```
cctcgttcag ccaggtcttg catacggccg ccagagcttc cacttggtca ggcagtagtt  23520
tgaagttcgc ctttagatcg ttatccacgt ggtacttgtc catcagcgcg cgcgcagcct  23580
ccatgccctt ctcccacgca gacacgatcg gcacactcag cgggttcatc accgtaattt  23640
cactttccgc ttcgctgggc tcttcctctt cctcttgcgt ccgcatacca cgcgccactg  23700
ggtcgtcttc attcagccgc cgcactgtgc gcttacctcc tttgccatgc ttgattagca  23760
ccggtgggtt gctgaaaccc accatttgta gcgccacatc ttctctttct tcctcgctgt  23820
ccacgattac ctctggtgat ggcgggcgct cgggcttggg agaagggcgc ttcttttttct  23880
tcttgggcgc aatggccaaa tccgccgccg aggtcgatgg ccgcgggctg ggtgtgcgcg  23940
gcaccagcgc gtcttgtgat gagtcttcct cgtcctcgga ctcgatacgc cgcctcatcc  24000
gcttttttgg gggcgcccgg ggaggcggcg gcgacgggga cggggacgac acgtcctcca  24060
tggttggggg acgtcgcgcc gcaccgcgtc cgcgctcggg ggtggtttcg cgctgctcct  24120
cttcccgact ggccatttcc ttctcctata ggcagaaaaa gatcatggag tcagtcgaga  24180
agaaggacag cctaaccgcc ccctctgagt tcgccaccac cgcctccacc gatgccgcca  24240
acgcgcctac caccttcccc gtcgaggcac ccccgcttga ggaggaggaa gtgattatcg  24300
agcaggaccc aggttttgta agcgaagacg acgaggaccg ctcagtacca acagaggata  24360
aaaagcaaga ccaggacaac gcagaggcaa acgaggaaca agtcgggcgg ggggacgaaa  24420
ggcatggcga ctacctagat gtgggagacg acgtgctgtt gaagcatctg cagcgccagt  24480
gcgccattat ctgcgacgcg ttgcaagagc gcagcgatgt gcccctcgcc atagcggatg  24540
tcagccttgc ctacgaacgc cacctattct caccgcgcgt accccccaaa cgccaagaaa  24600
acggcacatg cgagcccaac ccgcgcctca acttctaccc cgtatttgcc gtgccagagg  24660
tgcttgccac ctatcacatc tttttccaaa actgcaagat acccctatcc tgccgtgcca  24720
accgcagccg agcggacaag cagctggcct tgcggcaggg cgctgtcata cctgatatcg  24780
cctcgctcaa cgaagtgcca aaaatctttg agggtcttgg acgcgacgag aagcgcgcgg  24840
caaacgctct gcaacaggaa aacagcgaaa atgaaagtca ctctggagtg ttggtggaac  24900
tcgagggtga caacgcgcgc ctagccgtac taaaacgcag catcgaggtc acccactttg  24960
cctacccggc acttaaccta ccccccaagg tcatgagcac agtcatgagt gagctgatcg  25020
tgcgccgtgc gcagcccctg gagagggatg caaatttgca agaacaaaca gaggagggcc  25080
tacccgcagt tggcgacgag cagctagcgc gctggcttca aacgcgcgag cctgccgact  25140
tggaggagcg acgcaaacta atgatggccg cagtgctcgt taccgtggag cttgagtgca  25200
tgcagcggtt ctttgctgac ccggagatgc agcgcaagct agaggaaaca ttgcactaca  25260
cctttcgaca gggctacgta cgccaggcct gcaagatctc caacgtggag ctctgcaacc  25320
tggtctccta ccttggaatt ttgcacgaaa accgccttgg gcaaaacgtg cttcattcca  25380
cgctcaaggg cgaggcgcgc cgcgactacg tccgcgactg cgtttactta tttctatgct  25440
acacctggca gacggccatg ggcgtttggc agcagtgctt ggaggagtgc aacctcaagg  25500
agctgcagaa actgctaaag caaaacttga aggacctatg gacggccttc aacgagcgct  25560
ccgtggccgc gcacctggcg gacatcattt tccccgaacg cctgcttaaa accctgcaac  25620
agggtctgcc agacttcacc agtcaaagca tgttgcagaa ctttaggaac tttatcctag  25680
agcgctcagg aatcttgccc gccacctgct gtgcacttcc tagcgacttt gtgcccatta  25740
agtaccgcga atgccctccg ccgctttggg gccactgcta ccttctgcag ctagccaact  25800
accttgccta ccactctgac ataatggaag acgtgagcgg tgacggtcta ctggagtgtc  25860
```

```
actgtcgctg caacctatgc accccgcacc gctccctggt ttgcaattcg cagctgctta  25920
acgaaagtca aattatcggt acctttgagc tgcagggtcc ctcgcctgac gaaaagtccg  25980
cggctccggg gttgaaactc actccggggc tgtggacgtc ggcttacctt cgcaaatttg  26040
tacctgagga ctaccacgcc cacgagatta ggttctacga agaccaatcc cgcccgccaa  26100
atgcggagct taccgcctgc gtcattaccc agggccacat tcttggccaa ttgcaagcca  26160
tcaacaaagc ccgccaagag tttctgctac gaaagggacg gggggtttac ttggaccccc  26220
agtccggcga ggagctcaac ccaatccccc cgccgccgca gccctatcag cagcagccgc  26280
gggcccttgc ttcccaggat ggcacccaaa aagaagctgc agctgccgcc gccacccacg  26340
gacgaggagg aatactggga cagtcaggca gaggaggttt tggacgagga ggaggaggac  26400
atgatggaag actgggagag cctagacgag gaagcttccg aggtcgaaga ggtgtcagac  26460
gaaacaccgt caccctcggt cgcattcccc tcgccggcgc cccagaaatc ggcaaccggt  26520
tccagcatgg ctacaacctc cgctcctcag gcgccgccgg cactgcccgt tcgccgaccc  26580
aaccgtagat gggacaccac tggaaccagg gccggtaagt ccaagcagcc gccgccgtta  26640
gcccaagagc aacaacagcg ccaaggctac cgctcatggc gcgggcacaa gaacgccata  26700
gttgcttgct tgcaagactg tgggggcaac atctccttcg cccgccgctt tcttctctac  26760
catcacggcg tggccttccc ccgtaacatc ctgcattact accgtcatct ctacagccca  26820
tactgcaccg gcggcagcgg cagcggcagc aacagcagcg gccacacaga agcaaaggcg  26880
accggatagc aagactctga caaagcccaa gaaatccaca gcggcggcag cagcaggagg  26940
aggagcgctg cgtctggcgc ccaacgaacc cgtatcgacc cgcgagctta gaaacaggat  27000
ttttcccact ctgtatgcta tatttcaaca gagcaggggc caagaacaag agctgaaaat  27060
aaaaaacagg tctctgcgat ccctcacccg cagctgcctg tatcacaaaa gcgaagatca  27120
gcttcggcgc acgctggaag acgcggaggc tctcttcagt aaatactgcg cgctgactct  27180
taaggactag tttcgcgccc tttctcaaat ttaagcgcga aaactacgtc atctccagcg  27240
gccacacccg gcgccagcac ctgtcgtcag cgccattatg agcaaggaaa ttcccacgcc  27300
ctacatgtgg agttaccagc cacaaatggg acttgcggct ggagctgccc aagactactc  27360
aacccgaata aactacatga gcgcgggacc ccacatgata tcccgggtca acggaatccg  27420
cgcccaccga aaccgaattc tcttggaaca ggcggctatt accaccacac ctcgtaataa  27480
ccttaatccc cgtagttggc ccgctgccct ggtgtaccag gaaagtcccg ctcccaccac  27540
tgtggtactt cccagagacg cccaggccga agttcagatg actaactcag gggcgcagct  27600
tgcgggcggc tttcgtcaca gggtgcggtc gcccgggcag ggtataactc acctgacaat  27660
cagagggcga ggtattcagc tcaacgacga gtcggtgagc tcctcgcttg gtctccgtcc  27720
ggacgggaca tttcagatcg gcggcgccgg ccgctcttca ttcacgcctc gtcaggcaat  27780
cctaactctg cagacctcgt cctctgagcc gcgctctgga ggcattggaa ctctgcaatt  27840
tattgaggag tttgtgccat cggtctactt taacccettc tcgggacctc ccggccacta  27900
tccggatcaa tttattccta actttgacgc ggtaaaggac tcggcggatg gctacgactg  27960
aatgttaagt ggagaggcag agcaactgcg cctgaaacac ctggtccact gtcgccgcca  28020
caagtgcttt gcccgcgact ccggtgagtt ttgctacttt gaattgcccg aggatcatat  28080
cgagggcccg gcgcacggcg tccggcttac cgcccaggga gagcttgccc gtagcctgat  28140
tcgggagttt acccagcgcc ccctgctagt tgagcgggac aggggaccct gtgttctcac  28200
```

```
tgtgatttgc aactgtccta accctggatt acatcaagat ctttgttgcc atctctgtgc  28260
tgagtataat aaatacagaa attaaaatat actggggctc ctatcgccat cctgtaaacg  28320
ccaccgtctt cacccgccca agcaaaccaa ggcgaacctt acctggtact tttaacatct  28380
ctccctctgt gatttacaac agtttcaacc cagacggagt gagtctacga gagaacctct  28440
ccgagctcag ctactccatc agaaaaaaca ccaccctcct tacctgccgg gaacgtacga  28500
tgtggctgca gagcctgctg ctcttgggca ctgtggcctg cagcatctct gcacccgccc  28560
gctcgcccag ccccagcacg cagccctggg agcatgtgaa tgccatccag gaggcccggc  28620
gtctcctgaa cctgagtaga gacactgctg ctgagatgaa tgaaacagta gaagtcatct  28680
cagaaatgtt tgacctccag gagccgacct gcctacagac ccgcctggag ctgtacaagc  28740
agggcctgcg gggcagcctc accaagctca agggcccctt gaccatgatg gccagccact  28800
acaagcagca ctgccctcca accccggaaa cttcctgtgc aacccagact atcacctttg  28860
aaagtttcaa agagaacctg aaggactttc tgcttgtcat cccctttgac tgctgggagc  28920
cagtccagga gtgacaattg actctatgtg ggatatgctc cagcgctaca accttgaagt  28980
caggcttcct ggatgtcagc atctgacttt ggccagcacc tgtcccgcgg atttgttcca  29040
gtccaactac agcgacccac cctaacagag atgaccaaca caaccaacgc ggccgccgct  29100
accggactta catctaccac aaatacaccc caagtttctg cctttgtcaa taactgggat  29160
aacttgggca tgtggtggtt ctccatagcg cttatgtttg tatgccttat tattatgtgg  29220
ctcatctgct gcctaaagcg caaacgcgcc cgaccaccca tctatagtcc catcattgtg  29280
ctacacccaa acaatgatgg aatccataga ttggacggac tgaaacacat gttcttttct  29340
cttacagtat gattaaatga gacatgattc ctcgagtttt tatattactg acccttgttg  29400
cgcttttttg tgcgtgctcc acattggctg cggtttctca catcgaagta gactgcattc  29460
cagccttcac agtctatttg ctttacggat ttgtcaccct cacgctcatc tgcagcctca  29520
tcactgtggt catcgccttt atccagtgca ttgactgggt ctgtgtgcgc tttgcatatc  29580
tcagacacca tccccagtac agggacagga ctatagctga gcttcttaga attctttaat  29640
tatgaaattt actgtgactt ttctgctgat tatttgcacc ctatctgcgt tttgttcccc  29700
gacctccaag cctcaaagac atatatcatg cagattcact cgtatatgga atattccaag  29760
ttgctacaat gaaaaaagcg atctttccga agcctggtta tatgcaatca tctctgttat  29820
ggtgttctgc agtaccatct tagccctagc tatatatccc taccttgaca ttggctggaa  29880
acgaatagat gccatgaacc acccaacttt ccccgcgccc gctatgcttc cactgcaaca  29940
agttgttgcc ggcggctttg tcccagccaa tcagcctcgc cccacttctc ccacccccac  30000
tgaaatcagc tactttaatc taacaggagg agatgactga caccctagat ctagaaatgg  30060
acggaattat tacagagcag cgcctgctag aaagacgcag ggcagcggcc gagcaacagc  30120
gcatgaatca agagctccaa gacatggtta acttgcacca gtgcaaaagg ggtatctttt  30180
gtctggtaaa gcaggccaaa gtcacctacg acagtaatac caccggacac cgccttagct  30240
acaagttgcc aaccaagcgt cagaaattgg tggtcatggt gggagaaaag cccattacca  30300
taactcagca ctcggtagaa accgaaggct gcattcactc accttgtcaa ggacctgagg  30360
atctctgcac ccttattaag accctgtgcg gtctcaaaga tcttattccc tttaactaat  30420
aaaaaaaaat aataaagcat cacttactta aaatcagtta gcaaatttct gtccagttta  30480
ttcagcagca cctccttgcc ctcctcccag ctctggtatt gcagcttcct cctggctgca  30540
aactttctcc acaatctaaa tggaatgtca gtttcctcct gttcctgtcc atccgcaccc  30600
```

```
actatcttca tgttgttgca gatgaagcgc gcaagaccgt ctgaagatac cttcaacccc  30660
gtgtatccat atgacacgga aaccggtcct ccaactgtgc cttttcttac tcctcccttt  30720
gtatcccccca atgggtttca agagagtccc cctggggtac tctctttgcg cctatccgaa  30780
cctctagtta cctccaatgg catgcttgcg ctcaaaatgg gcaacggcct ctctctggac  30840
gaggccggca accttacctc ccaaaatgta accactgtga gcccacctct cggagccgga  30900
gcctcaaaca taaacctgga aatatctgca cccctcacag ttacctcaga agccctaact  30960
gtggctgccg ccgcacctct aatggtcgcg ggcaacacac tcaccatgca atcacaggcc  31020
ccgctaaccg tgcacgactc caaacttagc attgccaccc aaggacccct cacagtgtca  31080
gaaggaaagc tagccctgca aacatcaggc cccctcacca ccaccgatag cagtaccctt  31140
actatcactg cctcaccccc tctaactact gccactggta gcttgggcat tgacttgaaa  31200
gagcccattt atacacaaaa tggaaaacta ggactaaagt acggggctcc tttgcatgta  31260
acagacgacc taaacacttt gaccgtagca actggtccag gtgtgactat taataatact  31320
tccttgcaaa ctaaagttac tggagccttg ggttttgatt cacaaggcaa tatgcaactt  31380
aatgtagcag gaggactaag gattgattct caaaacagac gccttatact tgatgttagt  31440
tatccgtttg atgctcaaaa ccaactaaat ctaagactag gacagggccc tctttttata  31500
aactcagccc acaacttgga tattaactac aacaaaggcc tttacttgtt tacagcttca  31560
aacaattcca aaaagcttga ggttaaccta agcactgcca aggggttgat gtttgacgct  31620
acagccatag ccattaatgc aggagatggg cttgaatttg gttcacctaa tgcaccaaac  31680
acaaatcccc tcaaaacaaa aattggccat ggcctagaat ttgattcaaa caaggctatg  31740
gttcctaaac taggaactgg ccttagtttt gacagcacag gtgccattac agtaggaaac  31800
aaaaataatg ataagctaac cctatggaca ggtccaaaac cagaagccaa ctgcataatt  31860
gaatacggga aacaaaaccc agatagcaaa ctaactttaa tccttgtaaa aaatggagga  31920
attgttaatg gatatgtaac gctaatggga gcctcagact acgttaacac cttatttaaa  31980
aacaaaaatg tctccattaa tgtagaacta tactttgatg ccactggtca tatattacca  32040
gactcatctt ctcttaaaac agatctagaa ctaaaataca agcaaaccgc tgactttagt  32100
gcaagaggtt ttatgccaag tactacagcg tatccatttg tccttcctaa tgcgggaaca  32160
cataatgaaa attatatttt tggtcaatgc tactacaaag caagcgatgg tgcccttttt  32220
ccgttggaag ttactgttat gcttaataaa cgcctgccag atagtcgcac atcctatgtt  32280
atgacttttt tatggtcctt gaatgctggt ctagctccag aaactactca ggcaaccctc  32340
ataacctccc catttacctt ttcctatatt agagaagatg actaataaac tctaaagaat  32400
cgtttgtgtt atgtttcaac gtgtttattt ttcaattgca gaaaatttca agtcattttt  32460
cattcagtag tatagcccca ccaccacata gcttatacag atcaccgtac cttaatcaaa  32520
ctcacagaac cctagtattc aacctgccac ctccctccca acacacagag tacacagtcc  32580
tttctccccg gctggcctta aaaagcatca tatcatgggt aacagacata ttcttaggtg  32640
ttatattcca cacggtttcc tgtcgagcca aacgctcatc aagtgatatt aataaactcc  32700
ccgggcagct cacttaagtt catgtcgctg tccagctgct gagccacagg ctgctgtcca  32760
acttgcggtt gcttaacggg cggcgaagga gaagtccacg cctacatggg gggagagtca  32820
taatcgtgca tcaggatagg gcggtggtgc tgcagcagcg cgcgaataaa ctgctgccgc  32880
cgccgctccg tcctgcagga atacaacatg gcagtggtct cctcagcgat gattcgcacc  32940
```

-continued

```
gcccgcagca taaggcgcct tgtcctccgg gcacagcagc gcaccctgat ctcacttaaa  33000
tcagcacagt aactgcagca cagcaccaca atattgttca aaatcccaca gtgcaaggcg  33060
ctgtatccaa agctcatggc ggggaccaca gaacccacgt ggccatcata ccacaagcgc  33120
aggtagatta agtggcgacc cctcataaac acgctggaca taaacattac ctcttttggc  33180
atgttgtaat tcaccacctc ccggtaccat ataaacctct gattaaacat ggcgccatcc  33240
accaccatcc taaaccagct ggccaaaacc tgcccgccg ggntatacac tgcagggaac  33300
cgggactgga acaatgacag tggagagccc aggactcgta accatggatc atcatgctcg  33360
tcatgatatc aatgttggca caacacaggc acacgtgcat acacttcctc aggattacaa  33420
gctcctcccg cgttagaacc atatcccagg gaacaaccca ttcctgaatc agcgtaaatc  33480
ccacactgca gggaagacct cgcacgtaac tcacgttgtg cattgtcaaa gtgttacatt  33540
cgggcagcag cggatgatcc tccagtatgg tagcgcgggt ttctgtctca aaaggaggta  33600
gacgatccct actgtacgga gtgcgccgag acaaccgaga tcgtgttggt cgtagtgtca  33660
tgccaaatgg aacgccggac gtagtcatat ttcctgaagc aaaaccaggt gcgggcgtga  33720
caaacagatc tgcgtctccg gtctcgccgc ttagatcgct ctgtgtagta gttgtagtat  33780
atccactctc tcaaagcatc caggcgcccc ctggcttcgg gttctatgta aactccttca  33840
tgcgccgctg ccctgataac atccaccacc gcagaataag ccacacccag ccaacctaca  33900
cattcgttct gcgagtcaca cacgggagga gcgggaagag ctggaagaac catgtttttt  33960
tttttattcc aaaagattat ccaaaacctc aaaatgaaga tctattaagt gaacgcgctc  34020
ccctccggtg gcgtggtcaa actctacagc caaagaacag ataatggcat ttgtaagatg  34080
ttgcacaatg gcttccaaaa ggcaaacggc cctcacgtcc aagtggacgt aaaggctaaa  34140
cccttcaggg tgaatctcct ctataaacat tccagcacct tcaaccatgc ccaaataatt  34200
ctcatctcgc caccttctca atatatctct aagcaaatcc cgaatattaa gtccggccat  34260
tgtaaaaatt tggctccaga gcgccctcca ccttcagcct caagcagcga atcatgattg  34320
caaaaattca ggttcctcac agacctgtat aagattcaaa agcggaacat taacaaaaat  34380
accgcgatcc cgtaggtccc ttcgcagggc cagctgaaca taatcgtgca ggtctgcacg  34440
gaccagcgcg gccacttccc cgccaggaac catgacaaaa gaacccacac tgattatgac  34500
acgcatactc ggagctatgc taaccagcgt agccccgatg taagcttgtt gcatgggcgg  34560
cgatataaaa tgcaaggtgc tgctcaaaaa atcaggcaaa gcctcgcgca aaaaagaaag  34620
cacatcgtag tcatgctcat gcagataaag gcaggtaagc tccggaacca ccacagaaaa  34680
agacaccatt tttctctcaa acatgtctgc gggtttctgc ataaacacaa aataaaataa  34740
caaaaaaaca tttaaacatt agaagcctgt cttacaacag gaaaaacaac ccttataagc  34800
ataagacgga ctacggccat gccggcgtga ccgtaaaaaa actggtcacc gtgattaaaa  34860
agcaccaccg acagctcctc ggtcatgtcc ggagtcataa tgtaagactc ggtaaacaca  34920
tcaggttgat tcacatcggt cagtgctaaa aagcgaccga aatagcccgg gggaatacat  34980
acccgcaggc gtagagacaa cattacagcc cccataggag gtataacaaa attaatagga  35040
gagaaaaaca cataaacacc tgaaaaaccc tcctgcctag gcaaaatagc accctcccgc  35100
tccagaacaa catacagcgc ttccacagcg gcagccataa cagtcagcct taccagtaaa  35160
aaagaaaacc tattaaaaaa acaccactcg acacggcacc agctcaatca gtcacagtgt  35220
aaaaaagggc caagtgcaga gcgagtatat ataggactaa aaaatgacgt aacggttaaa  35280
gtccacaaaa aacacccaga aaccgcacgc cgaacctacg cccagaaacg aaagccaaaa  35340
```

aacccacaac ttcctcaaat cgtcacttcc gttttcccac gttacgtcac ttcccatttt 35400
aagaaaacta caattcccaa cacatacaag ttactccgcc ctaaaaccta cgtcacccgc 35460
cccgttccca cgccccgcgc cacgtcacaa actccacccc ctcattatca tattggcttc 35520
aatccaaaat aaggtatatt attgatgatg tta 35553

<210> SEQ ID NO 7
<211> LENGTH: 35745
<212> TYPE: DNA
<213> ORGANISM: Artificial Sequence
<220> FEATURE:
<223> OTHER INFORMATION: The nucleotide sequence encoding virus CGTG-607
<220> FEATURE:
<221> NAME/KEY: misc_feature
<222> LOCATION: (33475)..(33475)
<223> OTHER INFORMATION: n is a, c, g, or t

<400> SEQUENCE: 7
taacatcatc aataatatac cttattttgg attgaagcca atatgataat gagggggtgg 60
agtttgtgac gtggcgcggg gcgtgggaac ggggcgggtg acgtagtagt gtggcggaag 120
tgtgatgttg caagtgtggc ggaacacatg taagcgacgg atgtggcaaa agtgacgttt 180
ttggtgtgcg ccggtgtaca caggaagtga caattttcgc gcggttttag gcggatgttg 240
tagtaaattt gggcgtaacc gagtaagatt tggccatttt cgcgggaaaa ctgaataaga 300
ggaagtgaaa tctgaataat tttgtgttac tcatagcgcg taatactggt accgcggccg 360
ctggtaccat ccggacaaag cctgcgcgcg ccccgccccg ccattggccg taccgccccg 420
cgccgccgcc ccatcccgcc cctcgccgcc gggtccggcg cgttaaagcc aataggaacc 480
gccgccgttg ttcccgtcac ggccggggca gccaattgtg gcggcgctcg gcggctcgtg 540
gctctttcgc ggcaaaaagg atttggcgcg taaaagtggc cgggactttg caggcagcgg 600
cggccggggg cggagcggga tcgagccctc gccctcgagc tagaagcttg ttttctcctc 660
cgagccgctc cgacaccggg actgaaaatg agacatatta tctgccacgg aggtgttatt 720
accgaagaaa tggccgccag tcttttggac cagctgatcg aagaggtact ggctgataat 780
cttccacctc ctagccattt tgaaccacct acccttcacg aactgtatga tttagacgtg 840
acggcccccg aagatcccaa cgaggaggcg gtttcgcaga tttttcccga ctctgtaatg 900
ttggcggtgc aggaagggat tgacttactc acttttccgc cggcgcccgg ttctccggag 960
ccgcctcacc tttcccggca gcccgagcag ccggagcaga gagccttggg tccggtttct 1020
atgccaaacc ttgtaccgga ggtgatcgat ccacccagtg acgacgagga tgaagagggt 1080
gaggagtttg tgttagatta tgtggagcac cccgggcacg gttgcaggtc ttgtcattat 1140
caccggagga atacgggga cccagatatt atgtgttcgc tttgctatat gaggacctgt 1200
ggcatgtttg tctacagtaa gtgaaaatta tgggcagtgg gtgatagagt ggtgggtttg 1260
gtgtggtaat tttttttta atttttacag ttttgtggtt taaagaattt tgtattgtga 1320
tttttttaaa aggtcctgtg tctgaacctg agcctgagcc cgagccagaa ccggagcctg 1380
caagacctac ccgccgtcct aaaatggcgc ctgctatcct gagacgcccg acatcacctg 1440
tgtctagaga atgcaatagt agtacggata gctgtgactc cggtccttct aacacacctc 1500
ctgagataca cccggtggtc ccgctgtgcc ccattaaacc agttgccgtg agagttggtg 1560
ggcgtcgcca ggctgtggaa tgtatcgagg acttgcttaa cgagcctggg caacctttgg 1620
acttgagctg taaacgcccc aggccataag gtgtaaacct gtgattgcgt gtgtggttaa 1680

-continued

```
cgcctttgtt tgctgaatga gttgatgtaa gtttaataaa gggtgagata atgtttaact   1740
tgcatggcgt gttaaatggg gcggggctta aagggtatat aatgcgccgt gggctaatct   1800
tggttacatc tgacctcatg gaggcttggg agtgtttgga agatttttct gctgtgcgta   1860
acttgctgga acagagctct aacagtacct cttggttttg gaggtttctg tggggctcat   1920
cccaggcaaa gttagtctgc agaattaagg aggattacaa gtgggaattt gaagagcttt   1980
tgaaatcctg tggtgagctg tttgattctt tgaatctggg tcaccaggcg cttttccaag   2040
agaaggtcat caagactttg gatttttcca caccggggcg cgctgcggct gctgttgctt   2100
ttttgagttt tataaaggat aaatggagcg aagaaaccca tctgagcggg gggtacctgc   2160
tggattttct ggccatgcat ctgtggagag cggttgtgag acacaagaat cgcctgctac   2220
tgttgtcttc cgtccgcccg gcgataatac cgacggagga gcagcagcag cagcaggagg   2280
aagccaggcg gcggcggcag gagcagagcc catggaaccc gagagccggc ctggaccctc   2340
gggaatgaat gttgtacagg tggctgaact gtatccagaa ctgagacgca ttttgacaat   2400
tacagaggat gggcaggggc taaagggggt aaagagggag cgggggcctt gtgaggctac   2460
agaggaggct aggaatctag cttttagctt aatgaccaga caccgtcctg agtgtattac   2520
ttttcaacag atcaaggata attgcgctaa tgagcttgat ctgctggcgc agaagtattc   2580
catagagcag ctgaccactt actggctgca gccaggggat gattttgagg aggctattag   2640
ggtatatgca aaggtggcac ttaggccaga ttgcaagtac aagatcagca aacttgtaaa   2700
tatcaggaat tgttgctaca tttctgggaa cggggccgag gtggagatag atacggagga   2760
tagggtggcc tttagatgta gcatgataaa tatgtggccg gggtgcttg gcatggacgg    2820
ggtggttatt atgaatgtaa ggtttactgg ccccaatttt agcggtacgg ttttcctggc   2880
caataccaac cttatcctac acggtgtaag cttctatggg tttaacaata cctgtgtgga   2940
agcctggacc gatgtaaggg ttcggggctg tgccttttac tgctgctgga agggggtggt   3000
gtgtcgcccc aaaagcaggg cttcaattaa gaaatgcctc tttgaaaggt gtaccttggg   3060
tatcctgtct gagggtaact ccagggtgcg ccacaatgtg gcctccgact gtggttgctt   3120
catgctagtg aaaagcgtgg ctgtgattaa gcataacatg gtatgtggca actgcgagga   3180
cagggcctct cagatgctga cctgctcgga cggcaactgt cacctgctga agaccattca   3240
cgtagccagc cactctcgca aggcctggcc agtgtttgag cataacatac tgacccgctg   3300
ttccttgcat ttgggtaaca ggagggggt gttcctacct taccaatgca atttgagtca    3360
cactaagata ttgcttgagc ccgagagcat gtccaaggtg aacctgaacg gggtgtttga   3420
catgaccatg aagatctgga aggtgctgag gtacgatgag acccgcacca ggtgcagacc   3480
ctgcgagtgt ggcggtaaac atattaggaa ccagcctgtg atgctggatg tgaccgagga   3540
gctgaggccc gatcacttgg tgctggcctg cacccgcgct gagtttggct ctagcgatga   3600
agatacagat tgaggtactg aaatgtgtgg gcgtggctta agggtgggaa agaatatata   3660
aggtgggggt cttatgtagt tttgtatctg ttttgcagca gccgccgccg ccatgagcac   3720
caactcgttt gatggaagca ttgtgagctc atatttgaca acgcgcatgc ccccatgggc   3780
cggggtgcgt cagaatgtga tgggctccag cattgatggt cgccccgtcc tgcccgcaaa   3840
ctctactacc ttgacctacg agaccgtgtc tggaacgccg ttggagactg cagcctccgc   3900
cgccgcttca gccgctgcag ccaccgcccg cgggattgtg actgactttg ctttcctgag   3960
cccgcttgca agcagtgcag cttcccgttc atccgcccgc gatgacaagt tgacggctct   4020
tttggcacaa ttggattctt tgacccggga acttaatgtc gtttctcagc agctgttgga   4080
```

```
tctgcgccag caggtttctg ccctgaaggc ttcctcccct cccaatgcgg tttaaaacat   4140
aaataaaaaa ccagactctg tttggatttg gatcaagcaa gtgtcttgct gtctttattt   4200
aggggttttg cgcgcgcggt aggcccggga ccagcggtct cggtcgttga gggtcctgtg   4260
tattttttcc aggacgtggt aaaggtgact ctggatgttc agatacatgg gcataagccc   4320
gtctctgggg tggaggtagc accactgcag agcttcatgc tgcggggtgg tgttgtagat   4380
gatccagtcg tagcaggagc gctgggcgtg gtgcctaaaa atgtctttca gtagcaagct   4440
gattgccagg ggcaggccct tggtgtaagt gtttacaaag cggttaagct gggatgggtg   4500
catacgtggg gatatgagat gcatcttgga ctgtattttt aggttggcta tgttcccagc   4560
catatccctc cggggattca tgttgtgcag aaccaccagc acagtgtatc cggtgcactt   4620
gggaaatttg tcatgtagct tagaaggaaa tgcgtggaag aacttggaga cgcccttgtg   4680
acctccaaga ttttccatgc attcgtccat aatgatggca atgggcccac gggcggcggc   4740
ctgggcgaag atatttctgg gatcactaac gtcatagttg tgttccagga tgagatcgtc   4800
ataggccatt tttacaaagc gcgggcggag ggtgccagac tgcggtataa tggttccatc   4860
cggcccaggg gcgtagttac cctcacagat ttgcatttcc cacgctttga gttcagatgg   4920
ggggatcatg tctacctgcg gggcgatgaa gaaaacggtt tccggggtag gggagatcag   4980
ctgggaagaa agcaggttcc tgagcagctg cgacttaccg cagccggtgg gcccgtaaat   5040
cacacctatt accgggtgca actggtagtt aagagagctg cagctgccgt catccctgag   5100
caggggggcc acttcgttaa gcatgtccct gactcgcatg ttttccctga ccaaatccgc   5160
cagaaggcgc tcgccgccca gcgatagcag ttcttgcaag gaagcaaagt ttttcaacgg   5220
tttgagaccg tccgccgtag gcatgctttt gagcgtttga ccaagcagtt ccaggcggtc   5280
ccacagctcg gtcacctgct ctacggcatc tcgatccagc atatctcctc gtttcgcggg   5340
ttggggcggc tttcgctgta cggcagtagt cggtgctcgt ccagacgggc cagggtcatg   5400
tctttccacg ggcgcagggt cctcgtcagc gtagtctggg tcacggtgaa ggggtgcgct   5460
ccgggctgcg cgctggccag ggtgcgcttg aggctggtcc tgctggtgct gaagcgctgc   5520
cggtcttcgc cctgcgcgtc ggccaggtag catttgacca tggtgtcata gtccagcccc   5580
tccgcggcgt ggcccttggc gcgcagcttg cccttggagg aggcgccgca cgaggggcag   5640
tgcagacttt tgagggcgta gagcttgggc gcgagaaata ccgattccgg ggagtaggca   5700
tccgcgccgc aggccccgca gacggtctcg cattccacga gccaggtgag ctctggccgt   5760
tcggggtcaa aaaccaggtt tcccccatgc tttttgatgc gtttcttacc tctggtttcc   5820
atgagccggt gtccacgctc ggtgacgaaa aggctgtccg tgtccccgta tacagacttg   5880
agaggcctgt cctcgagcgg tgttccgcgg tcctcctcgt atagaaactc ggaccactct   5940
gagacaaagg ctcgcgtcca ggccagcacg aaggaggcta agtgggaggg gtagcggtcg   6000
ttgtccacta gggggtccac tcgctccagg gtgtgaagac acatgtcgcc ctcttcggca   6060
tcaaggaagg tgattggttt gtaggtgtag gccacgtgac cgggtgttcc tgaagggggg   6120
ctataaaagg gggtgggggc gcgttcgtcc tcactctctt ccgcatcgct gtctgcgagg   6180
gccagctgtt ggggtgagta ctccctctga aaagcgggca tgacttctgc gctaagattg   6240
tcagtttcca aaaacgagga ggatttgata ttcacctggc ccgcggtgat gcctttgagg   6300
gtggccgcat ccatctggtc agaaaagaca atctttttgt tgtcaagctt ggtggcaaac   6360
gacccgtaga gggcgttgga cagcaacttg gcgatggagc gcagggtttg gtttttgtcg   6420
```

-continued

```
cgatcggcgc gctccttggc cgcgatgttt agctgcacgt attcgcgcgc aacgcaccgc   6480
cattcgggaa agacggtggt gcgctcgtcg ggcaccaggt gcacgcgcca accgcggttg   6540
tgcagggtga caaggtcaac gctggtggct acctctccgc gtaggcgctc gttggtccag   6600
cagaggcggc cgcccttgcg cgagcagaat ggcggtaggg ggtctagctg cgtctcgtcc   6660
ggggggtctg cgtccacggt aaagaccccg ggcagcaggc gcgcgtcgaa gtagtctatc   6720
ttgcatcctt gcaagtctag cgcctgctgc catgcgcggg cggcaagcgc gcgctcgtat   6780
gggttgagtg ggggacccca tggcatgggg tgggtgagcg cggaggcgta catgccgcaa   6840
atgtcgtaaa cgtagagggg ctctctgagt attccaagat atgtagggta gcatcttcca   6900
ccgcggatgc tggcgcgcac gtaatcgtat agttcgtgcg agggagcgag gaggtcggga   6960
ccgaggttgc tacgggcggg ctgctctgct cggaagacta tctgcctgaa gatggcatgt   7020
gagttggatg atatggttgg acgctggaag acgttgaagc tggcgtctgt gagacctacc   7080
gcgtcacgca cgaaggaggc gtaggagtcg cgcagcttgt tgaccagctc ggcggtgacc   7140
tgcacgtcta gggcgcagta gtccagggtt tccttgatga tgtcatactt atcctgtccc   7200
ttttttttcc acagctcgcg gttgaggaca aactcttcgc ggtctttcca gtactcttgg   7260
atcggaaacc cgtcggcctc cgaacggtaa gagcctagca tgtagaactg gttgacggcc   7320
tggtaggcgc agcatccctt ttctacgggt agcgcgtatg cctgcgcggc cttccggagc   7380
gaggtgtggg tgagcgcaaa ggtgtccctg accatgactt tgaggtactg gtatttgaag   7440
tcagtgtcgt cgcatccgcc ctgctcccag agcaaaaagt ccgtgcgctt tttggaacgc   7500
ggatttggca gggcgaaggt gacatcgttg aagagtatct ttcccgcgcg aggcataaag   7560
ttgcgtgtga tgcggaaggg tcccggcacc tcggaacggt tgttaattac ctgggcggcg   7620
agcacgatct cgtcaaagcc gttgatgttg tggcccacaa tgtaaagttc caagaagcgc   7680
gggatgccct tgatggaagg caattttta agttcctcgt aggtgagctc ttcaggggag   7740
ctgagcccgt gctctgaaag ggcccagtct gcaagatgag ggttggaagc gacgaatgag   7800
ctccacaggt cacgggccat tagcatttgc aggtggtcgc gaaaggtcct aaactggcga   7860
cctatggcca ttttttctgg ggtgatgcag tagaaggtaa gcgggtcttg ttcccagcgg   7920
tcccatccaa ggttcgcggc taggtctcgc gcggcagtca ctagaggctc atctccgccg   7980
aacttcatga ccagcatgaa gggcacgagc tgcttcccaa aggcccccat ccaagtatag   8040
gtctctacat cgtaggtgac aaagagacgc tcggtgcgag gatgcgagcc gatcgggaag   8100
aactggatct cccgccacca attggaggag tggctattga tgtggtgaaa gtagaagtcc   8160
ctgcgacggg ccgaacactc gtgctggctt ttgtaaaaac gtgcgcagta ctggcagcgg   8220
tgcacgggct gtacatcctg cacgaggttg acctgacgac cgcgcacaag gaagcagagt   8280
gggaatttga gcccctcgcc tggcgggttt ggctggtggt cttctacttc ggctgcttgt   8340
ccttgaccgt ctggctgctc gaggggagtt acggtggatc ggaccaccac gccgcgcgag   8400
cccaaagtcc agatgtccgc gcgcggcggt cggagcttga tgacaacatc gcgcagatgg   8460
gagctgtcca tggtctggag ctcccgcggc gtcaggtcag gcgggagctc ctgcaggttt   8520
acctcgcata gacgggtcag ggcgcgggct agatccaggt gatacctaat ttccaggggc   8580
tggttggtgg cggcgtcgat ggcttgcaag aggccgcatc cccgcggcgc gactacggta   8640
ccgcgcggcg ggcggtgggc cgcgggggtg tccttggatg atgcatctaa aagcggtgac   8700
gcgggcgagc ccccggaggt aggggggggct ccggacccgc cgggagaggg ggcaggggca   8760
cgtcggcgcc gcgcgcgggc aggagctggt gctgcgcgcg taggttgctg gcgaacgcga   8820
```

```
cgacgcggcg gttgatctcc tgaatctggc gcctctgcgt gaagacgacg ggcccggtga   8880
gcttgagcct gaaagagagt tcgacagaat caatttcggt gtcgttgacg gcggcctggc   8940
gcaaaatctc ctgcacgtct cctgagttgt cttgataggc gatctcggcc atgaactgct   9000
cgatctcttc ctcctggaga tctccgcgtc cggctcgctc cacggtggcg gcgaggtcgt   9060
tggaaatgcg ggccatgagc tgcgagaagg cgttgaggcc tccctcgttc cagacgcggc   9120
tgtagaccac gccccccttcg gcatcgcggg cgcgcatgac cacctgcgcg agattgagct   9180
ccacgtgccg ggcgaagacg gcgtagtttc gcaggcgctg aaagaggtag ttgagggtgg   9240
tggcggtgtg ttctgccacg aagaagtaca taacccagcg tcgcaacgtg gattcgttga   9300
tatcccccaa ggcctcaagg cgctccatgg cctcgtagaa gtccacggcg aagttgaaaa   9360
actgggagtt gcgcgccgac acggttaact cctcctccag aagacggatg agctcggcga   9420
cagtgtcgcg cacctcgcgc tcaaaggcta caggggcctc ttcttcttct tcaatctcct   9480
cttccataag ggcctcccct tcttcttctt ctggcggcgg tgggggaggg gggacacggc   9540
ggcgacgacg gcgcaccggg aggcggtcga caaagcgctc gatcatctcc ccgcggcgac   9600
ggcgcatggt ctcggtgacg gcgcggccgt tctcgcgggg gcgcagttgg aagacgccgc   9660
ccgtcatgtc ccggttatgg gttggcgggg ggctgccatg cggcagggat acggcgctaa   9720
cgatgcatct caacaattgt tgtgtaggta ctccgccgcc gagggacctg agcgagtccg   9780
catcgaccgg atcggaaaac ctctcgagaa aggcgtctaa ccagtcacag tcgcaaggta   9840
ggctgagcac cgtggcgggc ggcagcgggc ggcggtcggg gttgtttctg gcggaggtgc   9900
tgctgatgat gtaattaaag taggcggtct tgagacggcg gatggtcgac agaagcacca   9960
tgtccttggg tccggcctgc tgaatgcgca ggcggtcggc catgccccag gcttcgtttt  10020
gacatcggcg caggtctttg tagtagtctt gcatgagcct ttctaccggc acttcttctt  10080
ctccttcctc ttgtcctgca tctcttgcat ctatcgctgc ggcggcggcg gagtttggcc  10140
gtaggtggcg ccctcttcct cccatgcgtg tgaccccgaa gcccctcatc ggctgaagca  10200
gggctaggtc ggcgacaacg cgctcggcta atatggcctg ctgcacctgc gtgagggtag  10260
actggaagtc atccatgtcc acaaagcggt ggtatgcgcc cgtgttgatg gtgtaagtgc  10320
agttggccat aacggaccag ttaacggtct ggtgacccgg ctgcgagagc tcggtgtacc  10380
tgagacgcga gtaagccctc gagtcaaata cgtagtcgtt gcaagtccgc accaggtact  10440
ggtatcccac caaaaagtgc ggcggcggct ggcggtagag gggccagcgt agggtggccg  10500
gggctccggg ggcgagatct tccaacataa ggcgatgata tccgtagatg tacctggaca  10560
tccaggtgat gccggcggcg gtggtggagg cgcgcggaaa gtcgcggacg cggttccaga  10620
tgttgcgcag cggcaaaaag tgctccatgg tcgggacgct ctggccggtc aggcgcgcgc  10680
aatcgttgac gctctagacc gtgcaaaagg agagcctgta agcgggcact cttccgtggt  10740
ctggtggata aattcgcaag ggtatcatgg cggacgaccg gggttcgagc cccgtatccg  10800
gccgtccgcc gtgatccatg cggttaccgc ccgcgtgtcg aacccaggtg tgcgacgtca  10860
gacaacgggg gagtgctcct tttggcttcc ttccaggcgc ggcggctgct gcgctagctt  10920
ttttggccac tggccgcgcg cagcgtaagc ggttaggctg gaaagcgaaa gcattaagtg  10980
gctcgctccc tgtagccgga gggttatttt ccaagggttg agtcgcggga cccccggttc  11040
gagtctcgga ccggccggac tgcggcgaac gggggtttgc ctccccgtca tgcaagaccc  11100
cgcttgcaaa ttcctccgga aacagggacg agcccctttt ttgcttttcc cagatgcatc  11160
```

```
cggtgctgcg gcagatgcgc ccccctcctc agcagcggca agagcaagag cagcggcaga  11220
catgcagggc accctcccct cctcctaccg cgtcaggagg ggcgacatcc gcggttgacg  11280
cggcagcaga tggtgattac gaacccccgc ggcgccgggc ccggcactac ctggacttgg  11340
aggagggcga gggcctggcg cggctaggag cgccctctcc tgagcggtac ccaagggtgc  11400
agctgaagcg tgatacgcgt gaggcgtacg tgccgcggca gaacctgttt cgcgaccgcg  11460
agggagagga gcccgaggag atgcgggatc gaaagttcca cgcagggcgc gagctgcggc  11520
atggcctgaa tcgcgagcgg ttgctgcgcg aggaggactt tgagcccgac gcgcgaaccg  11580
ggattagtcc cgcgcgcgca cacgtggcgg ccgccgacct ggtaaccgca tacgagcaga  11640
cggtgaacca ggagattaac tttcaaaaaa gctttaacaa ccacgtgcgt acgcttgtgg  11700
cgcgcgagga ggtggctata ggactgatgc atctgtggga ctttgtaagc gcgctggagc  11760
aaaacccaaa tagcaagccg ctcatggcgc agctgttcct tatagtgcag cacagcaggg  11820
acaacgaggc attcagggat gcgctgctaa acatagtaga gcccgagggc cgctggctgc  11880
tcgatttgat aaacatcctg cagagcatag tggtgcagga gcgcagcttg agcctggctg  11940
acaaggtggc cgccatcaac tattccatgc ttagcctggg caagttttac gcccgcaaga  12000
tataccatac cccttacgtt cccatagaca aggaggtaaa gatcgagggg ttctacatgc  12060
gcatggcgct gaaggtgctt accttgagcg acgacctggg cgtttatcgc aacgagcgca  12120
tccacaaggc cgtgagcgtg agccggcggc gcgagctcag cgaccgcgag ctgatgcaca  12180
gcctgcaaag ggccctggct ggcacgggca gcggcgatag agaggccgag tcctactttg  12240
acgcgggcgc tgacctgcgc tgggccccaa gccgacgcgc cctggaggca gctggggccg  12300
gacctgggct ggcggtggca cccgcgcgcg ctggcaacgt cggcggcgtg gaggaatatg  12360
acgaggacga tgagtacgag ccagaggacg gcgagtacta agcggtgatg tttctgatca  12420
gatgatgcaa gacgcaacgg acccggcggt gcgggcggcg ctgcagagcc agccgtccgg  12480
ccttaactcc acggacgact ggcgccaggt catggaccgc atcatgtcgc tgactgcgcg  12540
caatcctgac gcgttccggc agcagccgca ggccaaccgg ctctccgcaa ttctggaagc  12600
ggtggtcccg gcgcgcgcaa accccacgca cgagaaggtg ctggcgatcg taaacgcgct  12660
ggccgaaaac agggccatcc ggcccgacga ggccggcctg gtctacgacg cgctgcttca  12720
gcgcgtggct cgttacaaca gcggcaacgt gcagaccaac ctggaccggc tggtggggga  12780
tgtgcgcgag gccgtggcgc agcgtgagcg cgcgcagcag cagggcaacc tgggctccat  12840
ggttgcacta aacgccttcc tgagtacaca gcccgccaac gtgccgcggg gacaggagga  12900
ctacaccaac tttgtgagcg cactgcggct aatggtgact gagacaccgc aaagtgaggt  12960
gtaccagtct gggccagact atttttttcca gaccagtaga caaggcctgc agaccgtaaa  13020
cctgagccag gctttcaaaa acttgcaggg gctgtggggg gtgcgggctc ccacaggcga  13080
ccgcgcgacc gtgtctagct tgctgacgcc caactcgcgc ctgttgctgc tgctaatagc  13140
gcccttcacg gacagtggca gcgtgtcccg ggacacatac ctaggtcact tgctgacact  13200
gtaccgcgag gccataggtc aggcgcatgt ggacgagcat actttccagg agattacaag  13260
tgtcagccgc gcgctggggc aggaggacac gggcagcctg gaggcaaccc taaactacct  13320
gctgaccaac cggcggcaga agatcccctc gttgcacagt ttaaacagcg aggaggagcg  13380
cattttgcgc tacgtgcagc agagcgtgag ccttaacctg atgcgcgacg gggtaacgcc  13440
cagcgtggcg ctggacatga ccgcgcgcaa catggaaccg ggcatgtatg cctcaaaccg  13500
gccgtttatc aaccgcctaa tggactactt gcatcgcgcg gccgccgtga accccgagta  13560
```

```
tttcaccaat gccatcttga acccgcactg gctaccgccc cctggtttct acaccggggg  13620
attcgaggtg cccgagggta acgatggatt cctctgggac gacatagacg acagcgtgtt  13680
ttccccgcaa ccgcagaccc tgctagagtt gcaacagcgc gagcaggcag aggcggcgct  13740
gcgaaaggaa agcttccgca ggccaagcag cttgtccgat ctaggcgctg cggccccgcg  13800
gtcagatgct agtagcccat ttccaagctt gatagggtct cttaccagca ctcgcaccac  13860
ccgcccgcgc ctgctgggcg aggaggagta cctaaacaac tcgctgctgc agccgcagcg  13920
cgaaaaaaac ctgcctccgg catttcccaa caacgggata gagagcctag tggacaagat  13980
gagtagatgg aagacgtacg cgcaggagca cagggacgtg ccaggcccgc gcccgcccac  14040
ccgtcgtcaa aggcacgacc gtcagcgggg tctggtgtgg gaggacgatg actcggcaga  14100
cgacagcagc gtcctggatt tgggagggag tggcaacccg tttgcgcacc ttcgccccag  14160
gctggggaga atgttttaaa aaaaaaaaag catgatgcaa aataaaaaac tcaccaaggc  14220
catggcaccg agcgttggtt ttcttgtatt ccccttagta tgcggcgcgc ggcgatgtat  14280
gaggaaggtc ctcctccctc ctacgagagt gtggtgagcg cggcgccagt ggcggcggcg  14340
ctgggttctc ccttcgatgc tcccctggac ccgccgtttg tgcctccgcg gtacctgcgg  14400
cctaccgggg ggagaaacag catccgttac tctgagttgg cacccctatt cgacaccacc  14460
cgtgtgtacc tggtggacaa caagtcaacg gatgtggcat ccctgaacta ccagaacgac  14520
cacagcaact ttctgaccac ggtcattcaa aacaatgact acagcccggg ggaggcaagc  14580
acacagacca tcaatcttga cgaccggtcg cactggggcg gcgacctgaa aaccatcctg  14640
cataccaaca tgccaaatgt gaacgagttc atgtttacca ataagtttaa ggcgcgggtg  14700
atggtgtcgc gcttgcctac taaggacaat caggtggagc tgaaatacga gtgggtggag  14760
ttcacgctgc ccgagggcaa ctactccgag accatgacca tagaccttat gaacaacgcg  14820
atcgtggagc actacttgaa agtgggcaga cagaacgggg ttctggaaag cgacatcggg  14880
gtaaagtttg acacccgcaa cttcagactg gggtttgacc ccgtcactgg tcttgtcatg  14940
cctggggtat atacaaacga agccttccat ccagacatca ttttgctgcc aggatgcggg  15000
gtggacttca cccacagccg cctgagcaac ttgttgggca tccgcaagcg gcaacccttc  15060
caggagggct ttaggatcac ctacgatgat ctggagggtg gtaacattcc cgcactgttg  15120
gatgtggacg cctaccaggc gagcttgaaa gatgacaccg aacagggcgg gggtggcgca  15180
ggcggcagca acagcagtgg cagcggcgcg gaagagaact ccaacgcggc agccgcggca  15240
atgcagccgg tggaggacat gaacgatcat gccattcgcg gcgacacctt tgccacacgg  15300
gctgaggaga agcgcgctga ggccgaagca gcggccgaag ctgccgcccc cgctgcgcaa  15360
cccgaggtcg agaagcctca gaagaaaccg gtgatcaaac ccctgacaga ggacagcaag  15420
aaacgcagtt acaacctaat aagcaatgac agcaccttca cccagtaccg cagctggtac  15480
cttgcataca actacggcga ccctcagacc ggaatccgct catggaccct gctttgcact  15540
cctgacgtaa cctgcggctc ggagcaggtc tactggtcgt tgccagacat gatgcaagac  15600
cccgtgacct tccgctccac gcgccagatc agcaactttc cggtggtggg cgccgagctg  15660
ttgcccgtgc actccaagag cttctacaac gaccaggccg tctactccca actcatccgc  15720
cagtttacct ctctgaccca cgtgttcaat cgctttcccg agaaccagat tttggcgcgc  15780
ccgccagccc ccaccatcac caccgtcagt gaaaacgttc ctgctctcac agatcacggg  15840
acgctaccgc tgcgcaacag catcggagga gtccagcgag tgaccattac tgacgccaga  15900
```

-continued

```
cgccgcacct gcccctacgt ttacaaggcc ctgggcatag tctcgccgcg cgtcctatcg  15960
agccgcactt tttgagcaag catgtccatc cttatatcgc ccagcaataa cacaggctgg  16020
ggcctgcgct tcccaagcaa gatgtttggc ggggccaaga agcgctccga ccaacaccca  16080
gtgcgcgtgc gcgggcacta ccgcgcgccc tggggcgcgc acaaacgcgg ccgcactggg  16140
cgcaccaccg tcgatgacgc catcgacgcg gtggtggagg aggcgcgcaa ctacacgccc  16200
acgccgccac cagtgtccac agtggacgcg gccattcaga ccgtggtgcg cggagcccgg  16260
cgctatgcta aaatgaagag acggcggagg cgcgtagcac gtcgccaccg ccgccgaccc  16320
ggcactgccg cccaacgcgc ggcggcggcc ctgcttaacc gcgcacgtcg caccggccga  16380
cgggcggcca tgcgggccgc tcgaaggctg gccgcgggta ttgtcactgt gccccccagg  16440
tccaggcgac gagcggccgc cgcagcagcc gcggccatta gtgctatgac tcagggtcgc  16500
aggggcaacg tgtattgggt gcgcgactcg gttagcggcc tgcgcgtgcc cgtgcgcacc  16560
cgcccccccgc gcaactagat tgcaagaaaa aactacttag actcgtactg ttgtatgtat  16620
ccagcggcgg cggcgcgcaa cgaagctatg tccaagcgca aaatcaaaga agagatgctc  16680
caggtcatcg cgccggagat ctatggcccc ccgaagaagg aagagcagga ttacaagccc  16740
cgaaagctaa agcgggtcaa aaagaaaaag aaagatgatg atgatgaact tgacgacgag  16800
gtggaactgc tgcacgctac cgcgcccagg cgacgggtac agtggaaagg tcgacgcgta  16860
aaacgtgttt tgcgacccgg caccaccgta gtctttacgc ccggtgagcg ctccacccgc  16920
acctacaagc gcgtgtatga tgaggtgtac ggcgacgagg acctgcttga gcaggccaac  16980
gagcgcctcg gggagtttgc ctacggaaag cggcataagg acatgctggc gttgccgctg  17040
gacgagggca acccaacacc tagcctaaag cccgtaacac tgcagcaggt gctgcccgcg  17100
cttgcaccgt ccgaagaaaa gcgcggccta aagcgcgagt ctggtgactt ggcacccacc  17160
gtgcagctga tggtacccaa gcgccagcga ctggaagatg tcttggaaaa aatgaccgtg  17220
gaacctgggc tggagcccga ggtccgcgtg cggccaatca agcaggtggc gccgggactg  17280
ggcgtgcaga ccgtggacgt tcagataccc actaccagta gcaccagtat tgccaccgcc  17340
acagagggca tggagacaca aacgtccccg gttgcctcag cggtggcgga tgccgcggtg  17400
caggcggtcg ctgcggccgc gtccaagacc tctacggagg tgcaaacgga cccgtggatg  17460
tttcgcgttt cagcccccccg gcgcccgcgc ggttcgagga agtacggcgc cgccagcgcg  17520
ctactgcccg aatatgccct acatccttcc attgcgccta cccccggcta tcgtggctac  17580
acctaccgcc ccagaagacg agcaactacc cgacgccgaa ccaccactgg aacccgccgc  17640
cgccgtcgcc gtcgccagcc cgtgctggcc ccgatttccg tgcgcagggt ggctcgcgaa  17700
ggaggcagga ccctggtgct gccaacagcg cgctaccacc ccagcatcgt ttaaaagccg  17760
gtctttgtgg ttcttgcaga tatggccctc acctgccgcc tccgtttccc ggtgccggga  17820
ttccgaggaa gaatgcaccg taggaggggc atggccggcc acggcctgac gggcggcatg  17880
cgtcgtgcgc accaccggcg gcggcgcgcg tcgcaccgtc gcatgcgcgg cggtatcctg  17940
cccctcctta ttccactgat cgccgcggcg attggcgccg tgcccggaat tgcatccgtg  18000
gccttgcagg cgcagagaca ctgattaaaa acaagttgca tgtggaaaaa tcaaaataaa  18060
aagtctggac tctcacgctc gcttggtcct gtaactattt tgtagaatgg aagacatcaa  18120
ctttgcgtct ctggccccgc gacacggctc gcgcccgttc atgggaaact ggcaagatat  18180
cggcaccagc aatatgagcg gtggcgcctt cagctggggc tcgctgtgga gcggcattaa  18240
aaatttcggt tccaccgtta agaactatgg cagcaaggcc tggaacagca gcacaggcca  18300
```

```
gatgctgagg gataagttga aagagcaaaa tttccaacaa aaggtggtag atggcctggc  18360
ctctggcatt agcggggtgg tggacctggc caaccaggca gtgcaaaata agattaacag  18420
taagcttgat ccccgccctc ccgtagagga gcctccaccg gccgtggaga cagtgtctcc  18480
agaggggcgt ggcgaaaagc gtccgcgccc cgacagggaa gaaactctgg tgacgcaaat  18540
agacgagcct ccctcgtacg aggaggcact aaagcaaggc ctgcccacca cccgtcccat  18600
cgcgcccatg gctaccggag tgctgggcca gcacacaccc gtaacgctgg acctgcctcc  18660
ccccgccgac acccagcaga aacctgtgct gccaggcccg accgccgttg ttgtaacccg  18720
tcctagccgc gcgtccctgc gccgcgccgc cagcggtccg cgatcgttgc ggcccgtagc  18780
cagtggcaac tggcaaagca cactgaacag catcgtgggt ctgggggtgc aatccctgaa  18840
gcgccgacga tgcttctgaa tagctaacgt gtcgtatgtg tgtcatgtat gcgtccatgt  18900
cgccgccaga ggagctgctg agccgccgcg cgcccgcttt ccaagatggc taccccttcg  18960
atgatgccgc agtggtctta catgcacatc tcgggccagg acgcctcgga gtacctgagc  19020
cccgggctgg tgcagtttgc ccgcgccacc gagacgtact tcagcctgaa taacaagttt  19080
agaaacccca cggtggcgcc tacgcacgac gtgaccacag accggtccca gcgtttgacg  19140
ctgcggttca tccctgtgga ccgtgaggat actgcgtact cgtacaaggc gcggttcacc  19200
ctagctgtgg gtgataaccg tgtgctggac atggcttcca cgtactttga catccgcggc  19260
gtgctggaca ggggccctac ttttaagccc tactctggca ctgcctacaa cgccctggct  19320
cccaagggtg ccccaaatcc ttgcgaatgg gatgaagctg ctactgctct tgaaataaac  19380
ctagaagaag aggacgatga caacgaagac gaagtagacg agcaagctga gcagcaaaaa  19440
actcacgtat ttgggcaggc gccttattct ggtataaata ttacaaagga gggtattcaa  19500
ataggtgtcg aaggtcaaac acctaaatat gccgataaaa catttcaacc tgaacctcaa  19560
ataggagaat ctcagtggta cgaaactgaa attaatcatg cagctgggag agtccttaaa  19620
aagactaccc caatgaaacc atgttacggt tcatatgcaa aacccacaaa tgaaaatgga  19680
gggcaaggca ttcttgtaaa gcaacaaaat ggaaagctag aaagtcaagt ggaaatgcaa  19740
tttttctcaa ctactgaggc gaccgcaggc aatggtgata acttgactcc taaagtggta  19800
ttgtacagtg aagatgtaga tatagaaacc ccagacactc atatttctta catgcccact  19860
attaaggaag gtaactcacg agaactaatg ggccaacaat ctatgcccaa caggcctaat  19920
tacattgctt ttagggacaa ttttattggt ctaatgtatt acaacagcac gggtaatatg  19980
ggtgttctgg cgggccaagc atcgcagttg aatgctgttg tagatttgca agacagaaac  20040
acagagcttt cataccagct tttgcttgat tccattggtg atagaaccag gtacttttct  20100
atgtggaatc aggctgttga cagctatgat ccagatgtta gaattattga aaatcatgga  20160
actgaagatg aacttccaaa ttactgcttt ccactgggag gtgtgattaa tacagagact  20220
cttaccaagg taaaacctaa aacaggtcag gaaaatggat gggaaaaaga tgctacagaa  20280
ttttcagata aaaatgaaat aagagttgga aataatttg ccatggaaat caatctaaat  20340
gccaacctgt ggagaaattt cctgtactcc aacatagcgc tgtatttgcc cgacaagcta  20400
aagtacagtc cttccaacgt aaaaatttct gataacccaa acacctacga ctacatgaac  20460
aagcgagtgg tggctcccgg gttagtggac tgctacatta accttggagc acgctggtcc  20520
cttgactata tggacaacgt caacccattt aaccaccacc gcaatgctgg cctgcgctac  20580
cgctcaatgt tgctgggcaa tggtcgctat gtgcccttcc acatccaggt gcctcagaag  20640
```

```
ttctttgcca ttaaaaacct ccttctcctg ccgggctcat acacctacga gtggaacttc  20700
aggaaggatg ttaacatggt tctgcagagc tccctaggaa atgacctaag ggttgacgga  20760
gccagcatta agtttgatag catttgcctt tacgccacct tcttccccat ggcccacaac  20820
accgcctcca cgcttgaggc catgcttaga aacgacacca acgaccagtc ctttaacgac  20880
tatctctccg ccgccaacat gctctaccct atacccgcca acgctaccaa cgtgcccata  20940
tccatcccct cccgcaactg ggcggctttc cgcggctggg ccttcacgcg ccttaagact  21000
aaggaaaccc catcactggg ctcgggctac gacccttatt acacctactc tggctctata  21060
ccctacctag atggaacctt ttacctcaac cacaccttta agaaggtggc cattaccttt  21120
gactcttctg tcagctggcc tggcaatgac cgcctgctta cccccaacga gtttgaaatt  21180
aagcgctcag ttgacgggga gggttacaac gttgcccagt gtaacatgac caaagactgg  21240
ttcctggtac aaatgctagc taactacaac attggctacc agggcttcta tatcccagag  21300
agctacaagg accgcatgta ctccttcttt agaaacttcc agcccatgag ccgtcaggtg  21360
gtggatgata ctaaatacaa ggactaccaa caggtgggca tcctacacca acacaacaac  21420
tctggatttg ttggctacct tgcccccacc atgcgcgaag gacaggccta ccctgctaac  21480
ttcccctatc cgcttatagg caagaccgca gttgacagca ttacccagaa aaagtttctt  21540
tgcgatcgca ccctttggcg catcccattc tccagtaact ttatgtccat gggcgcactc  21600
acagacctgg gccaaaacct tctctacgcc aactccgccc acgcgctaga catgactttt  21660
gaggtggatc ccatggacga gcccaccctt ctttatgttt tgtttgaagt ctttgacgtg  21720
gtccgtgtgc accggccgca ccgcggcgtc atcgaaaccg tgtacctgcg cacgcccttc  21780
tcggccggca acgccacaac ataaagaagc aagcaacatc aacaacagct gccgccatgg  21840
gctccagtga gcaggaactg aaagccattg tcaaagatct tggttgtggg ccatattttt  21900
tgggcaccta tgacaagcgc tttccaggct ttgtttctcc acacaagctc gcctgcgcca  21960
tagtcaatac ggccggtcgc gagactgggg gcgtacactg gatggccttt gcctggaacc  22020
cgcactcaaa aacatgctac ctctttgagc cctttggctt ttctgaccag cgactcaagc  22080
aggtttacca gtttgagtac gagtcactcc tgcgccgtag cgccattgct tcttcccccg  22140
accgctgtat aacgctggaa aagtccaccc aaagcgtaca ggggcccaac tcggccgcct  22200
gtggactatt ctgctgcatg tttctccacg cctttgccaa ctggccccaa actcccatgg  22260
atcacaaccc caccatgaac cttattaccg gggtacccaa ctccatgctc aacagtcccc  22320
aggtacagcc caccctgcgt cgcaaccagg aacagctcta cagcttcctg gagcgccact  22380
cgccctactt ccgcagccac agtgcgcaga ttaggagcgc cacttctttt tgtcacttga  22440
aaaacatgta aaaataatgt actagagaca ctttcaataa aggcaaatgc ttttatttgt  22500
acactctcgg gtgattattt acccccaccc ttgccgtctg cgccgtttaa aaatcaaagg  22560
ggttctgccg cgcatcgcta tgcgccactg gcagggacac gttgcgatac tggtgtttag  22620
tgctccactt aaactcaggc acaaccatcc gcggcagctc ggtgaagttt tcactccaca  22680
ggctgcgcac catcaccaac gcgtttagca ggtcgggcgc cgatatcttg aagtcgcagt  22740
tggggcctcc gccctgcgcg cgcgagttgc gatacacagg gttgcagcac tggaacacta  22800
tcagcgccgg gtggtgcacg ctggccagca cgctcttgtc ggagatcaga tccgcgtcca  22860
ggtcctccgc gttgctcagg gcgaacggag tcaactttgg tagctgcctt cccaaaaagg  22920
gcgcgtgccc aggctttgag ttgcactcgc accgtagtgg catcaaaagg tgaccgtgcc  22980
cggtctgggc gttaggatac agcgcctgca taaaagcctt gatctgctta aaagccacct  23040
```

```
gagcctttgc gccttcagag aagaacatgc cgcaagactt gccggaaaac tgattggccg  23100
gacaggccgc gtcgtgcacg cagcaccttg cgtcggtgtt ggagatctgc accacatttc  23160
ggccccaccg gttcttcacg atcttggcct tgctagactg ctccttcagc gcgcgctgcc  23220
cgttttcgct cgtcacatcc atttcaatca cgtgctcctt atttatcata atgcttccgt  23280
gtagacactt aagctcgcct tcgatctcag cgcagcggtg cagccacaac gcgcagcccg  23340
tgggctcgtg atgcttgtag gtcacctctg caaacgactg caggtacgcc tgcaggaatc  23400
gccccatcat cgtcacaaag gtcttgttgc tggtgaaggt cagctgcaac ccgcggtgct  23460
cctcgttcag ccaggtcttg catacggccg ccagagcttc cacttggtca ggcagtagtt  23520
tgaagttcgc ctttagatcg ttatccacgt ggtacttgtc catcagcgcg cgcgcagcct  23580
ccatgccctt ctcccacgca gacacgatcg gcacactcag cgggttcatc accgtaattt  23640
cactttccgc ttcgctgggc tcttcctctt cctcttgcgt ccgcatacca cgcgccactg  23700
ggtcgtcttc attcagccgc cgcactgtgc gcttacctcc tttgccatgc ttgattagca  23760
ccggtgggtt gctgaaaccc accatttgta gcgccacatc ttctctttct tcctcgctgt  23820
ccacgattac ctctggtgat ggcgggcgct cgggcttggg agaagggcgc ttcttttttct  23880
tcttgggcgc aatggccaaa tccgccgccg aggtcgatgg ccgcgggctg ggtgtgcgcg  23940
gcaccagcgc gtcttgtgat gagtcttcct cgtcctcgga ctcgatacgc cgcctcatcc  24000
gctttttttgg gggcgcccgg ggaggcggcg gcgacgggga cggggacgac acgtcctcca  24060
tggttggggg acgtcgcgcc gcaccgcgtc cgcgctcggg ggtggtttcg cgctgctcct  24120
cttcccgact ggccatttcc ttctcctata ggcagaaaaa gatcatggag tcagtcgaga  24180
agaaggacag cctaaccgcc ccctctgagt tcgccaccac cgcctccacc gatgccgcca  24240
acgcgcctac caccttcccc gtcgaggcac ccccgcttga ggaggaggaa gtgattatcg  24300
agcaggaccc aggttttgta agcgaagacg acgaggaccg ctcagtacca acagaggata  24360
aaaagcaaga ccaggacaac gcagaggcaa acgaggaaca agtcgggcgg ggggacgaaa  24420
ggcatggcga ctacctagat gtgggagacg acgtgctgtt gaagcatctg cagcgccagt  24480
gcgccattat ctgcgacgcg ttgcaagagc gcagcgatgt gcccctcgcc atagcggatg  24540
tcagccttgc ctacgaacgc cacctattct caccgcgcgt acccccccaaa cgccaagaaa  24600
acggcacatg cgagcccaac ccgcgcctca acttctaccc cgtatttgcc gtgccagagg  24660
tgcttgccac ctatcacatc tttttccaaa actgcaagat accccctatcc tgccgtgcca  24720
accgcagccg agcggacaag cagctggcct tgcggcaggg cgctgtcata cctgatatcg  24780
cctcgctcaa cgaagtgcca aaaatctttg agggtcttgg acgcgacgag aagcgcgcgg  24840
caaacgctct gcaacaggaa aacagcgaaa atgaaagtca ctctggagtg ttggtggaac  24900
tcgagggtga caacgcgcgc ctagccgtac taaaacgcag catcgaggtc acccactttg  24960
cctacccggc acttaaccta ccccccaagg tcatgagcac agtcatgagt gagctgatcg  25020
tgcgccgtgc gcagcccctg gagagggatg caaatttgca agaacaaaca gaggagggcc  25080
tacccgcagt tggcgacgag cagctagcgc gctggcttca aacgcgcgag cctgccgact  25140
tggaggagcg acgcaaacta atgatggccg cagtgctcgt taccgtggag cttgagtgca  25200
tgcagcggtt ctttgctgac ccggagatgc agcgcaagct agaggaaaca ttgcactaca  25260
cctttcgaca gggctacgta cgccaggcct gcaagatctc caacgtggag ctctgcaacc  25320
tggtctccta ccttggaatt ttgcacgaaa accgccttgg gcaaaacgtg cttcattcca  25380
```

```
cgctcaaggg cgaggcgcgc cgcgactacg tccgcgactg cgtttactta tttctatgct  25440
acacctggca gacggccatg ggcgtttggc agcagtgctt ggaggagtgc aacctcaagg  25500
agctgcagaa actgctaaag caaaacttga aggacctatg gacggccttc aacgagcgct  25560
ccgtggccgc gcacctggcg gacatcattt tccccgaacg cctgcttaaa accctgcaac  25620
agggtctgcc agacttcacc agtcaaagca tgttgcagaa ctttaggaac tttatcctag  25680
agcgctcagg aatcttgccc gccacctgct gtgcacttcc tagcgacttt gtgcccatta  25740
agtaccgcga atgccctccg ccgctttggg gccactgcta ccttctgcag ctagccaact  25800
accttgccta ccactctgac ataatggaag acgtgagcgg tgacggtcta ctggagtgtc  25860
actgtcgctg caacctatgc accccgcacc gctccctggt ttgcaattcg cagctgctta  25920
acgaaagtca aattatcggt acctttgagc tgcagggtcc ctcgcctgac gaaaagtccg  25980
cggctccggg gttgaaactc actccggggc tgtggacgtc ggcttacctt cgcaaatttg  26040
tacctgagga ctaccacgcc cacgagatta ggttctacga agaccaatcc cgcccgccaa  26100
atgcggagct taccgcctgc gtcattaccc agggccacat tcttggccaa ttgcaagcca  26160
tcaacaaagc ccgccaagag tttctgctac gaaagggacg gggggtttac ttggaccccc  26220
agtccggcga ggagctcaac ccaatccccc cgccgccgca gccctatcag cagcagccgc  26280
gggcccttgc ttcccaggat ggcacccaaa aagaagctgc agctgccgcc gccacccacg  26340
gacgaggagg aatactggga cagtcaggca gaggaggttt tggacgagga ggaggaggac  26400
atgatggaag actgggagag cctagacgag gaagcttccg aggtcgaaga ggtgtcagac  26460
gaaacaccgt caccctcggt cgcattcccc tcgccggcgc cccagaaatc ggcaaccggt  26520
tccagcatgg ctacaacctc cgctcctcag gcgccgccgg cactgcccgt tcgccgaccc  26580
aaccgtagat gggacaccac tggaaccagg gccggtaagt ccaagcagcc gccgccgtta  26640
gcccaagagc aacaacagcg ccaaggctac cgctcatggc gcgggcacaa gaacgccata  26700
gttgcttgct tgcaagactg tgggggcaac atctccttcg cccgccgctt tcttctctac  26760
catcacggcg tggccttccc ccgtaacatc ctgcattact accgtcatct ctacagccca  26820
tactgcaccg gcggcagcgg cagcggcagc aacagcagcg gccacacaga agcaaaggcg  26880
accggatagc aagactctga caaagcccaa gaaatccaca gcggcggcag cagcaggagg  26940
aggagcgctg cgtctggcgc ccaacgaacc cgtatcgacc cgcgagctta gaaacaggat  27000
ttttcccact ctgtatgcta tatttcaaca gagcaggggc caagaacaag agctgaaaat  27060
aaaaaacagg tctctgcgat ccctcacccg cagctgcctg tatcacaaaa gcgaagatca  27120
gcttcggcgc acgctggaag acgcggaggc tctcttcagt aaatactgcg cgctgactct  27180
taaggactag tttcgcgccc tttctcaaat ttaagcgcga aaactacgtc atctccagcg  27240
gccacacccg gcgccagcac ctgtcgtcag cgccattatg agcaaggaaa ttcccacgcc  27300
ctacatgtgg agttaccagc cacaaatggg acttgcggct ggagctgccc aagactactc  27360
aacccgaata aactacatga gcgcgggacc ccacatgata tcccgggtca acggaatccg  27420
cgcccaccga aaccgaattc tcttggaaca ggcggctatt accaccacac ctcgtaataa  27480
ccttaatccc cgtagttggc ccgctgccct ggtgtaccag gaaagtcccg ctcccaccac  27540
tgtggtactt cccagagacg cccaggccga agttcagatg actaactcag gggcgcagct  27600
tgcgggcggc tttcgtcaca gggtgcggtc gcccgggcag ggtataactc acctgacaat  27660
cagagggcga ggtattcagc tcaacgacga gtcggtgagc tcctcgcttg gtctccgtcc  27720
ggacgggaca tttcagatcg gcggcgccgg ccgctcttca ttcacgcctc gtcaggcaat  27780
```

```
cctaactctg cagacctcgt cctctgagcc gcgctctgga ggcattggaa ctctgcaatt  27840
tattgaggag tttgtgccat cggtctactt taaccccttc tcgggacctc ccggccacta  27900
tccggatcaa tttattccta actttgacgc ggtaaaggac tcggcggatg gctacgactg  27960
aatgttaagt ggagaggcag agcaactgcg cctgaaacac ctggtccact gtcgccgcca  28020
caagtgcttt gcccgcgact ccggtgagtt ttgctacttt gaattgcccg aggatcatat  28080
cgagggcccg gcgcacggcg tccggcttac cgcccaggga gagcttgccc gtagcctgat  28140
tcgggagttt acccagcgcc ccctgctagt tgagcgggac aggggaccct gtgttctcac  28200
tgtgatttgc aactgtccta accctggatt acatcaagat ctttgttgcc atctctgtgc  28260
tgagtataat aaatacagaa attaaaatat actggggctc ctatcgccat cctgtaaacg  28320
ccaccgtctt cacccgccca agcaaaccaa ggcgaacctt acctggtact tttaacatct  28380
ctccctctgt gatttacaac agtttcaacc cagacggagt gagtctacga gagaacctct  28440
ccgagctcag ctactccatc agaaaaaaca ccaccctcct tacctgccgg gaacgtacga  28500
tgtggctgca gagcctgctg ctcttgggca ctgtggcctg cagcatctct gcacccgccc  28560
gctcgcccag ccccagcacg cagccctggg agcatgtgaa tgccatccag gaggcccggc  28620
gtctcctgaa cctgagtaga gacactgctg ctgagatgaa tgaaacagta gaagtcatct  28680
cagaaatgtt tgacctccag gagccgacct gcctacagac ccgcctggag ctgtacaagc  28740
agggcctgcg gggcagcctc accaagctca agggcccctt gaccatgatg gccagccact  28800
acaagcagca ctgccctcca accccggaaa cttcctgtgc aacccagact atcacctttg  28860
aaagtttcaa agagaacctg aaggactttc tgcttgtcat cccctttgac tgctgggagc  28920
cagtccagga gtgacaattg actctatgtg ggatatgctc cagcgctaca accttgaagt  28980
caggcttcct ggatgtcagc atctgacttt ggccatgaat tccatatgtc gtcgttttcg  29040
gcgcgcgccg aaattcgtcg ttttcggcgc gcgccgaaat tcgtcgtttt cggcgcgcgc  29100
cgaaatttcg tcgtcgttcg aacgacgttg ataaatttcg tcgtcgttcg aacgacgttg  29160
ataaatttcg tcgtcgttcg aacgacgttg atcatatgaa gtggccagca cctgtcccgc  29220
ggatttgttc cagtccaact acagcgaccc accctaacag agatgaccaa cacaaccaac  29280
gcggccgccg ctaccggact tacatctacc acaaatacac cccaagtttc tgcctttgtc  29340
aataactggg ataacttggg catgtggtgg ttctccatag cgcttatgtt tgtatgcctt  29400
attattatgt ggctcatctg ctgcctaaag cgcaaacgcg cccgaccacc catctatagt  29460
cccatcattg tgctacaccc aaacaatgat ggaatccata gattggacgg actgaaacac  29520
atgttctttt ctcttacagt atgattaaat gagacatgat tcctcgagtt tttatattac  29580
tgacccttgt tgcgcttttt tgtgcgtgct ccacattggc tgcggtttct cacatcgaag  29640
tagactgcat tccagccttc acagtctatt tgctttacgg atttgtcacc ctcacgctca  29700
tctgcagcct catcactgtg gtcatcgcct ttatccagtg cattgactgg gtctgtgtgc  29760
gctttgcata tctcagacac catccccagt acagggacag gactatagct gagcttctta  29820
gaattcttta attatgaaat ttactgtgac ttttctgctg attatttgca ccctatctgc  29880
gttttgttcc ccgacctcca agcctcaaag acatatatca tgcagattca ctcgtatatg  29940
gaatattcca agttgctaca atgaaaaaag cgatctttcc gaagcctggt tatatgcaat  30000
catctctgtt atggtgttct gcagtaccat cttagcccta gctatatatc cctaccttga  30060
cattggctgg aaacgaatag atgccatgaa ccacccaact ttccccgcgc ccgctatgct  30120
```

```
tccactgcaa caagttgttg ccggcggctt tgtcccagcc aatcagcctc gccccacttc  30180
tcccaccccc actgaaatca gctactttaa tctaacagga ggagatgact gacaccctag  30240
atctagaaat ggacggaatt attacagagc agcgcctgct agaaagacgc agggcagcgg  30300
ccgagcaaca gcgcatgaat caagagctcc aagacatggt taacttgcac cagtgcaaaa  30360
ggggtatctt ttgtctggta aagcaggcca aagtcaccta cgacagtaat accaccggac  30420
accgccttag ctacaagttg ccaaccaagc gtcagaaatt ggtggtcatg gtgggagaaa  30480
agcccattac cataactcag cactcggtag aaaccgaagg ctgcattcac tcaccttgtc  30540
aaggacctga ggatctctgc acccttatta agaccctgtg cggtctcaaa gatcttattc  30600
cctttaacta ataaaaaaaa ataataaagc atcacttact taaaatcagt tagcaaattt  30660
ctgtccagtt tattcagcag cacctccttg ccctcctccc agctctggta ttgcagcttc  30720
ctcctggctg caaactttct ccacaatcta aatggaatgt cagtttcctc ctgttcctgt  30780
ccatccgcac ccactatctt catgttgttg cagatgaagc gcgcaagacc gtctgaagat  30840
accttcaacc ccgtgtatcc atatgacacg gaaaccggtc ctccaactgt gccttttctt  30900
actcctccct ttgtatcccc caatgggttt caagagagtc cccctggggt actctctttg  30960
cgcctatccg aacctctagt tacctccaat ggcatgcttg cgctcaaaat gggcaacggc  31020
ctctctctgg acgaggccgg caaccttacc tcccaaaatg taaccactgt gagcccacct  31080
ctcggagccg gagcctcaaa cataaacctg gaaatatctg cacccctcac agttacctca  31140
gaagccctaa ctgtggctgc cgccgcacct ctaatggtcg cgggcaacac actcaccatg  31200
caatcacagg ccccgctaac cgtgcacgac tccaaactta gcattgccac ccaaggaccc  31260
ctcacagtgt cagaaggaaa gctagccctg caaacatcag gcccccctcac caccaccgat  31320
agcagtaccc ttactatcac tgcctcaccc cctctaacta ctgccactgg tagcttgggc  31380
attgacttga aagagcccat ttatacacaa aatggaaaac taggactaaa gtacggggct  31440
cctttgcatg taacagacga cctaaacact ttgaccgtag caactggtcc aggtgtgact  31500
attaataata cttccttgca aactaaagtt actggagcct tgggttttga ttcacaaggc  31560
aatatgcaac ttaatgtagc aggaggacta aggattgatt ctcaaaacag acgccttata  31620
cttgatgtta gttatccgtt tgatgctcaa aaccaactaa atctaagact aggacagggc  31680
cctcttttta taaactcagc ccacaacttg gatattaact acaacaaagg cctttacttg  31740
tttacagctt caaacaattc caaaaagctt gaggttaacc taagcactgc caaggggttg  31800
atgtttgacg ctacagccat agccattaat gcaggagatg ggcttgaatt tggttcacct  31860
aatgcaccaa acacaaatcc cctcaaaaca aaaattggcc atggcctaga atttgattca  31920
aacaaggcta tggttcctaa actaggaact ggccttagtt ttgacagcac aggtgccatt  31980
acagtaggaa acaaaaataa tgataagcta accctatgga caggtccaaa accagaagcc  32040
aactgcataa ttgaatacgg gaaacaaaac ccagatagca aactaacttt aatccttgta  32100
aaaaatggag gaattgttaa tggatatgta acgctaatgg gagcctcaga ctacgttaac  32160
accttattta aaaacaaaaa tgtctccatt aatgtagaac tatactttga tgccactggt  32220
catatattac cagactcatc ttctcttaaa acagatctag aactaaaata caagcaaacc  32280
gctgacttta gtgcaagagg ttttatgcca agtactacag cgtatccatt tgtccttcct  32340
aatgcgggaa cacataatga aaattatatt tttggtcaat gctactacaa agcaagcgat  32400
ggtgcccttt ttccgttgga agttactgtt atgcttaata aacgcctgcc agatagtcgc  32460
acatcctatg ttatgacttt tttatggtcc ttgaatgctg gtctagctcc agaaactact  32520
```

```
caggcaaccc tcataacctc cccatttacc ttttcctata ttagagaaga tgactaataa  32580
actctaaaga atcgtttgtg ttatgtttca acgtgtttat ttttcaattg cagaaaattt  32640
caagtcattt ttcattcagt agtatagccc caccaccaca tagcttatac agatcaccgt  32700
accttaatca aactcacaga accctagtat tcaacctgcc acctccctcc caacacacag  32760
agtacacagt cctttctccc cggctggcct taaaaagcat catatcatgg gtaacagaca  32820
tattcttagg tgttatattc cacacggttt cctgtcgagc caaacgctca tcaagtgata  32880
ttaataaact ccccgggcag ctcacttaag ttcatgtcgc tgtccagctg ctgagccaca  32940
ggctgctgtc caacttgcgg ttgcttaacg ggcggcgaag gagaagtcca cgcctacatg  33000
gggggagagt cataatcgtg catcaggata gggcggtggt gctgcagcag cgcgcgaata  33060
aactgctgcc gccgccgctc cgtcctgcag gaatacaaca tggcagtggt ctcctcagcg  33120
atgattcgca ccgcccgcag cataaggcgc cttgtcctcc gggcacagca gcgcaccctg  33180
atctcactta aatcagcaca gtaactgcag cacagcacca caatattgtt caaaatccca  33240
cagtgcaagg cgctgtatcc aaagctcatg gcggggacca cagaacccac gtggccatca  33300
taccacaagc gcaggtagat taagtggcga cccctcataa acacgctgga cataaacatt  33360
acctcttttg gcatgttgta attcaccacc tcccggtacc atataaacct ctgattaaac  33420
atggcgccat ccaccaccat cctaaaccag ctggccaaaa cctgccccgc cgggntatac  33480
actgcaggga accgggactg gaacaatgac agtggagagc ccaggactcg taaccatgga  33540
tcatcatgct cgtcatgata tcaatgttgg cacaacacag gcacacgtgc atacacttcc  33600
tcaggattac aagctcctcc cgcgttagaa ccatatccca gggaacaacc cattcctgaa  33660
tcagcgtaaa tcccacactg cagggaagac ctcgcacgta actcacgttg tgcattgtca  33720
aagtgttaca ttcgggcagc agcggatgat cctccagtat ggtagcgcgg gtttctgtct  33780
caaaaggagg tagacgatcc ctactgtacg gagtgcgccg agacaaccga gatcgtgttg  33840
gtcgtagtgt catgccaaat ggaacgccgg acgtagtcat atttcctgaa gcaaaaccag  33900
gtgcgggcgt gacaaacaga tctgcgtctc cggtctcgcc gcttagatcg ctctgtgtag  33960
tagttgtagt atatccactc tctcaaagca tccaggcgcc ccctggcttc gggttctatg  34020
taaactcctt catgcgccgc tgccctgata acatccacca ccgcagaata agccacaccc  34080
agccaaccta cacattcgtt ctgcgagtca cacacgggag gagcgggaag agctggaaga  34140
accatgtttt tttttttatt ccaaaagatt atccaaaacc tcaaaatgaa gatctattaa  34200
gtgaacgcgc tcccctccgg tggcgtggtc aaactctaca gccaaagaac agataatggc  34260
atttgtaaga tgttgcacaa tggcttccaa aaggcaaacg gccctcacgt ccaagtggac  34320
gtaaaggcta aacccttcag ggtgaatctc ctctataaac attccagcac cttcaaccat  34380
gcccaaataa ttctcatctc gccaccttct caatatatct ctaagcaaat cccgaatatt  34440
aagtccggcc attgtaaaaa tttggctcca gagcgccctc caccttcagc ctcaagcagc  34500
gaatcatgat tgcaaaaatt caggttcctc acagacctgt ataagattca aaagcggaac  34560
attaacaaaa ataccgcgat cccgtaggtc ccttcgcagg gccagctgaa cataatcgtg  34620
caggtctgca cggaccagcg cggccacttc cccgccagga accatgacaa aagaacccac  34680
actgattatg acacgcatac tcggagctat gctaaccagc gtagccccga tgtaagcttg  34740
ttgcatgggc ggcgatataa aatgcaaggt gctgctcaaa aaatcaggca aagcctcgcg  34800
caaaaaagaa agcacatcgt agtcatgctc atgcagataa aggcaggtaa gctccggaac  34860
```

caccacagaa aaagacacca tttttctctc aaacatgtct gcgggtttct gcataaacac 34920
aaaataaaat aacaaaaaaa catttaaaca ttagaagcct gtcttacaac aggaaaaaca 34980
acccttataa gcataagacg gactacggcc atgccggcgt gaccgtaaaa aaactggtca 35040
ccgtgattaa aaagcaccac cgacagctcc tcggtcatgt ccggagtcat aatgtaagac 35100
tcggtaaaca catcaggttg attcacatcg gtcagtgcta aaaagcgacc gaaatagccc 35160
gggggaatac atacccgcag gcgtagagac aacattacag cccccatagg aggtataaca 35220
aaattaatag gagagaaaaa cacataaaca cctgaaaaac cctcctgcct aggcaaaata 35280
gcaccctccc gctccagaac aacatacagc gcttccacag cggcagccat aacagtcagc 35340
cttaccagta aaaaagaaaa cctattaaaa aaacaccact cgacacggca ccagctcaat 35400
cagtcacagt gtaaaaaagg gccaagtgca gagcgagtat atataggact aaaaaatgac 35460
gtaacggtta aagtccacaa aaaacaccca gaaaaccgca cgcgaaccta cgcccagaaa 35520
cgaaagccaa aaaacccaca acttcctcaa atcgtcactt ccgttttccc acgttacgtc 35580
acttcccatt ttaagaaaac tacaattccc aacacataca agttactccg ccctaaaacc 35640
tacgtcaccc gccccgttcc cacgccccgc gccacgtcac aaactccacc ccctcattat 35700
catattggct tcaatccaaa ataaggtata ttattgatga tgtta 35745

<210> SEQ ID NO 8
<211> LENGTH: 9794
<212> TYPE: DNA
<213> ORGANISM: Artificial Sequence
<220> FEATURE:
<223> OTHER INFORMATION: The nucleotide sequence encoding plasmid pE2F.E1.D24
<220> FEATURE:
<221> NAME/KEY: misc_feature
<222> LOCATION: (5859)..(5861)
<223> OTHER INFORMATION: n is a, c, g, or t
<220> FEATURE:
<221> NAME/KEY: misc_feature
<222> LOCATION: (5876)..(5878)
<223> OTHER INFORMATION: n is a, c, g, or t
<220> FEATURE:
<221> NAME/KEY: misc_feature
<222> LOCATION: (6861)..(6863)
<223> OTHER INFORMATION: n is a, c, g, or t
<220> FEATURE:
<221> NAME/KEY: misc_feature
<222> LOCATION: (6878)..(6880)
<223> OTHER INFORMATION: n is a, c, g, or t
<220> FEATURE:
<221> NAME/KEY: misc_feature
<222> LOCATION: (8181)..(8186)
<223> OTHER INFORMATION: n is a, c, g, or t

<400> SEQUENCE: 8
ttttggattg aagccaatat gataatgagg gggtggagtt tgtgacgtgg cgcggggcgt 60
gggaacgggg cgggtgacgt agtagtgtgg cggaagtgtg atgttgcaag tgtggcggaa 120
cacatgtaag cgacggatgt ggcaaaagtg acgtttttgg tgtgcgccgg tgtacacagg 180
aagtgacaat tttcgcgcgg ttttaggcgg atgttgtagt aaatttgggc gtaaccgagt 240
aagatttggc cattttcgcg ggaaaactga ataagaggaa gtgaaatctg aataattttg 300
tgttactcat agcgcgtaat actggtaccg cggccgctgg taccatccgg acaaagcctg 360
cgcgcgcccc gccccgccat tggccgtacc gccccgcgcc gccgccccat cccgcccctc 420
gccgccgggt ccggcgcgtt aaagccaata ggaaccgccg ccgttgttcc cgtcacggcc 480
ggggcagcca attgtggcgg cgctcggcgg ctcgtggctc tttcgcggca aaaaggattt 540

```
ggcgcgtaaa agtggccggg actttgcagg cagcggcggc cgggggcgga gcgggatcga    600
gccctcgccc tcgagctaga agcttgtttt ctcctccgag ccgctccgac accgggactg    660
aaaatgagac atattatctg ccacggaggt gttattaccg aagaaatggc cgccagtctt    720
ttggaccagc tgatcgaaga ggtactggct gataatcttc cacctcctag ccattttgaa    780
ccacctaccc ttcacgaact gtatgattta gacgtgacgg cccccgaaga tcccaacgag    840
gaggcggttt cgcagatttt tcccgactct gtaatgttgg cggtgcagga agggattgac    900
ttactcactt ttccgccggc gcccggttct ccggccggag ccgcctcacc tttcccggca    960
gcccgagcag ccggagcaga gagccttggg tccggtttct atgccaaacc ttgtaccgga   1020
ggtgatcgat ccacccagtg acgacgagga tgaagagggt gaggagtttg tgttagatta   1080
tgtggagcac ccccgggcacg gttgcaggtc ttgtcattat caccggagga atacggggga   1140
cccagatatt atgtgttcgc tttgctatat gaggacctgt ggcatgtttg tctacagtaa   1200
gtgaaaatta tgggcagtgg gtgatagagt ggtgggtttg gtgtggtaat tttttttta    1260
atttttacag ttttgtggtt taaagaattt tgtattgtga tttttttaaa aggtcctgtg   1320
tctgaacctg agcctgagcc cgagccagaa ccggagcctg caagacctac ccgccgtcct   1380
aaaatggcgc ctgctatcct gagacgcccg acatcacctg tgtctagaga atgcaatagt   1440
agtacggata gctgtgactc cggtccttct aacacacctc ctgagataca cccggtggtc   1500
ccgctgtgcc ccattaaacc agttgccgtg agagttggtg ggcgtcgcca ggctgtggaa   1560
tgtatcgagg acttgcttaa cgagcctggg caacctttgg acttgagctg taaacgcccc   1620
aggccataag gtgtaaacct gtgattgcgt gtgtggttaa cgcctttgtt tgctgaatga   1680
gttgatgtaa gtttaataaa gggtgagata atgtttaact tgcatggcgt gttaaatggg   1740
gcggggctta aagggtatat aatgcgccgt gggctaatct tggttacatc tgacctcatg   1800
gaggcttggg agtgtttgga agatttttct gctgtgcgta acttgctgga acagagctct   1860
aacagtacct cttggttttg gaggtttctg tggggctcat cccaggcaaa gttagtctgc   1920
agaattaagg aggattacaa gtgggaattt gaagagcttt tgaaatcctg tggtgagctg   1980
tttgattctt tgaatctggg tcaccaggcg cttttccaag agaaggtcat caagactttg   2040
gatttttcca caccggggcg cgctgcggct gctgttgctt ttttgagttt tataaaggat   2100
aaatggagcg aagaaaccca tctgagcggg gggtacctgc tggattttct ggccatgcat   2160
ctgtggagag cggttgtgag acacaagaat cgcctgctac tgttgtcttc cgtccgcccg   2220
gcgataatac cgacggagga gcagcagcag cagcaggagg aagccaggcg gcggcggcag   2280
gagcagagcc catggaaccc gagagccggc ctggaccctc gggaatgaat gttgtacagg   2340
tggctgaact gtatccagaa ctgagacgca ttttgacaat tacagaggat gggcaggggc   2400
taaagggggt aaagagggag cggggggctt gtgaggctac agaggaggct aggaatctag   2460
cttttagctt aatgaccaga caccgtcctg agtgtattac ttttcaacag atcaaggata   2520
attgcgctaa tgagcttgat ctgctggcgc agaagtattc catagagcag ctgaccactt   2580
actggctgca gccaggggat gattttgagg aggctattag ggtatatgca aaggtggcac   2640
ttaggccaga ttgcaagtac aagatcagca aacttgtaaa tatcaggaat tgttgctaca   2700
tttctgggaa cggggccgag gtggagatag atacggagga tagggtggcc tttagatgta   2760
gcatgataaa tatgtggccg gggggtgcttg gcatggacgg ggtggttatt atgaatgtaa   2820
ggtttactgg ccccaatttt agcggtacgg ttttcctggc caataccaac cttatcctac   2880
acggtgtaag cttctatggg tttaacaata cctgtgtgga agcctggacc gatgtaaggg   2940
```

```
ttcggggctg tgccttttac tgctgctgga agggggtggt gtgtcgcccc aaaagcaggg   3000
cttcaattaa gaaatgcctc tttgaaaggt gtaccttggg tatcctgtct gagggtaact   3060
ccagggtgcg ccacaatgtg gcctccgact gtggttgctt catgctagtg aaaagcgtgg   3120
ctgtgattaa gcataacatg gtatgtggca actgcgagga cagggcctct cagatgctga   3180
cctgctcgga cggcaactgt cacctgctga agaccattca cgtagccagc cactctcgca   3240
aggcctggcc agtgtttgag cataacatac tgacccgctg ttccttgcat ttgggtaaca   3300
ggaggggggt gttcctacct taccaatgca atttgagtca cactaagata ttgcttgagc   3360
ccgagagcat gtccaaggtg aacctgaacg gggtgtttga catgaccatg aagatctgga   3420
aggtgctgag gtacgatgag acccgcacca ggtgcagacc ctgcgagtgt ggcggtaaac   3480
atattaggaa ccagcctgtg atgctggatg tgaccgagga gctgaggccc gatcacttgg   3540
tgctggcctg cacccgcgct gagtttggct ctagcgatga agatacagat tgaggtactg   3600
aaatgtgtgg gcgtggctta agggtgggaa agaatatata aggtgggggt cttatgtagt   3660
tttgtatctg ttttgcagca gccgccgccg ccatgagcac caactcgttt gatggaagca   3720
ttgtgagctc atatttgaca acgcgcatgc ccccatgggc cggggtgcgt cagaatgtga   3780
tgggctccag cattgatggt cgccccgtcc tgcccgcaaa ctctactacc ttgacctacg   3840
agaccgtgtc tggaacgccg ttggagactg cagcctccgc cgccgcttca gccgctgcag   3900
ccaccgcccg cgggattgtg actgactttg ctttcctgag cccgcttgca agcagtgcag   3960
cttcccgttc atccgcccgc gatgacaagt tgacggctct tttggcacaa ttggattctt   4020
tgacccggga acttaatgtc gtttctcagc agctgttgga tctgcgccag caggtttctg   4080
ccctgaaggc ttcctcccct cccaatgcgg tttaaaacat aaataaaaaa ccagactctg   4140
tttggatttg gatcaagcaa gtgtcttgct gtctttattt aggggttttg cgcgcgcggt   4200
aggcccggga ccagcggtct cggtcgttga gggtcctgtg tatttttttcc aggacgtggt   4260
aaaggtgact ctggatgttc agatacatgg gcataagccc gtctctgggg tggaggtagc   4320
accactgcag agcttcatgc tgcggggtgg tgttgtagat gatccagtcg tagcaggagc   4380
gctgggcgtg gtgcctaaaa atgtctttca gtagcaagct gattgccagg ggcaggccct   4440
tggtgtaagt gtttacaaag cggttaagct gggatgggtg catacgtggg gatatgagat   4500
gcatcttgga ctgtattttt aggttggcta tgttcccagc catatccctc cggggattca   4560
tgttgtgcag aaccaccagc acagtgtatc cggtgcactt gggaaatttg tcatgtagct   4620
tagaaggaaa tgcgtggaag aacttggaga cgcccttgtg acctccaaga ttttccatgc   4680
attcgtccat aatgatggca atgggcccac gggcggcggc ctgggcgaag atatttctgg   4740
gatcactaac gtcatagttg tgttccagga tgagatcgtc ataggccatt tttacaaagc   4800
gcgggcggag ggtgccagac tgcggtataa tggttccatc cggcccaggg gcgtagttac   4860
cctcacagat ttgcatttcc cacgctttga gttcagatgg ggggatcatg tctacctgcg   4920
gggcgatgaa gaaaacggtt tccggggtag gggagatcag ctgggaagaa agcaggttcc   4980
tgagcagctg cgacttaccg cagccggtgg gcccgtaaat cacacctatt accgggtgca   5040
actggtagtt aagagagctg cagctgccgt catccctgag caggggggcc acttcgttaa   5100
gcatgtccct gactcgcatg ttttccctga ccaaatccgc cagaaggcgc tcgccgccca   5160
gcgatagcag ttcttgcaag gaagcaaagt ttttcaacgg tttgagaccg tccgccgtag   5220
gcatgctttt gagcgtttga ccaagcagtt ccaggcggtc ccacagctcg gtcacctgct   5280
```

```
ctacggcatc tcgatccagc atatctcctc gtttcgcggg ttggggcggc tttcgctgta   5340
cggcagtagt cggtgctcgt ccagacgggc cagggtcatg tctttccacg ggcgcagggt   5400
cctcgtcagc gtagtctggg tcacggtgaa ggggtgcgct ccgggctgcg cgctggccag   5460
ggtgcgcttg aggctggtcc tgctggtgct gaagcgctgc cggtcttcgc cctgcgcgtc   5520
ggccaggtag catttgacca tggtgtcata gtccagcccc tccgcggcgt ggcccttggc   5580
gcgcagcttg cccttggagg aggcgccgca cgaggggcag tgcagacttt tgagggcgta   5640
gagcttgggc gcgagaaata ccgattccgg ggagtaggca tccgcgccgc aggccccgca   5700
gacggtctcg cattccacga gccaggtgag ctctggccgt tcggggtcaa aaaccaggtt   5760
tcccccatgc tttttgatgc gtttcttacc tctggtttcc atgagccggt gtccacgctc   5820
ggtgacgaaa aggctgtccg tgtccccgta tacagactnn ngtttaaacg aattcnnnta   5880
taaaatgcaa ggtgctgctc aaaaaatcag gcaaagcctc gcgcaaaaaa gaaagcacat   5940
cgtagtcatg ctcatgcaga taaaggcagg taagctccgg aaccaccaca gaaaaagaca   6000
ccatttttct ctcaaacatg tctgcgggtt tctgcataaa cacaaaataa aataacaaaa   6060
aaacatttaa acattagaag cctgtcttac aacaggaaaa acaaccctta taagcataag   6120
acggactacg gccatgccgg cgtgaccgta aaaaaactgg tcaccgtgat taaaaagcac   6180
caccgacagc tcctcggtca tgtccggagt cataatgtaa gactcggtaa acacatcagg   6240
ttgattcatc ggtcagtgct aaaaagcgac cgaaatagcc cgggggaata catacccgca   6300
ggcgtagaga caacattaca gcccccatag gaggtataac aaaattaata ggagagaaaa   6360
acacataaac acctgaaaaa ccctcctgcc taggcaaaat agcaccctcc cgctccagaa   6420
caacatacag cgcttcacag cggcagccta acagtcagcc ttaccagtaa aaaagaaaac   6480
ctattaaaaa aacaccactc gacacggcac cagctcaatc agtcacagtg taaaaaaggg   6540
ccaagtgcag agcgagtata tataggacta aaaaatgacg taacggttaa agtccacaaa   6600
aaacacccag aaaaccgcac gcgaacctac gcccagaaac gaaagccaaa aaacccacaa   6660
cttcctcaaa tcgtcacttc cgttttccca cgttacgtaa cttcccattt taagaaaact   6720
acaattccca acacatacaa gttactccgc cctaaaacct acgtcacccg ccccgttccc   6780
acgccccgcg ccacgtcaca aactccaccc cctcattatc atattggctt caatccaaaa   6840
taaggtatat tattgatgat nnnttaatta aggatccnnn cggtgtgaaa taccgcacag   6900
atgcgtaagg agaaaatacc gcatcaggcg ctcttccgct tcctcgctca ctgactcgct   6960
gcgctcggtc gttcggctgc ggcgagcggt atcagctcac tcaaaggcgg taatacggtt   7020
atccacagaa tcaggggata acgcaggaaa gaacatgtga gcaaaaggcc agcaaaaggc   7080
caggaaccgt aaaaaggccg cgttgctggc gtttttccat aggctccgcc cccctgacga   7140
gcatcacaaa aatcgacgct caagtcagag gtggcgaaac ccgacaggac tataaagata   7200
ccaggcgttt ccccctggaa gctccctcgt gcgctctcct gttccgaccc tgccgcttac   7260
cggatacctg tccgcctttc tcccttcggg aagcgtggcg ctttctcata gctcacgctg   7320
taggtatctc agttcggtgt aggtcgttcg ctccaagctg ggctgtgtgc acgaaccccc   7380
cgttcagccc gaccgctgcg ccttatccgg taactatcgt cttgagtcca acccggtaag   7440
acacgactta tcgccactgg cagcagccac tggtaacagg attagcagag cgaggtatgt   7500
aggcggtgct acagagttct tgaagtggtg gcctaactac ggctacacta gaaggacagt   7560
atttggtatc tgcgctctgc tgaagccagt taccttcgga aaaagagttg gtagctcttg   7620
atccggcaaa caaaccaccg ctggtagcgg tggttttttt gtttgcaagc agcagattac   7680
```

```
gcgcagaaaa aaaggatctc aagaagatcc tttgatcttt tctacggggt ctgacgctca    7740
gtggaacgaa aactcacgtt aagggatttt ggtcatgaga ttatcaaaaa ggatcttcac    7800
ctagatcctt ttaaattaaa aatgaagttt taaatcaatc taaagtatat atgagtaaac    7860
ttggtctgac agttaccaat gcttaatcag tgaggcacct atctcagcga tctgtctatt    7920
tcgttcatcc atagttgcct gactccccgt cgtgtagata actacgatac gggagggctt    7980
accatctggc cccagtgctg caatgatacc gcgagaccca cgctcaccgg ctccagattt    8040
atcagcaata aaccagccag ccggaagggc cgagcgcaga agtggtcctg caactttatc    8100
cgcctccatc cagtctatta attgttgccg ggaagctaga gtaagtagtt cgccagttaa    8160
tagtttgcgc aacgttgttg nnnnnnaaaa aggatcttca cctagatcct tttcacgtag    8220
aaagccagtc cgcagaaacg gtgctgaccc cggatgaatg tcagctactg ggctatctgg    8280
acaagggaaa acgcaagcgc aaagagaaag caggtagctt gcagtgggct tacatggcga    8340
tagctagact gggcggtttt atggacagca agcgaaccgg aattgccagc tggggcgccc    8400
tctggtaagg ttgggaagcc ctgcaaagta aactggatgg ctttctcgcc gccaaggatc    8460
tgatggcgca ggggatcaag ctctgatcaa gagacaggat gaggatcgtt tcgcatgatt    8520
gaacaagatg gattgcacgc aggttctccg gccgcttggg tggagaggct attcggctat    8580
gactgggcac aacagacaat cggctgctct gatgccgccg tgttccggct gtcagcgcag    8640
gggcgcccgg ttctttttgt caagaccgac ctgtccggtg ccctgaatga actgcaagac    8700
gaggcagcgc ggctatcgtg gctggccacg acgggcgttc cttgcgcagc tgtgctcgac    8760
gttgtcactg aagcgggaag ggactggctg ctattgggcg aagtgccggg gcaggatctc    8820
ctgtcatctc accttgctcc tgccgagaaa gtatccatca tggctgatgc aatgcggcgg    8880
ctgcatacgc ttgatccggc tacctgccca ttcgaccacc aagcgaaaca tcgcatcgag    8940
cgagcacgta ctcggatgga agccggtctt gtcgatcagg atgatctgga cgaagagcat    9000
caggggctcg cgccagccga actgttcgcc aggctcaagg cgagcatgcc cgacggcgag    9060
gatctcgtcg tgacccatgg cgatgcctgc ttgccgaata tcatggtgga aaatggccgc    9120
ttttctggat tcatcgactg tggccggctg ggtgtggcgg accgctatca ggacatagcg    9180
ttggctaccc gtgatattgc tgaagagctt ggcggcgaat gggctgaccg cttcctcgtg    9240
ctttacggta tcgccgctcc cgattcgcag cgcatcgcct tctatcgcct tcttgacgag    9300
ttcttctgaa ttttgttaaa atttttgtta aatcagctca ttttttaacc aataggccga    9360
aatcggcaac atcccttata aatcaaaaga atagaccgcg atagggttga gtgttgttcc    9420
agtttggaac aagagtccac tattaaagaa cgtggactcc aacgtcaaag ggcgaaaaac    9480
cgtctatcag ggcgatggcc cactacgtga accatcaccc aaatcaagtt ttttgcggtc    9540
gaggtgccgt aaagctctaa atcggaaccc taaagggagc ccccgattta gagcttgacg    9600
gggaaagccg gcgaacgtgg cgagaaagga agggaagaaa gcgaaaggag cgggcgctag    9660
ggcgctggca agtgtagcgg tcacgctgcg cgtaaccacc acacccgcgc gcttaatgcg    9720
ccgctacagg gcgcgtccat tcgccattca ggatcgaatt aattcttaat taacatcatc    9780
aataatatac ctta                                                      9794
```

<210> SEQ ID NO 9
<211> LENGTH: 40117
<212> TYPE: DNA
<213> ORGANISM: Artificial Sequence
<220> FEATURE:

<223> OTHER INFORMATION: The nucleotide sequence encoding plasmid pAd5/3-E2F-D24-GMCSF
<220> FEATURE:
<221> NAME/KEY: misc_feature
<222> LOCATION: (33283)..(33283)
<223> OTHER INFORMATION: n is a, c, g, or t
<220> FEATURE:
<221> NAME/KEY: misc_feature
<222> LOCATION: (38528)..(38533)
<223> OTHER INFORMATION: n is a, c, g, or t

<400> SEQUENCE: 9

```
taacatcatc aataatatac cttattttgg attgaagcca atatgataat gaggggggtgg     60
agtttgtgac gtggcgcggg gcgtgggaac ggggcgggtg acgtagtagt gtggcggaag    120
tgtgatgttg caagtgtggc ggaacacatg taagcgacgg atgtggcaaa agtgacgttt    180
ttggtgtgcg ccggtgtaca caggaagtga caattttcgc gcggttttag gcggatgttg    240
tagtaaattt gggcgtaacc gagtaagatt tggccatttt cgcgggaaaa ctgaataaga    300
ggaagtgaaa tctgaataat tttgtgttac tcatagcgcg taatactggt accgcggccg    360
ctggtaccat ccggacaaag cctgcgcgcg ccccgccccg ccattggccg taccgccccg    420
cgccgccgcc ccatcccgcc cctcgccgcc gggtccggcg cgttaaagcc aataggaacc    480
gccgccgttg ttcccgtcac ggccggggca gccaattgtg gcggcgctcg gcggctcgtg    540
gctctttcgc ggcaaaaagg atttggcgcg taaaagtggc cgggactttg caggcagcgg    600
cggccggggg cggagcggga tcgagccctc gccctcgagc tagaagcttg ttttctcctc    660
cgagccgctc cgacaccggg actgaaaatg agacatatta tctgccacgg aggtgttatt    720
accgaagaaa tggccgccag tcttttggac cagctgatcg aagaggtact ggctgataat    780
cttccacctc ctagccattt tgaaccacct acccttcacg aactgtatga tttagacgtg    840
acggcccccg aagatcccaa cgaggaggcg gtttcgcaga tttttcccga ctctgtaatg    900
ttggcggtgc aggaagggat tgacttactc acttttccgc cggcgcccgg ttctccggag    960
ccgcctcacc tttcccggca gcccgagcag ccggagcaga gagccttggg tccggtttct   1020
atgccaaacc ttgtaccgga ggtgatcgat ccacccagtg acgacgagga tgaagagggt   1080
gaggagtttg tgttagatta tgtggagcac ccccgggcacg gttgcaggtc ttgtcattat   1140
caccggagga atacgggggga cccagatatt atgtgttcgc tttgctatat gaggacctgt   1200
ggcatgtttg tctacagtaa gtgaaaatta tgggcagtgg gtgatagagt ggtgggtttg   1260
gtgtggtaat tttttttta atttttacag ttttgtggtt taaagaattt tgtattgtga   1320
tttttttaaa aggtcctgtg tctgaacctg agcctgagcc cgagccagaa ccggagcctg   1380
caagacctac ccgccgtcct aaaatggcgc ctgctatcct gagacgcccg acatcacctg   1440
tgtctagaga atgcaatagt agtacggata gctgtgactc cggtccttct aacacacctc   1500
ctgagataca cccggtggtc ccgctgtgcc ccattaaacc agttgccgtg agagttggtg   1560
ggcgtcgcca ggctgtggaa tgtatcgagg acttgcttaa cgagcctggg caacctttgg   1620
acttgagctg taaacgcccc aggccataag gtgtaaacct gtgattgcgt gtgtggttaa   1680
cgcctttgtt tgctgaatga gttgatgtaa gtttaataaa gggtgagata atgtttaact   1740
tgcatggcgt gttaaatggg gcggggctta aagggtatat aatgcgccgt gggctaatct   1800
tggttacatc tgacctcatg gaggcttggg agtgtttgga agatttttct gctgtgcgta   1860
acttgctgga acagagctct aacagtacct cttggttttg gaggtttctg tggggctcat   1920
cccaggcaaa gttagtctgc agaattaagg aggattacaa gtgggaattt gaagagcttt   1980
```

```
tgaaatcctg tggtgagctg tttgattctt tgaatctggg tcaccaggcg cttttccaag   2040
agaaggtcat caagactttg gatttttcca caccggggcg cgctgcggct gctgttgctt   2100
ttttgagttt tataaaggat aaatggagcg aagaaaccca tctgagcggg gggtacctgc   2160
tggattttct ggccatgcat ctgtggagag cggttgtgag acacaagaat cgcctgctac   2220
tgttgtcttc cgtccgcccg gcgataatac cgacggagga gcagcagcag cagcaggagg   2280
aagccaggcg gcggcggcag gagcagagcc catggaaccc gagagccggc ctggaccctc   2340
gggaatgaat gttgtacagg tggctgaact gtatccagaa ctgagacgca ttttgacaat   2400
tacagaggat gggcaggggc taaagggggt aaagagggag cgggggcctt gtgaggctac   2460
agaggaggct aggaatctag cttttagctt aatgaccaga caccgtcctg agtgtattac   2520
ttttcaacag atcaaggata attgcgctaa tgagcttgat ctgctggcgc agaagtattc   2580
catagagcag ctgaccactt actggctgca gccaggggat gattttgagg aggctattag   2640
ggtatatgca aaggtggcac ttaggccaga ttgcaagtac aagatcagca aacttgtaaa   2700
tatcaggaat tgttgctaca tttctgggaa cggggccgag gtggagatag atacggagga   2760
tagggtggcc tttagatgta gcatgataaa tatgtggccg gggtgcttg  gcatggacgg   2820
ggtggttatt atgaatgtaa ggtttactgg ccccaatttt agcggtacgg ttttcctggc   2880
caataccaac cttatcctac acggtgtaag cttctatggg tttaacaata cctgtgtgga   2940
agcctggacc gatgtaaggg ttcggggctg tgccttttac tgctgctgga agggggtggt   3000
gtgtcgcccc aaaagcaggg cttcaattaa gaaatgcctc tttgaaaggt gtaccttggg   3060
tatcctgtct gagggtaact ccagggtgcg ccacaatgtg gcctccgact gtggttgctt   3120
catgctagtg aaaagcgtgg ctgtgattaa gcataacatg gtatgtggca actgcgagga   3180
cagggcctct cagatgctga cctgctcgga cggcaactgt cacctgctga agaccattca   3240
cgtagccagc cactctcgca aggcctggcc agtgtttgag cataacatac tgacccgctg   3300
ttccttgcat ttgggtaaca ggaggggggt gttcctacct taccaatgca atttgagtca   3360
cactaagata ttgcttgagc ccgagagcat gtccaaggtg aacctgaacg gggtgtttga   3420
catgaccatg aagatctgga aggtgctgag gtacgatgag acccgcacca ggtgcagacc   3480
ctgcgagtgt ggcggtaaac atattaggaa ccagcctgtg atgctggatg tgaccgagga   3540
gctgaggccc gatcacttgg tgctggcctg cacccgcgct gagtttggct ctagcgatga   3600
agatacagat tgaggtactg aaatgtgtgg gcgtggctta agggtgggaa agaatatata   3660
aggtgggggt cttatgtagt tttgtatctg ttttgcagca gccgccgccg ccatgagcac   3720
caactcgttt gatggaagca ttgtgagctc atatttgaca acgcgcatgc ccccatgggc   3780
cggggtgcgt cagaatgtga tgggctccag cattgatggt cgccccgtcc tgcccgcaaa   3840
ctctactacc ttgacctacg agaccgtgtc tggaacgccg ttggagactg cagcctccgc   3900
cgccgcttca gccgctgcag ccaccgcccg cgggattgtg actgactttg ctttcctgag   3960
cccgcttgca agcagtgcag cttcccgttc atccgcccgc gatgacaagt tgacggctct   4020
tttggcacaa ttggattctt tgacccggga acttaatgtc gtttctcagc agctgttgga   4080
tctgcgccag caggtttctg ccctgaaggc ttcctcccct cccaatgcgg tttaaaacat   4140
aaataaaaaa ccagactctg tttggatttg gatcaagcaa gtgtcttgct gtctttattt   4200
aggggttttg cgcgcgcggt aggcccggga ccagcggtct cggtcgttga gggtcctgtg   4260
tattttttcc aggacgtggt aaaggtgact ctggatgttc agatacatgg gcataagccc   4320
gtctctgggg tggaggtagc accactgcag agcttcatgc tgcggggtgg tgttgtagat   4380
```

```
gatccagtcg tagcaggagc gctgggcgtg gtgcctaaaa atgtctttca gtagcaagct   4440
gattgccagg ggcaggccct tggtgtaagt gtttacaaag cggttaagct gggatgggtg   4500
catacgtggg gatatgagat gcatcttgga ctgtattttt aggttggcta tgttcccagc   4560
catatccctc cggggattca tgttgtgcag aaccaccagc acagtgtatc cggtgcactt   4620
gggaaatttg tcatgtagct tagaaggaaa tgcgtggaag aacttggaga cgcccttgtg   4680
acctccaaga ttttccatgc attcgtccat aatgatggca atgggcccac gggcggcggc   4740
ctgggcgaag atatttctgg gatcactaac gtcatagttg tgttccagga tgagatcgtc   4800
ataggccatt tttacaaagc gcgggcggag ggtgccagac tgcggtataa tggttccatc   4860
cggcccaggg gcgtagttac cctcacagat ttgcatttcc cacgctttga gttcagatgg   4920
ggggatcatg tctacctgcg gggcgatgaa gaaaacggtt tccggggtag gggagatcag   4980
ctgggaagaa agcaggttcc tgagcagctg cgacttaccg cagccggtgg gcccgtaaat   5040
cacacctatt accgggtgca actggtagtt aagagagctg cagctgccgt catccctgag   5100
caggggggcc acttcgttaa gcatgtccct gactcgcatg ttttccctga ccaaatccgc   5160
cagaaggcgc tcgccgccca gcgatagcag ttcttgcaag gaagcaaagt ttttcaacgg   5220
tttgagaccg tccgccgtag gcatgctttt gagcgtttga ccaagcagtt ccaggcggtc   5280
ccacagctcg gtcacctgct ctacggcatc tcgatccagc atatctcctc gtttcgcggg   5340
ttggggcggc tttcgctgta cggcagtagt cggtgctcgt ccagacgggc cagggtcatg   5400
tctttccacg ggcgcagggt cctcgtcagc gtagtctggg tcacggtgaa ggggtgcgct   5460
ccgggctgcg cgctggccag ggtgcgcttg aggctggtcc tgctggtgct gaagcgctgc   5520
cggtcttcgc cctgcgcgtc ggccaggtag catttgacca tggtgtcata gtccagcccc   5580
tccgcggcgt ggcccttggc gcgcagcttg cccttggagg aggcgccgca cgaggggcag   5640
tgcagacttt tgagggcgta gagcttgggc gcgagaaata ccgattccgg ggagtaggca   5700
tccgcgccgc aggccccgca gacggtctcg cattccacga gccaggtgag ctctggccgt   5760
tcggggtcaa aaaccaggtt tcccccatgc tttttgatgc gtttcttacc tctggtttcc   5820
atgagccggt gtccacgctc ggtgacgaaa aggctgtccg tgtccccgta tacagacttg   5880
agaggcctgt cctcgagcgg tgttccgcgg tcctcctcgt atagaaactc ggaccactct   5940
gagacaaagg ctcgcgtcca ggccagcacg aaggaggcta agtgggaggg gtagcggtcg   6000
ttgtccacta gggggtccac tcgctccagg gtgtgaagac acatgtcgcc ctcttcggca   6060
tcaaggaagg tgattggttt gtaggtgtag gccacgtgac cgggtgttcc tgaagggggg   6120
ctataaaagg gggtgggggc gcgttcgtcc tcactctctt ccgcatcgct gtctgcgagg   6180
gccagctgtt ggggtgagta ctccctctga aaagcgggca tgacttctgc gctaagattg   6240
tcagtttcca aaaacgagga ggatttgata ttcacctggc ccgcggtgat gcctttgagg   6300
gtggccgcat ccatctggtc agaaaagaca atctttttgt tgtcaagctt ggtggcaaac   6360
gacccgtaga gggcgttgga cagcaacttg gcgatggagc gcagggtttg gtttttgtcg   6420
cgatcggcgc gctccttggc cgcgatgttt agctgcacgt attcgcgcgc aacgcaccgc   6480
cattcgggaa agacggtggt gcgctcgtcg ggcaccaggt gcacgcgcca accgcggttg   6540
tgcagggtga caaggtcaac gctggtggct acctctccgc gtaggcgctc gttggtccag   6600
cagaggcggc cgcccttgcg cgagcagaat ggcggtaggg ggtctagctg cgtctcgtcc   6660
ggggggtctg cgtccacggt aaagaccccg ggcagcaggc gcgcgtcgaa gtagtctatc   6720
```

```
ttgcatcctt gcaagtctag cgcctgctgc catgcgcggg cggcaagcgc gcgctcgtat   6780
gggttgagtg ggggacccca tggcatgggg tgggtgagcg cggaggcgta catgccgcaa   6840
atgtcgtaaa cgtagagggg ctctctgagt attccaagat atgtagggta gcatcttcca   6900
ccgcggatgc tggcgcgcac gtaatcgtat agttcgtgcg agggagcgag gaggtcggga   6960
ccgaggttgc tacgggcggg ctgctctgct cggaagacta tctgcctgaa gatggcatgt   7020
gagttggatg atatggttgg acgctggaag acgttgaagc tggcgtctgt gagacctacc   7080
gcgtcacgca cgaaggaggc gtaggagtcg cgcagcttgt tgaccagctc ggcggtgacc   7140
tgcacgtcta gggcgcagta gtccagggtt tccttgatga tgtcatactt atcctgtccc   7200
ttttttttcc acagctcgcg gttgaggaca aactcttcgc ggtctttcca gtactcttgg   7260
atcggaaacc cgtcggcctc cgaacggtaa gagcctagca tgtagaactg gttgacggcc   7320
tggtaggcgc agcatccctt ttctacgggt agcgcgtatg cctgcgcggc cttccggagc   7380
gaggtgtggg tgagcgcaaa ggtgtccctg accatgactt tgaggtactg gtatttgaag   7440
tcagtgtcgt cgcatccgcc ctgctcccag agcaaaaagt ccgtgcgctt tttggaacgc   7500
ggatttggca gggcgaaggt gacatcgttg aagagtatct ttcccgcgcg aggcataaag   7560
ttgcgtgtga tgcggaaggg tcccggcacc tcggaacggt tgttaattac ctgggcggcg   7620
agcacgatct cgtcaaagcc gttgatgttg tggcccacaa tgtaaagttc caagaagcgc   7680
gggatgccct tgatggaagg caatttttta agttcctcgt aggtgagctc ttcaggggag   7740
ctgagcccgt gctctgaaag ggcccagtct gcaagatgag ggttggaagc gacgaatgag   7800
ctccacaggt cacgggccat tagcatttgc aggtggtcgc gaaaggtcct aaactggcga   7860
cctatggcca tttttctgg ggtgatgcag tagaaggtaa gcgggtcttg ttcccagcgg   7920
tcccatccaa ggttcgcggc taggtctcgc gcggcagtca ctagaggctc atctccgccg   7980
aacttcatga ccagcatgaa gggcacgagc tgcttcccaa aggcccccat ccaagtatag   8040
gtctctacat cgtaggtgac aaagagacgc tcggtgcgag gatgcgagcc gatcgggaag   8100
aactggatct cccgccacca attggaggag tggctattga tgtggtgaaa gtagaagtcc   8160
ctgcgacggg ccgaacactc gtgctggctt ttgtaaaaac gtgcgcagta ctggcagcgg   8220
tgcacgggct gtacatcctg cacgaggttg acctgacgac cgcgcacaag gaagcagagt   8280
gggaatttga gcccctcgcc tggcgggttt ggctggtggt cttctacttc ggctgcttgt   8340
ccttgaccgt ctggctgctc gaggggagtt acggtggatc ggaccaccac gccgcgcgag   8400
cccaaagtcc agatgtccgc gcgcggcggt cggagcttga tgacaacatc gcgcagatgg   8460
gagctgtcca tggtctggag ctcccgcggc gtcaggtcag gcgggagctc ctgcaggttt   8520
acctcgcata gacgggtcag ggcgcgggct agatccaggt gatacctaat ttccaggggc   8580
tggttggtgg cggcgtcgat ggcttgcaag aggccgcatc cccgcggcgc gactacggta   8640
ccgcgcggcg ggcggtgggc cgcgggggtg tccttggatg atgcatctaa aagcggtgac   8700
gcgggcgagc cccggaggt agggggggct ccggacccgc cgggagaggg ggcaggggca   8760
cgtcggcgcc gcgcgcgggc aggagctggt gctgcgcgcg taggttgctg gcgaacgcga   8820
cgacgcggcg gttgatctcc tgaatctggc gcctctgcgt gaagacgacg ggcccggtga   8880
gcttgagcct gaaagagagt tcgacagaat caatttcggt gtcgttgacg gcggcctggc   8940
gcaaaatctc ctgcacgtct cctgagttgt cttgataggc gatctcggcc atgaactgct   9000
cgatctcttc ctcctggaga tctccgcgtc cggctcgctc cacggtggcg gcgaggtcgt   9060
tggaaatgcg ggccatgagc tgcgagaagg cgttgaggcc tccctcgttc cagacgcggc   9120
```

```
tgtagaccac gcccccttcg gcatcgcggg cgcgcatgac cacctgcgcg agattgagct   9180
ccacgtgccg ggcgaagacg gcgtagtttc gcaggcgctg aaagaggtag ttgagggtgg   9240
tggcggtgtg ttctgccacg aagaagtaca taacccagcg tcgcaacgtg gattcgttga   9300
tatcccccaa ggcctcaagg cgctccatgg cctcgtagaa gtccacggcg aagttgaaaa   9360
actgggagtt gcgcgccgac acggttaact cctcctccag aagacggatg agctcggcga   9420
cagtgtcgcg cacctcgcgc tcaaaggcta caggggcctc ttcttcttct tcaatctcct   9480
cttccataag ggcctcccct tcttcttctt ctggcggcgg tgggggaggg gggacacggc   9540
ggcgacgacg gcgcaccggg aggcggtcga caaagcgctc gatcatctcc ccgcggcgac   9600
ggcgcatggt ctcggtgacg gcgcggccgt tctcgcgggg gcgcagttgg aagacgccgc   9660
ccgtcatgtc ccggttatgg gttggcgggg ggctgccatg cggcagggat acggcgctaa   9720
cgatgcatct caacaattgt tgtgtaggta ctccgccgcc gagggacctg agcgagtccg   9780
catcgaccgg atcggaaaac ctctcgagaa aggcgtctaa ccagtcacag tcgcaaggta   9840
ggctgagcac cgtggcgggc ggcagcgggc ggcggtcggg gttgtttctg gcggaggtgc   9900
tgctgatgat gtaattaaag taggcggtct tgagacggcg gatggtcgac agaagcacca   9960
tgtccttggg tccggcctgc tgaatgcgca ggcggtcggc catgccccag gcttcgtttt  10020
gacatcggcg caggtctttg tagtagtctt gcatgagcct ttctaccggc acttcttctt  10080
ctccttcctc ttgtcctgca tctcttgcat ctatcgctgc ggcggcggcg gagtttggcc  10140
gtaggtggcg ccctcttcct cccatgcgtg tgaccccgaa gcccctcatc ggctgaagca  10200
gggctaggtc ggcgacaacg cgctcggcta atatggcctg ctgcacctgc gtgagggtag  10260
actggaagtc atccatgtcc acaaagcggt ggtatgcgcc cgtgttgatg gtgtaagtgc  10320
agttggccat aacggaccag ttaacggtct ggtgacccgg ctgcgagagc tcggtgtacc  10380
tgagacgcga gtaagccctc gagtcaaata cgtagtcgtt gcaagtccgc accaggtact  10440
ggtatcccac caaaaagtgc ggcggcggct ggcggtagag gggccagcgt agggtggccg  10500
gggctccggg ggcgagatct tccaacataa ggcgatgata tccgtagatg tacctggaca  10560
tccaggtgat gccggcggcg gtggtggagg cgcgcggaaa gtcgcggacg cggttccaga  10620
tgttgcgcag cggcaaaaag tgctccatgg tcgggacgct ctggccggtc aggcgcgcgc  10680
aatcgttgac gctctagacc gtgcaaaagg agagcctgta agcgggcact cttccgtggt  10740
ctggtggata aattcgcaag ggtatcatgg cggacgaccg gggttcgagc cccgtatccg  10800
gccgtccgcc gtgatccatg cggttaccgc ccgcgtgtcg aacccaggtg tgcgacgtca  10860
gacaacgggg gagtgctcct tttggcttcc ttccaggcgc ggcggctgct gcgctagctt  10920
ttttggccac tggccgcgcg cagcgtaagc ggttaggctg gaaagcgaaa gcattaagtg  10980
gctcgctccc tgtagccgga gggttatttt ccaagggttg agtcgcggga cccccggttc  11040
gagtctcgga ccggccggac tgcggcgaac gggggtttgc ctccccgtca tgcaagaccc  11100
cgcttgcaaa ttcctccgga aacagggacg agcccctttt ttgcttttcc cagatgcatc  11160
cggtgctgcg gcagatgcgc ccccctcctc agcagcggca agagcaagag cagcggcaga  11220
catgcagggc accctcccct cctcctaccg cgtcaggagg ggcgacatcc gcggttgacg  11280
cggcagcaga tggtgattac gaacccccgc ggcgccgggc ccggcactac ctggacttgg  11340
aggagggcga gggcctggcg cggctaggag cgccctctcc tgagcggtac ccaagggtgc  11400
agctgaagcg tgatacgcgt gaggcgtacg tgccgcggca gaacctgttt cgcgaccgcg  11460
```

```
agggagagga gcccgaggag atgcgggatc gaaagttcca cgcagggcgc gagctgcggc  11520
atggcctgaa tcgcgagcgg ttgctgcgcg aggaggactt tgagcccgac gcgcgaaccg  11580
ggattagtcc cgcgcgcgca cacgtggcgg ccgccgacct ggtaaccgca tacgagcaga  11640
cggtgaacca ggagattaac tttcaaaaaa gctttaacaa ccacgtgcgt acgcttgtgg  11700
cgcgcgagga ggtggctata ggactgatgc atctgtggga ctttgtaagc gcgctggagc  11760
aaaacccaaa tagcaagccg ctcatggcgc agctgttcct tatagtgcag cacagcaggg  11820
acaacgaggc attcagggat gcgctgctaa acatagtaga gcccgagggc cgctggctgc  11880
tcgatttgat aaacatcctg cagagcatag tggtgcagga gcgcagcttg agcctggctg  11940
acaaggtggc cgccatcaac tattccatgc ttagcctggg caagttttac gcccgcaaga  12000
tataccatac cccttacgtt cccatagaca aggaggtaaa gatcgagggg ttctacatgc  12060
gcatggcgct gaaggtgctt accttgagcg acgacctggg cgtttatcgc aacgagcgca  12120
tccacaaggc cgtgagcgtg agccggcggc gcgagctcag cgaccgcgag ctgatgcaca  12180
gcctgcaaag ggccctggct ggcacgggca gcggcgatag agaggccgag tcctactttg  12240
acgcgggcgc tgacctgcgc tgggccccaa gccgacgcgc cctggaggca gctggggccg  12300
gacctgggct ggcggtggca cccgcgcgcg ctggcaacgt cggcggcgtg gaggaatatg  12360
acgaggacga tgagtacgag ccagaggacg gcgagtacta agcggtgatg tttctgatca  12420
gatgatgcaa gacgcaacgg acccggcggt gcgggcggcg ctgcagagcc agccgtccgg  12480
ccttaactcc acggacgact ggcgccaggt catggaccgc atcatgtcgc tgactgcgcg  12540
caatcctgac gcgttccggc agcagccgca ggccaaccgg ctctccgcaa ttctggaagc  12600
ggtggtcccg gcgcgcgcaa accccacgca cgagaaggtg ctggcgatcg taaacgcgct  12660
ggccgaaaac agggccatcc ggcccgacga ggccggcctg gtctacgacg cgctgcttca  12720
gcgcgtggct cgttacaaca gcggcaacgt gcagaccaac ctggaccggc tggtgggga   12780
tgtgcgcgag gccgtggcgc agcgtgagcg cgcgcagcag cagggcaacc tgggctccat  12840
ggttgcacta aacgccttcc tgagtacaca gcccgccaac gtgccgcggg gacaggagga  12900
ctacaccaac tttgtgagcg cactgcggct aatggtgact gagacaccgc aaagtgaggt  12960
gtaccagtct gggccagact attttttcca gaccagtaga caaggcctgc agaccgtaaa  13020
cctgagccag gctttcaaaa acttgcaggg gctgtggggg gtgcgggctc ccacaggcga  13080
ccgcgcgacc gtgtctagct tgctgacgcc caactcgcgc ctgttgctgc tgctaatagc  13140
gcccttcacg gacagtggca gcgtgtcccg ggacacatac ctaggtcact tgctgacact  13200
gtaccgcgag gccataggtc aggcgcatgt ggacgagcat actttccagg agattacaag  13260
tgtcagccgc gcgctggggc aggaggacac gggcagcctg gaggcaaccc taaactacct  13320
gctgaccaac cggcggcaga agatcccctc gttgcacagt ttaaacagcg aggaggagcg  13380
cattttgcgc tacgtgcagc agagcgtgag ccttaacctg atgcgcgacg ggtaacgcc   13440
cagcgtggcg ctggacatga ccgcgcgcaa catggaaccg ggcatgtatg cctcaaaccg  13500
gccgtttatc aaccgcctaa tggactactt gcatcgcgcg gccgccgtga accccgagta  13560
tttcaccaat gccatcttga acccgcactg gctaccgccc cctggtttct acaccggggg  13620
attcgaggtg cccgagggta acgatggatt cctctgggac gacatagacg acagcgtgtt  13680
ttccccgcaa ccgcagaccc tgctagagtt gcaacagcgc gagcaggcag aggcggcgct  13740
gcgaaaggaa agcttccgca ggccaagcag cttgtccgat ctaggcgctg cggccccgcg  13800
gtcagatgct agtagcccat ttccaagctt gatagggtct cttaccagca ctcgcaccac  13860
```

```
ccgcccgcgc ctgctgggcg aggaggagta cctaaacaac tcgctgctgc agccgcagcg  13920
cgaaaaaaac ctgcctccgg catttcccaa caacgggata gagagcctag tggacaagat  13980
gagtagatgg aagacgtacg cgcaggagca cagggacgtg ccaggcccgc gcccgcccac  14040
ccgtcgtcaa aggcacgacc gtcagcgggg tctggtgtgg gaggacgatg actcggcaga  14100
cgacagcagc gtcctggatt tgggagggag tggcaacccg tttgcgcacc ttcgccccag  14160
gctggggaga atgttttaaa aaaaaaaaag catgatgcaa aataaaaaac tcaccaaggc  14220
catggcaccg agcgttggtt ttcttgtatt ccccttagta tgcggcgcgc ggcgatgtat  14280
gaggaaggtc ctcctccctc ctacgagagt gtggtgagcg cggcgccagt ggcggcggcg  14340
ctgggttctc ccttcgatgc tcccctggac ccgccgtttg tgcctccgcg gtacctgcgg  14400
cctaccgggg ggagaaacag catccgttac tctgagttgg caccccctatt cgacaccacc  14460
cgtgtgtacc tggtggacaa caagtcaacg gatgtggcat ccctgaacta ccagaacgac  14520
cacagcaact ttctgaccac ggtcattcaa aacaatgact acagcccggg ggaggcaagc  14580
acacagacca tcaatcttga cgaccggtcg cactggggcg gcgacctgaa aaccatcctg  14640
cataccaaca tgccaaatgt gaacgagttc atgtttacca ataagtttaa ggcgcgggtg  14700
atggtgtcgc gcttgcctac taaggacaat caggtggagc tgaaatacga gtgggtggag  14760
ttcacgctgc ccgagggcaa ctactccgag accatgacca tagaccttat gaacaacgcg  14820
atcgtggagc actacttgaa agtgggcaga cagaacgggg ttctggaaag cgacatcggg  14880
gtaaagtttg acacccgcaa cttcagactg ggtttgacc ccgtcactgg tcttgtcatg  14940
cctggggtat atacaaacga agccttccat ccagacatca ttttgctgcc aggatgcggg  15000
gtggacttca cccacagccg cctgagcaac ttgttgggca tccgcaagcg gcaacccttc  15060
caggagggct ttaggatcac ctacgatgat ctggagggtg gtaacattcc cgcactgttg  15120
gatgtggacg cctaccaggc gagcttgaaa gatgacaccg aacagggcgg gggtggcgca  15180
ggcggcagca acagcagtgg cagcggcgcg gaagagaact ccaacgcggc agccgcggca  15240
atgcagccgg tggaggacat gaacgatcat gccattcgcg gcgacacctt tgccacacgg  15300
gctgaggaga agcgcgctga ggccgaagca gcggccgaag ctgccgcccc cgctgcgcaa  15360
cccgaggtcg agaagcctca gaagaaaccg gtgatcaaac ccctgacaga ggacagcaag  15420
aaacgcagtt acaacctaat aagcaatgac agcaccttca cccagtaccg cagctggtac  15480
cttgcataca actacggcga ccctcagacc ggaatccgct catggaccct gctttgcact  15540
cctgacgtaa cctgcggctc ggagcaggtc tactggtcgt tgccagacat gatgcaagac  15600
cccgtgacct tccgctccac gcgccagatc agcaactttc cggtggtggg cgccgagctg  15660
ttgcccgtgc actccaagag cttctacaac gaccaggccg tctactccca actcatccgc  15720
cagtttacct ctctgaccca cgtgttcaat cgctttcccg agaaccagat tttggcgcgc  15780
ccgccagccc ccaccatcac caccgtcagt gaaaacgttc ctgctctcac agatcacggg  15840
acgctaccgc tgcgcaacag catcggagga gtccagcgag tgaccattac tgacgccaga  15900
cgccgcacct gcccctacgt ttacaaggcc ctgggcatag tctcgccgcg cgtcctatcg  15960
agccgcactt tttgagcaag catgtccatc cttatatcgc ccagcaataa cacaggctgg  16020
ggcctgcgct tcccaagcaa gatgtttggc ggggccaaga agcgctccga ccaacaccca  16080
gtgcgcgtgc gcgggcacta ccgcgcgccc tggggcgcgc acaaacgcgg ccgcactggg  16140
cgcaccaccg tcgatgacgc catcgacgcg gtggtggagg aggcgcgcaa ctacacgccc  16200
```

```
acgccgccac cagtgtccac agtggacgcg gccattcaga ccgtggtgcg cggagcccgg  16260
cgctatgcta aaatgaagag acggcggagg cgcgtagcac gtcgccaccg ccgccgaccc  16320
ggcactgccg cccaacgcgc ggcggcggcc ctgcttaacc gcgcacgtcg caccggccga  16380
cgggcggcca tgcgggccgc tcgaaggctg gccgcgggta ttgtcactgt gccccccagg  16440
tccaggcgac gagcggccgc cgcagcagcc gcggccatta gtgctatgac tcagggtcgc  16500
aggggcaacg tgtattgggt gcgcgactcg gttagcggcc tgcgcgtgcc cgtgcgcacc  16560
cgcccccgc gcaactagat tgcaagaaaa aactacttag actcgtactg ttgtatgtat  16620
ccagcggcgg cggcgcgcaa cgaagctatg tccaagcgca aaatcaaaga agagatgctc  16680
caggtcatcg cgccggagat ctatggcccc ccgaagaagg aagagcagga ttacaagccc  16740
cgaaagctaa agcgggtcaa aaagaaaaag aaagatgatg atgatgaact tgacgacgag  16800
gtggaactgc tgcacgctac cgcgcccagg cgacgggtac agtggaaagg tcgacgcgta  16860
aaacgtgttt tgcgacccgg caccaccgta gtctttacgc ccggtgagcg ctccacccgc  16920
acctacaagc gcgtgtatga tgaggtgtac ggcgacgagg acctgcttga gcaggccaac  16980
gagcgcctcg gggagtttgc ctacggaaag cggcataagg acatgctggc gttgccgctg  17040
gacgagggca acccaacacc tagcctaaag cccgtaacac tgcagcaggt gctgcccgcg  17100
cttgcaccgt ccgaagaaaa gcgcggccta aagcgcgagt ctggtgactt ggcacccacc  17160
gtgcagctga tggtacccaa gcgccagcga ctggaagatg tcttggaaaa aatgaccgtg  17220
gaacctgggc tggagcccga ggtccgcgtg cggccaatca agcaggtggc gccgggactg  17280
ggcgtgcaga ccgtggacgt tcagataccc actaccagta gcaccagtat tgccaccgcc  17340
acagagggca tggagacaca aacgtccccg gttgcctcag cggtggcgga tgccgcggtg  17400
caggcggtcg ctgcggccgc gtccaagacc tctacggagg tgcaaacgga cccgtggatg  17460
tttcgcgttt cagccccccg gcgcccgcgc ggttcgagga agtacggcgc cgccagcgcg  17520
ctactgcccg aatatgccct acatccttcc attgcgccta cccccggcta tcgtggctac  17580
acctaccgcc ccagaagacg agcaactacc cgacgccgaa ccaccactgg aacccgccgc  17640
cgccgtcgcc gtcgccagcc cgtgctggcc ccgatttccg tgcgcagggt ggctcgcgaa  17700
ggaggcagga ccctggtgct gccaacagcg cgctaccacc ccagcatcgt ttaaaagccg  17760
gtctttgtgg ttcttgcaga tatggccctc acctgccgcc tccgtttccc ggtgccggga  17820
ttccgaggaa gaatgcaccg taggaggggc atggccggcc acggcctgac gggcggcatg  17880
cgtcgtgcgc accaccggcg gcggcgcgcg tcgcaccgtc gcatgcgcgg cggtatcctg  17940
cccctcctta ttccactgat cgccgcggcg attggcgccg tgcccggaat tgcatccgtg  18000
gccttgcagg cgcagagaca ctgattaaaa acaagttgca tgtggaaaaa tcaaaataaa  18060
aagtctggac tctcacgctc gcttggtcct gtaactattt tgtagaatgg aagacatcaa  18120
ctttgcgtct ctggccccgc gacacggctc gcgcccgttc atgggaaact ggcaagatat  18180
cggcaccagc aatatgagcg gtggcgcctt cagctggggc tcgctgtgga gcggcattaa  18240
aaatttcggt tccaccgtta agaactatgg cagcaaggcc tggaacagca gcacaggcca  18300
gatgctgagg gataagttga aagagcaaaa tttccaacaa aaggtggtag atggcctggc  18360
ctctggcatt agcggggtgg tggacctggc caaccaggca gtgcaaaata agattaacag  18420
taagcttgat ccccgccctc ccgtagagga gcctccaccg gccgtggaga cagtgtctcc  18480
agaggggcgt ggcgaaaagc gtccgcgccc cgacagggaa gaaactctgg tgacgcaaat  18540
agacgagcct ccctcgtacg aggaggcact aaagcaaggc ctgcccacca cccgtcccat  18600
```

```
cgcgcccatg gctaccggag tgctgggcca gcacacaccc gtaacgctgg acctgcctcc  18660
ccccgccgac acccagcaga aacctgtgct gccaggcccg accgccgttg ttgtaacccg  18720
tcctagccgc gcgtccctgc gccgcgccgc cagcggtccg cgatcgttgc ggcccgtagc  18780
cagtggcaac tggcaaagca cactgaacag catcgtgggt ctgggggtgc aatccctgaa  18840
gcgccgacga tgcttctgaa tagctaacgt gtcgtatgtg tgtcatgtat gcgtccatgt  18900
cgccgccaga ggagctgctg agccgccgcg cgcccgcttt ccaagatggc taccccttcg  18960
atgatgccgc agtggtctta catgcacatc tcgggccagg acgcctcgga gtacctgagc  19020
cccgggctgg tgcagtttgc ccgcgccacc gagacgtact tcagcctgaa taacaagttt  19080
agaaacccca cggtggcgcc tacgcacgac gtgaccacag accggtccca gcgtttgacg  19140
ctgcggttca tccctgtgga ccgtgaggat actgcgtact cgtacaaggc gcggttcacc  19200
ctagctgtgg gtgataaccg tgtgctggac atggcttcca cgtactttga catccgcggc  19260
gtgctggaca ggggccctac ttttaagccc tactctggca ctgcctacaa cgccctggct  19320
cccaagggtg ccccaaatcc ttgcgaatgg gatgaagctg ctactgctct tgaaataaac  19380
ctagaagaag aggacgatga caacgaagac gaagtagacg agcaagctga gcagcaaaaa  19440
actcacgtat ttgggcaggc gccttattct ggtataaata ttacaaagga gggtattcaa  19500
ataggtgtcg aaggtcaaac acctaaatat gccgataaaa catttcaacc tgaacctcaa  19560
ataggagaat ctcagtggta cgaaactgaa attaatcatg cagctgggag agtccttaaa  19620
aagactaccc caatgaaacc atgttacggt tcatatgcaa aacccacaaa tgaaaatgga  19680
gggcaaggca ttcttgtaaa gcaacaaaat ggaaagctag aaagtcaagt ggaaatgcaa  19740
tttttctcaa ctactgaggc gaccgcaggc aatggtgata acttgactcc taaagtggta  19800
ttgtacagtg aagatgtaga tatagaaacc ccagacactc atatttctta catgcccact  19860
attaaggaag gtaactcacg agaactaatg ggccaacaat ctatgcccaa caggcctaat  19920
tacattgctt ttagggacaa ttttattggt ctaatgtatt acaacagcac gggtaatatg  19980
ggtgttctgg cgggccaagc atcgcagttg aatgctgttg tagatttgca agacagaaac  20040
acagagcttt cataccagct tttgcttgat tccattggtg atagaaccag gtacttttct  20100
atgtggaatc aggctgttga cagctatgat ccagatgtta gaattattga aaatcatgga  20160
actgaagatg aacttccaaa ttactgcttt ccactgggag gtgtgattaa tacagagact  20220
cttaccaagg taaaacctaa aacaggtcag gaaaatggat gggaaaaaga tgctacagaa  20280
ttttcagata aaaatgaaat aagagttgga aataatttg ccatggaaat caatctaaat  20340
gccaacctgt ggagaaattt cctgtactcc aacatagcgc tgtatttgcc cgacaagcta  20400
aagtacagtc cttccaacgt aaaaatttct gataacccaa acacctacga ctacatgaac  20460
aagcgagtgg tggctcccgg gttagtggac tgctacatta accttggagc acgctggtcc  20520
cttgactata tggacaacgt caacccattt aaccaccacc gcaatgctgg cctgcgctac  20580
cgctcaatgt tgctgggcaa tggtcgctat gtgcccttcc acatccaggt gcctcagaag  20640
ttctttgcca ttaaaaacct ccttctcctg ccgggctcat acacctacga gtggaacttc  20700
aggaaggatg ttaacatggt tctgcagagc tccctaggaa atgacctaag ggttgacgga  20760
gccagcatta agtttgatag catttgcctt tacgccacct tcttccccat ggcccacaac  20820
accgcctcca cgcttgaggc catgcttaga aacgacacca acgaccagtc ctttaacgac  20880
tatctctccg ccgccaacat gctctaccct atacccgcca acgctaccaa cgtgcccata  20940
```

```
tccatcccct cccgcaactg ggcggctttc cgcggctggg ccttcacgcg ccttaagact  21000
aaggaaaccc catcactggg ctcgggctac gacccttatt acacctactc tggctctata  21060
ccctacctag atggaacctt ttacctcaac cacaccttta agaaggtggc cattaccttt  21120
gactcttctg tcagctggcc tggcaatgac cgcctgctta cccccaacga gtttgaaatt  21180
aagcgctcag ttgacgggga gggttacaac gttgcccagt gtaacatgac caaagactgg  21240
ttcctggtac aaatgctagc taactacaac attggctacc agggcttcta tatcccagag  21300
agctacaagg accgcatgta ctccttcttt agaaacttcc agcccatgag ccgtcaggtg  21360
gtggatgata ctaaatacaa ggactaccaa caggtgggca tcctacacca acacaacaac  21420
tctggatttg ttggctacct tgcccccacc atgcgcgaag gacaggccta ccctgctaac  21480
ttcccctatc cgcttatagg caagaccgca gttgacagca ttacccagaa aaagtttctt  21540
tgcgatcgca ccctttggcg catcccattc tccagtaact ttatgtccat gggcgcactc  21600
acagacctgg gccaaaacct tctctacgcc aactccgccc acgcgctaga catgactttt  21660
gaggtggatc ccatggacga gcccaccctt ctttatgttt tgtttgaagt ctttgacgtg  21720
gtccgtgtgc accggccgca ccgcggcgtc atcgaaaccg tgtacctgcg cacgcccttc  21780
tcggccggca acgccacaac ataaagaagc aagcaacatc aacaacagct gccgccatgg  21840
gctccagtga gcaggaactg aaagccattg tcaaagatct tggttgtggg ccatattttt  21900
tgggcaccta tgacaagcgc tttccaggct ttgtttctcc acacaagctc gcctgcgcca  21960
tagtcaatac ggccggtcgc gagactgggg gcgtacactg gatggccttt gcctggaacc  22020
cgcactcaaa aacatgctac ctctttgagc cctttggctt ttctgaccag cgactcaagc  22080
aggtttacca gtttgagtac gagtcactcc tgcgccgtag cgccattgct tcttcccccg  22140
accgctgtat aacgctggaa aagtccaccc aaagcgtaca ggggcccaac tcggccgcct  22200
gtggactatt ctgctgcatg tttctccacg cctttgccaa ctggccccaa actcccatgg  22260
atcacaaccc caccatgaac cttattaccg gggtacccaa ctccatgctc aacagtcccc  22320
aggtacagcc caccctgcgt cgcaaccagg aacagctcta cagcttcctg gagcgccact  22380
cgccctactt ccgcagccac agtgcgcaga ttaggagcgc cacttctttt tgtcacttga  22440
aaaacatgta aaaataatgt actagagaca ctttcaataa aggcaaatgc ttttatttgt  22500
acactctcgg gtgattattt acccccaccc ttgccgtctg cgccgtttaa aaatcaaagg  22560
ggttctgccg cgcatcgcta tgcgccactg gcagggacac gttgcgatac tggtgtttag  22620
tgctccactt aaactcaggc acaaccatcc gcggcagctc ggtgaagttt tcactccaca  22680
ggctgcgcac catcaccaac gcgtttagca ggtcgggcgc cgatatcttg aagtcgcagt  22740
tggggcctcc gccctgcgcg cgcgagttgc gatacacagg gttgcagcac tggaacacta  22800
tcagcgccgg gtggtgcacg ctggccagca cgctcttgtc ggagatcaga tccgcgtcca  22860
ggtcctccgc gttgctcagg gcgaacggag tcaactttgg tagctgcctt cccaaaaagg  22920
gcgcgtgccc aggctttgag ttgcactcgc accgtagtgg catcaaaagg tgaccgtgcc  22980
cggtctgggc gttaggatac agcgcctgca taaaagcctt gatctgctta aaagccacct  23040
gagcctttgc gccttcagag aagaacatgc cgcaagactt gccggaaaac tgattggccg  23100
gacaggccgc gtcgtgcacg cagcaccttg cgtcggtgtt ggagatctgc accacatttc  23160
ggccccaccg gttcttcacg atcttggcct tgctagactg ctccttcagc gcgcgctgcc  23220
cgttttcgct cgtcacatcc atttcaatca cgtgctcctt atttatcata atgcttccgt  23280
gtagacactt aagctcgcct tcgatctcag cgcagcggtg cagccacaac gcgcagcccg  23340
```

```
tgggctcgtg atgcttgtag gtcacctctg caaacgactg caggtacgcc tgcaggaatc  23400
gccccatcat cgtcacaaag gtcttgttgc tggtgaaggt cagctgcaac ccgcggtgct  23460
cctcgttcag ccaggtcttg catacggccg ccagagcttc cacttggtca ggcagtagtt  23520
tgaagttcgc ctttagatcg ttatccacgt ggtacttgtc catcagcgcg cgcgcagcct  23580
ccatgccctt ctcccacgca gacacgatcg gcacactcag cgggttcatc accgtaattt  23640
cactttccgc ttcgctgggc tcttcctctt cctcttgcgt ccgcatacca cgcgccactg  23700
ggtcgtcttc attcagccgc cgcactgtgc gcttacctcc tttgccatgc ttgattagca  23760
ccggtgggtt gctgaaaccc accatttgta gcgccacatc ttctctttct tcctcgctgt  23820
ccacgattac ctctggtgat ggcgggcgct cgggcttggg agaagggcgc ttcttttttct  23880
tcttgggcgc aatggccaaa tccgccgccg aggtcgatgg ccgcgggctg ggtgtgcgcg  23940
gcaccagcgc gtcttgtgat gagtcttcct cgtcctcgga ctcgatacgc cgcctcatcc  24000
gctttttttgg gggcgcccgg ggaggcggcg gcgacgggga cggggacgac acgtcctcca  24060
tggttggggg acgtcgcgcc gcaccgcgtc cgcgctcggg ggtggtttcg cgctgctcct  24120
cttcccgact ggccatttcc ttctcctata ggcagaaaaa gatcatggag tcagtcgaga  24180
agaaggacag cctaaccgcc ccctctgagt tcgccaccac cgcctccacc gatgccgcca  24240
acgcgcctac caccttcccc gtcgaggcac ccccgcttga ggaggaggaa gtgattatcg  24300
agcaggaccc aggttttgta agcgaagacg acgaggaccg ctcagtacca acagaggata  24360
aaaagcaaga ccaggacaac gcagaggcaa acgaggaaca agtcgggcgg ggggacgaaa  24420
ggcatggcga ctacctagat gtgggagacg acgtgctgtt gaagcatctg cagcgccagt  24480
gcgccattat ctgcgacgcg ttgcaagagc gcagcgatgt gcccctcgcc atagcggatg  24540
tcagccttgc ctacgaacgc cacctattct caccgcgcgt acccccccaaa cgccaagaaa  24600
acggcacatg cgagcccaac ccgcgcctca acttctaccc cgtatttgcc gtgccagagg  24660
tgcttgccac ctatcacatc tttttccaaa actgcaagat acccctatcc tgccgtgcca  24720
accgcagccg agcggacaag cagctggcct tgcggcaggg cgctgtcata cctgatatcg  24780
cctcgctcaa cgaagtgcca aaaatctttg agggtcttgg acgcgacgag aagcgcgcgg  24840
caaacgctct gcaacaggaa aacagcgaaa atgaaagtca ctctggagtg ttggtggaac  24900
tcgagggtga caacgcgcgc ctagccgtac taaaacgcag catcgaggtc acccactttg  24960
cctacccggc acttaaccta ccccccaagg tcatgagcac agtcatgagt gagctgatcg  25020
tgcgccgtgc gcagcccctg gagagggatg caaatttgca agaacaaaca gaggagggcc  25080
tacccgcagt tggcgacgag cagctagcgc gctggcttca aacgcgcgag cctgccgact  25140
tggaggagcg acgcaaacta atgatggccg cagtgctcgt taccgtggag cttgagtgca  25200
tgcagcggtt ctttgctgac ccggagatgc agcgcaagct agaggaaaca ttgcactaca  25260
cctttcgaca gggctacgta cgccaggcct gcaagatctc caacgtggag ctctgcaacc  25320
tggtctccta ccttggaatt ttgcacgaaa accgccttgg gcaaaacgtg cttcattcca  25380
cgctcaaggg cgaggcgcgc cgcgactacg tccgcgactg cgtttactta tttctatgct  25440
acacctggca gacggccatg ggcgtttggc agcagtgctt ggaggagtgc aacctcaagg  25500
agctgcagaa actgctaaag caaaacttga aggacctatg gacggccttc aacgagcgct  25560
ccgtggccgc gcacctggcg gacatcattt tccccgaacg cctgcttaaa accctgcaac  25620
agggtctgcc agacttcacc agtcaaagca tgttgcagaa ctttaggaac tttatcctag  25680
```

```
agcgctcagg aatcttgccc gccacctgct gtgcacttcc tagcgacttt gtgcccatta  25740
agtaccgcga atgccctccg ccgctttggg gccactgcta ccttctgcag ctagccaact  25800
accttgccta ccactctgac ataatggaag acgtgagcgg tgacggtcta ctggagtgtc  25860
actgtcgctg caacctatgc accccgcacc gctccctggt ttgcaattcg cagctgctta  25920
acgaaagtca aattatcggt acctttgagc tgcagggtcc ctcgcctgac gaaaagtccg  25980
cggctccggg gttgaaactc actccggggc tgtggacgtc ggcttacctt cgcaaatttg  26040
tacctgagga ctaccacgcc cacgagatta ggttctacga agaccaatcc cgcccgccaa  26100
atgcggagct taccgcctgc gtcattaccc agggccacat tcttggccaa ttgcaagcca  26160
tcaacaaagc ccgccaagag tttctgctac gaaagggacg gggggtttac ttggaccccc  26220
agtccggcga ggagctcaac ccaatccccc cgccgccgca gccctatcag cagcagccgc  26280
gggcccttgc ttcccaggat ggcacccaaa aagaagctgc agctgccgcc gccacccacg  26340
gacgaggagg aatactggga cagtcaggca gaggaggttt tggacgagga ggaggaggac  26400
atgatggaag actgggagag cctagacgag gaagcttccg aggtcgaaga ggtgtcagac  26460
gaaacaccgt caccctcggt cgcattcccc tcgccggcgc cccagaaatc ggcaaccggt  26520
tccagcatgg ctacaacctc cgctcctcag gcgccgccgg cactgcccgt tcgccgaccc  26580
aaccgtagat gggacaccac tggaaccagg gccggtaagt ccaagcagcc gccgccgtta  26640
gcccaagagc aacaacagcg ccaaggctac cgctcatggc gcgggcacaa gaacgccata  26700
gttgcttgct tgcaagactg tgggggcaac atctccttcg cccgccgctt tcttctctac  26760
catcacggcg tggccttccc ccgtaacatc ctgcattact accgtcatct ctacagccca  26820
tactgcaccg gcggcagcgg cagcggcagc aacagcagcg gccacacaga agcaaaggcg  26880
accggatagc aagactctga caaagcccaa gaaatccaca gcggcggcag cagcaggagg  26940
aggagcgctg cgtctggcgc ccaacgaacc cgtatcgacc cgcgagctta gaaacaggat  27000
ttttcccact ctgtatgcta tatttcaaca gagcaggggc caagaacaag agctgaaaat  27060
aaaaaacagg tctctgcgat ccctcacccg cagctgcctg tatcacaaaa gcgaagatca  27120
gcttcggcgc acgctggaag acgcggaggc tctcttcagt aaatactgcg cgctgactct  27180
taaggactag tttcgcgccc tttctcaaat ttaagcgcga aaactacgtc atctccagcg  27240
gccacacccg gcgccagcac ctgtcgtcag cgccattatg agcaaggaaa ttcccacgcc  27300
ctacatgtgg agttaccagc cacaaatggg acttgcggct ggagctgccc aagactactc  27360
aacccgaata aactacatga gcgcgggacc ccacatgata tcccgggtca acggaatccg  27420
cgcccaccga aaccgaattc tcttggaaca ggcggctatt accaccacac ctcgtaataa  27480
ccttaatccc cgtagttggc ccgctgccct ggtgtaccag gaaagtcccg ctcccaccac  27540
tgtggtactt cccagagacg cccaggccga agttcagatg actaactcag gggcgcagct  27600
tgcgggcggc tttcgtcaca gggtgcggtc gcccgggcag ggtataactc acctgacaat  27660
cagagggcga ggtattcagc tcaacgacga gtcggtgagc tcctcgcttg gtctccgtcc  27720
ggacgggaca tttcagatcg gcggcgccgg ccgctcttca ttcacgcctc gtcaggcaat  27780
cctaactctg cagacctcgt cctctgagcc gcgctctgga ggcattggaa ctctgcaatt  27840
tattgaggag tttgtgccat cggtctactt taacccctta tcgggacctc ccggccacta  27900
tccggatcaa tttattccta actttgacgc ggtaaaggac tcggcggatg gctacgactg  27960
aatgttaagt ggagaggcag agcaactgcg cctgaaacac ctggtccact gtcgccgcca  28020
caagtgcttt gcccgcgact ccggtgagtt ttgctacttt gaattgcccg aggatcatat  28080
```

```
cgagggcccg gcgcacggcg tccggcttac cgcccaggga gagcttgccc gtagcctgat  28140
tcgggagttt acccagcgcc ccctgctagt tgagcgggac aggggaccct gtgttctcac  28200
tgtgatttgc aactgtccta accctggatt acatcaagat ctttgttgcc atctctgtgc  28260
tgagtataat aaatacagaa attaaaatat actggggctc ctatcgccat cctgtaaacg  28320
ccaccgtctt cacccgccca agcaaaccaa ggcgaacctt acctggtact tttaacatct  28380
ctccctctgt gatttacaac agtttcaacc cagacggagt gagtctacga gagaacctct  28440
ccgagctcag ctactccatc agaaaaaaca ccaccctcct tacctgccgg gaacgtacga  28500
tgtggctgca gagcctgctg ctcttgggca ctgtggcctg cagcatctct gcacccgccc  28560
gctcgcccag ccccagcacg cagccctggg agcatgtgaa tgccatccag gaggcccggc  28620
gtctcctgaa cctgagtaga gacactgctg ctgagatgaa tgaaacagta gaagtcatct  28680
cagaaatgtt tgacctccag gagccgacct gcctacagac ccgcctggag ctgtacaagc  28740
agggcctgcg gggcagcctc accaagctca agggcccctt gaccatgatg gccagccact  28800
acaagcagca ctgccctcca accccggaaa cttcctgtgc aacccagact atcacctttg  28860
aaagtttcaa agagaacctg aaggactttc tgcttgtcat cccctttgac tgctgggagc  28920
cagtccagga gtgacaattg actctatgtg ggatatgctc cagcgctaca accttgaagt  28980
caggcttcct ggatgtcagc atctgacttt ggccagcacc tgtcccgcgg atttgttcca  29040
gtccaactac agcgacccac cctaacagag atgaccaaca caaccaacgc ggccgccgct  29100
accggactta catctaccac aaatacaccc caagtttctg cctttgtcaa taactgggat  29160
aacttgggca tgtggtggtt ctccatagcg cttatgtttg tatgccttat tattatgtgg  29220
ctcatctgct gcctaaagcg caaacgcgcc cgaccaccca tctatagtcc catcattgtg  29280
ctacacccaa acaatgatgg aatccataga ttggacggac tgaaacacat gttcttttct  29340
cttacagtat gattaaatga gacatgattc ctcgagtttt tatattactg acccttgttg  29400
cgcttttttg tgcgtgctcc acattggctg cggtttctca catcgaagta gactgcattc  29460
cagccttcac agtctatttg ctttacggat ttgtcaccct cacgctcatc tgcagcctca  29520
tcactgtggt catcgccttt atccagtgca ttgactgggt ctgtgtgcgc tttgcatatc  29580
tcagacacca tccccagtac agggacagga ctatagctga gcttcttaga attctttaat  29640
tatgaaattt actgtgactt ttctgctgat tatttgcacc ctatctgcgt tttgttcccc  29700
gacctccaag cctcaaagac atatatcatg cagattcact cgtatatgga atattccaag  29760
ttgctacaat gaaaaaagcg atctttccga agcctggtta tatgcaatca tctctgttat  29820
ggtgttctgc agtaccatct tagccctagc tatatatccc taccttgaca ttggctggaa  29880
acgaatagat gccatgaacc acccaacttt ccccgcgccc gctatgcttc cactgcaaca  29940
agttgttgcc ggcggctttg tcccagccaa tcagcctcgc cccacttctc ccaccccac  30000
tgaaatcagc tactttaatc taacaggagg agatgactga caccctagat ctagaaatgg  30060
acggaattat tacagagcag cgcctgctag aaagacgcag ggcagcggcc gagcaacagc  30120
gcatgaatca agagctccaa gacatggtta acttgcacca gtgcaaaagg ggtatctttt  30180
gtctggtaaa gcaggccaaa gtcacctacg acagtaatac caccggacac cgccttagct  30240
acaagttgcc aaccaagcgt cagaaattgg tggtcatggt gggagaaaag cccattacca  30300
taactcagca ctcggtagaa accgaaggct gcattcactc accttgtcaa ggacctgagg  30360
atctctgcac ccttattaag accctgtgcg gtctcaaaga tcttattccc tttaactaat  30420
```

```
aaaaaaaaat aataaagcat cacttactta aaatcagtta gcaaatttct gtccagttta  30480
ttcagcagca cctccttgcc ctcctcccag ctctggtatt gcagcttcct cctggctgca  30540
aactttctcc acaatctaaa tggaatgtca gtttcctcct gttcctgtcc atccgcaccc  30600
actatcttca tgttgttgca gatgaagcgc gcaagaccgt ctgaagatac cttcaacccc  30660
gtgtatccat atgacacgga aaccggtcct ccaactgtgc cttttcttac tcctcccttt  30720
gtatccccca atgggtttca agagagtccc cctggggtac tctctttgcg cctatccgaa  30780
cctctagtta cctccaatgg catgcttgcg ctcaaaatgg gcaacggcct ctctctggac  30840
gaggccggca accttacctc ccaaaatgta accactgtga gcccacctct caaaaaaacc  30900
aagtcaaaca taaacctgga aatatctgca cccctcacag ttacctcaga agccctaact  30960
gtggctgccg ccgcacctct aatggtcgcg ggcaacacac tcaccatgca atcacaggcc  31020
ccgctaaccg tgcacgactc caaacttagc attgccaccc aaggacccct cacagtgtca  31080
gaaggaaagc tagccctgca aacatcaggc cccctcacca ccaccgatag cagtaccctt  31140
actatcactg cctcaccccc tctaactact gccactggta gcttgggcat tgacttgaaa  31200
gagcccattt atacacaaaa tggaaaacta ggactaaagt acggggctcc tttgcatgta  31260
acagacgacc taaacacttt gaccgtagca actggtccag gtgtgactat taataatact  31320
tccttgcaaa ctaaagttac tggagccttg ggttttgatt cacaaggcaa tatgcaactt  31380
aatgtagcag gaggactaag gattgattct caaaacagac gccttatact tgatgttagt  31440
tatccgtttg atgctcaaaa ccaactaaat ctaagactag gacagggccc tctttttata  31500
aactcagccc acaacttgga tattaactac aacaaaggcc tttacttgtt tacagcttca  31560
aacaattcca aaaagcttga ggttaaccta agcactgcca aggggttgat gtttgacgct  31620
acagccatag ccattaatgc aggagatggg cttgaatttg gttcacctaa tgcaccaaac  31680
acaaatcccc tcaaaacaaa aattggccat ggcctagaat ttgattcaaa caaggctatg  31740
gttcctaaac taggaactgg ccttagtttt gacagcacag gtgccattac agtaggaaac  31800
aaaaataatg ataagctaac cctatggaca ggtccaaaac cagaagccaa ctgcataatt  31860
gaatacggga aacaaaaccc agatagcaaa ctaactttaa tccttgtaaa aaatggagga  31920
attgttaatg gatatgtaac gctaatggga gcctcagact acgttaacac cttatttaaa  31980
aacaaaaatg tctccattaa tgtagaacta tactttgatg ccactggtca tatattacca  32040
gactcatctt ctcttaaaac agatctagaa ctaaaataca agcaaaccgc tgactttagt  32100
gcaagaggtt ttatgccaag tactacagcg tatccatttg tccttcctaa tgcgggaaca  32160
cataatgaaa attatatttt tggtcaatgc tactacaaag caagcgatgg tgcccttttt  32220
ccgttggaag ttactgttat gcttaataaa cgcctgccag atagtcgcac atcctatgtt  32280
atgacttttt tatggtcctt gaatgctggt ctagctccag aaactactca ggcaaccctc  32340
ataacctccc catttacctt ttcctatatt agagaagatg actaataaac tctaaagaat  32400
cgtttgtgtt atgtttcaac gtgtttattt ttcaattgca gaaaatttca agtcattttt  32460
cattcagtag tatagcccca ccaccacata gcttatacag atcaccgtac cttaatcaaa  32520
ctcacagaac cctagtattc aacctgccac ctccctccca acacacagag tacacagtcc  32580
tttctccccg gctggcctta aaaagcatca tatcatgggt aacagacata ttcttaggtg  32640
ttatattcca cacggtttcc tgtcgagcca aacgctcatc aagtgatatt aataaactcc  32700
ccgggcagct cacttaagtt catgtcgctg tccagctgct gagccacagg ctgctgtcca  32760
acttgcggtt gcttaacggg cggcgaagga gaagtccacg cctacatggg ggagagtca   32820
```

```
taatcgtgca tcaggatagg gcggtggtgc tgcagcagcg cgcgaataaa ctgctgccgc  32880
cgccgctccg tcctgcagga atacaacatg gcagtggtct cctcagcgat gattcgcacc  32940
gcccgcagca taaggcgcct tgtcctccgg gcacagcagc gcaccctgat ctcacttaaa  33000
tcagcacagt aactgcagca cagcaccaca atattgttca aaatcccaca gtgcaaggcg  33060
ctgtatccaa agctcatggc ggggaccaca gaacccacgt ggccatcata ccacaagcgc  33120
aggtagatta agtggcgacc cctcataaac acgctggaca taaacattac ctcttttggc  33180
atgttgtaat tcaccacctc ccggtaccat ataaacctct gattaaacat ggcgccatcc  33240
accaccatcc taaaccagct ggccaaaacc tgcccccgccg ggntatacac tgcagggaac  33300
cgggactgga acaatgacag tggagagccc aggactcgta accatggatc atcatgctcg  33360
tcatgatatc aatgttggca caacacaggc acacgtgcat acacttcctc aggattacaa  33420
gctcctcccg cgttagaacc atatcccagg gaacaaccca ttcctgaatc agcgtaaatc  33480
ccacactgca gggaagacct cgcacgtaac tcacgttgtg cattgtcaaa gtgttacatt  33540
cgggcagcag cggatgatcc tccagtatgg tagcgcgggt ttctgtctca aaaggaggta  33600
gacgatccct actgtacgga gtgcgccgag acaaccgaga tcgtgttggt cgtagtgtca  33660
tgccaaatgg aacgccggac gtagtcatat ttcctgaagc aaaaccaggt gcgggcgtga  33720
caaacagatc tgcgtctccg gtctcgccgc ttagatcgct ctgtgtagta gttgtagtat  33780
atccactctc tcaaagcatc caggcgcccc ctggcttcgg gttctatgta aactccttca  33840
tgcgccgctg ccctgataac atccaccacc gcagaataag ccacacccag ccaacctaca  33900
cattcgttct gcgagtcaca cacgggagga gcgggaagag ctggaagaac catgtttttt  33960
tttttattcc aaaagattat ccaaaacctc aaaatgaaga tctattaagt gaacgcgctc  34020
ccctccggtg gcgtggtcaa actctacagc caaagaacag ataatggcat ttgtaagatg  34080
ttgcacaatg gcttccaaaa ggcaaacggc cctcacgtcc aagtggacgt aaaggctaaa  34140
cccttcaggg tgaatctcct ctataaacat tccagcacct tcaaccatgc ccaaataatt  34200
ctcatctcgc caccttctca atatatctct aagcaaatcc cgaatattaa gtccggccat  34260
tgtaaaaatt tggctccaga gcgccctcca ccttcagcct caagcagcga atcatgattg  34320
caaaaattca ggttcctcac agacctgtat aagattcaaa agcggaacat taacaaaaat  34380
accgcgatcc cgtaggtccc ttcgcagggc cagctgaaca taatcgtgca ggtctgcacg  34440
gaccagcgcg gccacttccc cgccaggaac catgacaaaa gaacccacac tgattatgac  34500
acgcatactc ggagctatgc taaccagcgt agccccgatg taagcttgtt gcatgggcgg  34560
cgatataaaa tgcaaggtgc tgctcaaaaa atcaggcaaa gcctcgcgca aaaaagaaag  34620
cacatcgtag tcatgctcat gcagataaag gcaggtaagc tccggaacca ccacagaaaa  34680
agacaccatt tttctctcaa acatgtctgc gggtttctgc ataaacacaa aataaaataa  34740
caaaaaaaca tttaaacatt agaagcctgt cttacaacag gaaaaacaac ccttataagc  34800
ataagacgga ctacggccat gccggcgtga ccgtaaaaaa actggtcacc gtgattaaaa  34860
agcaccaccg acagctcctc ggtcatgtcc ggagtcataa tgtaagactc ggtaaacaca  34920
tcaggttgat tcacatcggt cagtgctaaa aagcgaccga aatagcccgg gggaatacat  34980
acccgcaggc gtagagacaa cattacagcc cccataggag gtataacaaa attaatagga  35040
gagaaaaaca cataaacacc tgaaaaaccc tcctgcctag gcaaaatagc accctcccgc  35100
tccagaacaa catacagcgc ttccacagcg gcagccataa cagtcagcct taccagtaaa  35160
```

```
aaagaaaacc tattaaaaaa acaccactcg acacggcacc agctcaatca gtcacagtgt  35220
aaaaaagggc caagtgcaga gcgagtatat ataggactaa aaaatgacgt aacggttaaa  35280
gtccacaaaa aacacccaga aaaccgcacg cgaacctacg cccagaaacg aaagccaaaa  35340
aacccacaac ttcctcaaat cgtcacttcc gttttcccac gttacgtcac ttcccatttt  35400
aagaaaacta caattcccaa cacatacaag ttactccgcc ctaaaaccta cgtcacccgc  35460
cccgttccca cgccccgcgc cacgtcacaa actccacccc ctcattatca tattggcttc  35520
aatccaaaat aaggtatatt attgatgatg ttaattaaca tgcatggatc ctcgtctcga  35580
cgatgccctt gagagccttc aacccagtca gctccttccg gtgggcgcgg ggcatgacta  35640
tcgtcgccgc acttatgact gtcttcttta tcatgcaact cgtaggacag gtgccggcag  35700
cgctctgggt cattttcggc gaggaccgct ttcgctggag cgcgacgatg atcggcctgt  35760
cgcttgcggt attcggaatc ttgcacgccc tcgctcaagc cttcgtcact ggtcccgcca  35820
ccaaacgttt cggcgagaag caggccatta tcgccggcat ggcggccgac gcgctgggct  35880
acgtcttgct ggcgttcgcg acgcgaggct ggatggcctt ccccattatg attcttctcg  35940
cttccggcgg catcgggatg cccgcgttgc aggccatgct gtccaggcag gtagatgacg  36000
accatcaggg acagcttcaa ggatcgctcg cggctcttac cagcctaact tcgatcactg  36060
gaccgctgat cgtcacggcg atttatgccg cctcggcgag cacatggaac gggttggcat  36120
ggattgtagg cgccgcccta taccttgtct gcctccccgc gttgcgtcgc ggtgcatgga  36180
gccgggccac ctcgacctga atggaagccg gcggcacctc gctaacggat tcaccactcc  36240
aagaattgga gccaatcaat tcttgcggag aactgtgaat gcgcaaacca acccttggca  36300
gaacatatcc atcgcgtccg ccatctccag cagccgcacg cggcgcatct cgggcagcgt  36360
tgggtcctgg ccacgggtgc gcatgatcgt gctcctgtcg ttgaggaccc ggctaggctg  36420
gcggggttgc cttactggtt agcagaatga atcaccgata cgcgagcgaa cgtgaagcga  36480
ctgctgctgc aaaacgtctg cgacctgagc aacaacatga atggtcttcg gtttccgtgt  36540
ttcgtaaagt ctggaaacgc ggaagtcagc gccctgcacc attatgttcc ggatctgcat  36600
cgcaggatgc tgctggctac cctgtggaac acctacatct gtattaacga agcgctggca  36660
ttgaccctga gtgatttttc tctggtcccg ccgcatccat accgccagtt gtttaccctc  36720
acaacgttcc agtaaccggg catgttcatc atcagtaacc cgtatcgtga gcatcctctc  36780
tcgtttcatc ggtatcatta cccccatgaa cagaaattcc cccttacacg gaggcatcaa  36840
gtgaccaaac aggaaaaaac cgcccttaac atggcccgct ttatcagaag ccagacatta  36900
acgcttctgg agaaactcaa cgagctggac gcggatgaac aggcagacat ctgtgaatcg  36960
cttcacgacc acgctgatga gctttaccgc agctgcctcg cgcgtttcgg tgatgacggt  37020
gaaaacctct gacacatgca gctcccggag acggtcacag cttgtctgta agcggatgcc  37080
gggagcagac aagcccgtca gggcgcgtca gcgggtgttg gcgggtgtcg gggcgcagcc  37140
atgacccagt cacgtagcga tagcggagtg tatactggct taactatgcg gcatcagagc  37200
agattgtact gagagtgcac catatgcggt gtgaaatacc gcacagatgc gtaaggagaa  37260
aataccgcat caggcgctct tccgcttcct cgctcactga ctcgctgcgc tcggtcgttc  37320
ggctgcggcg agcggtatca gctcactcaa aggcggtaat acggttatcc acagaatcag  37380
gggataacgc aggaaagaac atgtgagcaa aaggccagca aaaggccagg aaccgtaaaa  37440
aggccgcgtt gctggcgttt ttccataggc tccgcccccc tgacgagcat cacaaaaatc  37500
gacgctcaag tcagaggtgg cgaaacccga caggactata aagataccag gcgtttcccc  37560
```

```
ctggaagctc cctcgtgcgc tctcctgttc cgaccctgcc gcttaccgga tacctgtccg  37620
cctttctccc ttcgggaagc gtggcgcttt ctcaatgctc acgctgtagg tatctcagtt  37680
cggtgtaggt cgttcgctcc aagctgggct gtgtgcacga accccccgtt cagcccgacc  37740
gctgcgcctt atccggtaac tatcgtcttg agtccaaccc ggtaagacac gacttatcgc  37800
cactggcagc agccactggt aacaggatta gcagagcgag gtatgtaggc ggtgctacag  37860
agttcttgaa gtggtggcct aactacggct acactagaag gacagtattt ggtatctgcg  37920
ctctgctgaa gccagttacc ttcggaaaaa gagttggtag ctcttgatcc ggcaaacaaa  37980
ccaccgctgg tagcggtggt ttttttgttt gcaagcagca gattacgcgc agaaaaaaag  38040
gatctcaaga agatcctttg atcttttcta cggggtctga cgctcagtgg aacgaaaact  38100
cacgttaagg gattttggtc atgagattat caaaaaggat cttcacctag atccttttaa  38160
attaaaaatg aagttttaaa tcaatctaaa gtatatatga gtaaacttgg tctgacagtt  38220
accaatgctt aatcagtgag gcacctatct cagcgatctg tctatttcgt tcatccatag  38280
ttgcctgact ccccgtcgtg tagataacta cgatacggga gggcttacca tctggcccca  38340
gtgctgcaat gataccgcga gacccacgct caccggctcc agatttatca gcaataaacc  38400
agccagccgg aagggccgag cgcagaagtg gtcctgcaac tttatccgcc tccatccagt  38460
ctattaattg ttgccgggaa gctagagtaa gtagttcgcc agttaatagt ttgcgcaacg  38520
ttggttgnnn nnnaaaaagg atcttcacct agatcctttt cacgtagaaa gccagtccgc  38580
agaaacggtg ctgaccccgg atgaatgtca gctactgggc tatctggaca agggaaaacg  38640
caagcgcaaa gagaaagcag gtagcttgca gtgggcttac atggcgatag ctagactggg  38700
cggttttatg gacagcaagc gaaccggaat tgccagctgg ggcgccctct ggtaaggttg  38760
ggaagccctg caaagtaaac tggatggctt tctcgccgcc aaggatctga tggcgcaggg  38820
gatcaagctc tgatcaagag acaggatgag gatcgtttcg catgattgaa caagatggat  38880
tgcacgcagg ttctccggcc gcttgggtgg agaggctatt cggctatgac tgggcacaac  38940
agacaatcgg ctgctctgat gccgccgtgt tccggctgtc agcgcagggg cgcccggttc  39000
tttttgtcaa gaccgacctg tccggtgccc tgaatgaact gcaagacgag gcagcgcggc  39060
tatcgtggct ggccacgacg ggcgttcctt gcgcagctgt gctcgacgtt gtcactgaag  39120
cgggaaggga ctggctgcta ttgggcgaag tgccggggca ggatctcctg tcatctcacc  39180
ttgctcctgc cgagaaagta tccatcatgg ctgatgcaat gcggcggctg catacgcttg  39240
atccggctac ctgcccattc gaccaccaag cgaaacatcg catcgagcga gcacgtactc  39300
ggatggaagc cggtcttgtc gatcaggatg atctggacga agagcatcag gggctcgcgc  39360
cagccgaact gttcgccagg ctcaaggcga gcatgcccga cggcgaggat ctcgtcgtga  39420
cccatggcga tgcctgcttg ccgaatatca tggtggaaaa tggccgcttt tctggattca  39480
tcgactgtgg ccggctgggt gtggcggacc gctatcagga catagcgttg gctacccgtg  39540
atattgctga agagcttggc ggcgaatggg ctgaccgctt cctcgtgctt tacggtatcg  39600
ccgctcccga ttcgcagcgc atcgccttct atcgccttct tgacgagttc ttctgaattt  39660
tgttaaaatt tttgttaaat cagctcattt tttaaccaat aggccgaaat cggcaacatc  39720
ccttataaat caaaagaata gaccgcgata gggttgagtg ttgttccagt ttggaacaag  39780
agtccactat taaagaacgt ggactccaac gtcaaagggc gaaaaaccgt ctatcagggc  39840
gatggcccac tacgtgaacc atcacccaaa tcaagttttt tgcggtcgag gtgccgtaaa  39900
```

```
gctctaaatc ggaaccctaa agggagcccc cgatttagag cttgacgggg aaagccggcg  39960

aacgtggcga gaaaggaagg gaagaaagcg aaaggagcgg gcgctagggc gctggcaagt  40020

gtagcggtca cgctgcgcgt aaccaccaca cccgcgcgct taatgcgccg ctacagggcg  40080

cgtccattcg ccattcagga tcgaattaat tcttaat                           40117
```

```
<210> SEQ ID NO 10
<211> LENGTH: 18
<212> TYPE: DNA
<213> ORGANISM: Artificial Sequence
<220> FEATURE:
<223> OTHER INFORMATION: The nucleotide sequence of primer E4-forward

<400> SEQUENCE: 10

ggagtgcgcc gagacaac                                                   18


<210> SEQ ID NO 11
<211> LENGTH: 18
<212> TYPE: DNA
<213> ORGANISM: Artificial Sequence
<220> FEATURE:
<223> OTHER INFORMATION: The nucleotide sequence of primer E4-reverse

<400> SEQUENCE: 11

actacgtccg gcgttcca                                                   18


<210> SEQ ID NO 12
<211> LENGTH: 28
<212> TYPE: DNA
<213> ORGANISM: Artificial Sequence
<220> FEATURE:
<223> OTHER INFORMATION: The nucleotide sequence of probe E4

<400> SEQUENCE: 12

tggcatgaca ctacgaccaa cacgatct                                        28


<210> SEQ ID NO 13
<211> LENGTH: 20
<212> TYPE: DNA
<213> ORGANISM: Artificial Sequence
<220> FEATURE:
<223> OTHER INFORMATION: The nucleotide sequence of primer GAPDH-forward

<400> SEQUENCE: 13

caccgaggac caggttgtct                                                 20


<210> SEQ ID NO 14
<211> LENGTH: 24
<212> TYPE: DNA
<213> ORGANISM: Artificial Sequence
<220> FEATURE:
<223> OTHER INFORMATION: The nucleotide sequence of primer GAPDH-reverse

<400> SEQUENCE: 14

cataccagga gatgagcttt acga                                            24


<210> SEQ ID NO 15
<211> LENGTH: 30
<212> TYPE: DNA
<213> ORGANISM: Artificial Sequence
<220> FEATURE:
<223> OTHER INFORMATION: The nucleotide sequence of probe GAPDH

<400> SEQUENCE: 15

caagagtgac tcccactctt ccacctttga                                      30
```

<210> SEQ ID NO 16
<211> LENGTH: 21
<212> TYPE: DNA
<213> ORGANISM: Artificial Sequence
<220> FEATURE:
<223> OTHER INFORMATION: The nucleotide sequence of E1-forward primer

<400> SEQUENCE: 16
tccggtttct atgccaaacc t 21

<210> SEQ ID NO 17
<211> LENGTH: 22
<212> TYPE: DNA
<213> ORGANISM: Artificial Sequence
<220> FEATURE:
<223> OTHER INFORMATION: The nucleotide sequence of E1-reverse primer

<400> SEQUENCE: 17
tcctccggtg ataatgacaa ga 22

<210> SEQ ID NO 18
<211> LENGTH: 19
<212> TYPE: DNA
<213> ORGANISM: Artificial Sequence
<220> FEATURE:
<223> OTHER INFORMATION: The nucleotide sequence of probe “onco”

<400> SEQUENCE: 18
tgatcgatcc acccagtga 19

<210> SEQ ID NO 19
<211> LENGTH: 16
<212> TYPE: DNA
<213> ORGANISM: Artificial Sequence
<220> FEATURE:
<223> OTHER INFORMATION: The nucleotide sequence of probe “wt”

<400> SEQUENCE: 19
tacctgccac gaggct 16

<210> SEQ ID NO 20
<211> LENGTH: 21
<212> TYPE: DNA
<213> ORGANISM: Artificial Sequence
<220> FEATURE:
<223> OTHER INFORMATION: The nucleotide sequence of GM-CSF-forward

<400> SEQUENCE: 20
aaacaccacc ctccttacct g 21

<210> SEQ ID NO 21
<211> LENGTH: 21
<212> TYPE: DNA
<213> ORGANISM: Artificial Sequence
<220> FEATURE:
<223> OTHER INFORMATION: The nucleotide sequence of GM-CSF-reverse primer

<400> SEQUENCE: 21
tcattcatct cagcagcagt g 21

<210> SEQ ID NO 22
<211> LENGTH: 21
<212> TYPE: DNA
<213> ORGANISM: Artificial Sequence

```
<220> FEATURE:
<223> OTHER INFORMATION: The nucleotide sequence of human beta-actin-
      forward primer

<400> SEQUENCE: 22

cagcagatgt ggatcagcaa g                                              21


<210> SEQ ID NO 23
<211> LENGTH: 21
<212> TYPE: DNA
<213> ORGANISM: Artificial Sequence
<220> FEATURE:
<223> OTHER INFORMATION: The nucleotide sequence of human beta-actin-
      reverse primer

<400> SEQUENCE: 23

ctagaagcat ttgcggtgga c                                              21


<210> SEQ ID NO 24
<211> LENGTH: 22
<212> TYPE: DNA
<213> ORGANISM: Artificial Sequence
<220> FEATURE:
<223> OTHER INFORMATION: The nucleotide sequence of human beta-actin
      probe
<220> FEATURE:
<221> NAME/KEY: misc_feature
<223> OTHER INFORMATION: 6FAM marker in 5' end TAMRA marker in 3' end

<400> SEQUENCE: 24

aggagtatga cgaaggcccc tc                                             22


<210> SEQ ID NO 25
<211> LENGTH: 16
<212> TYPE: DNA
<213> ORGANISM: Artificial Sequence
<220> FEATURE:
<223> OTHER INFORMATION: The nucleotide sequence of mouse beta-actin-
      forward primer

<400> SEQUENCE: 25

cgagcggttc cgatgc                                                    16


<210> SEQ ID NO 26
<211> LENGTH: 20
<212> TYPE: DNA
<213> ORGANISM: Artificial Sequence
<220> FEATURE:
<223> OTHER INFORMATION: The nucleotide sequence of mouse beta-actin-
      reverse primer

<400> SEQUENCE: 26

tggatgccac aggattccat                                                20


<210> SEQ ID NO 27
<211> LENGTH: 27
<212> TYPE: DNA
<213> ORGANISM: Artificial Sequence
<220> FEATURE:
<223> OTHER INFORMATION: The nucleotide sequence of mouse beta-actin
      probe
<220> FEATURE:
<221> NAME/KEY: misc_feature
<223> OTHER INFORMATION: 6FAM marker in 5' end TAMRA marker in 3' end

<400> SEQUENCE: 27

aggctctttt ccagccttcc ttcttgg                                        27
```

```
<210> SEQ ID NO 28
<211> LENGTH: 4
<212> TYPE: PRT
<213> ORGANISM: Artificial Sequence
<220> FEATURE:
<223> OTHER INFORMATION: Synthetic peptide

<400> SEQUENCE: 28

Gly Ala Gly Ala
1


<210> SEQ ID NO 29
<211> LENGTH: 4
<212> TYPE: PRT
<213> ORGANISM: Artificial Sequence
<220> FEATURE:
<223> OTHER INFORMATION: Synthetic peptide

<400> SEQUENCE: 29

Lys Lys Thr Lys
1
```

RECOMBINANT SEROTYPE 5 (AD5) ADENOVIRAL VECTORS

CROSS-REFERENCE TO RELATED APPLICATIONS

This application is a 35 U.S.C. §371 National Phase Entry Application of International Application No. PCT/FI12/51162 filed Nov. 23, 2012, and which claims benefit under 35 U.S.C. §119(e) of U.S. Provisional Application Ser. No. 61/563,634 filed Nov. 25, 2011, and Finnish Application No. 20116181, filed on Nov. 25, 2011 the contents of which are incorporated herein by reference in their entireties.

SEQUENCE LISTING

The instant application contains a Sequence Listing which has been submitted in ASCII format via EFS-Web and is hereby incorporated by reference in its entirety. Said ASCII copy, created on Dec. 23, 2015, is named ONCT-002N01US_ST25.txt and is 401,668 bytes in size.

FIELD OF THE INVENTION

The present invention relates to the field of medicine. Specifically, the present invention relates to novel strategies to construct oncolytic adenoviral vectors for cancer therapy allowing safe and efficient treatment.

BACKGROUND OF THE INVENTION

Typically, cancer is treated with conventional treatment regimens such as surgery, hormonal therapies, chemotherapies, radiotherapies and/or other therapies. However, in many cases cancers which often are characterized by an advanced stage cannot be cured with present therapies. Despite progress in conventional cancer treatment regimens, metastatic disease essentially remains incurable and new treatment alternatives are desperately needed.

Virotherapy is a relatively novel treatment approach, which harnesses the natural ability of some viruses to kill the cells in which they proliferate and the ability to spread to neighboring cells, thereby amplifying the therapeutic effect of the initial input dose. Requirements of optimal viral vectors include an efficient capability to find specific target cells and express the viral genome in the target cells. Furthermore, therapeutically optimal vectors have to stay active in the target tissues or cells long enough to exert their therapeutic efficacy while causing minimal effects in normal cells. There has been some progress in developing these beneficial properties of therapeutic viral vectors during the last decades and, for example, retroviral, adenoviral and adeno-associated viral vectors have been widely studied in biomedicine.

Contrary to the viral gene therapy approach, in which foreign genetic material is introduced in cells to correct genetic defects, oncolytic virotherapy takes advantage of the similarities between cellular mechanisms of carcinogenesis and DNA virus replication to direct the cell lysing activity of an oncolytic virus to tumor. In virotherapy the cancer cell transduction and viral replication are carefully controlled by genetic engineering of the viral genome to gain effective and safe tumor eradication. In other words, the use of replicating, oncolytic viruses for cancer treatment necessitates introduction of various genetic modifications to the viral genome, thereby restraining replication exclusively to tumor cells and eventually obtaining selective eradication of the tumor without side effects to healthy tissue.

Upon infection, adenoviruses need to induce a cell cycle S-phase-like state in order to transcribe and replicate the viral genome. E1A is the first viral protein to be expressed in a transduced cell and it can activate transcription of other early viral genes by interactions with cellular check point proteins. Importantly, E1A expression results in the activation of the Eta promoter and the E2 region transcription, leading to the expression of adenoviral replication machinery (Berk 1986, Annu Rev Genet 20: 45-79).

Specific deletions on adenoviral key regulatory genes have been utilized to create dysfunctional proteins or the lack of their expression that leads to dependence on a specific genetic feature present in target cells. Partial deletions of E1A result in restricted replication in normal cells but allow replication in target cells, such as cancer cells. Conditionally replicating viruses featuring a 24 base pair deletion in the CR2 (constant region 2) have been created and shown to be potent and selective in the treatment of glioma and breast cancer xenografts (Fueyo et al. 2000, Oncogene 19:2-12; Heise et al. 2000, Nat Med 6:1134-9). Their cancer specificity results from the inability of dysfunctional E1A to release E2F1 transcription factor, which leads to the requirement of free E2F1. E2F1 is abundant in cancer cells, where the pRb pathway is most often disrupted (Hanahan and Weinberg 2000, Cell 100: 57-70).

Most clinical trials have been performed with early generation adenoviruses based on adenovirus 5 (Ad5). The antitumor effect of oncolytic adenoviruses depends on their capacity for gene delivery. Unfortunately, most tumors have low expression of the main Ad5 receptor, coxsackie-adenovirus receptor (CAR).

Currently most oncolytic viruses in clinical use are highly attenuated in terms of replication due to several deletions in critical viral genes. These viruses have shown excellent safety record, but the antitumor efficacy has been limited. However, clinical and preclinical results show that treatment with unarmed oncolytic viruses is not immunostimulatory enough to result in sustained anti-tumoral therapeutic immune responses. In this regard, oncolytic viruses have been armed to be more immunostimulatory. Virally infected cells are superior at delivery of nonviral antigen (i.e. tumor antigen) for cross-presentation (Schulz et al. 2005, Nature 433:887-92), and virally induced cell death would be expected to enhance the availability of tumor-associated antigens for uptake by dendritic cells (DCs) (Moehler et al. 2005, Hum Gene Ther 16:996-1005) and subsequently enhance stimulation of cytotoxic T-cells. Furthermore, viral infection may alter the balance of cytokine production from the tumor, and subsequently affect the nature of the immune reaction to the tumor, that is, by counteracting the immunosuppressive nature of the tumor microenvironment (Prestwich et al. 2008, Expert Rev Anticancer Ther 8:1581-8). Most importantly, viruses can be engineered to express highly immunogenic proteins such as granulocyte-macrophage colony-stimulating factor (GM-CSF). When immunogenic proteins are expressed within tumor cells, they are potent stimulators of specific and long-lasting antitumor immunity. Introduction of immunotherapeutic genes into tumor cells and, furthermore, their translation into proteins, leads to the activation of the immune response and to more efficient destruction of tumor cells. The most relevant immune cells in this regard are natural killer cells (NK) and cytotoxic CD8+ T-cells.

Adenoviral Vectors

Adenoviruses are non-enveloped viruses 70-90 nm in diameter with an icosahedral capsid. Their genome is linear, double stranded DNA varying between 25-45 kilobases in size with inverted terminal repeats (ITRs) at both termini and a terminal protein attached to the 5' ends (Russell 2000, J gen Virol 90:1-20).

The icosahedral capsid is formed by three major proteins, of which the hexon trimers are most abundant (Nemerow et al. 2009, Virology 384:380-8). Each of the twelve vertices of the capsid also contains a pentameric protein, a penton base that is covalently attached to the fiber. The fiber is a trimeric protein that protrudes from the penton base and is a knobbed rod-like structure. Other viral proteins Ma, IVa2, VI, VIII and IX are also associated with the viral capsid. The proteins VII, small peptide mu and a terminal protein (TP) are associated with DNA. Protein V provides a structural link to the capsid via protein VI.

All human adenoviruses have similarities in their fiber architecture. Each has an N-terminal tail, a shaft with repeating sequences, and a C-terminal knob domain with a globular structure. The knob domain is principally responsible for binding the target cellular receptor and its globular structure presents a large surface for lateral and apical binding. The fiber proteins of adenoviruses from different subgroups most distinctively differ in length and ability to bend.

The fiber participates in attachment of the virus to the target cell. First, the knob domain of the fiber protein binds to the receptor of the target cell, secondly, the virus interacts with an integrin molecule, and thirdly, the virus is endocytosed into the target cell. Next, the viral genome is transported from endosomes into the nucleus and the replication of the viral genome can begin (Russell W. C. 2000, J General Virol 81, 2573-2604).

Adenoviruses are dependent on the cellular machinery to replicate the viral genome. They can infect quiescent cells and induce them into a cell cycle S-phase-like state enabling viral DNA replication. The adenoviral genome can be divided into immediate early (E1A), early (E1B, E2, E3, E4), intermediate (IX, Iva), and late (L1-L5) genes (Russell 2000).

Adenoviral transcription can be described as a two-phase-event, early and late, characterized by the expression of different viral genes and separated by the onset of viral DNA replication (Russell 2000, J gen Virol 90:1-20). The first transcription unit to be expressed is the E1A. The E1A proteins stimulate the transcription of other early genes and modulate the expression of cellular genes involved in the transition into S-phase, making the cell more susceptible to viral DNA replication (Berk 1986, Annu Rev Genet 20: 45-79). The E1B proteins suppress cell death elicited in response to unregulated cell proliferation signals, including those mediated by E1A (Moran 1993, FASEB J 7:880-5). The E2 gene products provide the replication machinery for viral gene products.

E3 gene products are not essential for virus replication in vitro, but are dedicated to the control of various host immune responses. E3-gp19K inhibits the transport of the class 1 major histocompatibility complex (MHC) from the endoplasmic reticulum (ER) to the plasma membrane, thereby preventing the presentation of peptides to T lymphocytes by MHC (Rawle et al. 1989, J Immunol 143:2031-7). Other E3 proteins inhibit apoptosis elicited by various cellular proteins such as the tumor necrosis factor α (TNFα) (Wold 1993, J Cell Biochem 53:329-35). As an exception, E3 derived adenoviral death protein (ADP) functions late in the viral cycle to promote cell death, presumably to aid in the release of the virus after all the replicative functions have been completed. E4 gene products have been implicated in many events that occur as the late program begins. E4 proteins augment viral DNA synthesis and messenger RNA (mRNA) transport, late viral gene expression, shutoff of host protein synthesis, and production of progeny virions. The late gene transcription leads to the production of viral structural components and the encapsidation and maturation of the viral particles in the nucleus.

More than 50 different serotypes of adenoviruses have been found in humans. Serotypes are classified into six subgroups A-F and different serotypes are known to be associated with different conditions i.e. respiratory diseases, conjunctivitis and gastroenteritis. Adenovirus serotype 5 (Ad5) is known to cause respiratory diseases and it is the most common serotype studied in the field of gene therapy. In the first Ad5 vectors E1 and/or E3 regions were deleted enabling insertion of foreign DNA to the vectors (Danthinne and Imperiale 2000, Gene Ther 7:1707-14). Furthermore, deletions of other regions as well as further mutations have provided extra properties to viral vectors. Indeed, various modifications of adenoviruses have been suggested for achieving efficient anti-tumor effects.

EP1377671 B1 (Cell Genesys, Inc.) and application US2003/0104625 A1 (Cheng C. et al.) describe an oncolytic adenoviral vector encoding an immunotherapeutic protein granulocyte-macrophage colony-stimulating factor (GM-CSF).

EP1767642 A1 (Chengdu Kanghong Biotechnologies Co., Ltd.) discloses oncolytic adenoviral vectors having improved effects on human immune response.

WO2010072900 discloses oncolytic adenoviral vectors having a modified viral genome and an immunostimulatory GM-CSF.

SUMMARY OF THE INVENTION

An object of the present invention is to provide novel oncolytic adenoviruses for cancer therapy and to solve problems relating to conventional cancer therapy and manufacture of therapeutically effective and safe viral therapies for cancer.

Modifications in the E1-Region

Pan-cancer promoters target hallmark cancer pathways making them broadly applicable for targeting approaches in various cancer types. Examples of such promoters are E2F-1, the human telomerase reverse transcriptase (hTERT) promoter, and the multidrug resistance promoter (Mdr1). In the viruses of the present application the native E1A promoter has been replaced by a human E2F-1 promoter to control the expression of E1A and subsequent viral replication. E2F transcription factors regulate the expression of a diverse set of genes involved in key cellular events by binding to their promoters (Johnson and Schneider-Broussard 1998, Front Biosci 3:447-8). E2F transcription factors also activate their own promoters. In a resting cell E2F transcription factors are bound in a complex with retinoblastoma (pRb) protein. The pRb/E2F-1 complex inactivates the E2F-1 promoter and E2F-1 promoter activation requires free E2F-1 transcription factor. The pRb pathway is disrupted in nearly all human cancers, resulting in abundant free E2F-1 in cancer cells. This creates a broad target spectrum for E2F-1 promoter usage in replication control of oncolytic viruses in cancer treatment.

The rationale behind the use of a 24 base pair deletion in the E1A gene for restricting viral replication to cancer cells is similar to the use of E2F-1 promoter. The adenoviral E1A protein was originally described as a pRb binding protein capable of inducing DNA replication in quiescent normal cells (Ruley 1983, Nature 304:602-6). One of the key functions of E1A protein is to disrupt the pRb-E2F interactions, thereby releasing E2F transcription factors to activate the E2F responsive promoters and transcription of the genes they control, such as adenoviral E2A (Raychaudhuri et al. 1991, Genes Dev 5:1200-11). The conserved region 2 (CR2) in E1A protein forms a strong interaction with the pocket binding domain of pRb and CR1 mediates the actual disruption of the E2F binding of pRb (Fattaey et al. 1993, Mol Cell Biol 13:7267-77). Conditionally replicating viruses featuring a 24 base pair deletion in the CR2 were created and shown to be potent and selective in the treatment of glioma and breast cancer xenografts (Fueyo et al. 2000, Oncogene 19:2-12; Heise et al. 2000, Nat Med 6:1134-9). Their cancer specificity results from the inability of dysfunctional E1A to release E2F1 transcription factor, which leads to the requirement of free E2F1, similarly as when controlling the E1A expression with E2F-1 promoter.

However, one critical aspect has been neglected in previous viruses featuring the E2F-1 promoter. Since the promoter has E2F-1 binding sites, and is therefore effectively self-activated, even minute amounts of free E2F-1 (as found in normal cells) would lead to activation of the promoter, for release of more E2F-1 as a result of E1A binding to Rb. Eventually, this vicious loop leads to replication of such viruses in normal cells. Therefore, selectivity of the promoter can only be retained by inactivating binding of Rb by E1A, as described in this patent.

Modifications in the E3 Region

Adenoviruses are immunogenic viruses (Cerullo et al. 2007, Mol Ther 15:378-85), and since it seems that the immune response is a major determinant of the antitumor effect of oncolytic viruses (Tuve et al. 2009, Vaccine 27:4225-39), they have a great potential for cancer therapy utilities. Based on the "danger signal" paradigm (Matzinger 1994, Annu Rev Immunol 12:991-1045), the presence of oncolytic viruses within a tumor can act as a danger signal for the immune system. Further, tumor associated antigens (TAAs) are self-derived molecules that are converted immunogenic due to various genetic alterations and, as such, can be viewed as a second danger signal when released from cells undergoing abnormal death by viral oncolysis. The immunity related to adenoviral replication within the tumor and the release of tumor epitopes is not sufficient to cause antitumor response, however, and thus arming adenovirus with immunostimulatory molecules may augment the immune responses against tumor antigens, thereby presenting a third danger signal.

Oncolytic adenoviruses that express granulocyte-macrophage colony-stimulating factor (GM-CSF) induce anticancer immunity while acting directly on cancer cells by oncolysis. GM-CSF is a potent inducer of systemic antitumor immunity associated with recruitment and maturation of antigen presenting cells (APCs), mainly dendritic cells, as well as recruitment of cells of the innate immunity arm. However, systemically elevated cytokine levels represent a risk for toxic side-effects. Besides the direct risk of side effects mediated by high serums concentrations of GMCSF, an indirect risk results from recruitment of myeloid derived suppressor cells (MDSC). While the immunosuppressive effect of MDSC is potentially harmful for cancer patients in general, it could be particularly counterproductive in the context of cancer immunotherapy.

Further, the adenoviral E1A-protein is also toxic to cells. It is therefore important that therapeutic adenoviruses expressing GM-CSF can be directed to cells in which the intended therapy is required and healthy cells are left intact. Thus, there exists a great need to be able to control the replication of therapeutic oncolytic adenoviruses coding for GM-CSF. Other immunostimulatory molecules that could be expressed from the viral backbone include CD40 ligand and monoclonal antibody against CTLA-4.

E3 promoter activation requires the transactivating function of E1A protein (Berk 1986). Thus, when E1A protein production is controlled under the E2F-1 promoter, simultaneously an indirect control over E3 gene products is elicited.

Another way which has been used to induce anti-cancer immunity is through CpG island which can be inserted into the E3 region downstream from the GM-CSF transgene. Insertion of CpG dinucleotide islands into the nucleotide backbone of the virus activates toll-like receptor 9 (TLR9) expressed on B cells and dendritic cells (DC). Specifically, binding of CpG to TLR9 causes a conformational shift in the receptor, causing the recruitment of the adapter protein MyD88, activation of signaling pathways and subsequent activation of nuclear factor-κB (NF-κB) (Latz et al. 2007, Nat Immunol, 8, 772-779). On a cellular level TLR9 activation initiates a cascade of innate and adaptive immune responses, such as activation of DCs and subsequent secretion of chemokines, activation of NK-cells and expansion of T-cell populations, which may help initiate an immune response against infected tumor cells, and, via epitope spreading, against noninfected tumor cells as well. Previously CpG oligonucleotides have been studied as cancer vaccine adjuvants, but CpG islands have not been incorporated into oncolytic adenoviruses to enhance the immune reaction towards infected tumor cells. Since CpG islands represent patterns typical of microbes, it is unexepected that they could be of utility in the context of treatment of humans.

Modifications in the Fiber

Loss of CAR expression correlates with tumor progression, which implies low expression levels of CAR in advanced disease (Okegawa et al. 2004). Cells expressing low levels of CAR are refractory to Ad5 infection, at least in vitro. CAR dependency results in a scenario in which the target tissue of adenoviral gene therapy is poorly transduced, i.e. viruses enter target cells inefficiently, while non-target tissue with high CAR expression is efficiently transduced (Kim et al. 2002).

Fiber chimerism results in CAR binding ablation and alternate receptor recognition, but is limited to the tropic behavior of the characterized serotype adenoviruses. Increased transduction of ovarian cancer cells has been achieved by replacing the Ad5 knob with the knob from Ad3 (Krasnykh et al. 1996; Kanerva et al. 2002). Desmoglein 2 has recently been identified as the primary receptor for serotype 3 adenoviruses (Wang et al. 2011, Nature Medicine, 17, 96-105). Desmoglein 2 is a calcium-binding transmembrane glycoprotein from the cadherin protein family, and is a component of the cell-cell adhesion structure in epithelial cells. Desmoglein 2 is overexpressed in various epithelial malignancies, including gastric, bladder and metastatic prostate cancer as well as squamous cell carcinomas and melanoma (Biedermann et al. 2005, J Pathol, 207, 199-206; Abbod et al. 2009, Expert Rev Anticancer Ther, 9, 867-870; Trojan et al. 2005, Anticancer Res, 25, 183-191; Harada et al. 1996, Acta Derm Venereol, 76, 417-420; Schmitt et al. 2007, J Invest dermatol, 127, 2191-2206).

Genetic modification of the capsid is a conceptually elegant approach to redirect adenoviral tropism. In short, the goal of genetic targeting is to create a single-component vector that can transduce cells via non-native receptors. CAR independent gene delivery can be achieved by incorporating peptide ligands into the knob. This approach does not abrogate the native tropism, as the CAR binding ability is retained, but rather expands the vectors tropism. Ligands can be incorporated into two distinct locales of the knob: the HI loop or the carboxy (C)-terminus. An RGD (arg-gly-asp)-ligand, targeting adenoviruses into integrins, or a polylysine (pK) motif, targeting them into heparan sulphate proteoglycans (HSPGs), have been incorporated into the C-terminus (Wickham et al. 1993, Cell 73:309-19; Borovjagin et al. 2005 Cancer Gene Ther 12:475-86) and HI-loop (Krasnykh et al. 1998, J Virol 70:6839-46). In an aspect of the present invention the polylysine introduced in the C-terminus may comprise one or more than one lysine residues, e.g. from 1 to 10 ($Lys_{1-10}$), 1 to 7 ($Lys_{1-7}$) or 1, 2, 3, 4, 5, 6, 7, 8, 9 or 10 lysines.

Further, Ad5 capsid in therapeutic adenoviruses has been modified to alter the biodistribution of systemically administered adenoviruses to gain a more favorable tumor to liver ratio and, subsequently, less treatment related liver toxicity and inflammatory cytokine responses. A mutation in the putative HSPG binding motif (KKTK) of the Ad5 fiber shaft has been shown to result in substantial reduction in liver transduction and inflammatory cytokine responses (Smith et al. 2003a, Hum Gene Ther 14, 777-87; Smith et al. 2003b, Human Gene Ther 14, 1595-1604). However, all previous approaches exploring mutation of the HSPG region have been unable to retain or increase tumor targeting. Thus, reduction of liver uptake has been associated with reduction in tumor uptake. It is quite surprising that the Ad3 knob in a KKTK mutated Ad5 fiber seems to be able to achieve this critical goal.

Despite attempts to develop effective adenoviral therapies with high safety profile, there still remains a great demand and growing need for efficient and accurate gene transfer as well as increased specificity and sufficient tumor killing ability of gene therapies. The task of developing such therapies is particularly difficult because of safety requirements set for human therapies and the difficulties in avoiding clearance of the therapeutic virus due to host immune response. Of note, immunotherapies cannot be studied in vitro since an intact immune system is required. Moreover, since human adenoviruses are quite species specific, model systems do not capture the immunostimulatory effect of oncolysis on anti-tumor immunity. This is compounded by the species specificity of immunostimulatory molecules with regard to activity and signaling. In other words, mouse GMCSF does not work in humans and vice versa, and mouse GMCSF works differently in mice than human GMCSF in humans. Of all oncolytic adenovirus candidates tested today, only few have provided a level of therapeutic efficacy enabling successful clinical use. This application describes strategies and provides methods and means to both effectively recruit the host's immune system against malignant cells and simultaneously provide direct oncolytic activity in malignant cells, while maintaining an excellent safety record.

Aspects of the invention are directed to novel methods and means for achieving efficient and accurate gene transfer as well as increased specificity and sufficient tumor killing ability in cancer gene therapy. The present application describes construction of recombinant viral vectors, methods relating to manufacturing said vectors, and use of said vectors in tumor cells lines, animal models and cancer patients. The invention is also directed to host cells, compositions and kits comprising said vectors.

In an aspect of the invention, the oncolytic adenoviruses according to the invention can be used for improving, preventing and treating cancer in a subject.

In another aspect of the invention, the present invention relates to oncolytic adenoviruses derived from serotype 5 adenovirus. The inventive adenoviruses have one, some or all of the following modifications in their genome: the native E1A promoter controlling the expression E1A gene has been replaced by human E2F-1 promoter; a 24 base pair deletion has been introduced to the E1A gene CR2 region, which results in a dysfunctional E1A protein unable to bind cellular retinoblastoma protein and subsequently release E2F transcription factors for the activation of downstream viral gene expression; 965 base pairs coding for the viral genes gp19K and 6.7K have been deleted from the E3 region and a transgene GM-CSF has been introduced to replace them; the knob region of the fiber protein on the viral capsid has been replaced by a knob from serotype 3 adenovirus resulting in a 5/3 chimeric fiber protein, enabling viral entry via desmoglein 2 protein instead of the native receptor for serotype 5 adenovirus, the coxsackie-adenovirus receptor (CAR). Alternatively, an RGD motif has been introduced into the HI loop of the native fiber knob or a polylysine (pK) motif has been introduced into the C terminus of the native fiber knob. In combination with the modification of the knob a KKTK mutation has been introduced into the shaft of the fiber and a CpG island has been introduced in the E3 region.

In another aspect of the invention, the present invention relates to oncolytic CGTG-602 adenovirus which comprises serotype 5 adenovirus having the following modifications in the genome while the other regions of the genome are intact: the native E1A promoter controlling the expression E1A gene has been replaced by human E2F-1 promoter; a 24 base pair deletion has been introduced to the E1A gene CR2 region, which results in a dysfunctional E1A protein unable to bind cellular retinoblastoma protein and subsequently release E2F transcription factors for the activation of downstream viral gene expression; 965 base pairs coding for the viral genes gp19K and 6.7K have been deleted from the E3 region and a transgene GM-CSF has been introduced to replace them; the knob region of the fiber protein on the viral capsid has been replaced by a knob from serotype 3 adenovirus resulting in a 5/3 chimeric fiber protein, enabling viral entry via desmoglein 2 protein instead of the native receptor for serotype 5 adenovirus, the coxsackie-adenovirus receptor (CAR).

In other aspects of the invention, the invention relates to following serotype 5 based adenoviruses:

CGTG-601 is otherwise identical to CGTG-602, but it has an intact serotype 5 fiber.

CGTG-603 is otherwise identical to CGTG-601, but it has an RGD-4C motif (Arg-Gly-Asp and 4 cys) inserted in the HI-loop of the serotype 5 fiber knob. This modification enables viral entry to cells via cellular integrins in addition to the native receptor CAR.

CGTG-604 is otherwise identical to CGTG-601, but it has seven lysines introduced to the C-terminus of the serotype 5 fiber knob. This modification enables viral entry to cells via heparin sulphate proteoglycans in addition to the native receptor CAR.

CGTG-605 is otherwise identical to CGTG-602, but it has CpG islands inserted in the E3 downstream from the transgene GM-CSF.

CGTG-606 is otherwise identical to CGTG-602, but it has the KKTK motif of the serotype 5 fiber shaft mutated and replaced by a GAGA motif.

CGTG-607 is otherwise identical to CGTG-602, but it has CpG islands inserted in E3 downstream from the transgene GM-CSF and the KKTK motif of the serotype 5 fiber shaft mutated and replaced by a GAGA motif.

In another aspect of the invention, the present invention provides a method of treating cancer in a subject, wherein the method comprises administering the vector or pharmaceutical composition comprising the vector according to the invention to a subject, the method comprising the steps of a) carrying a vehicle comprising an oncolytic adenoviral vector of the invention to a cell, and b) expressing GM-CSF of said vector in the cell.

In another aspect of the invention, the present invention provides a method of increasing tumor specific immune response in a subject, wherein the method comprises:

a) carrying a vehicle comprising an oncolytic adenoviral vector according to the invention to a target cell or tissue,
b) expressing recombinant GM-CSF of said vector in the target cell, and
c) Increasing amount of cytotoxic T cells and/or natural killer cells in said target cell or tissue.

In another aspect of the invention, the present invention provides a use of the oncolytic adenoviral vector of the invention for producing GM-CSF in a cell.

In another aspect of the invention, the present invention provides an oncolytic adenoviral vector of the invention for producing GM-CSF in a cell.

In another aspect of the invention, the present invention provides a use of the oncolytic adenoviral vector of the invention for increasing tumor specific immune response in a subject.

In another aspect of the invention, the present invention provides an oncolytic adenoviral vector of the invention for increasing tumor specific immune response in a subject.

BRIEF DESCRIPTION OF THE DRAWINGS

The following figures are included to further demonstrate certain aspects and features of the present invention. The invention may be better understood by reference to one or more of these drawings in combination with the detailed description of specific aspects, including examples.

FIG. 3 represents results of MTS assay showing cell killing efficiency of the novel virus CGTG-602 compared to CGTG-102—a control virus bearing the genetically intact E1A promoter—a wild type serotype 5 virus and a non-replicating control virus Ad5/3 luc1 in A549 lung cancer cells, SKOV3ip.1 ovarian cancer cells and PC3-MM2 prostate cancer cells.

FIG. 9A represents the frequency of IFN-gamma producing peptide specific PBMCs, FIG. 9B the proportion of the peptide specific IFN-gamma producing PBMC from all activated PBMC (per million cells.

SEQUENCE LISTINGS

Figure 1A:
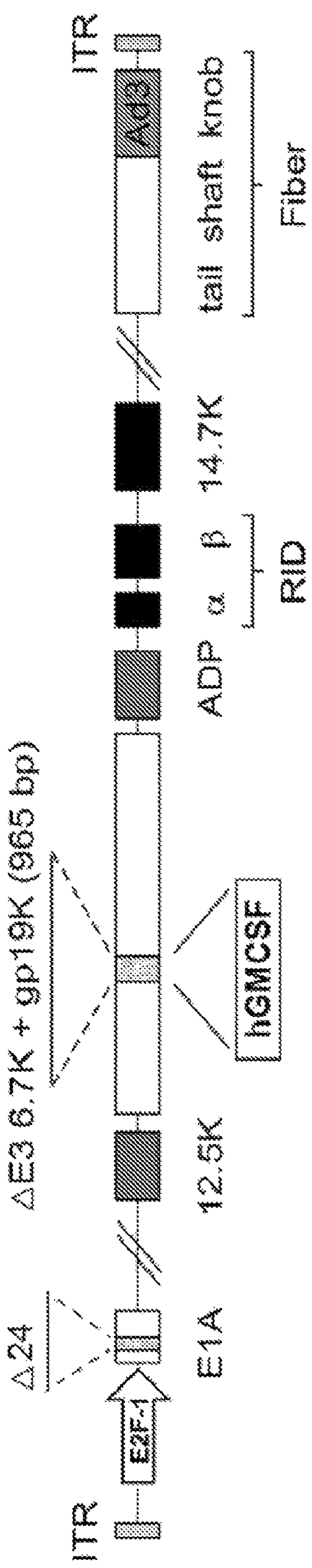
FIG. 1. A schema of CGTG-602 (Ad5/3-E2F1.D24-GMCSF, SEQ ID NO:2) (a), CGTG-601 (Ad5-E2F.D24-GMCSF, SEQ ID NO:1) (b), CGTG-603 (Ad5-RGD-E2F.D24-GMCSF, SEQ ID NO:3) (c), CGTG-604 (Ad5-pK7-E2F.D24-GMCSF, SEQ ID NO:4) (d), CGTG-605 (Ad5/3-E2F.D24-GMCSF-CpG, SEQ ID NO:5) (e) CGTG-606 (Ad5/3-E2F1.D24-GMCSF-KKTK, SEQ ID NO:6) (f) and CGTG-607 (Ad5/3-E2F1.D24-GMCSF-CpG-KKTK, SEQ ID NO:7) (g) genome. The viruses have their E1A promoter replaced by a human E2F-1 promoter, which controls the transcription of the E1A gene. The E1A gene bears a 24 base pair deletion in the constant region 2 to avoid the selfactivation of the promoter by E2F-1 released by E1A-Rb interaction, a critical fault in previous designs with an intact E1A gene. gp19k and 6.7K in E3 have been replaced with the cDNA of human GM-CSF. ADP refers to the adenovirus death protein. CGTG-605 has a CpG dinucleotide island inserted into the E3 region. CGTG-602 (SEQ ID NO: 2), CGTG-605 (SEQ ID NO:5) and CGTG-606 (SEQ ID NO:6) have a chimeric 5/3 fiber, where the serotype 5 (Ad5) knob has been replaced by the serotype 3 (Ad3) knob. Additionally, CGTG-606 (SEQ ID NO:6) has a KKTK motif replaced by GAGA on the fiber shaft. CGTG-607 (SEQ ID NO:7) has the features of CGTG-605 and CGTG-606 combined. CGTG-603 (SEQ ID NO:3) has an RGD-4C (Arg-Gly-Asp and 4×Cys) motif inserted in the HI-loop of the Ad5 knob. CGTG-604 (SEQ ID NO:4) has a polylysine motif inserted into the C-terminus of the Ad5 knob. CGTG-601 (SEQ ID NO:1) has a genetically intact Ad5 fiber.
Figure 1B:
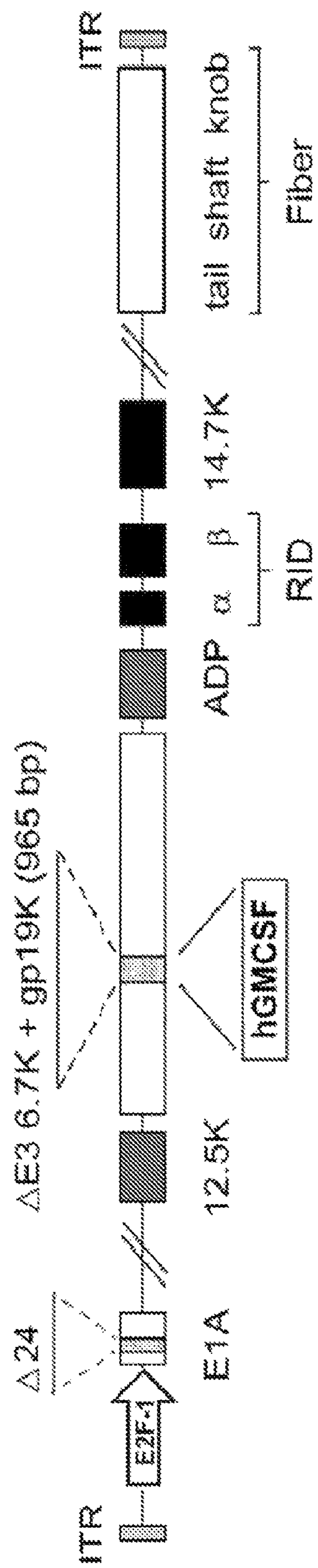
Figure 1C:
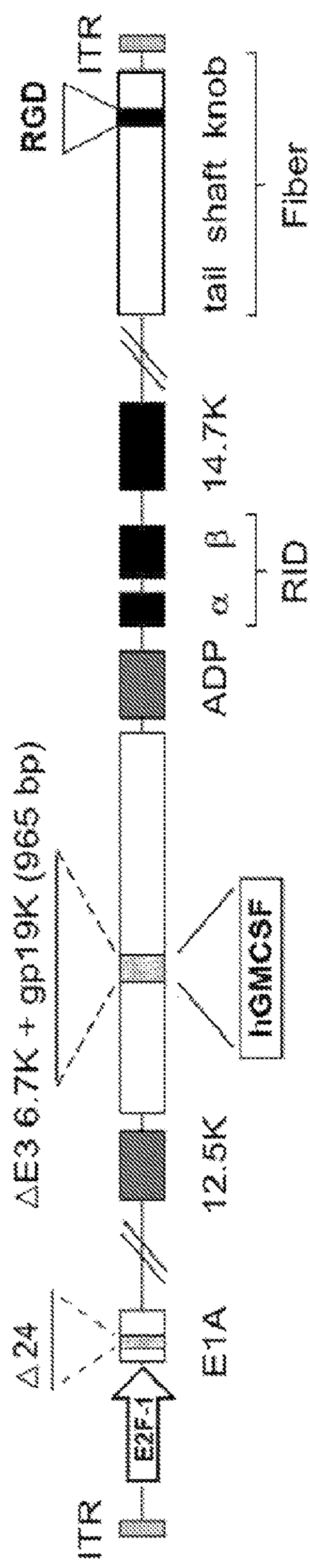
Figure 1D:
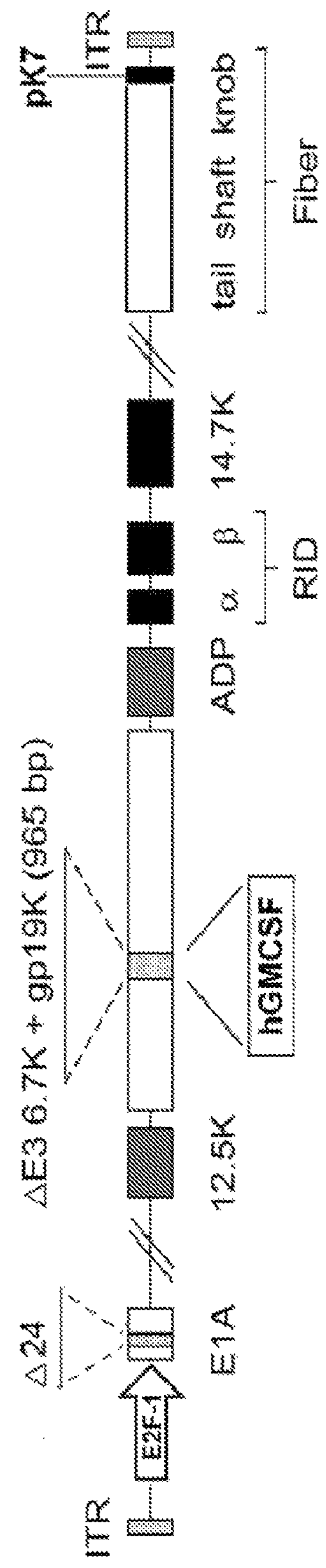
Figure 2:
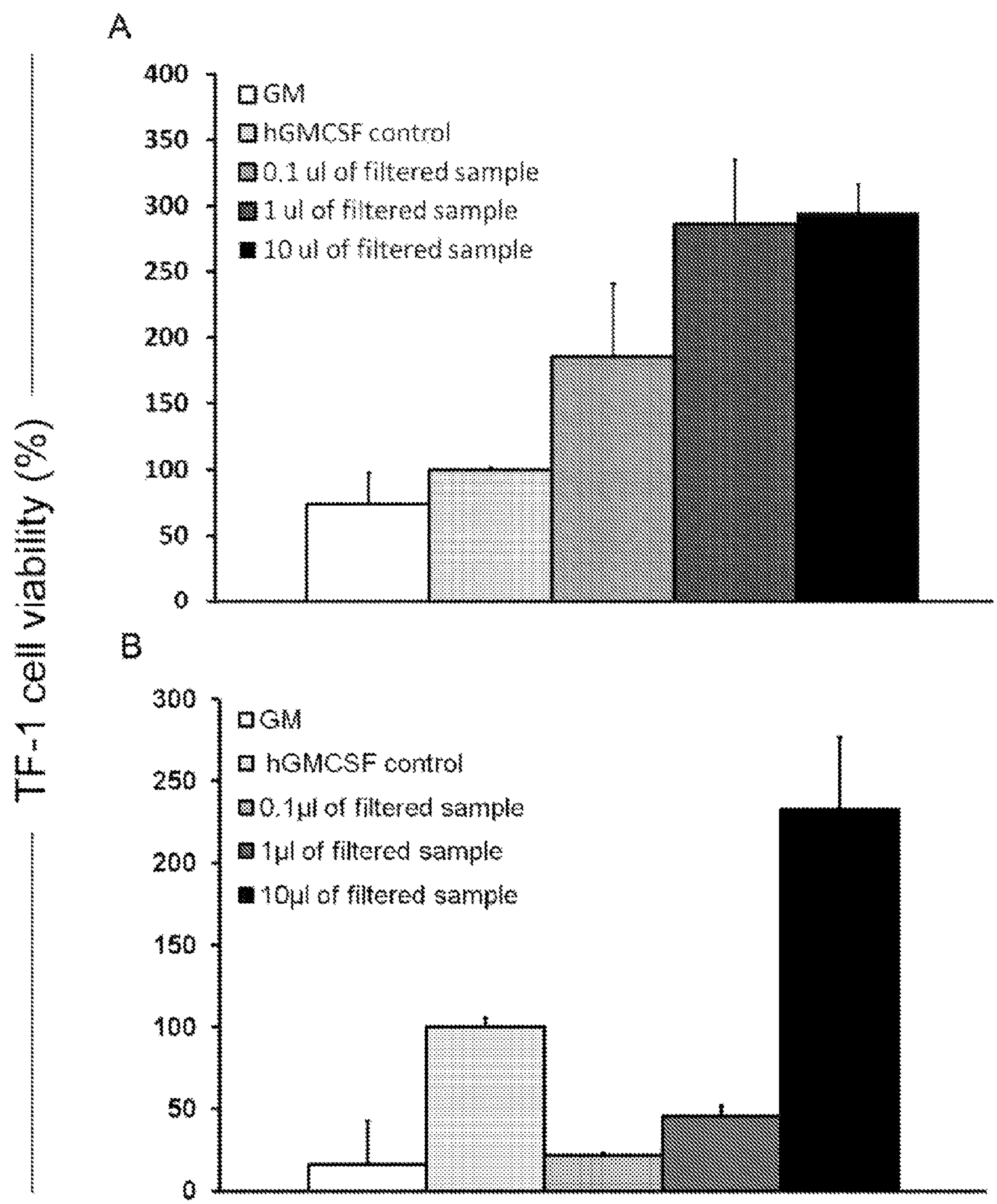
FIG. 2 shows that adenovirus-expressed GMCSF retains its biological activity in human lymphocytes. TF1 cells, which require human GMCSF for staying alive, were cultured in the presence of human recombinant GMCSF (*E. coli*-produced, purchased from Sigma) or supernatant from CGTG-602 (a) or CGTG-603 (b) infected cells. The viability of TF1-cells treated with recombinant hGMCSF was set as 100%.

SEQ ID NO: 1 is the nucleotide sequence encoding the virus CGTG-601.

SEQ ID NO: 2 is the nucleotide sequence encoding the virus CGTG-602.

SEQ ID NO: 3 is the nucleotide sequence encoding the virus CGTG-603.

SEQ ID NO: 4 is the nucleotide sequence encoding the virus CGTG-604.

SEQ ID NO: 5 is the nucleotide sequence encoding the virus CGTG-605.

SEQ ID NO: 6 is the nucleotide sequence encoding the virus CGTG-606.

SEQ ID NO: 7 is the nucleotide sequence encoding the virus CGTG-607.

SEQ ID NO: 8 is the nucleotide sequence encoding the plasmid pE2F.E1.D24.

SEQ ID NO: 9 is the nucleotide sequence encoding the plasmid pAd5/3-E2F-D24-GMCSF.

SEQ ID NO: 10 is the nucleotide sequence of the primer E4-forward.

SEQ ID NO: 11 is the nucleotide sequence of the primer E4-reverse.

SEQ ID NO: 12 is the nucleotide sequence of the probe E4.

SEQ ID NO: 13 is the nucleotide sequence of the primer GAPDH-forward.

SEQ ID NO: 14 is the nucleotide sequence of the primer GAPDH-reverse.

SEQ ID NO: 15 is the nucleotide sequence of the probe GAPDH.

SEQ ID NO: 16 is the nucleotide sequence of the E1-forward primer.

SEQ ID NO: 17 is the nucleotide sequence of the E1-reverse primer.

SEQ ID NO: 18 is the nucleotide sequence of the probe "onco".

SEQ ID NO: 19 is the nucleotide sequence of the probe "wt".

SEQ ID NO: 20 is the nucleotide sequence of the GM-CSF-forward.

SEQ ID NO: 21 is the nucleotide sequence of GM-CSF-reverse primer.

SEQ ID NO: 22 is the nucleotide sequence of human beta-actin-forward primer.

SEQ ID NO: 23 is the nucleotide sequence of human beta-actin-reverse primer.

SEQ ID NO: 24 is the nucleotide sequence of human beta-actin probe having 6FAM marker in the 5' end and TAMRA marker in the 3' end.

SEQ ID NO: 25 is the nucleotide sequence of mouse beta-actin-forward primer.

SEQ ID NO: 26 is the nucleotide sequence of mouse beta-actin-reverse primer.

SEQ ID NO: 27 is the nucleotide sequence of mouse beta-actin probe having 6FAM marker in the 5' end and TAMRA marker in the 3' end.

DETAILED DESCRIPTION OF THE INVENTION

Unless defined otherwise, all technical and scientific terms used in this application have the same meaning as commonly understood by one of ordinary skill in the art to which this invention pertains. Standard one-letter notations for nucleic acids and three-letter and one-letter notations for amino acids are used interchangeably herein.

As used herein, the expression "adenovirus serotype 5 (Ad5) nucleic acid backbone" or "virus genome" refers to the genome or partial genome of Ad5, which comprises one or several regions selected from the group consisting of partial E1, pIX, pIVa2, E2, VA1, VA2, L1, L2, L3, L4, partial E3, L5 and E4 of Ad5 origin. One preferred vector of the invention comprises nucleic acid backbone of Ad5. In another preferred vector, the adenoviral nucleic acid backbone is mostly derived from Ad5 and combined with a portion (e.g. a part of the capsid structure) of Ad3.

As used herein, expression "partial" as used in the context of regions of viral DNA refers to a region, which lacks any part compared to a corresponding wild type virus region. "Partial E1" refers to E1 region with D24 deletion and "partial E3" refers to E3 region lacking gp19k/6.7K.

As used herein, the terms "VA1" and "VA2" refer to virus associated RNAs 1 and 2, which are transcribed by the adenovirus but are not translated. VA1 and VA2 have a role in combating cellular defence mechanisms.

As used herein, the expression "a viral packaging signal" refers to a part of virus DNA, which consists of a series of AT-rich sequences and governs the encapsidation process.

As used herein the term "capsid" refers to the protein shell of the virus, which includes hexon, fiber and penton base proteins.

As used herein, the expression "Ad5/3 chimerism" of the capsid refers to a chimerism, wherein the knob part of the fiber is from Ad serotype 3, and the rest of the fiber is from Ad serotype 5.

As used herein, the expression "RGD region" refers to the arginine-glycine-aspartic acid (RGD) motif, which is exposed on the penton base and interacts with cellular av integrins supporting adenovirus internalization.

As used herein, a "KKTK mutation" refers to a nucleotide sequence aaaaaaaccaag (base pairs 30892-30903, translating into KKTK) replaced by nucleotide sequence ggagccggagcc (translating into GAGA).

As used herein, the expression "expression cassette" refers to a DNA vector or a part thereof comprising nucleotide sequences, which encode cDNAs or genes, and nucleotide sequences, which control and/or regulate the expression of said cDNAs or genes. Similar or different expression cassettes may be inserted to one vector or to several different vectors. Ad5 vectors of the present invention may comprise either several or one expression cassettes.

The term "mutation" as used herein refers to a deletion, an insertion of nucleic acid, an inversion, or a substitution as commonly understood in the art.

The term "gene" as used herein refers to a segment of nucleic acid that encodes an individual protein or RNA (also referred to as a "coding sequence" or "coding region"), optionally together with the associated regulatory regions such as promoters, operators, terminators and the like, that may be located upstream or downstream of the coding sequence.

The terms "mutant virus", "modified virus" and "modified virus vector" as used herein refer to a virus comprising one or more mutations in its genome, including but not limited to deletions, insertions of nucleic acids, inversions, substitutions or combinations thereof.

The term "naturally-occurring", "native" and similar expressions as used herein with reference to a virus indicates that the virus is in the form in which it can be found in nature, i.e. it can be isolated from a source in nature in this form and it has not been intentionally modified.

The term "wild-type virus" as used herein refers to the most frequent genotype of a virus found in nature and against which mutants are defined.

The term "anti-viral response" as used herein refers to a cell's response to viral infection and includes, for example, production of interferons, cytokine release, production of chemokines, production of lymphokines or a combination thereof.

The expressions "normal host cell" and "normal tissue" as used herein refer to a non-cancerous, non-infected cell or tissue with an intact anti-viral response.

The term "oncolytic agent" as used herein refers to an agent capable of inhibiting the growth of and/or killing tumour cells.

The term "subject" as used herein refers to any living organism, including humans and animals, human and animal tissue, and human and animal cells.

An object of the present invention was to develop novel therapeutically effective oncolytic adenoviruses with improved safety properties for cancer therapy and to solve problems encountered in conventional cancer therapy and in cancer virotherapy.

The inventors have surprisingly found an oncolytic adenoviral vector which is both therapeutically effective and safe in use. The recombinant adenovirus according to the invention comprises one or more of the following elements: an adenovirus serotype 5 (Ad5) nucleic acid backbone; a nucleic acid sequence encoding a tumor specific human E2F-1 promoter replacing the E1A promoter for the control of the of E1A gene transcription; a 24 bp deletion (D24) in the Rb binding constant region 2 of adenoviral E1; a nucleic acid sequence encoding a granulocyte-macrophage colony-stimulating factor (GM-CSF) in the place of the deleted gp19k/6.7K in the adenoviral E3 region; a nucleic acid sequence replacing the serotype 5 adenoviral fiber knob region with that of a serotype 3 adenovirus knob region; with or without a nucleic acid sequence comprising CpG island in the E3 region after GMCSF-gene; with or without a mutated KKTK-region in the fiber shaft region. The unexpected efficacy of the inventive oncolytic adenovirus provides a significant improvement in the therapeutic efficacy as demonstrated in in vivo studies in comparison to previous oncolytic adenoviruses. The safety record of the inventive oncolytic adenovirus is also excellent. Efficacy and safety of the agents was found to be unexpectedly good especially in human patients.

In some aspects, the present invention provides cells comprising the adenoviral vector of the invention.

In some aspects, the present invention provides a pharmaceutical composition comprising adenoviral vectors of the invention. A pharmaceutical composition of the invention comprises at least one type of the vectors of the invention. Furthermore, the composition may comprise at least two, three, four or more different vectors of the invention. In addition to the vector of the invention, a pharmaceutical composition of the invention may comprise any other vectors, such as other adenoviral vectors, other therapeutically effective agents, any other agents such as pharmaceutically acceptable carriers, buffers, excipients, adjuvants, antiseptics, filling, stabilising or thickening agents, and/or any components normally found in corresponding products.

The pharmaceutical composition may be in any form, such as solid, semisolid or liquid form suitable for administration. A formulation can be selected from a group consisting of, but not limited to, solutions, emulsions, suspensions, tablets, pellets and capsules.

In an aspect of the invention, the oncolytic adenoviral vector or pharmaceutical composition acts as an in situ cancer vaccine. As used herein "in situ cancer vaccine" refers to a cancer vaccine, which both kills tumor cells and also increases the immune response against tumor cells. Virus replication is a strong danger signal to the immune system (=needed for a TH1 type response), and thus acts as a powerful costimulatory phenomenon to GM-CSF mediated maturation and activation of APCs, and recruitment of NK cells. Tumor cell lysis also helps to present tumor fragments and epitopes to APCs and furthermore, costimulation is produced by inflammation. Thus, an epitope independent (i.e. not HLA restricted) response is produced in the context of each tumor and therefore takes place in situ. Tumor specific immune response is activated in the target cell as well as the surrounding cells, e.g. in the target tissue.

The effective dose of vectors depends on at least the subject in need of the treatment, tumor type, location of the tumor and stage of the tumor. The dose may vary for example from about 10e8 viral particles (VP) to about 10e14 VP, preferably from about 5×10e9 VP to about 10e13 VP and more preferably from about 8×10e9 VP to about 10e12 VP. In one specific aspect of the invention the dose is in the range of about 5×10e10-5×10e11 VP.

The pharmaceutical compositions may be produced by any conventional processes known in the art, for example by utilizing any one of the following: batch, fed-batch and perfusion culture modes, column-chromatography purification, CsCl gradient purification and perfusion modes with low-shear cell retention devices.

The vector or pharmaceutical composition of the invention may be administered to any eukaryotic subject selected from the group consisting of plants, animals and human beings. In a preferred aspect of the invention, the subject is a human or an animal. An animal may be selected from a group consisting of pets, domestic animals and production animals. In an aspect of the invention the subject is human.

Any conventional method may be used for administration of the vector or composition to a subject. The route of administration depends on the formulation or form of the composition, the disease, location of tumors, the patient, comorbidities and other factors. In a preferred aspect of the invention, the administration is conducted through an intratumoral, intramuscular, intra-arterial, intravenous, intrapleural, intravesicular, intracavitary or peritoneal injection, or an oral administration. Therapeutic compositions are formulated relative to the particular administration route.

In an aspect, in the present invention oncolytic adenoviral vectors are administered in a single administration to achieve therapeutic effects. However, in a preferred aspect of the invention, oncolytic adenoviral vectors or pharmaceutical compositions are administered several times during the treatment period. Oncolytic adenoviral vectors or pharmaceutical compositions may be administered for example from 1 to 10 times in the first 2 weeks, 4 weeks, monthly or during the treatment period. In an aspect of the invention, administration is done three to seven times in the first 2 weeks, then at 4 weeks and then monthly. In an aspect of the invention administration is done four times in the first 2 weeks, then at 4 weeks and then monthly. The length of the treatment period may vary, and for example may last from two to 12 months or more.

In order to avoid neutralizing antibodies in a subject, the vectors of the invention may vary between treatments. In a preferred aspect of the invention, the oncolytic adenoviral vector having a different fiber knob of the capsid compared to the vector of the earlier treatment is administered to a subject. As used herein "fiber knob of the capsid" refers to the knob part of the fiber protein (FIG. 1).

The therapy of the invention is effective alone, but combination of adenoviral gene therapy with other therapies, such as traditional therapy, may be more effective than either one alone. For example, each agent of the combination therapy may work independently in the tumor tissue, the adenoviral vectors may sensitize cells to chemotherapy or radiotherapy and/or chemotherapeutic agents may enhance the level of virus replication or effect the receptor status of the target cells. The agents of combination therapy may be administered simultaneously or sequentially.

In a preferred aspect of the invention, the method or use further comprises administration of concurrent radiotherapy to a subject. In another preferred aspect of the invention, the method or use further comprises administration of concurrent chemotherapy to a subject. As used herein "concurrent" refers to a therapy, which has been administered before, after or simultaneously with the gene therapy of the invention. The period for a concurrent therapy may vary from minutes to several weeks. Preferably the concurrent therapy lasts for some hours.

Agents suitable for combination therapy or which can be used as virus sensitizers include but are not limited to All-trans retinoic acid, Azacitidine, Azathioprine, Bleomycin, Carboplatin, Capecitabine, Cisplatin, Chlorambucil, Cyclophosphamide, Cytarabine, Daunorubicin, Docetaxel, Doxifluridine, Doxorubicin, Epirubicin, Epothilone, erlotinib, Etoposide, Fluorouracil, Gemcitabine, Hydroxyurea, Idarubicin, Imatinib, Mechlorethamine, Mercaptopurine, Methotrexate, Mitoxantrone, Oxaliplatin, Paclitaxel, Pemetrexed, Temozolomide, Teniposide, Tioguanine, Valrubicin, Vinblastine, Vincristine, Vindesine and Vinorelbine.

In a preferred aspect of the invention, the method or use further comprises administration of verapamil or another calcium channel blocker to a subject. "Calcium channel blocker" refers to a class of drugs and natural substances which disrupt the conduction of calcium channels, and it may be selected from a group consisting of verapamil, dihydropyridines, gallopamil, diltiazem, mibefradil, bepridil, fluspirilene and fendiline.

In a preferred aspect of the invention, the method or use further comprises administration of autophagy inducing agents to a subject. Autophagy refers to a catabolic process involving the degradation of a cell's own components through the lysosomal machinery. "Autophagy inducing agents" refer to agents capable of inducing autophagy and may be selected from a group consisting of, but not limited to, mTOR inhibitors, PI3K inhibitors, lithium, tamoxifen, chloroquine, bafilomycin, temsirolimus, sirolimus and temozolomide. In a specific aspect of the invention, the method further comprises administration of temozolomide to a subject. Temozolomide may be either oral or intravenous temozolomide.

In one aspect of the invention, the method or use further comprises administration of chemotherapy or anti-CD20 therapy or other approaches for blocking of neutralizing antibodies. "Anti-CD20 therapy" refers to agents capable of killing CD20 positive cells, and may be selected from a group consisting of rituximab and other anti-CD20 monoclonal antibodies. "Approaches for blocking of neutralizing antibodies" refers to agents capable of inhibiting the generation of anti-viral antibodies that normally result from infection and may be selected from a group consisting of different chemotherapeutics, immunomodulatory substances, corticoids and other drugs. These substances may be selected from a group consisting of, but not limited to, cyclophosphamide, cyclosporin, azathioprine, methylprenisolone, etoposide, CD40L, CTLA4Ig4, FK506 (tacrolismus), IL-12, IFN-gamma, interleukin 10, anti-CD8, anti-CD4 antibodies, myeloablation and oral adenoviral proteins.

The oncolytic adenoviral vector of the invention induces virion mediated oncolysis of tumor cells and activates human immune response against tumor cells. In a preferred aspect of the invention, the method or use further comprises administration of substances capable of downregulating regulatory T-cells in a subject. "Substances capable of downregulating regulatory T-cells" refers to agents that reduce the amount of cells identified as T-suppressor or Regulatory T-cells. These cells have been identified as consisting one or many of the following immunophenotypic markers: CD4+, CD25+, FoxP3+, CD127− and GITR+. Such agents reducing T-suppressor or Regulatory T-cells may be selected from a group consisting of anti-CD25 antibodies or chemotherapeutics.

In a preferred aspect of the invention, the method or use further comprises administration of cyclophosphamide to a subject. Cyclophosphamide is a common chemotherapeutic agent, which has also been used in some autoimmune disorders. In the present invention, cyclophosphamide can be used as a virus sensitizer to enhance viral replication and the effects of GM-CSF induced stimulation of NK and cytotoxic T-cells for enhanced immune response against the tumor. It can be used as intravenous bolus doses or low-dose oral metronomic administration. Other suitable virus sensitizers that can be used in aspects of present invention include temozolomide and erlotinib.

Any method or use of the invention may be either in vivo, ex vivo or in vitro method or use.

The present invention also relates to a method of treating cancer in a subject, wherein the method comprises administering the vector or pharmaceutical composition of the invention to a subject; carrying a vehicle comprising an oncolytic adenoviral vector of the invention into a cell; and expressing GM-CSF of said vector in the cell.

Furthermore, the present invention relates to a method of increasing tumor specific immune response in a subject, wherein the method comprises carrying a vehicle comprising an oncolytic adenoviral vector of the invention to a target cell or tissue; expressing immunostimulatory GM-CSF of said vector in the cell; and increasing amount of cytotoxic T cells and/or natural killer cells in said target cell or tissue.

Furthermore, the present invention provides use of the oncolytic adenoviral vector of the invention for producing GM-CSF in a cell.

Furthermore, the present invention provides an oncolytic adenoviral vector for producing GM-CSF in a cell.

Furthermore, the present invention provides use of the oncolytic adenoviral vector for increasing tumor specific immune response in a subject.

Furthermore, the present invention provides oncolytic adenoviral vector for increasing tumor specific immune response in a subject.

Furthermore, the present invention provides tool for treatment of cancers, which are refractory to current approaches. Also, restrictions regarding tumor types suitable for treatment remain few compared to many other treatments. In fact all solid tumors may be treated with the present invention. Larger tumors by mass and more complex tumors can be cured by the present invention. The treatment can be given intratumorally, intracavitary, intravenously and in a combination of these. The approach can give systemic efficacy despite local injection. The approach can also eradicate cells proposed as tumor initiating ("cancer stem cells").

In an aspect of the invention the oncolytic adenoviral vector comprises a human E2F-1 promoter replacing the viral E1A promoter upstream of the E1A region, lacks 24 base pairs from CR2 in E1A gene, and gp19k and 6.7K in E3 region, and comprises a human GM-CSF in place of the deleted sequence in E3.

In another aspect of the invention, the adenoviral vector of the invention comprises a capsid modification in the fiber of the virus, a CpG island in the E3 region and/or a KKTK mutation in the fiber gene in the shaft region.

In another aspect of the invention, in addition to partial regions E1 and E3, the oncolytic adenoviral vector of the invention may further comprise one or more regions or elements selected from the group consisting of viral early genes, viral intermediate genes and viral late genes, preferably E2, E4, and late regions.

In another aspect of the invention, the oncolytic adenoviral vector comprises the following regions or elements: a left ITR, partial E1, pIX, pIVa2, E2, VA1, VA2, L1, L2, L3, L4, partial E3, L5, E4, and a right ITR. In another aspect of the invention the regions or elements may be in any order in the vector, but in a preferred aspect the regions are in a sequential order in the 5' to 3' direction. Open reading frames (ORFs) may be in the same DNA strand or in different DNA strands. In a preferred aspect of the invention, the E1 region comprises a viral packaging signal.

In an aspect of the invention, a gene encoding an immunostimulatory protein, preferably human GM-CSF, is incorporated in the virus vector for immunostimulatory effect. As is obvious to persons skilled in the art, other proteins exerting similar immunostimulatory effect and being pharmaceutically acceptable, such as genes encoding human CD40 ligand and human anti-CTLA-4 antibody may also be used in the vector instead of GM-CSF.

In an aspect the present invention provides recombinant serotype 5 (Ad5) adenovirus being capable of replicating and having lytic activity in target cells wherein the virus comprises in the genome thereof a nucleic acid sequence encoding a target cell specific promoter replacing the natural E1A adenoviral promoter; at least one modification in the Rb binding constant region 2 of adenoviral E1 disrupting the ability to bind Rb and preventing virus replication outside target cells; at least one modification in the viral E3 genes disrupting the ability to control host immune response; and a nucleic acid sequence encoding an immunostimulatory protein operably linked to the promoter of adenoviral E3.

In an embodiment the present invention provides a recombinant serotype 5 (Ad5) adenovirus being capable of replicating and having lytic activity in target cells characterized in that the virus comprises in the genome thereof a nucleic acid sequence encoding E2F-1 promoter replacing the natural E1A adenoviral promoter; at least a 24 bp deletion (D24) in the Rb binding constant region 2 of adenoviral E1 disrupting the ability to bind Rb and preventing virus replication outside target cells; at least a deletion in gp19k/6.7K in any of the viral E3 genes disrupting the ability to control host immune response and an insertion of an immunostimulatory transgene in the deleted region operably linked to the promoter of adenoviral E3; and a nucleic acid element which activates TLR9.

In an aspect the present invention provides recombinant Ad5 adenovirus above wherein the nucleic acid sequence encoding a target cell specific promoter replacing the natural E1A adenoviral comprises E2F-1 promoter.

In an aspect the present invention provides recombinant Ad5 adenovirus above, wherein the at least one modification in the Rb binding constant region 2 of adenoviral E1 disrupting the ability to bind Rb comprises a 24 bp deletion (D24) in the Rb binding constant region 2 of the adenoviral E1.

In an aspect the present invention provides recombinant Ad5 adenovirus above, wherein the at least one modification in any of the viral E3 genes disrupting the ability to control host immune response comprises a deletion in gp19k/6.7K of the adenoviral E3 region comprising the viral E3 genes and an operably linked insertion of an immunostimulatory transgene, preferably a GM-CSF, in the deleted region.

In an aspect the present invention provides recombinant Ad5 adenovirus above, wherein the adenovirus genome comprises a capsid modification.

In an aspect the present invention provides the recombinant Ad5 adenovirus above, wherein the capsid modification is a fiber knob region substitution wherein a region encoding Ad5 adenoviral fiber knob is replaced by the corresponding region from another adenovirus serotype, preferably from Ad3.

In an aspect the present invention provides the recombinant Ad5 adenovirus above, wherein the adenovirus genome comprises a nucleic acid element which activates TLR9.

In an aspect the present invention provides the recombinant Ad5 adenovirus above, wherein the nucleic acid element which activates TLR9 comprises CpG island inserted in the E3 region downstream of the transgene encoding the immunostimulatory protein.

In an aspect the present invention provides the recombinant Ad5 adenovirus above, wherein when the fiber knob region comprises Ad5 adenoviral fiber knob the adenovirus genome comprises an RGD motif (Arg-Gly-Asp) inserted in the HI loop of the adenoviral fiber knob.

In an aspect the present invention provides the recombinant Ad5 adenovirus above, wherein when the fiber knob region comprises Ad5 adenoviral fiber knob the adenovirus genome comprises a polylysine motif ($Lys_{1-7}$) introduced in the C terminus of the fiber knob.

In an aspect the present invention provides the recombinant Ad5 adenovirus above, wherein when the fiber knob region comprises Ad3 adenoviral fiber knob, the nucleic acid modification in the fiber shaft region comprises a mutation in a KKTK motif, preferably a GAGA motif substituted for the KKTK motif.

In an aspect the present invention provides the recombinant Ad5 adenovirus above, wherein the virus genome further comprises at least one element selected from the group consisting of viral immediate early genes, intermediate genes, and late genes.

In an aspect the present invention provides the recombinant Ad5 adenovirus above for use in therapy.

In an aspect the present invention provides the recombinant Ad5 adenovirus above, wherein the therapy is for treating and/or preventing any condition susceptible of being improved or prevented by said recombinant Ad5 adenovirus.

In an aspect the present invention provides the recombinant Ad5 adenovirus above, wherein the therapy is for cancer.

In an aspect the present invention provides the recombinant Ad5 adenovirus above, wherein the cancer is selected from a group consisting of nasopharyngeal cancer, synovial cancer, hepatocellular cancer, renal cancer, cancer of connective tissues, melanoma, lung cancer, bowel cancer, colon cancer, rectal cancer, colorectal cancer, brain cancer, throat cancer, oral cancer, liver cancer, bone cancer, pancreatic cancer, choriocarcinoma, gastrinoma, pheochromocytoma, prolactinoma, T-cell leukemia/lymphoma, neuroma, von Hippel-Lindau disease, Zollinger-Ellison syndrome, adrenal cancer, anal cancer, bile duct cancer, bladder cancer, ureter cancer, oligodendroglioma, neuroblastoma, meningioma, spinal cord tumor, osteochondroma, chondrosarcoma, Ewing's sarcoma, cancer of unknown primary site, carcinoid, carcinoid of gastrointestinal tract, fibrosarcoma, breast cancer, Paget's disease, cervical cancer, esophagus cancer, gall bladder cancer, head cancer, eye cancer, neck cancer, kidney cancer, Wilms' tumor, Kaposi's sarcoma, prostate cancer, testicular cancer, Hodgkin's disease, non-Hodgkin's lymphoma, skin cancer, mesothelioma, multiple myeloma, ovarian cancer, endocrine pancreatic cancer, glucagonoma, pancreatic cancer, parathyroid cancer, penis cancer, pituitary cancer, soft tissue sarcoma, retinoblastoma, small intestine cancer, stomach cancer, thymus cancer, thyroid cancer, trophoblastic cancer, hydatidiform mole, uterine cancer, endometrial cancer, vagina cancer, vulva cancer, acoustic neuroma, mycosis fungoides, insulinoma, carcinoid syndrome, somatostatinoma, gum cancer, heart cancer, lip cancer, meninges cancer, mouth cancer, nerve 5 cancer, palate cancer, parotid gland cancer, peritoneum cancer, pharynx cancer, pleural cancer, salivary gland cancer, tongue cancer, and tonsil cancer.

In an aspect the present invention provides the recombinant Ad5 adenovirus above, wherein the virus comprises the nucleic acid sequence according to SEQ ID NO: 1, 2, 3, 4, 5, 6, 7, 8, or 9.

In an aspect the present invention provides a method of producing recombinant Ad5 adenovirus particles, wherein the method comprises providing recombinant Ad5 adenovirus above inside a host cell permissive for adenovirus replication, culturing the host cells under conditions allowing said recombinant Ad5 adenovirus to propagate to form recombinant Ad5 adenovirus particles, and recovering said infectious recombinant Ad5 adenovirus particles.

In an aspect the present invention provides a pharmaceutical composition which comprises the recombinant Ad5 adenovirus above and a pharmaceutically acceptable carrier.

In an aspect the present invention provides a virus particle which comprises the recombinant Ad5 adenovirus above.

In an aspect the present invention provides a host cell which comprises the recombinant Ad5 adenovirus above or the virus particle above.

In an aspect the present invention provides the recombinant Ad5 adenovirus above, the pharmaceutical composition above, the virus particle above, or the host cell above for inducing immunity directed against cancer, treating tumors and/or preventing tumors.

In an aspect the present invention provides a method of using the recombinant Ad5 adenovirus above, the pharmaceutical composition above, the virus particle above, or the host cell above for inducing immunity directed against cancers, treating tumors and/or preventing tumors.

In an aspect the present invention provides a method of cancer therapy wherein the method comprises administering the recombinant Ad5 adenovirus above, the pharmaceutical composition above, the virus particle above, or the host cell above to a subject.

In an aspect the present invention provides a method for manufacturing a medicament for therapy intended for any condition susceptible of being improved or prevented by administering said medicament, wherein the recombinant Ad5 adenovirus above, the virus particle above, or the host cell above is used.

In an aspect the present invention provides the recombinant Ad5 serotype adenovirus above or the method of cancer therapy above, wherein the recombinant Ad5 adenovirus is administered several times.

In an aspect the present invention provides the recombinant Ad5 serotype adenovirus above or the method of cancer therapy above, wherein the recombinant Ad5 adenovirus is administered several times and the adenovirus used in subsequent administrations is different from the recombinant Ad5 adenovirus used in the first administration.

In an aspect the present invention provides the recombinant Ad5 serotype adenovirus according to any one of claims 13-17 or the method of cancer therapy above, wherein the therapy comprises radiotherapy, surgery, or administering one ore more agent selected from the group consisting of a virus sensitizer, chemotherapeutic agent, verapamil, calcium channel blocker, anti-CD20 therapy, and autophagy inducing agent.

Besides enabling the transport of the vector to the site of interest the adenovirus vector of the invention also assures the expression and persistence of the transgene. Furthermore, immune response against the vector as well as the transgene is minimized.

The present invention solves problems related to therapeutic resistance to conventional treatments. Furthermore, the present invention provides tools and methods for selective treatments, with less toxicity or damages in healthy tissues. Advantages of the present invention include also different and reduced side effects in comparison to other therapeutics. Importantly, the approach is synergistic with many other forms of therapy including chemotherapy and radiation therapy, and is therefore suitable for use in combination regimens.

Induction of an immune reaction towards cells that allow replication of unarmed viruses is normally not strong enough to lead to development of therapeutic tumor immunity. In order to overcome this weakness, the present invention provides armed viruses with a potent inducer of anti-tumor immunity. The present invention achieves cancer therapy, wherein tumor cells are destroyed by virion caused oncolysis. In addition, various different mechanisms activating human immune response, including activation of natural killer cells (NK) and dendritic cells (DC) are recruited for therapeutic use in the present invention.

Compared to adenoviral tools of the prior art, the present invention provides a more simple, more effective, inexpensive, non-toxic and safer tool for cancer therapy. Furthermore, the present invention makes it unnecessary to use any helper viruses that are required in prior viral therapies.

The novel products of the invention enable further improvements in cancer therapy.

EXAMPLES

The following examples are given solely for the purpose of illustrating various aspects of the invention and they are not meant to limit the present invention. One skilled in the art will appreciate readily that the present invention is well adapted to carry out the objects and obtain the aims and advantages mentioned above, as well as those objects, aims and advantages inherent herein. Changes therein and other uses which are encompassed within the spirit of the invention as defined by the scope of the claims will occur to those skilled in the art.

Example 1

Cloning of CGTG-602 (SEQ ID NO:2)

CGTG-602 was constructed as follows. A pAdEasy-1-derived plasmid containing a chimeric 5/3 fiber, pAdEasy5/3, was created by homologous recombination in *E. coli* of Ad5/3 luc1 viral genome and BstXI-digested 8.9 kb fragment of pAdEasy-1. Next, a shuttle vector containing a 24-bp deletion in E1A (pShuttleD24) was linearized with PmeI and recombined with pAdEasy5/3 resulting in pAd5/3-D24. In order to insert human GMCSF gene into E3 region, an E3-cloning vector pTHSN was created by inserting SpeI to NdeI fragment from Ad5 genome into the multi-cloning site of pGEM5Zf+ (Promega, Madison, Wis.). pTHSN was further digested with SunI/MunI creating a 965-bp deletion in E3 region (6.7K and gp19K deleted) (described in Kanerva et al. 2005, Gene Ther 12:87-94). The 432 bp cDNA encoding human GMCSF (Invitrogen, Carlsbad Calif.) was amplified with primers featuring specific restriction sites SunI/MunI flanking the gene and then inserted into SunI/MunI-digested pTHSN to create pTHSN-GMCSF (described in Cerullo et al. 2010, Cancer Res 70:4297-309). pAd5/3-D24-GMCSF was generated by homologous recombination in *E. coli* between FspI-linearized pTHSN-GMCSF and SilI-linearized pAd5/3-D24 (described in Kanerva et al. 2003, Mol Ther 3:449-58). The E2F-1 promoter was amplified by PCR with specific primers with restriction enzyme cutting sites for NotI and XhoI designed so that the promoter could be inserted into a pSE1.D24 plasmid (described in Nettelbeck et al. 2002, Cancer Res 62:4663-70 as pScsΔ24) to control E1A. The resulting plasmid, pE2F.E1.D24 (SEQ ID NO: 8), contains the E2F-1 promoter controlling E1A gene that has a 24 bp deletion in CR2. pAd5/3-E2F-D24-GM-CSF (SEQ ID NO: 9) was generated by homologous recombination in *E. coli* between PmeI-linearized pE2F.E1.D24 and SilI-linearized rescue plasmid pAd5/3-D24-GMCSF (described in Koski et al. 2010, Mol Ther 18:1874-84). CGTG-602 virus genome was released by PacI digestion and transfection to A549 cells for amplification and rescue. All phases of the cloning were confirmed by multiple PCRs and restriction digestions as well as sequencing for the relevant areas of the plasmids. All phases of the virus production, including transfection, were done on A549 cells to avoid risk of wild type recombination. Other cancer cell lines known in the art that grow as an even cell layer when cultured in vitro can also be used for producing the virus.

Example 2

In Vitro Analysis of CGTG-602 Virus

Functionality of the CGTG-602 produced GM-CSF was tested by analyzing the proliferative activity of the GM-CSF dependent TF-1 erythroleukemia cells upon addition of filtered supernatant from CGTG-602 infected A549 cells. GM-CSF dependent TF-1 erythroleukemia cells (Sigma Aldrich) were cultured in suspension in complete growth medium supplemented with 2 ng recombinant hGM-CSF and kept on a shaker. A549 cells were grown in growth medium supplemented with 2% FCS and infected with 10 VP/cell of Ad5/3-E2F.D24-GM-CSF. 48 hours later the supernatant was collected and filtered through a 0.02 μm inorganic filter (Whatman, Maidstone, UK). TF1 cells were centrifuged and resuspended into growth medium without hGM-CSF, seeded on a 96-well plate at a density of $1\times10^4$ cells/well and kept on a shaker. 0.1, 1 and 10 μl of filtered supernatant from Ad5/3-E2F.D24-GM-CSF infected A549 cells was added on TF1 cells (6 wells per each) and hGM-CSF was added on positive control cells. TF-1 cells without supplementation were used as negative control. Three days later fresh growth medium without hGM-CSF was added on the cells. Cell viability was analyzed with a (3-(4,5-dimethylthiazol-2-yl)-5-(3-carboxymethoxyphenyl)-2-(4-sulphophenyl)-2H-tetrazolium) (MTS) cytotoxicity assay (Promega) after 5 days of incubation as previously described (Koski et al. 2010, Mol Ther 18:1874-84). The viability of positive control cells were depicted as 100%.

Figure 3:
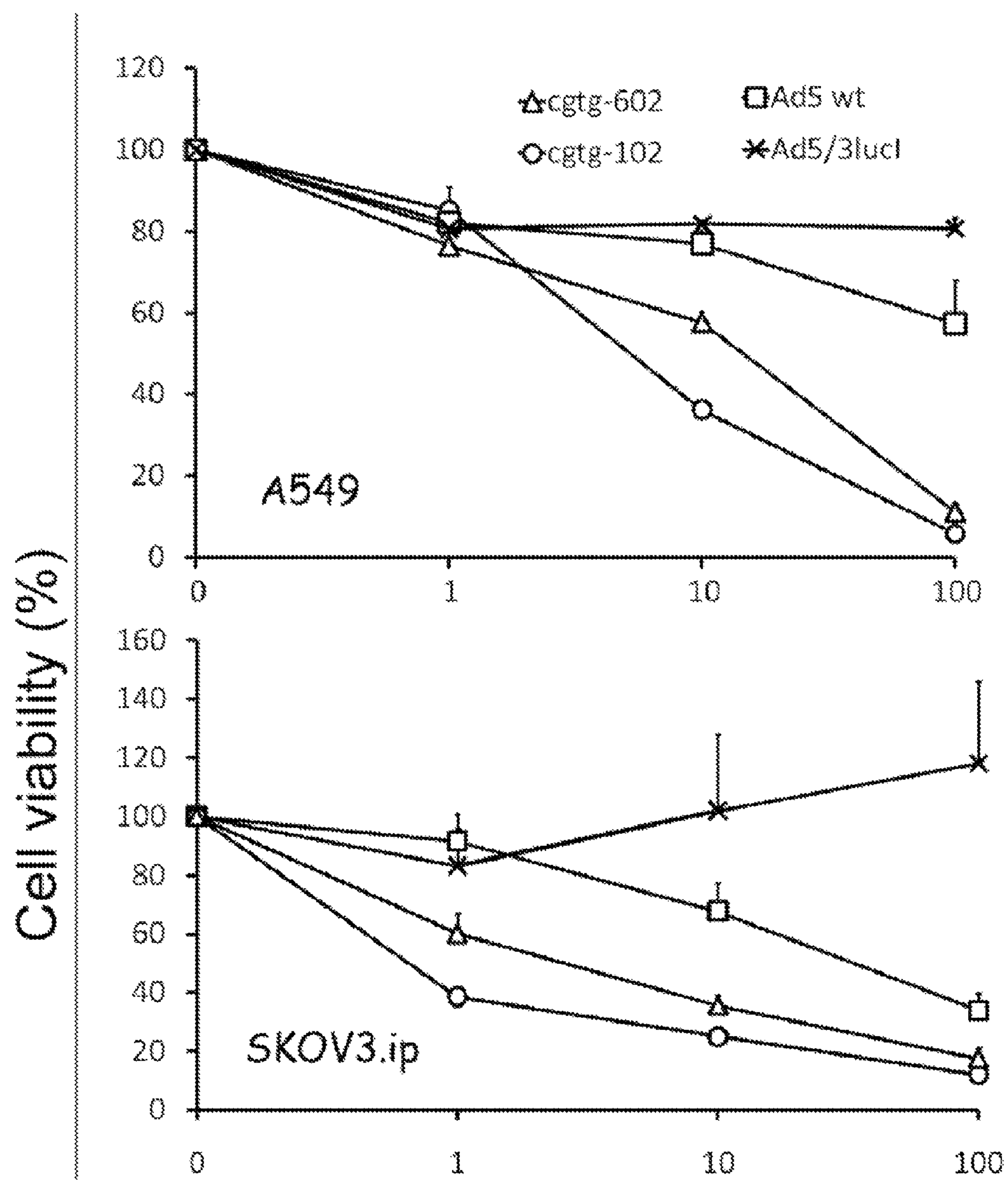
FIG. 3 shows that replacing the native E1A promoter with E2F-1 promoter does not impair virus replication and cell killing effect in vitro.
Figure 3:
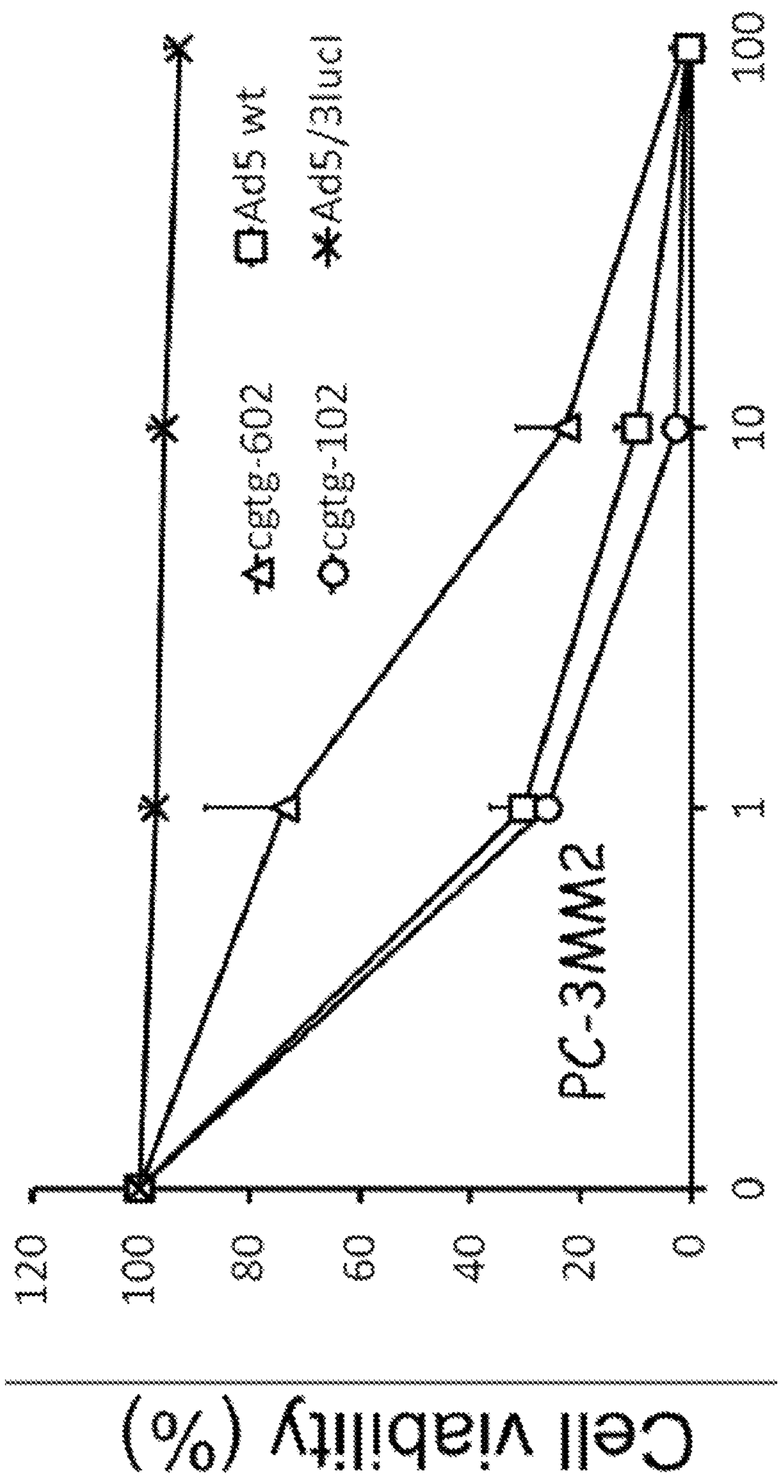

In vitro efficacy of CGTG-602 virus was studied in lung cancer cells (A549), ovarian cancer cells (SKOV3.ip1) and prostate cancer cells (PC3-MM2) by utilizing MTS cell killing assays. MTS assay is currently the standard method to assess cell viability in cancer gene therapy publications. Ad5/3 Luc1 is a replication deficient virus and acts as a negative control. Ad5 wt is a wild type Ad5 virus (strain Ad300 wt) and was used as a positive control. Ad5/3-D24-GMCSF is an otherwise isogenic control virus that has the native E1A promoter. VP indicates virus particles. Cells were seeded on a 96-well plate at a density of $1\times10^4$ cells/well and infected after 24 hours with 1, 10 or 100 VP/cell. Infection was done in 50 μl of growth media supplemented with 2% FCS and 1 hour later growth media with 10% FCS was added on cells. Thereafter, cells were maintained in 10% media and followed daily. MTS-assay was performed as previously described 6 days (A549 and PC3-MM2) or 14 days (SKOV3.ip1) later, when 100% cell killing with the highest viral dose was observed. In summary, CGTG-602 had oncolytic activity similar to positive control virus Ad5/3-D24-GMCSF in vitro, and therefore the insertion of E2F-1 promoter did not compromise the oncolytic potency of the virus (FIG. 3).

Figure 4:
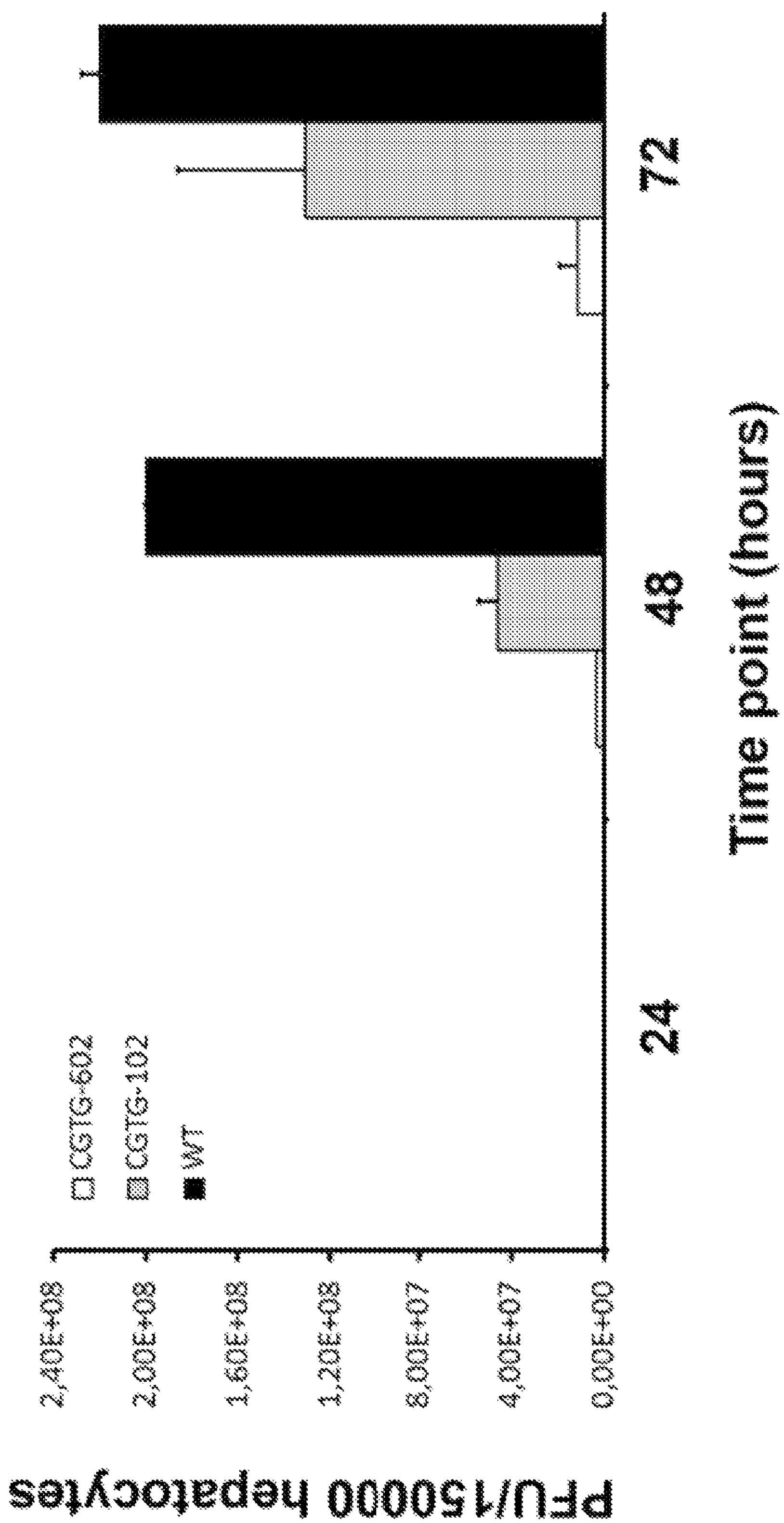
FIG. 4 shows that the E2F-1 promoter improves the in vitro selectivity of CGTG-602 replication. Human primary hepatocytes were infected with CGTG-602 or control viruses CGTG-102, Ad5 wt, Ad5/3-D24-Cox2L or mock-infected. Cells and supernatant were collected 24, 48 or 72 hours later and analyzed for infective virus particles by standard plaque assay on 293 cells.
Figure 5:
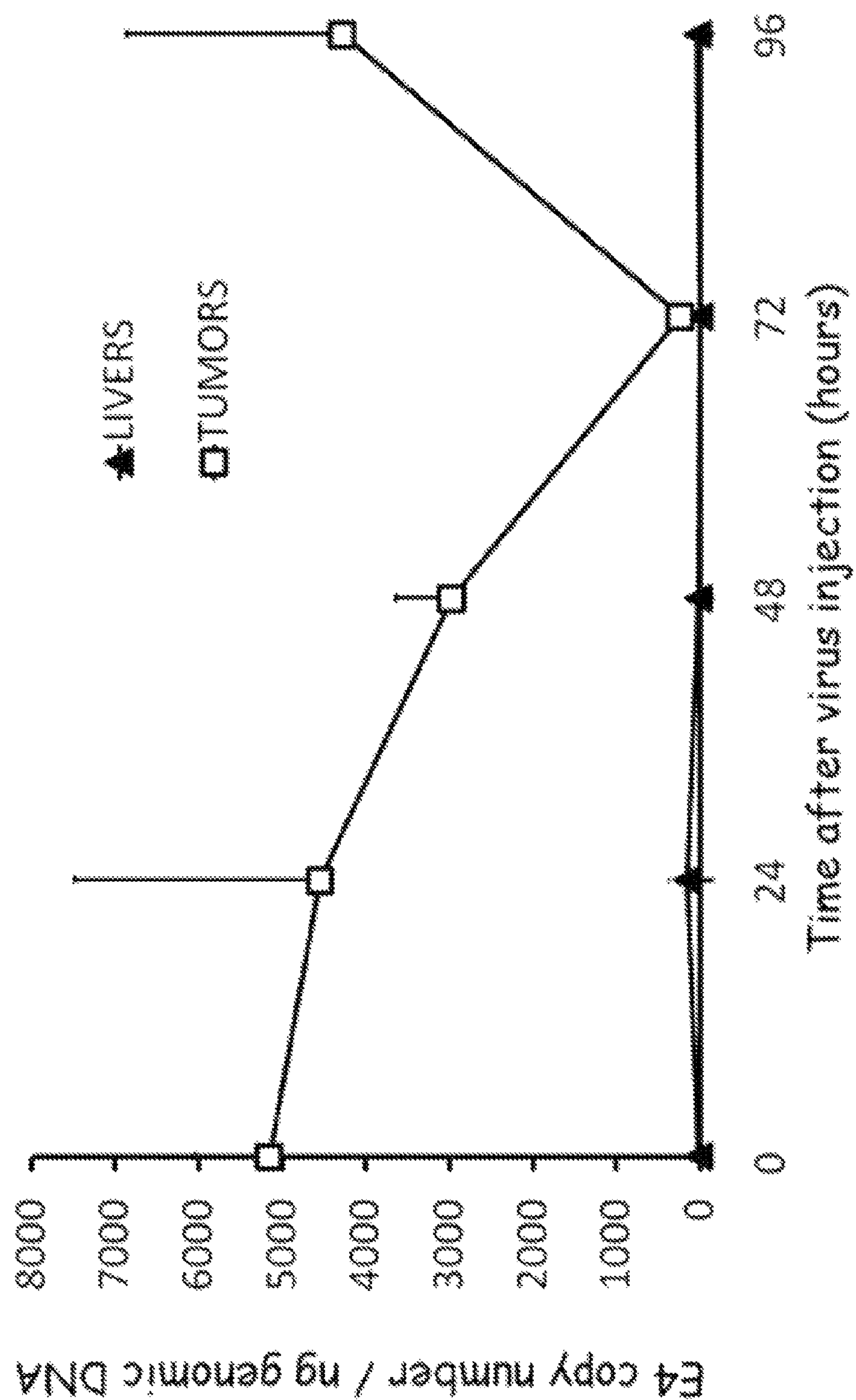
FIG. 5 shows in vivo selectivity of CGTG-602 in Syrian hamsters. CGTG-602 was injected intratumorally in HAPT-1 pancreatic cancer tumors or straight into livers of animals without tumors and the tumors or livers were collected 0.5, 24, 48, 72 or 96 hours later and the amount of viral DNA was analyzed by qPCR. Results are depicted as viral E4 copy numbers relative to hamster genomic dna (ng).

In vitro selectivity of CGTG-602 was analyzed by viral burst assay from primary human hepatocytes (Lonza). 24-well plate was coated with 0.5 mg/ml Rat tail type 1 collagen in 1 mM acetic acid for 30 minutes. $1.5\times10^5$ primary human h NHEPS hepatocytes (Lonza) were seeded per well in HCM medium with 2% FBS. Cells were let to rest for 3 hours in 37° C. and the growth media was changed to HCM without FBS. 24 hours later the hepatocytes were infected with 10 VP/cell of CGTG-602, CGTG102, Ad5 wt or growth media only. Growth media was changed after 2 hours of infection. Cells and supernatant were collected 24, 48 and 72 hours after infection and frozen at −80° C. Cells and supernatant went through 4 cycles of freezing and thawing prior to the subsequent plaque assay. Standard plaque assay was performed with serially diluted ($10^{-1}$ to $10^{-11}$) supernatant from the samples centrifuged for 25 minutes at 4000 rpm prior to infection. Each analysis contained a mock infected well for comparison. In summary, CGTG-602 titers were 11-37-fold lower than CGTG-102 titers and, at best, 64-fold lower than Ad5 wt titers (FIG. 4), representing enhanced selectivity of CGTG-602 in human primary hepatocytes in vitro due to the E2F-1 promoter.

Example 5

In Vivo Analysis of CGTG-602 Virus in Animals

The in vivo specificity of CGTG-602 was analyzed in immunocompetent Syrian hamsters, which are semipermissive for human adenovirus replication (mice are non-permissive) (Ying B. et al. 2009, Cancer Gene Ther doi:10.1038/cgt.2009.6.). Hamster HAPT-1 tumors were induced into the flanks of the hamsters. After the tumors reached approximately the size of 0.5 cm (7 days), $3\times10^8$ VP of CGTG-602 was injected intratumorally (n=8 tumors/timepoint). Hamsters without tumors (n=2/timepoint) were injected directly into the liver. Animals were killed and tumors or livers collected 0.5, 24, 48, 72 or 96 hours after virus injection and stored at −80° C.

For quantitative PCR, frozen tissues were homogenized and total DNA was extracted using the QIAamp Mini Kit (Qiagen, Valencia, Calif.) according to the manufacturer's instructions. Adenoviral E4 gene was used as the target for quantitative PCR and hamster glyceraldehyde 3-phosphate dehydrogenase (GAPDH) gene was used as an internal control target and to normalize viral DNA copies per amount of genomic DNA. Quantitative PCR was done using primers E4-forward (GGAGTGCGCCGAGACAAC, SEQ ID NO:10) and E4-reverse (ACTACGTCCGGCGTTCCA, SEQ ID NO:11) for E4, GAPDH-forward (CACCGAGGACCAGGTTGTCT, SEQ ID NO:13) and GAPDH-reverse (CATACCAGGAGATGAGCTTTACGA, SEQ ID NO:14) for GAPDH and probes E4-probe (6-FAM-TGGCATGACACTACGACCAACACGATCT-TAMRA, SEQ ID NO:12) for E4 and GAPDH-probe (6-FAM-CAAGAGTGACTCCCACTCTTCCACCTTTGA-TAM RA, SEQ ID NO:15) for GAPDH. A regression standard curve for GAPDH was established using known amounts of DNA extracted from cultured cells (1,800-0.18 ng).

Figure 6:
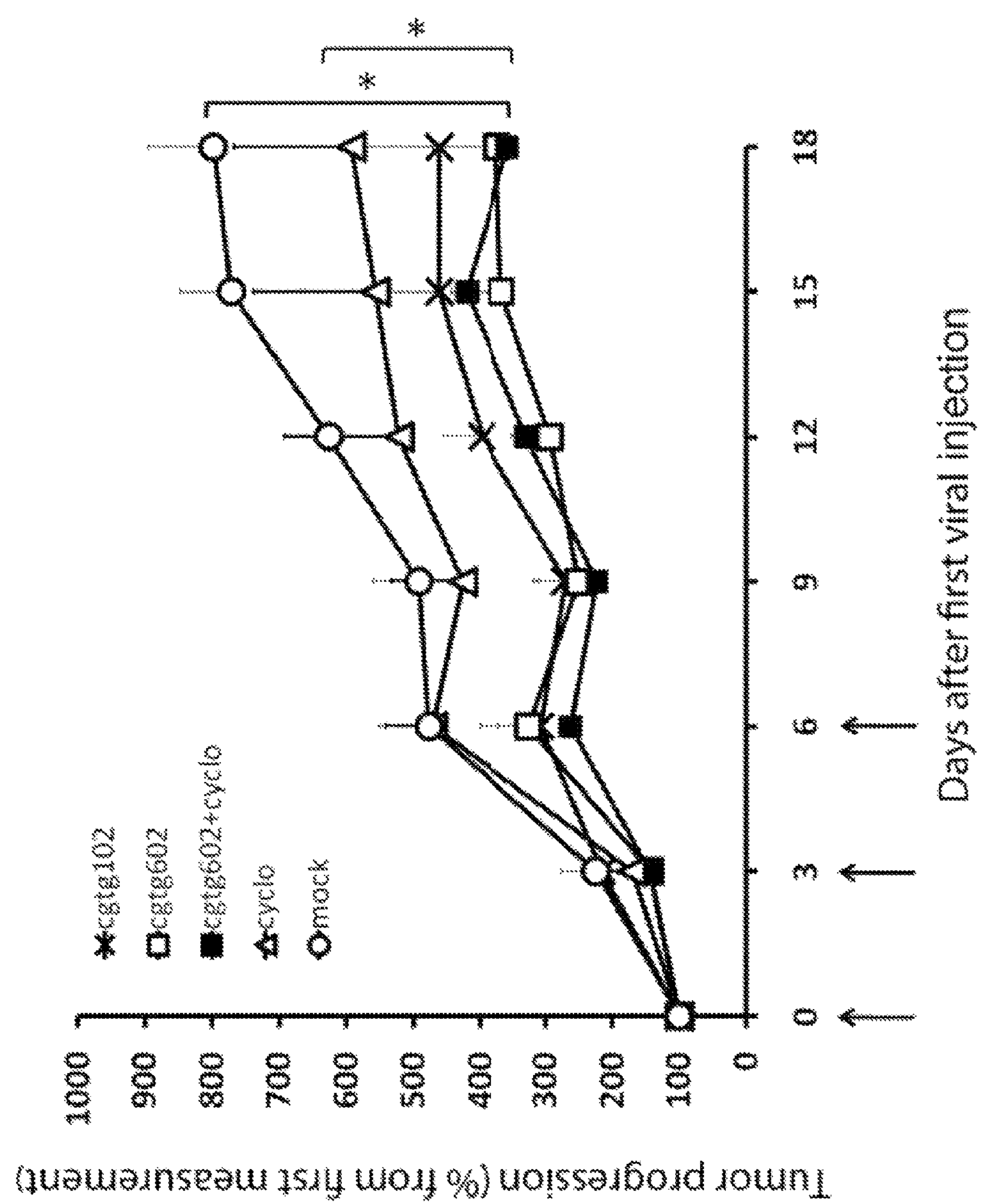
FIG. 6 shows in vivo efficiency of CGTG-602 in Syrian Hamsters (semipermissive for human adenovirus replication) bearing pancreatic cancer tumors. CGTG-602 significantly ($P<0.01$) slowed down tumor progression, and was more potent than the control virus CGTG-102. $3\times10^8$ VP of virus was administered intratumorally on days 0, 3 and 6. The smallest tumors were seen in the group which received concomitant low-dose cyclophosphamide (2 mg/hamster).
Figure 7A:
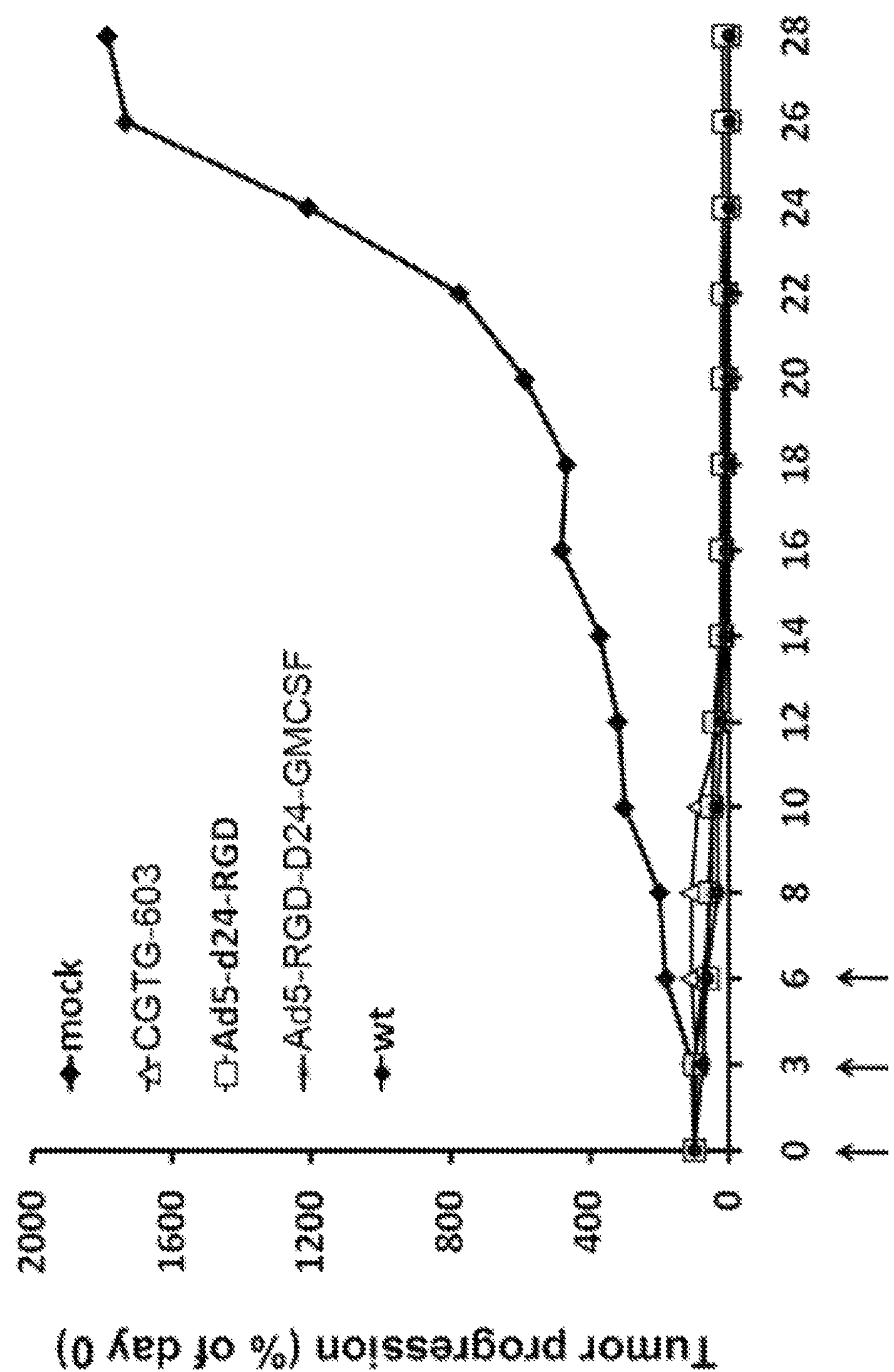
FIG. 7A shows in vivo efficiency of CGTG-603 in Syrian Hamsters bearing pancreatic cancer tumors. $1\times10^9$ VP of virus was administered on days 0, 2 and 4. Ad5-D24-RGD (lacks E2F-1 promoter and GM-CSF gene), Ad5-RGD-D24-GMCSF (lacks E2F-1 promoter) and Ad5 wt were used as control viruses. Mock treated animals received growth medium only. All viruses eradicate the tumors within 16 days following the treatments.
Figure 7B:
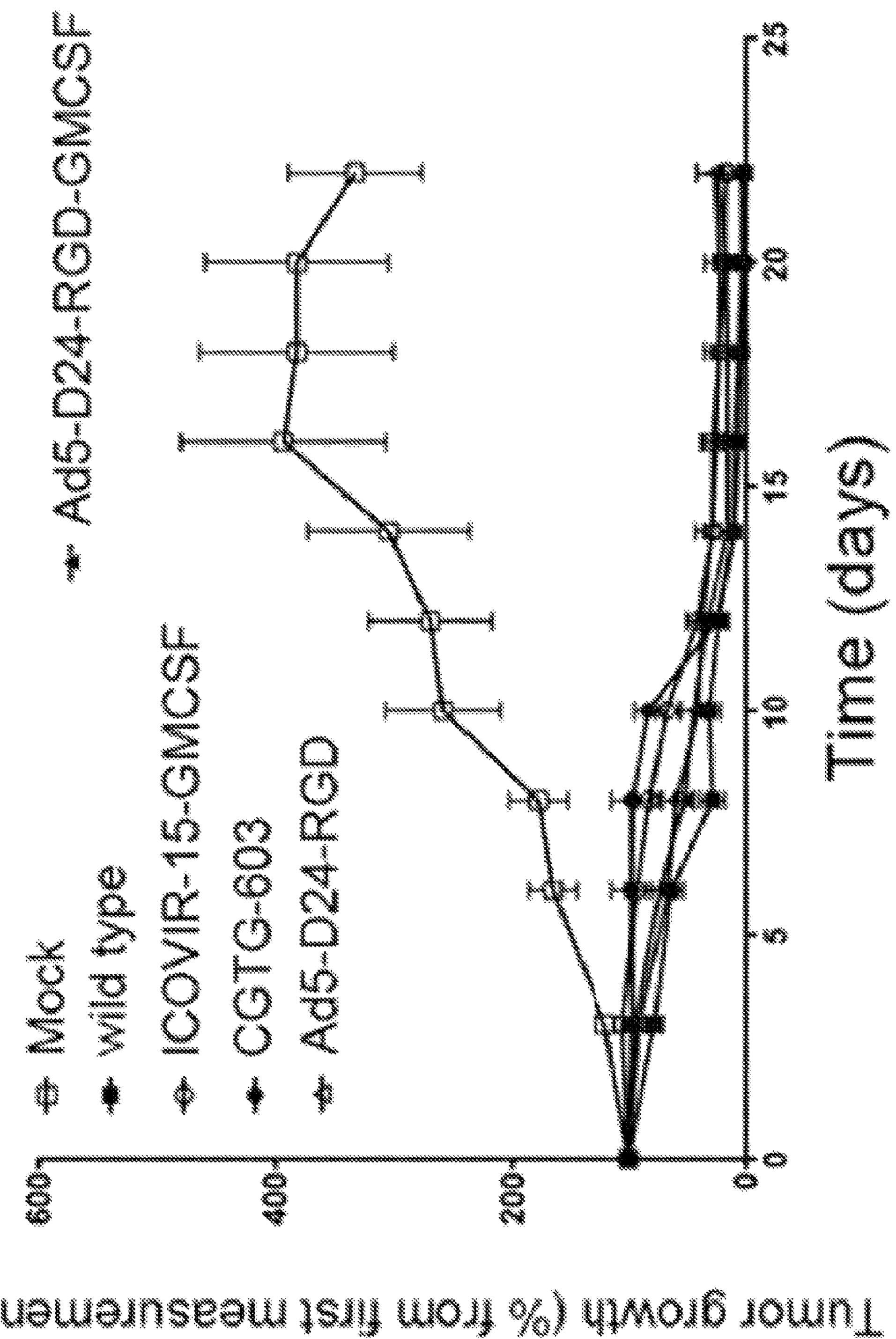
FIGS. 7B-C show a rechallenge experiment with the same viruses and a GM-CSF producing ICOVIR-15 virus (an adenovirus with a modified E2F-1 promoter and an RGD-modified capsid) as an additional control virus. Hamster HAPT-1 tumors were treated intratumorally with $1\times10^9$ VP of each virus as described above and tumor growth was followed for 20 days (B). Tumors were surgically removed, hamsters were re-challenged with HAPT-1 tumors and re-treated (C). All hamsters treated with virus showed delay in tumor growth, but only those hamsters that had been previously treated with CGTG-603 or one of the other viruses containing GM-CSF as a transgene showed a complete protection against tumor re-challenge.
Figure 7C:
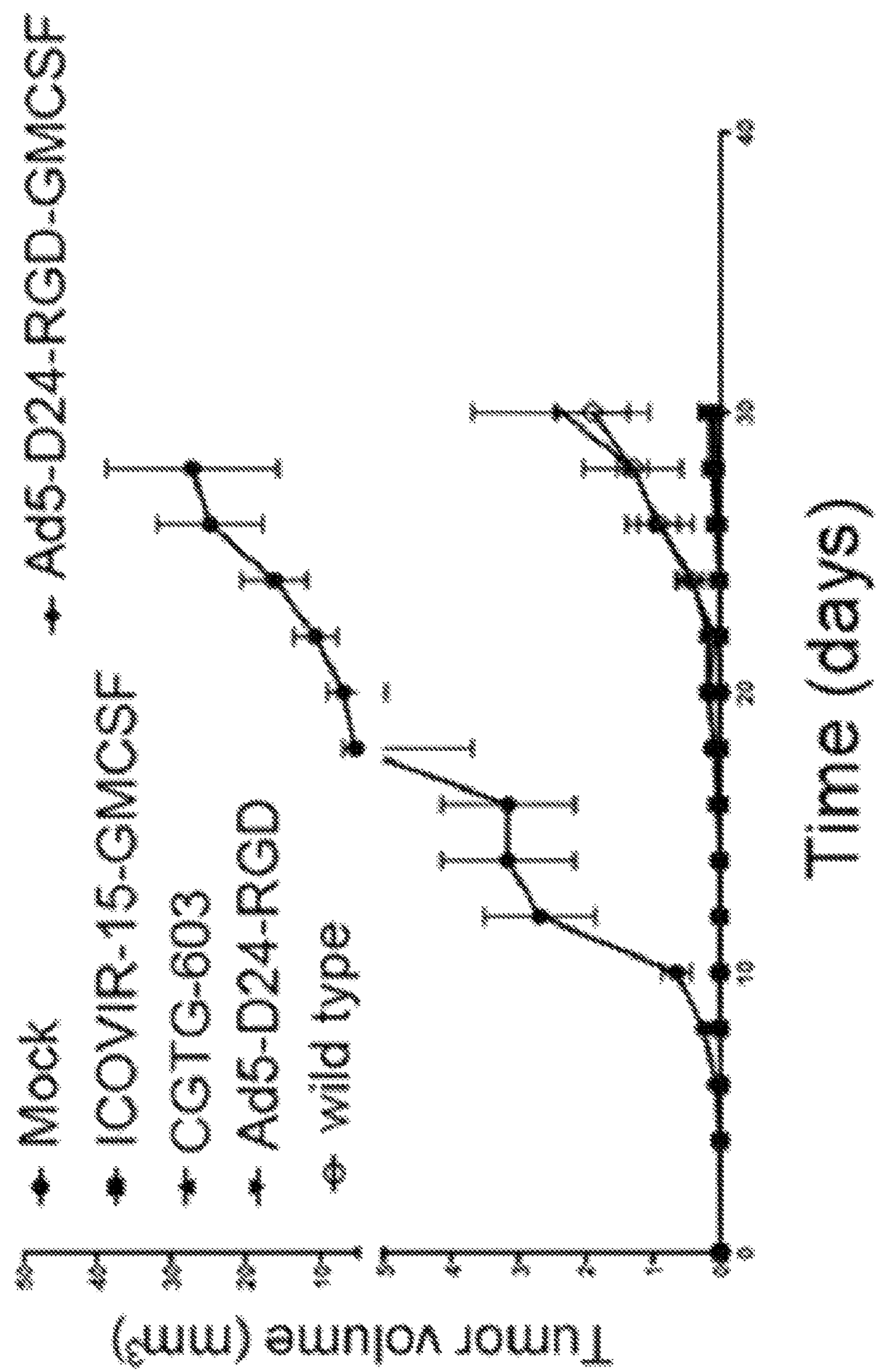

In vivo efficacy of CGTG-602 was tested in immune competent Syrian hamsters, which are semipermissive for human adenovirus replication (mice are non-permissive) (Ying B. et al. 2009, Cancer Gene Ther doi:10.1038/cgt.2009.6.). $7\times10^6$ HapT1 pancreatic cancer cells were injected subcutaneously into flanks, and when the tumors reached a diameter of approximately 0.5 cm, they were injected intratumorally with $3\times10^8$ VP of either CGTG-602 (n=6 hamsters, 24 tumors) or CGTG-102 (n=5 hamsters, 20 tumors) 3 times every 3 days, and the tumor volumes were followed (FIG. 6). Further, 5 animals received 2 mg/hamster cyclophosphamide intraperitoneally in a combination with CGTG-602, 5 hamsters received cyclophosphamide only and 4 animals were mock-treated with intratumoral growth medium injections. Treatments with CGTG-602 slowed down the tumor progression significantly when compared to the mock treatments. There was no significant difference between CGTG-602 and CGTG-102 treatments in efficacy (although tumors in the former group were smaller), which is in line with the hypothesis that they are expected to be as effective, but CGTG-602 has improved safety properties. Further, the combination treatment with cyclophosphamide did not significantly enhance the efficacy of virus alone, even if mean tumor size the combination group was slightly smaller. The HAPT-1 tumor model is such an aggressive model that tumor growth in control groups limited the length of the experiment. Therefore, the immunological benefit of low-dose cyclophosphamide probably did not have enough time to become visible. This is supported by the observation that tumors were becoming smaller in the combination group at the last time point while tumors were growing in all other groups. The model is not optimal for efficacy studied as hamster cells are likely to express only low levels of desmoglein 2, which is the primary receptor for Ad3 based vectors. This is highlighted in other experiments, where CGTG-603, a virus with an Ad5 knob featuring an RGD modification, was used (FIGS. 7A-C). The receptors for this virus are known to be expressed in hamster tissues. $1\times10^9$ VP of virus was administered on days 0, 2 and 4. Ad5-D24-RGD (lacks E2F-1 promoter and GM-CSF gene), Ad5-RGD-D24-GMCSF (lacks E2F-1 promoter) and Ad5 wt were used as control viruses. Mock treated animals received growth medium only. All viruses eradicate the tumors within 16 days following the treatments (FIG. 7A). A similar setup was used for the re-challenge experiment, where HAPT-1 tumors were first allowed to grow and were treated as mentioned above (FIG. 7 B), and subsequently were surgically removed. The same hamsters were re-challenged with HAPT-1 cells and treated as above. CGTG-603 treatment resulted in complete protection against tumor re-challenge, highlighting the immunostimulatory role of the transgnene GM-CSF (FIG. 7C).

Example 6

Analysis of CGTG-602 in Human Patients

I. Patients

Patients with advanced and treatment refractory solid tumors were enrolled in a FIMEA regulated Advanced Therapy Access Program treatment protocol (ISRCTN 10141600, EC/1394/2007). Information of patients receiving CGTG-602 is listed in Table 1.

14 patients with advanced solid tumors refractory to standard therapies (Table 1) were serially treated with CGTG-602 intravenously and intratumorally (Table 2). Intratumoral injection was performed intraperitoneally or intrapleurally in the case of carcinomatosis or pleural metastases, respectively. Inclusion criteria were solid tumors refractory to conventional therapies, WHO performance score 2 or less and no major organ function deficiencies. Exclusion criteria were organ transplant, HIV, severe cardiovascular, metabolic or pulmonary disease or other symptoms, findings or diseases preventing oncolytic virus treatment. Written informed consent was obtained and treatments were administered according to Good Clinical Practice and the Declaration of Helsinki.

II. Treatments with Adenoviral Vector Encoding GM-CSF a) CGTG-602 Treatments

13/14 patients were serially treated with CGTG-602 for 2-4 times approximately every 3 weeks. One patient received 1 treatment of CGTG-602 (C332) and subsequently serial treatment with another virus. This patient is included only for an immunohistochemical analysis of CD8+ T-cells from a tumor sample that was obtained 3 weeks after treatment with CGTG-602 and for assessment of adverse events after the single treatment, and is not included in any of the response evaluations.

Virus administration was performed by ultrasound-guided intratumoral injection and circa one fifth of the dose was given intravenously in the first injection. In subsequent injections the entire dose was given intratumorally. Viral doses ranging from $3\times10^{10}$ VP to a maximum of $1\times10^{12}$ VP were used based on safety results previously published with Ad5/3-D24-GM-CSF (Koski et al. 2010, Mol Ther 18:1874-84).

Virus was diluted in sterile saline solution at the time of administration under appropriate condition. Following virus administration all patients were monitored overnight at the hospital and subsequently during the whole treatment period and after the last treatment for 4 weeks as outpatients. Physical assessment and medical history were done at each visit and clinically relevant laboratory values were followed. Side effects of treatment were recorded and scored according to Common Terminology for Adverse Events v3.0 (CTCAE).

Because many cancer patients have symptoms due to disease, pre-existing symptoms were not scored if they did not become worse. However, if the symptom became more severe, e.g. pre-treatment grade 1 changed to grade 2 after treatment, it was scored as grade 2. Tumor size was assessed by positron emission tomography-contrast-enhanced computer tomography (PET-CT) scanning. A modification of the PET Response Criteria in Solid Tumors 30 were applied to overall disease, including injected and non-injected lesions. No adjustments for fat % or body surface area were performed. The five most active lesions, maximum two lesions per organ, were evaluated for SUVmax and the values were summed. Lymph node signal increase was not considered progression as lymph node metabolism increases during inflammation and eg. after vaccination. Progressive metabolic disease (PMD)=30% increase of Summed SUVmax or >2 cm PET positive new lesion. Stable metabolic disease (SMD)=−9%-+29% change, minor metabolic response (MMR)=−29%-10% decline, partial metabolic response (PMR)=−30% decline in Summed SUVmax. Complete metabolic response (CMR)=disappearance of all metabolically active tumor. Tumor markers were measured from serum when elevated at baseline, and the same percentages were used.

Table 3 reports the efficacy evaluation of CGTG-602 according to the criteria described above.

b) Safety of CGTG-602 in Cancer Patients

Treatments were well tolerated up to the highest dose used: $1\times10^{12}$ VP/patient. Table 4 summarizes all the adverse events that were recorded during CGTG-602 treatment rounds. Adverse events are reported as frequency per all 39 treatment rounds. All the adverse events have been graded according to Common Terminology for Adverse Events v3.0 (CTCAE). No grade 4-5 adverse events were seen. Fever (22/39 treatment rounds), fatigue (22/39 treatment rounds) or upper respiratory symptoms (7/39 treatment rounds) were common grade 1-2 flu-like symptoms. AST elevation (11/39), pain in the injection site (6/39 treatment rounds), abdominal pain (15/39 treatment rounds), nausea (11/39 treatment rounds), vomiting (7 treatment rounds) and oedema (6/39 treatment rounds) were also relatively common grade 1-2 adverse events. Grade 3 symptoms were seen in 11/39 treatment rounds: fever (2/39), neuropathy (1/39), pain (5/39), upper respiratory symptoms (2/39), oedema (1/39) and flushing (1/39). Asymptomatic and self-limiting grade 3 hematological or metabolic side effects were seen in 6/39 treatment rounds: anemia (2/39), hyponatremia (2/39), leucosytopenia (1/39) and creatinine elevation (1/39).

III. Virus Replication

Serum samples were collected from patients treated with CGTG-602 and conventional PCR was carried out with primers and conditions according to Takayama et al. 2007, J. Med. Virol. 79:278-284. Briefly, total DNA was extracted by adding 3 μg of carrier DNA (polydeoxyadenylic acid; Roche, Mannheim, Germany) to 400 μl of serum and using the QIAamp DNA mini kit. Extracted DNA was eluted in 60 μl nuclease-free water and DNA concentration was measured by spectrophotometry. PCR amplification was based on primers and probe targeting the E1A region flanking the 24-bp deletion (E1 forward primer 5"-TCCGGTTTCTATGCCAAACCT-3 (SEQ ID NO:16), E1 reverse primer 5'-TCCTCCGGTGATAATGACAAGA-3' (SEQ ID NO:17) and probe onco $5'^{FAM}$-TGATCGATCCACCCAGTGA-$3'^{MGBNFQ}$ (SEQ ID NO:18)). In addition, a probe complementary to a sequence included in the 24-bp region targeted for deletion was used to test the samples for the presence of wild-type adenovirus infection (probe wt $5'^{VIC}$-tacctgccacgaggct-$3'^{MGBNFQ}$ (SEQ ID NO:19)).

The real-time PCR conditions for each 25 μl reaction were as follows: 2× LightCycler480 Probes Master Mix (Roche, Mannheim, Germany), 800 nM each forward and reverse primer, 200 nM each probe and 250 ng extracted DNA. PCR reactions were carried out in a LightCycler (Roche, Mannheim, Germany) under the following cycling conditions: 10 min at 95° C., 50 cycles of 10 s at 95° C., 30 s at 62° C. and 20 sec at 72° C. and 10 min at 40° C. All samples were tested in duplicate. TaqMan exogenous internal positive control reagents (Applied Biosystems) were used in the same PCR runs to test each sample for the presence of PCR inhibitors.

A regression standard curve was generated using DNA extracted from serial dilutions of Ad5/3-D24-Cox2L ($1\times10^{8}$-10 vp/ml) in normal human serum. The limit of detection and limit of quantification for the assay were 500 vp/ml of serum.

Positive samples were confirmed by real-time PCR using LightCycler480 SYBR Green I Master mix (Roche, Mannheim, Germany) and primers specific for adenovirus and GM-CSF sequences (GM-CSF forward primer 5"-AAACACCACCCTCCTTACCTG-3' (SEQ ID NO:20) and GM-CSF reverse primer 5"-TCATTCATCTCAGCAGCAGTG-3' (SEQ ID NO:21)).

All patients evaluated for the presence of CGTG-602 in serum were negative for CGTG-602 prior to the treatment (Table 3). On day 1 after the first treatment 9/11 evaluable patients had measurable levels of virus genomes in the serum, with the highest titer being 1141 VP/ml serum. From samples taken during days 3-7 2/4 evaluable patients were positive, with the highest titer of 11523 VP/ml serum, suggesting virus replication at tumors.

III. Detection of CD8+ T-Cells from Tumor

Figure 8A:
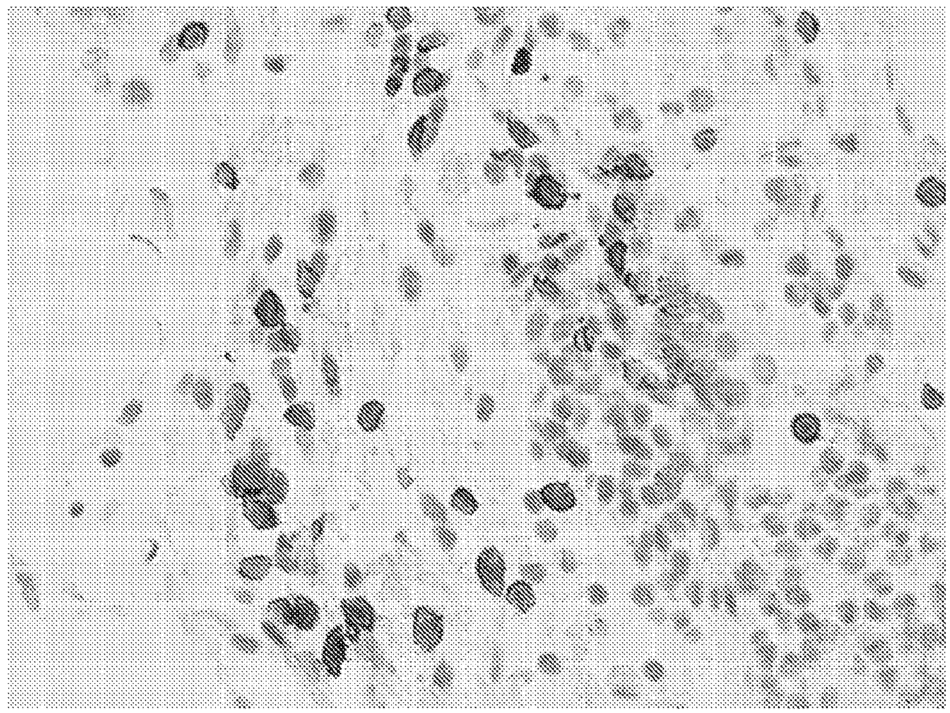
FIGS. 8A-B show CGTG-602 induced CD8+ T-cell infiltration in A) human tumor tissue but not in B) normal peritoneal lining obtained from patient C332 1 month after treatment with CGTG-602. Cells stained positive for CD8 appear as brown.
Figure 8B:
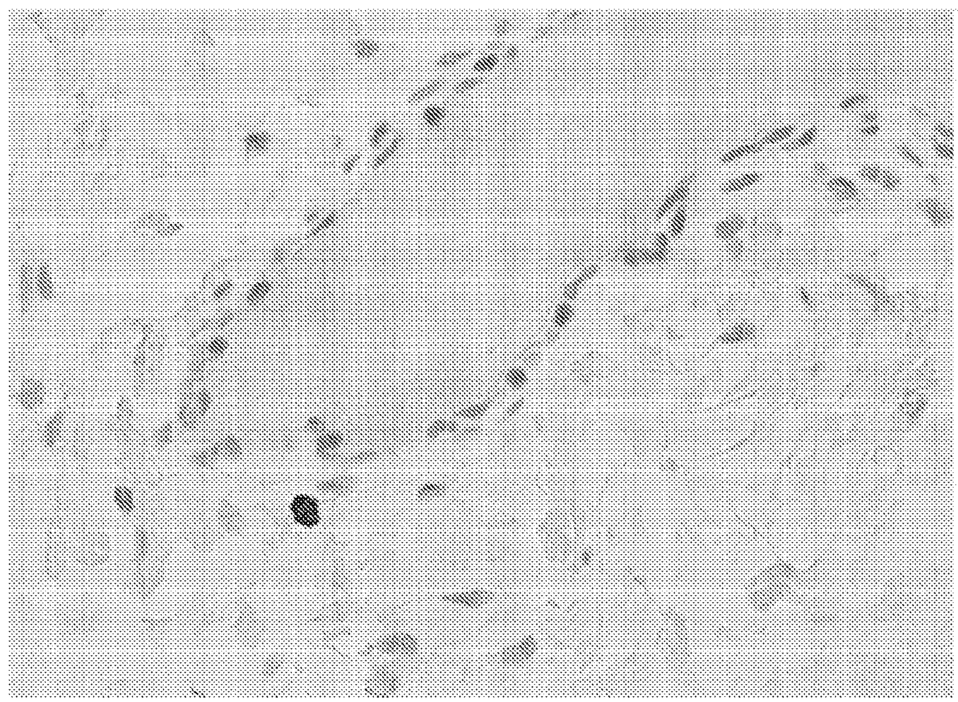

Tumor sample from patient C332 was obtained 4 weeks after treatment with CGTG-602. Tumor and normal peritoneal lining were fixed in 4% formalin and paraffin blocks were made. For analysis of CD8 positive cells, i.e. cytotoxic T-cells, tissue sections of 4 μm thickness were prepared, deparaffinized, rehydrated and incubated with a primary mouse anti-CD8 antibody (NCL-CD8-4B11; Novocastra, Newcastle Upon Tyne, United Kingdom) at a dilution of 1:25 in antibody diluent S0809 (DakoCytomation, Carpinteria, Calif., USA). Sections were washed and incubated with a secondary anti-mouse antibody labeled with horseradish peroxide (HRP) and counterstained for hematoxyline. Pictures were taken with an Axioplan2 microscope (Carl Zeiss) equipped with Axiocam (Zeiss). Infiltration of CD8+ T-cells was seen in tumor samples but not in normal peritoneal lining, suggesting anti-tumor immunity induction by CGTG-602 (FIGS. 8A and 8B).

IV. Efficacy of CGTG-602

All patients had progressing tumors prior to treatment. 7 patients could be assessed for radiological benefit according to PERCIST (Table 3). Of the 6 evaluable patients, 1 patient had a complete response (CMR), 1 patient had partial response (PMR) and a complete response in a non-injected mediastinal lesion, 1 patient had minor response (MMR), 2 patients had a stable disease (SMD) and 1 patient had progressive disease (PMD). Therefore, the radiological disease control rate was 83% of the 6 radiologically evaluable patients while the response rate (including MMR) was 50%.

Figure 13:
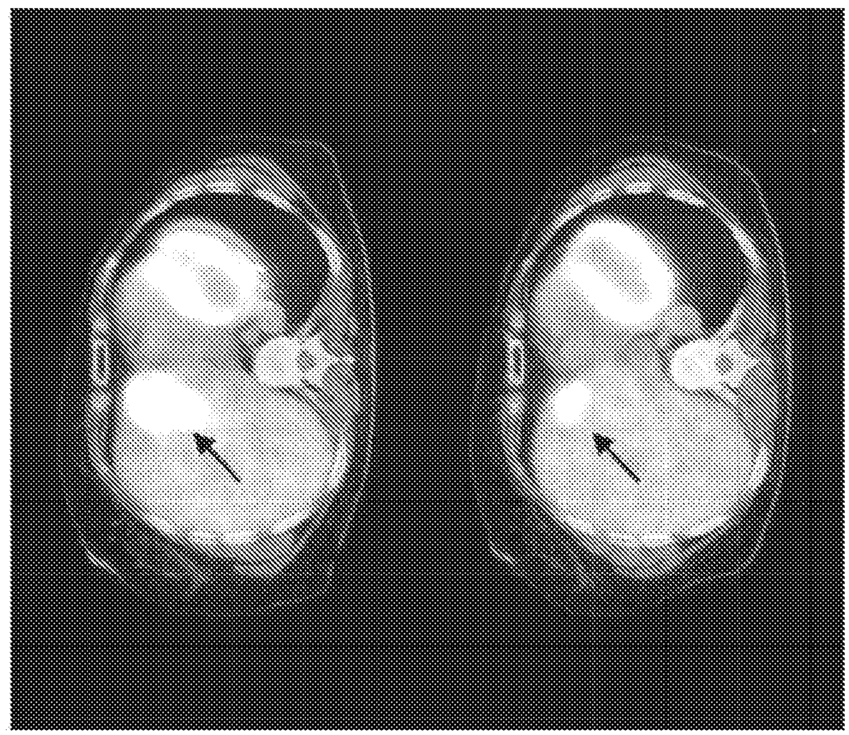
FIG. 13 shows a disappearance of a non-injected mediastinal lesion (A before treatment, B after treatment) and a 49.1% reduction in the metabolic activity of an injected liver lesion (C before treatment, D after treatment) of patient R319.
Figure 13:
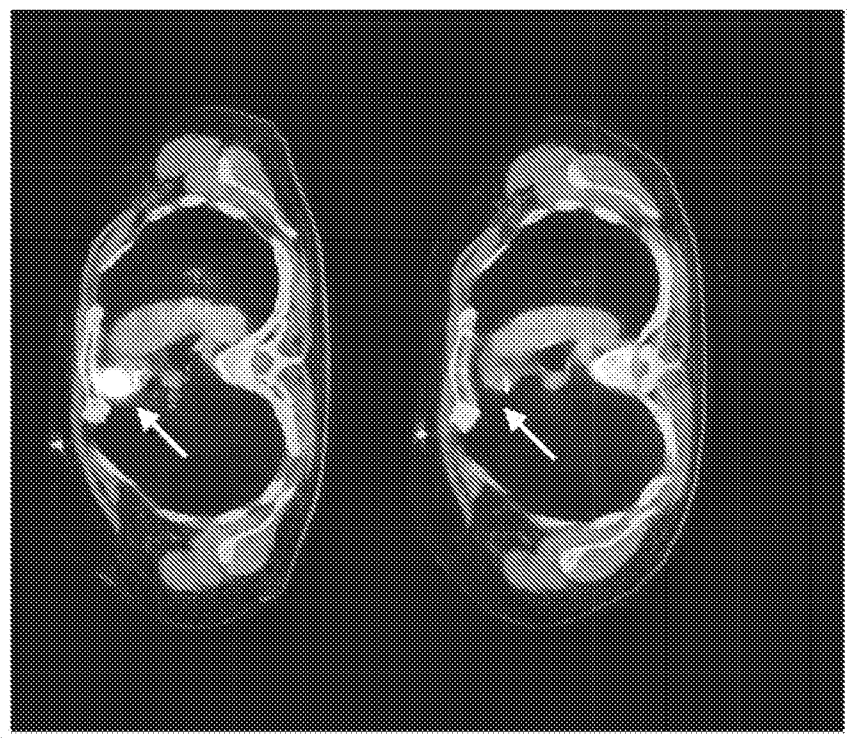

Patient R319 had a 49.1% reduction in metabolic activity of an injected liver lesion (FIGS. 13 C-D) and a non-injected mediastinal lesion disappeared (FIG. 13 A-B) after treatment.

Figure 14:
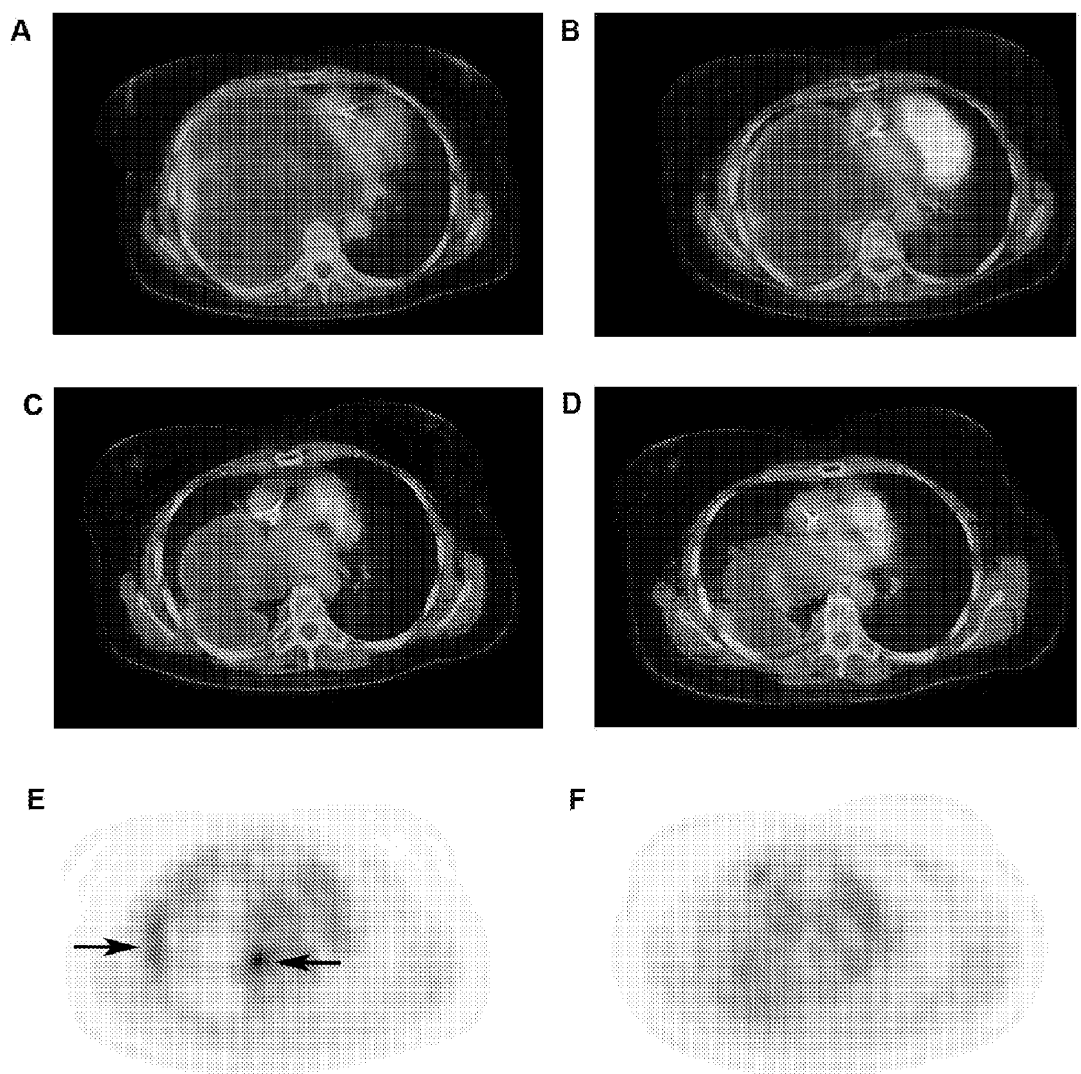
FIG. 14 shows positron emission tomography-computed tomography (PET-CT) fusion images from patients R319 and S354. A) baseline, B) after 3 months of treatment, C) after 6 months, D) after 9 months. Tumor size started diminishing at 6 months. E-F) a different plane of PET analysis from the same patient at baseline and after 3 months, arrows indicate PET active regions of the tumor.

A complete metabolic response was seen in PETCT imaging tumor of the tumor in the right lung of patient S354 (FIG. 14): A) baseline, B) after 3 months of treatment, C) after 6 months, D) after 9 months. Tumor size started diminishing at 6 months. E-F) a different plane of PET analysis from the same patient at baseline and after 3 months, arrows indicate PET active regions of the tumor.

Figure 11:
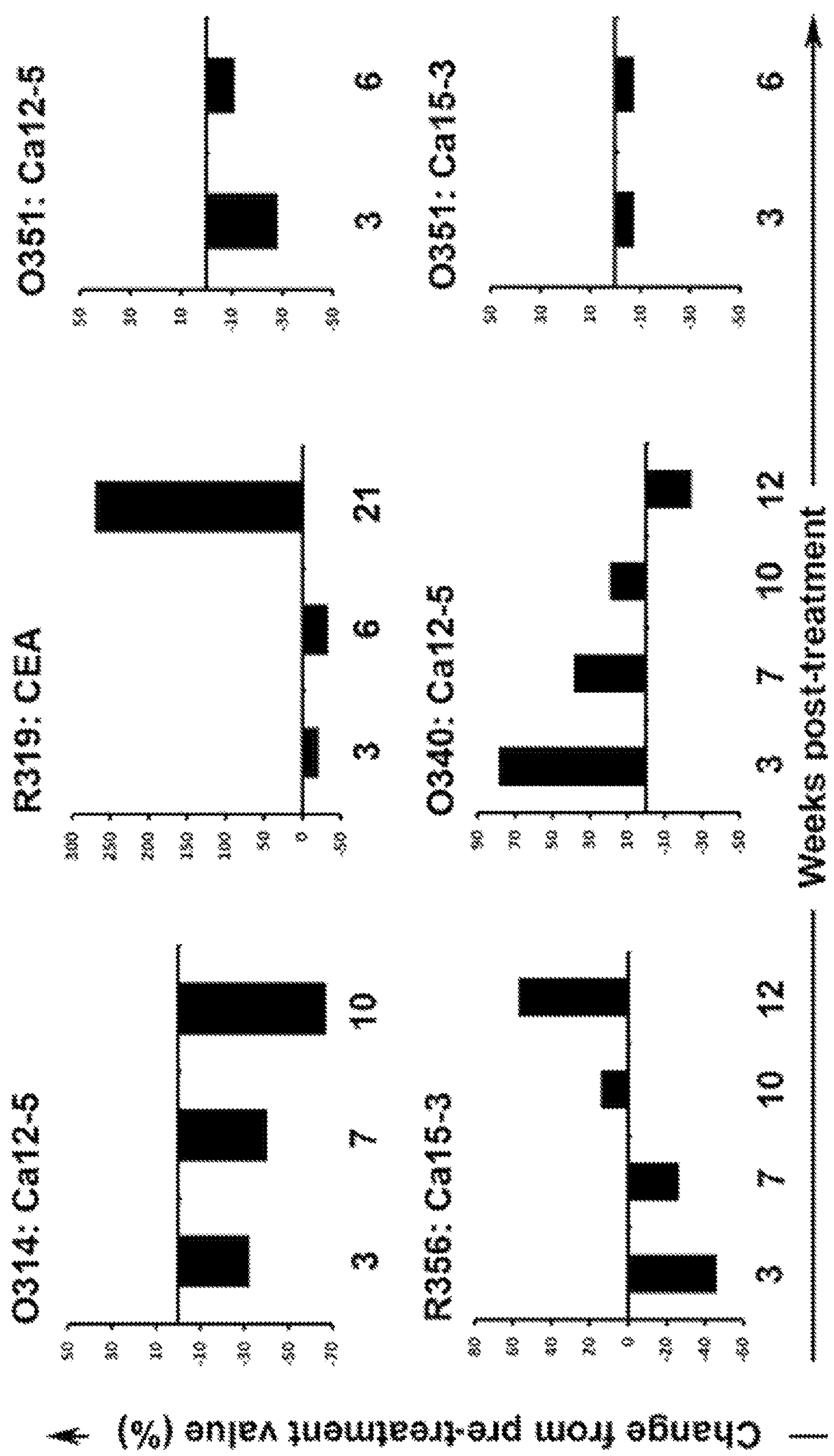
FIG. 11 shows the patient serum marker levels for CEA, Ca12-5, Ca15-3 and/or Ca19-9 after treatment.
Figure 11:
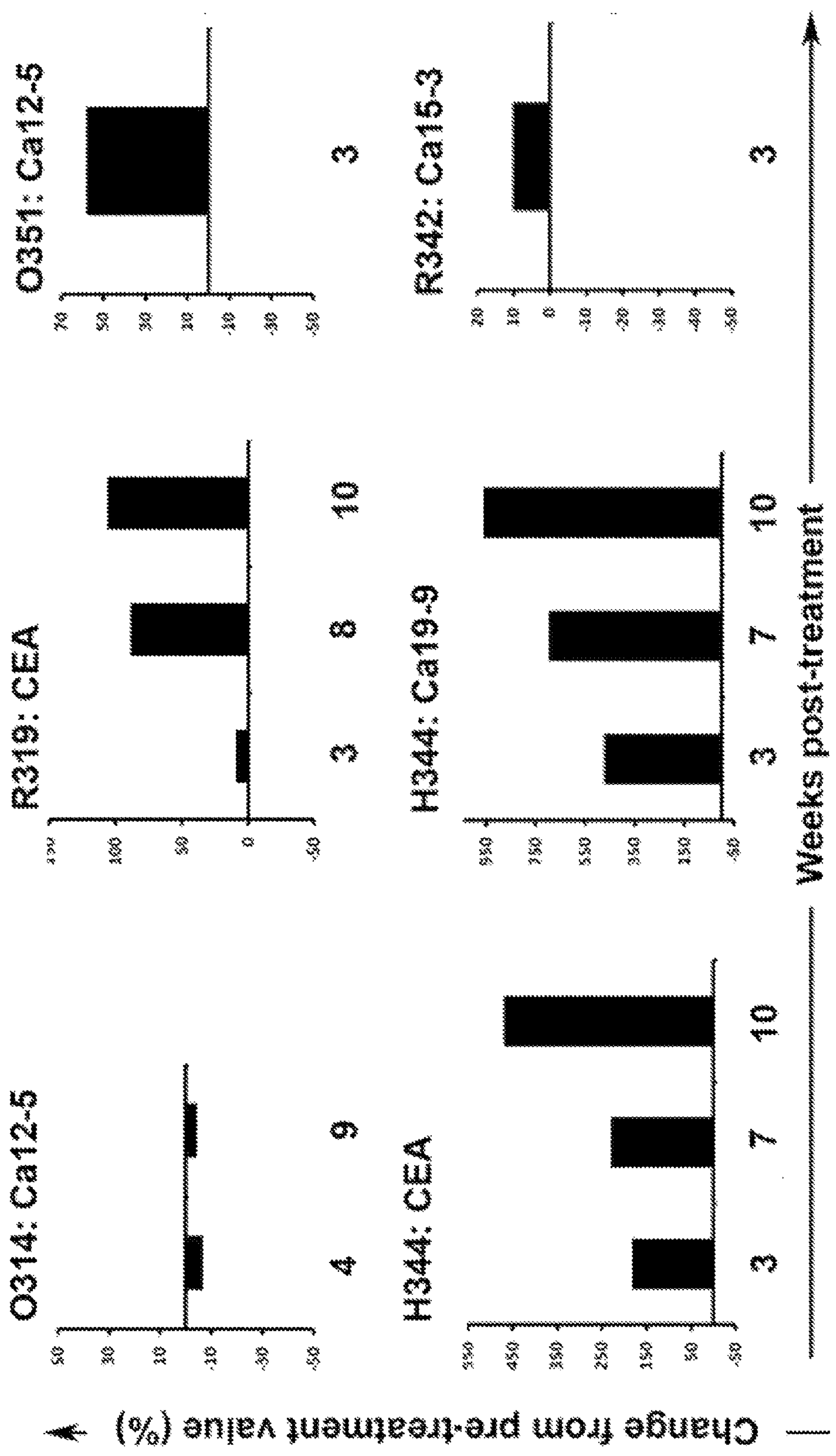

With regard to tumor markers, assessed for patients who had elevated markers at baseline, 3/9 patients had reduction of marker levels, 2/9 had initial reduction and subsequent elevation of marker levels, 1 patient had initial elevation and subsequent reduction and 3/9 had elevation of marker levels (FIG. 11).

Figure 12:
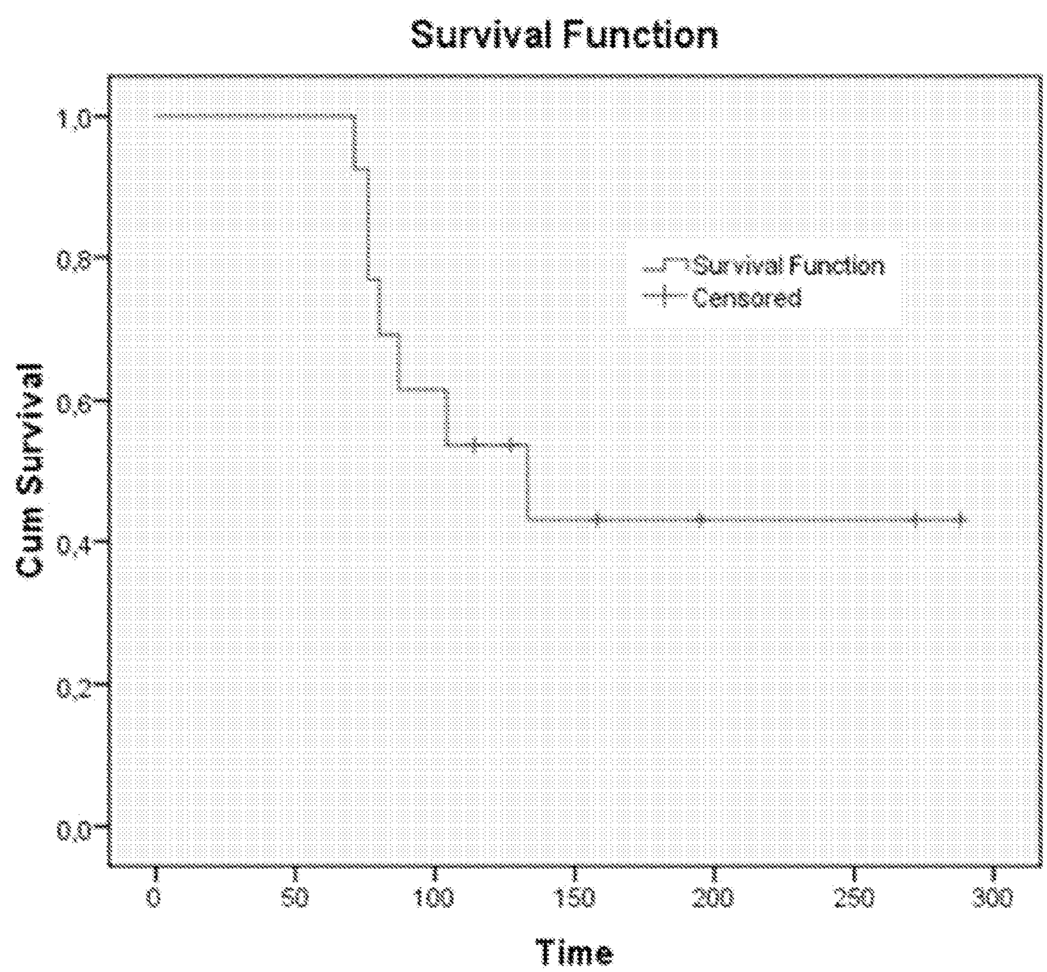
FIG. 12 shows a survival plot for CGTG-602 treated patients.

Overall, with regard to tumor marker or radiological responses, signs of antitumor efficacy were seen in 9/12 evaluable patients (75%). These patients lived a median of 135 days while the median survival of the other three was 80 days. Overall survival of all patients discussed here is shown in FIG. 12.

V. Immune Responses Elicited by the Treatment a. T-Cell Responses

Figure 9A:
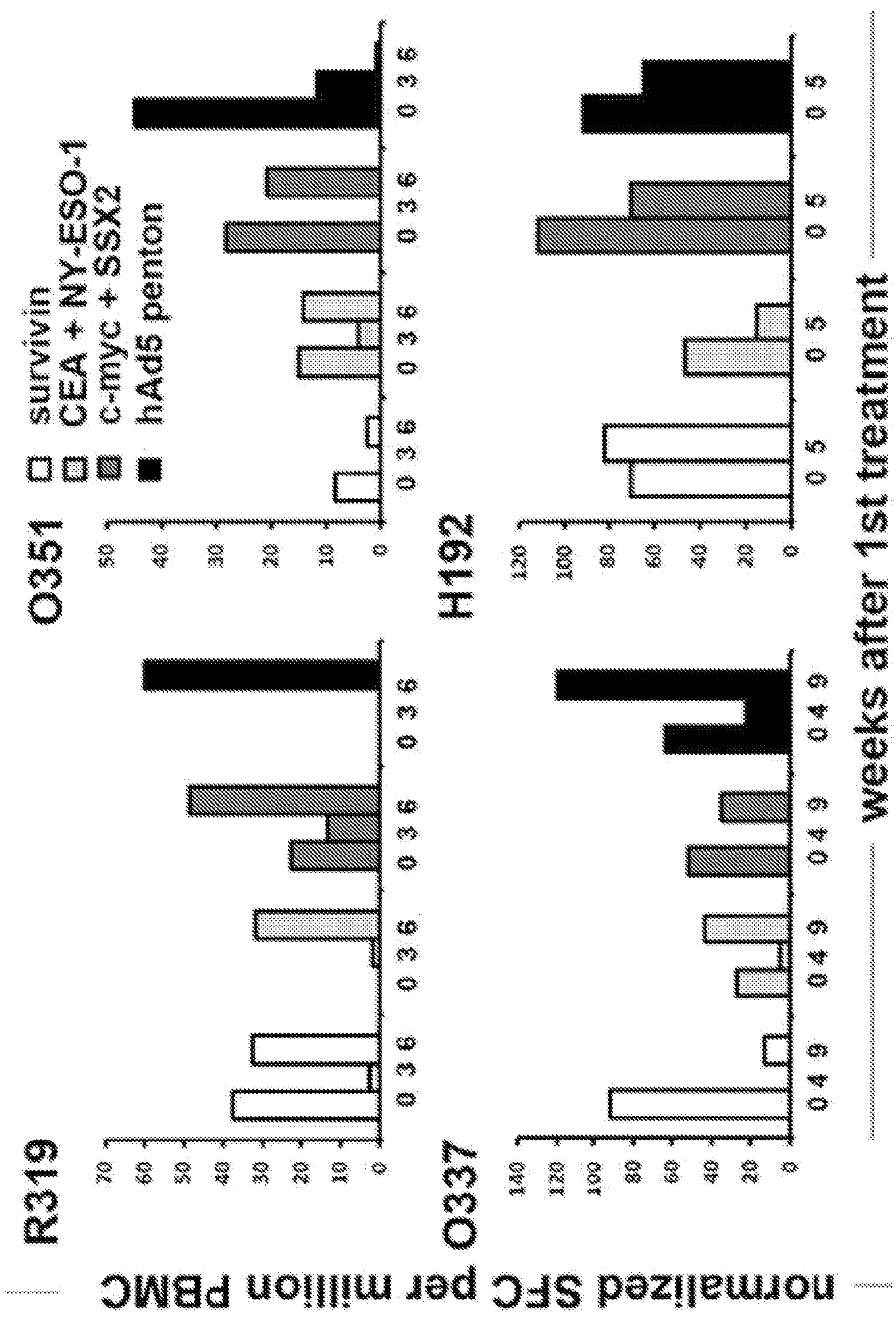
FIGS. 9A-B show that CGTG-602 elicited a T cell-response against both tumor epitopes and adenovirus (present in tumor cells). PBMCs harvested from patients treated with CGTG-602 were analyzed by IFN-gamma ELISPOT upon stimulation with a mix of peptide from Adenovirus 5 and mixes of peptides from tumor antigens CEA and NY-ESO-1 (pool1), c-myc and SSX2 (pool2) and survivin alone.
Figure 9A:
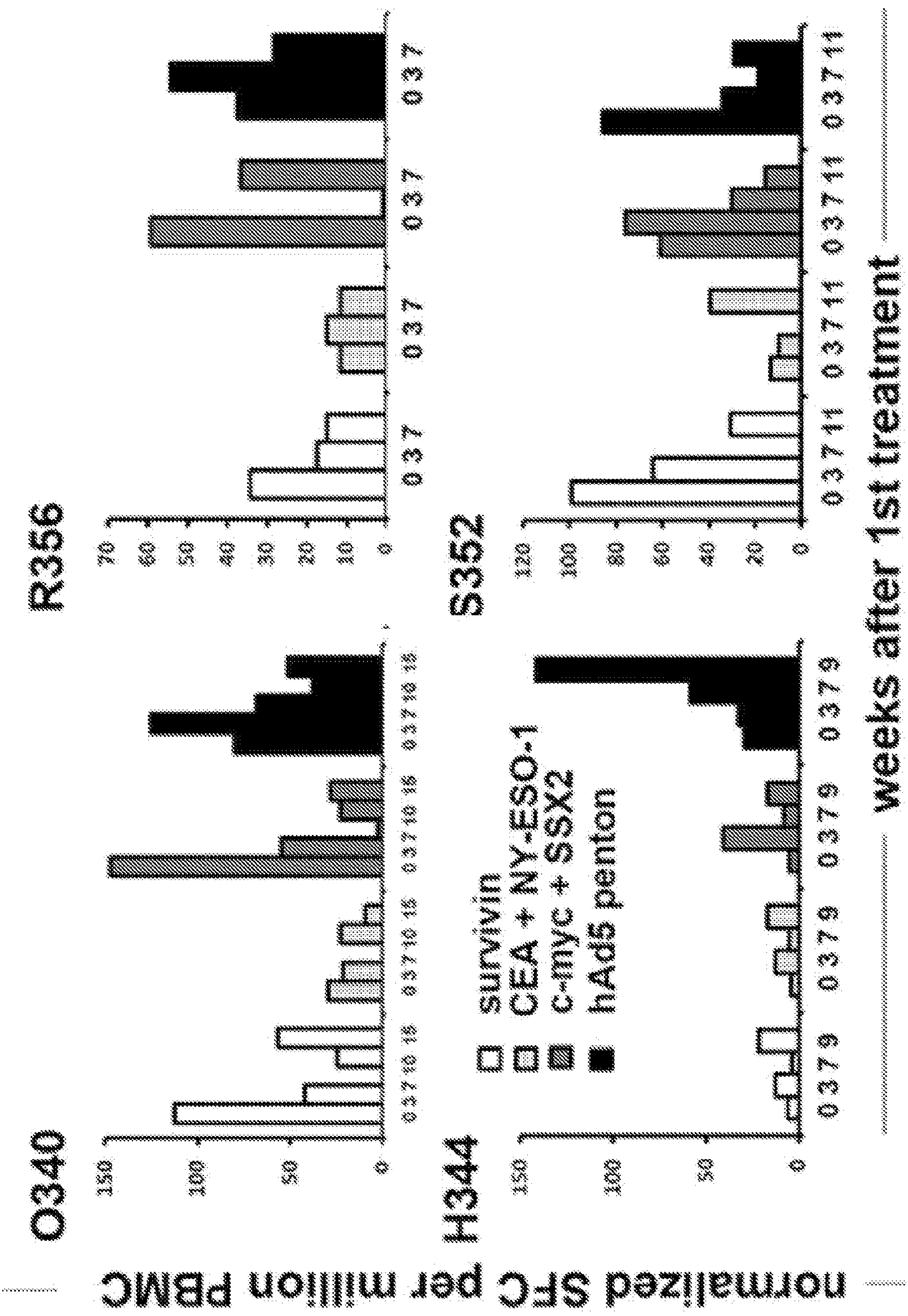
Figure 9A:
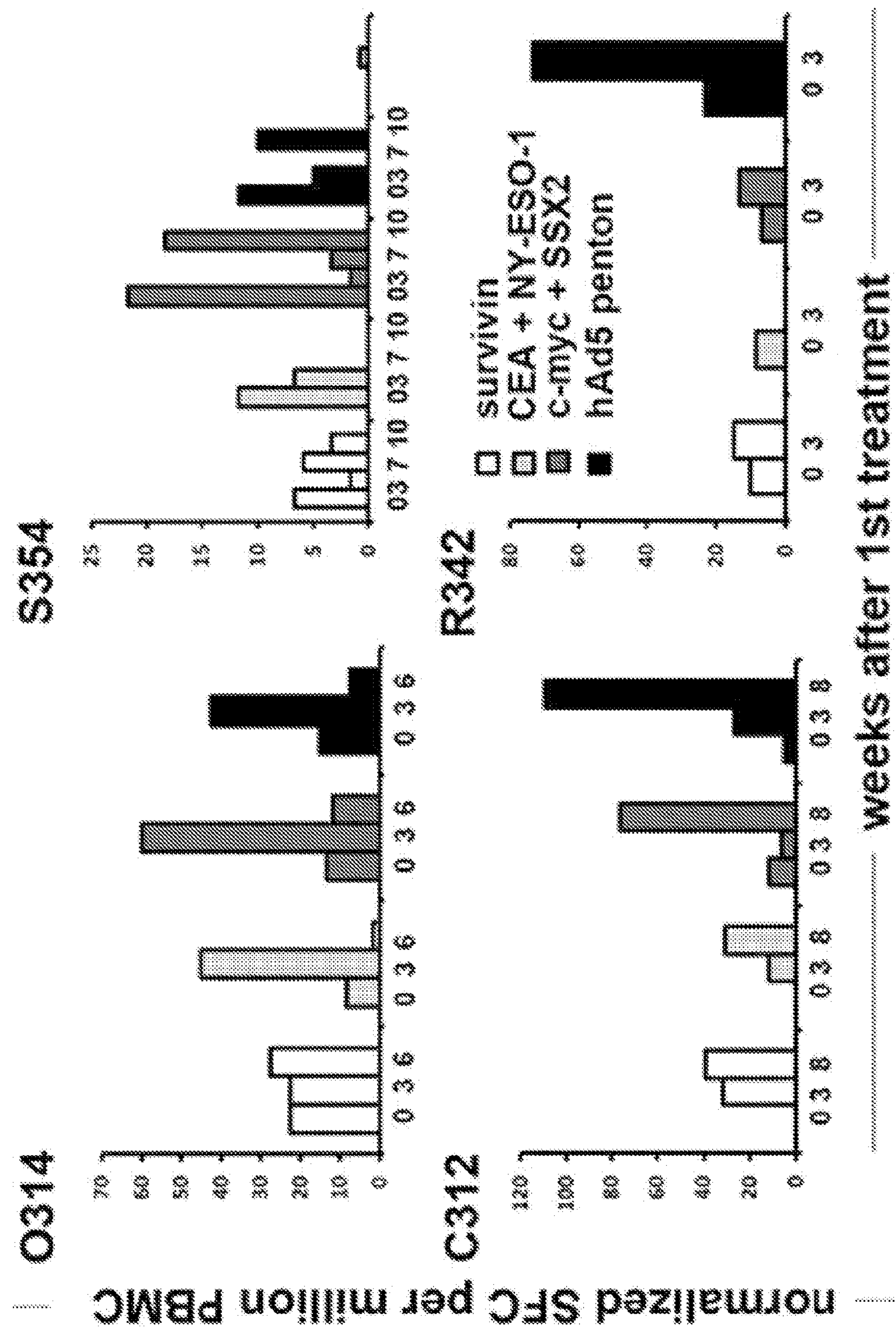
Figure 9A:
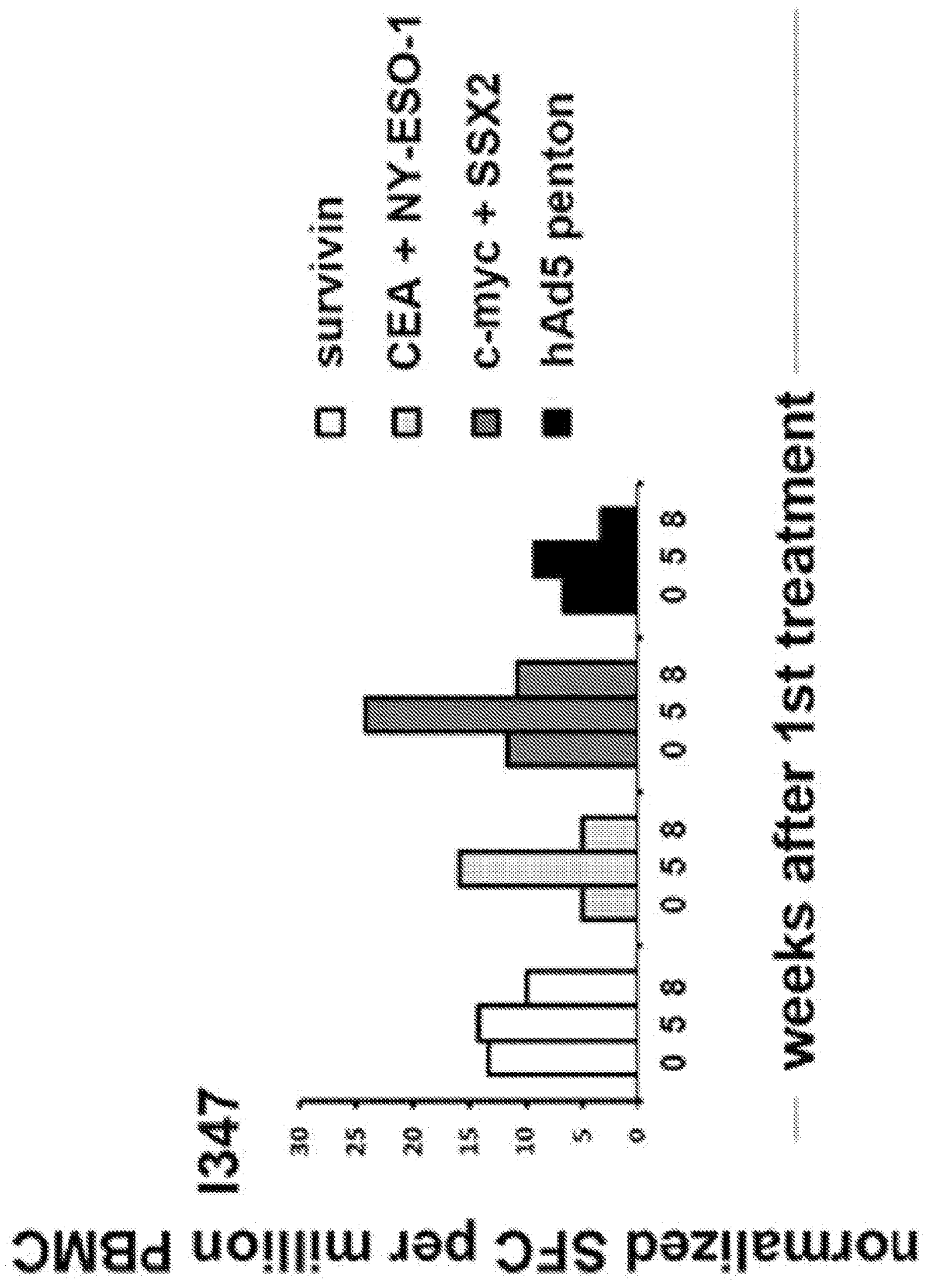

Oncolytic cell death allows the immune system to gain the capacity for recognizing and killing tumor cells. This is potentially beneficial for tumor eradication and may facilitate cures. Adenovirus is cleared out from the body in a relatively short time following the administration; hence it becomes of key importance to stimulate the immune system to be able to recognize specific tumor-antigen so that the treatment can result in a sustained beneficial effect for the patient. In addition, in the presence of antibody, the virus is neutralized so that it can lose its efficacy of infecting metastasis. However, effector T or NK cells induced against the tumor are free to circulate and eventually kill metastasis far from the injected tumor. In order to demonstrate that the GMCSF-expressing adenovirus is able to elicit adenovirus- and tumor specific immunity, PBMCs collected from treated patients were analyzed by IFN-gamma ELISPOT (IFN-gamma is a specific activation marker of stimulated T cells). In FIG. 9A are illustrated the results from such analysis. The frequency of IFN-gamma producing tumor associated antigen (TAA) (survivin alone, CEA+NY-ESO-1 or cmyc+SSX2) specific PBMCs increased 6/13 patients and decreased in 4/13 patients after treatment (FIG. 9A). The frequency of adenovirus specific (penton) IFN-gamma producing PBMCs increased in 9/13 patients after treatment. These results suggest that the PBMC-population gained “anti-tumor” characteristics. Further, reduction of the frequency of stimulated PBMCs in the blood may suggest trafficking from the periphery to the tumor site.

Figure 9B:
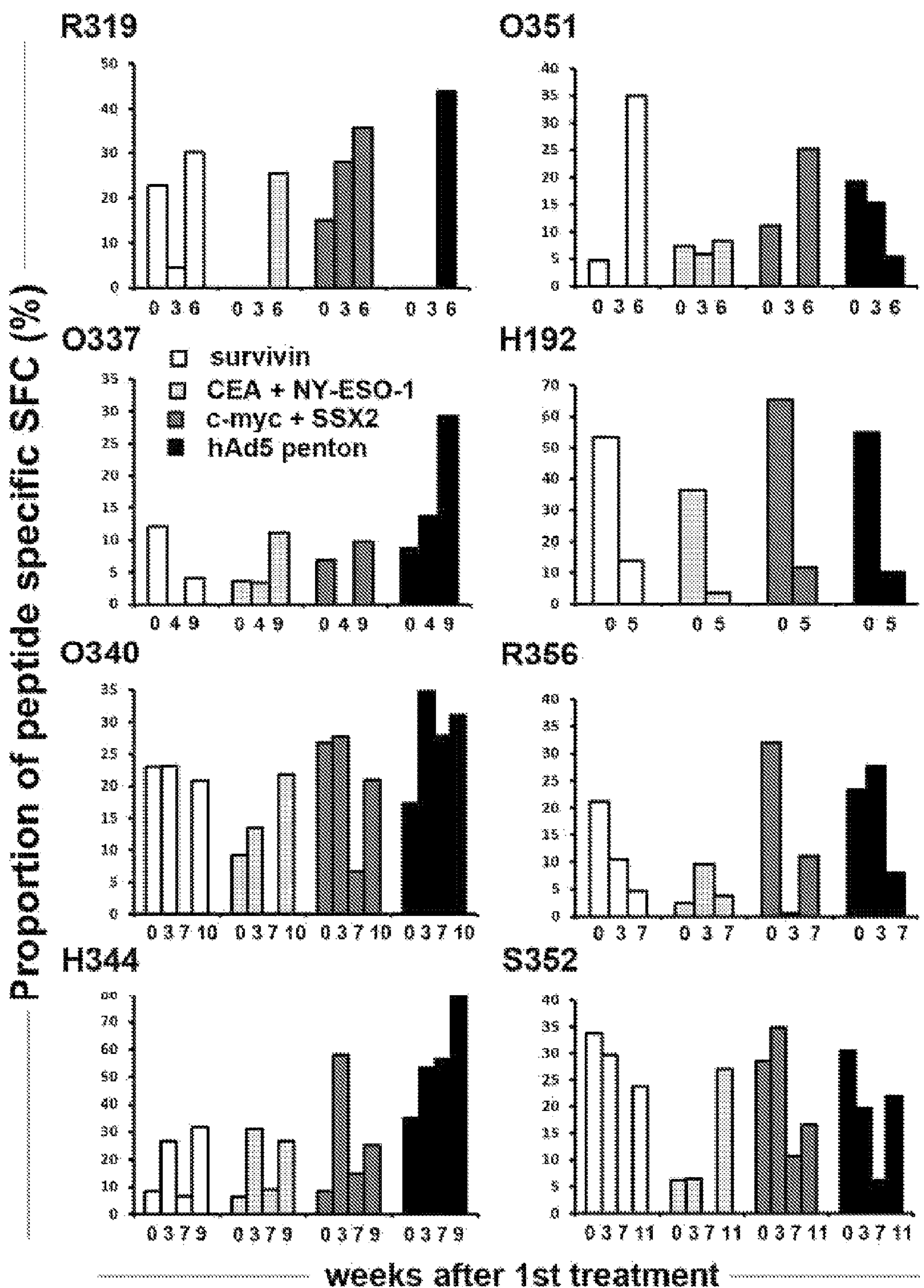
Figure 9B:
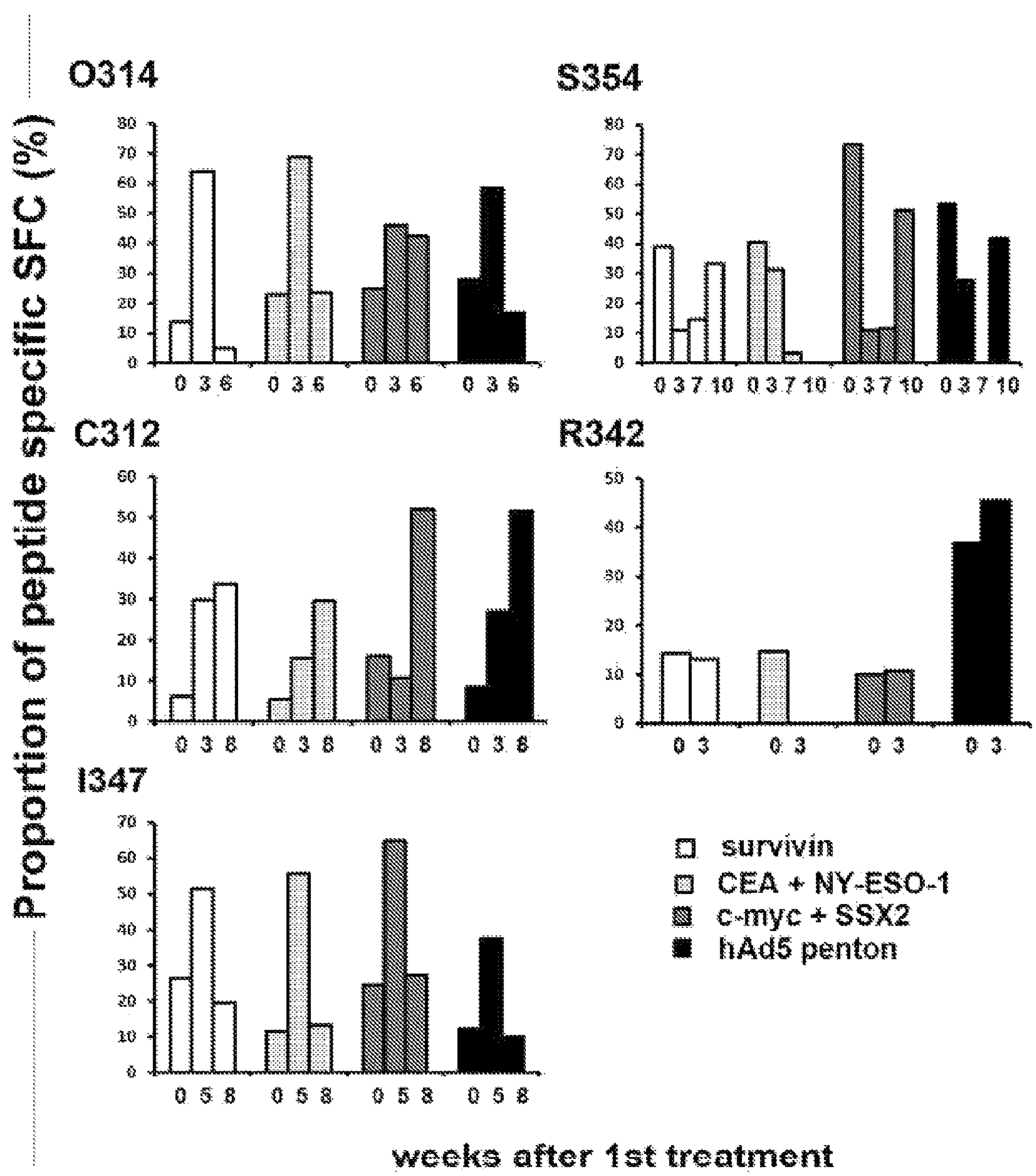

Interestingly, we discovered that there was a 75% concordance in induction of antiviral and antitumor cells on a patient level (FIG. 9A). In other words, if there was an increase in anti-viral cells, most of those patients also featured an increase in one or more classes of anti-tumor T-cells. Unexpectedly, this finding reveals that in humans, anti-viral response corresponds and may contribute to anti-tumor response through epitope spreading and reduction of tumor-associated immunological tolerance. The concordance in induction of antiviral and antitumor cells was 100% when the antigen specific PBMCs was viewed proportionate to all IFN-gamma producing PBMCS (FIG. 9B).

b. Antibody Responses to Tumor Antigens

Antibodies against tumor associated antigens (TAA) are often elevated in cancer patients. Serum samples from patients treated with CGTG-602 were analyzed with indirect ELISA for antibodies against NY-ESO-1 MUC-1 (Ca15-3), CEA and survivin. Shortly, 200 μl of proteins (NY-ESO-1 and CEA) or peptides (survivin and MUC-1) in a concentration of 0.5 μg/ml were added on immulon 2HB plates (Thermo scientific, Milford, Mass., USA) for overnight coating at 4° C. Free binding sites were blocked with 2.5% BSA at room temperature. Serum samples were diluted 1:100 and added on the wells incubated at room temperature for 2 hours. After washing, plates were incubated with anti-human IgG conjugated to alkaline phosphatase and after washing, 1 step PNPP substrate (Pierce) was added for appropriate color reaction. After incubation for 30 minutes, reaction was stopped with 2M NaOH and absorbance at 405 nm was read. As a control, serum from 5 healthy donors was used to establish a cutoff value for elevated antibody level. Cutoff value was determined as the mean absorbance of the normal samples plus 2 standard deviations.

Figure 10:
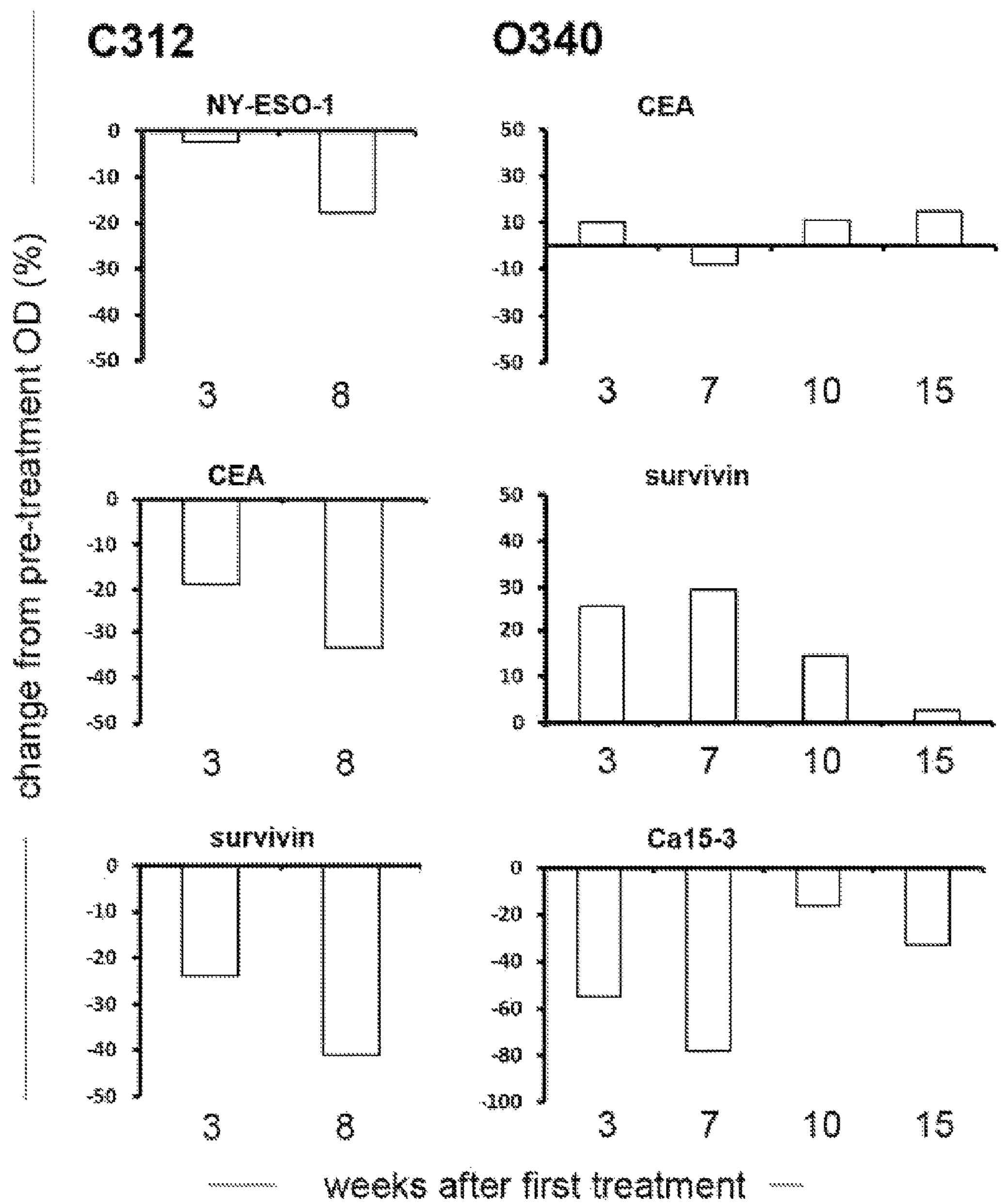
FIG. 10 shows the results obtained when antibodies against tumor associated antigens (TAAs) NY-ESO-1, CA-15-3, CEA and survivin were analyzed from patient serum (a) and ascites fluid and cells of patient O314 (b) before and after viral treatment, and the data is presented as proportional change (%) of antibody levels from pre-treatment value. (a) Treatment often resulted in decrease of elevated levels of antibodies against TAAs in patients that showed a concomitant decrease in marker levels (patients O314, R356, R319, O340). (b) Malignant ascites (resulting from peritoneal tumor masses) was removed from the peritoneal cavity of patient O314 before and 19 and 40 days after virus administration. Results were compared to control serum levels and data for those TAAs that were elevated at any time point are shown.
Figure 10:
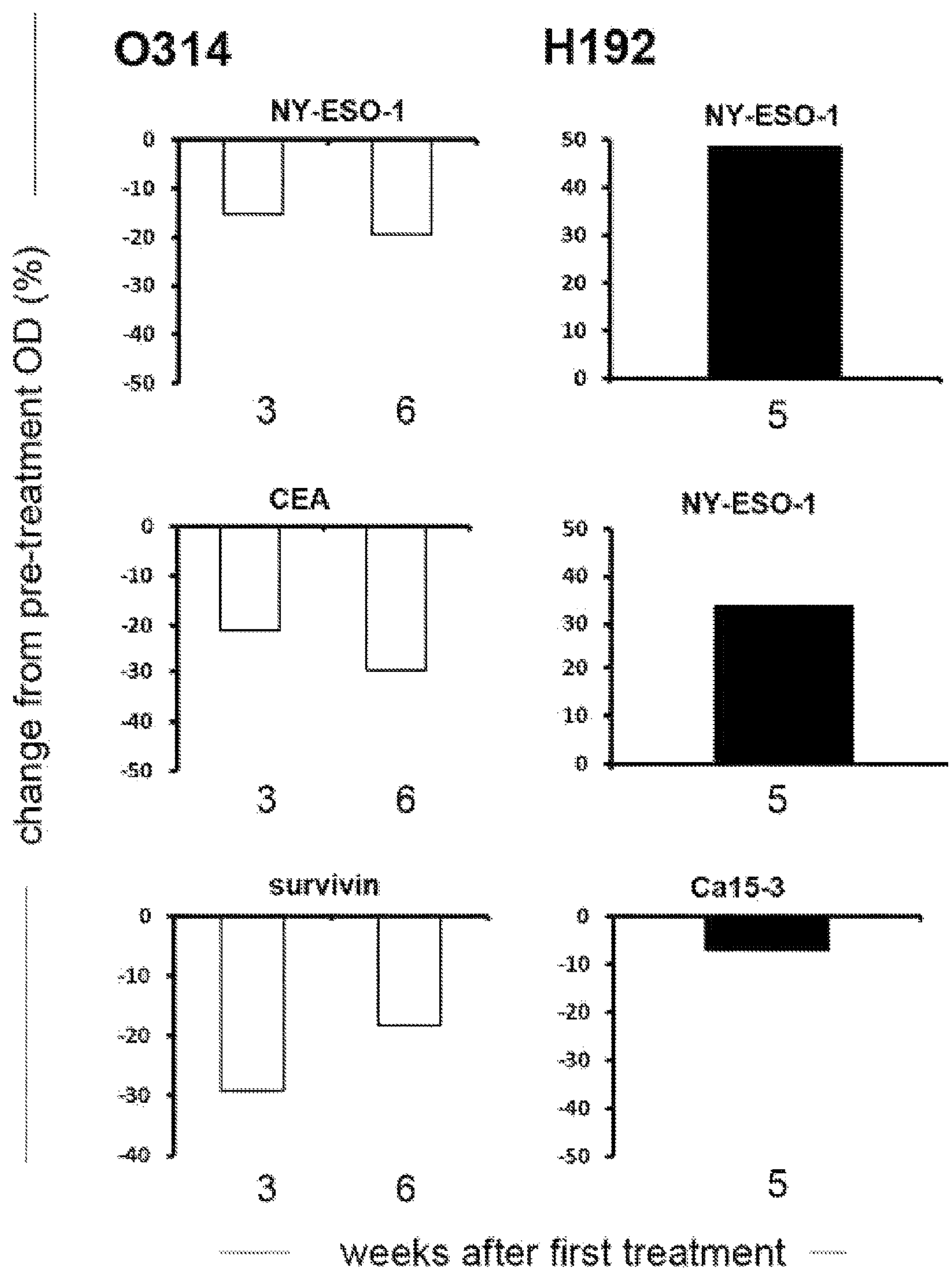
Figure 10:
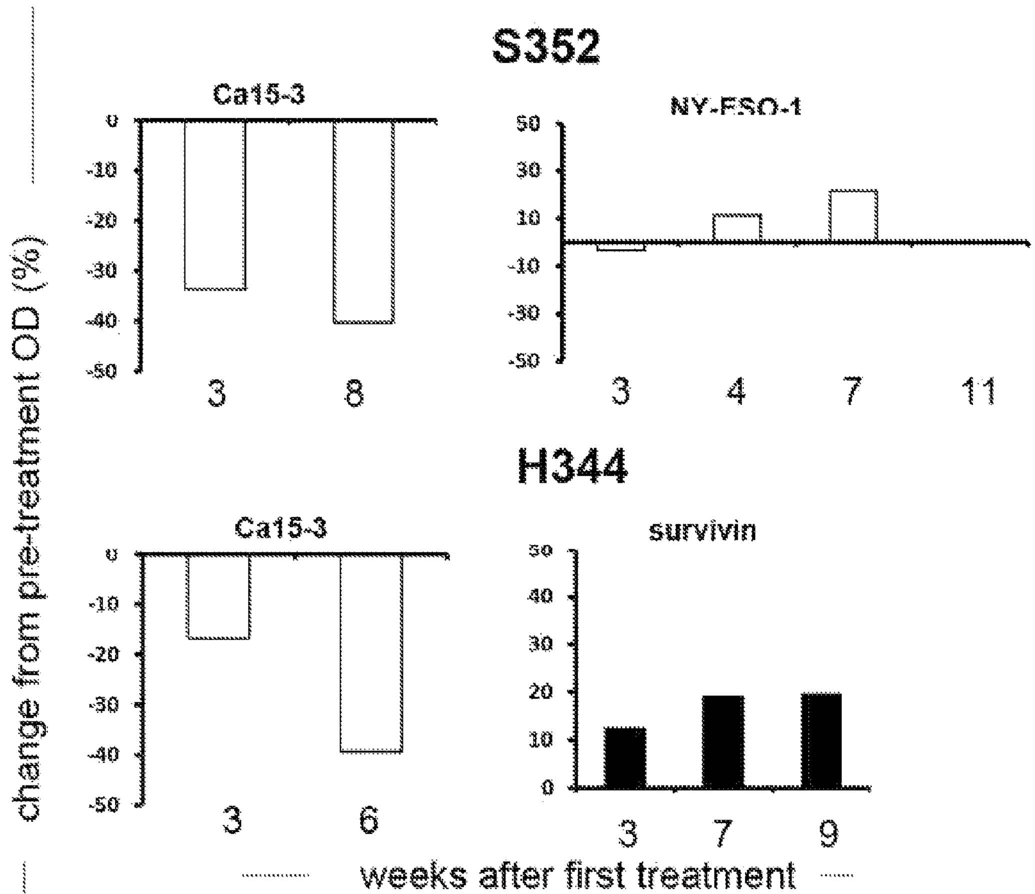
Figure 10:
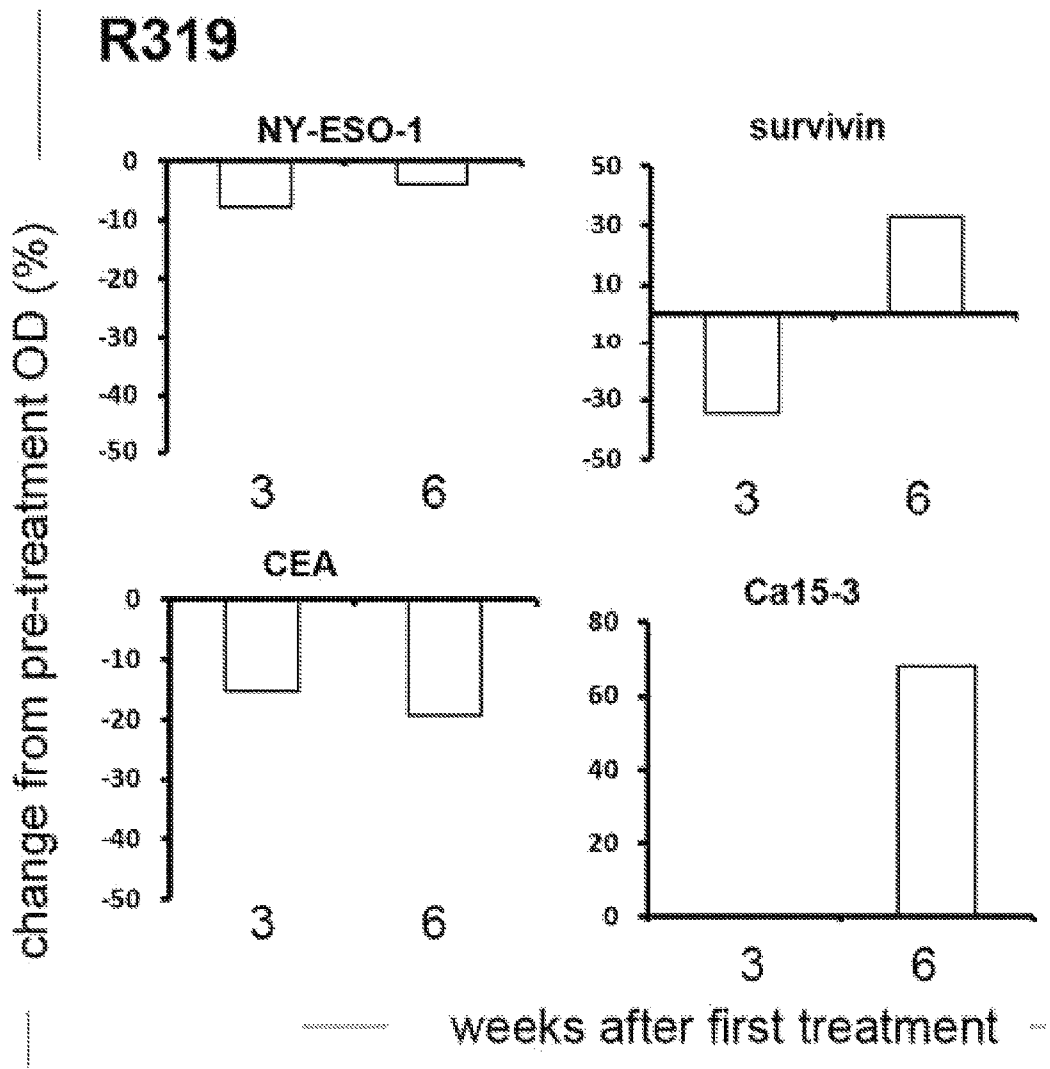
Figure 10:
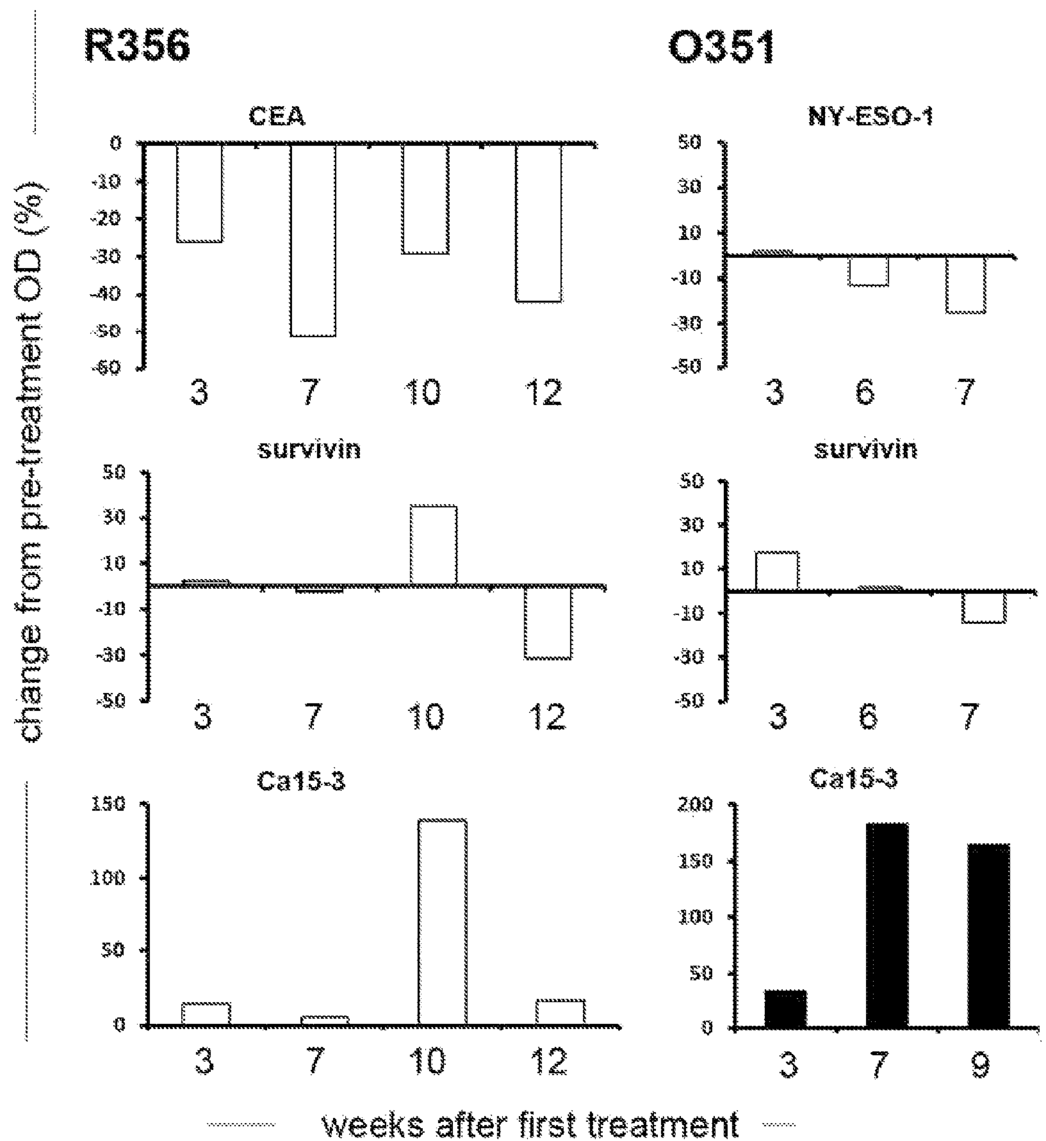

The changes in the antibody levels of those patients that had an elevated level at any timepoint are presented as percentage of the pre-treatment level in FIG. 10. Frequently, the elevated antibody levels decreased to normal levels due to the treatment with patients that otherwise benefited from the treatment (i.e. had decrease in elevated tumor marker levels or radiologic response). On the contrary, two of the patients that did not benefit from the treatment showed clear elevation in the antibody levels despite treatment (represented as black bars in FIG. 10). To this end, it was previously shown that a decrease in NY-ESO-1 antibody titers are associated with tumor regression (Jager et a. 1999, Int J Cancer 84:506-510). Furthermore, decrease of antibody levels in serum may indicate trafficking to tumor site.

Example 8

The Effect of KKTK Mutation on Viral Transduction

Figure 15:
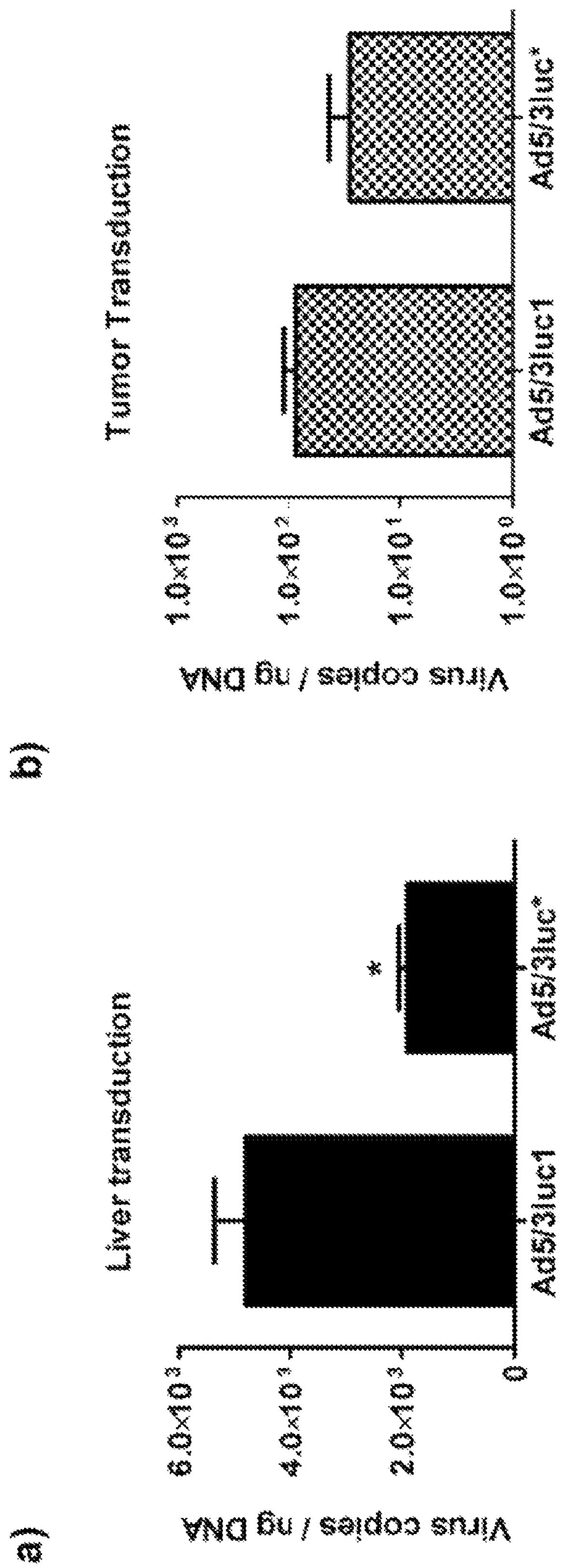
FIG. 15 shows that the mutation of the KKTK motif significantly reduces the viral transduction to liver (a), but contrary to previous reports does not significantly alter the transduction efficacy to tumors (b). Briefly, a non-replicating virus with a 5/3 chimeric capsid was used for intravenous injections in tumor bearing mice and the viral load in tissue was quantitated by qPCR.

To study the effect of the mutation on KKTK motif on viral transduction to cancer and liver, viral load was analyzed in liver and tumors of intravenously treated mice. Briefly, $2\times10^6$ M4A4-LM3 cells were inoculated to both upper most mammary fat pads of Nude NMRI mice and tumors were let to develop until circa 5 mm in diameters. $5\times10^{10}$ VP of Ad5/3 luc*(KKTK mutated virus) or the control virus Ad5/3 luc1 or Ad5 luc1 were administered by a single intravenous injection to the tail vein. After 30 minutes mice were sacrificed and livers and tumors collected. Viral load in the tissues was quantified by qPCR with primers and probes against adenoviral e4 region. qPCR for mouse 3-actin (primer mouse beta-actin-forward: CGACGCGTTCCGATGC, SEQ ID NO:25; primer mouse-beta-actin-reverse: TGGATGCCACAGGATTCCAT, SEQ ID NO:26; probe mouse beta-actin: $^6$FAM-AGGCTCTTTTCCAGCCTTCCTTCTTGG-TAMRA, SEQ ID NO:27) and human β-actin (primer Human beta-actin-forward: CAGCAGATGTGGATCAGCAAG, SEQ ID NO:22; primer Human beta-actin-reverse: CTAGAAGCATTTGCGGTGGAC, SEQ ID NO:23; probe Human beta-actin: $^6$FAM-AGGAGTATGACGAAGGCCCCTC-TAMRA, SEQ ID NO:24), for liver and tumor tissues respectively, was used to normalize viral titers to tissue DNA. The results indicate that the KKTK mutated Ad5/3 luc*exhibits reduced liver transduction while retaining tumor transduction in vivo (FIG. 15).

Figure 16:
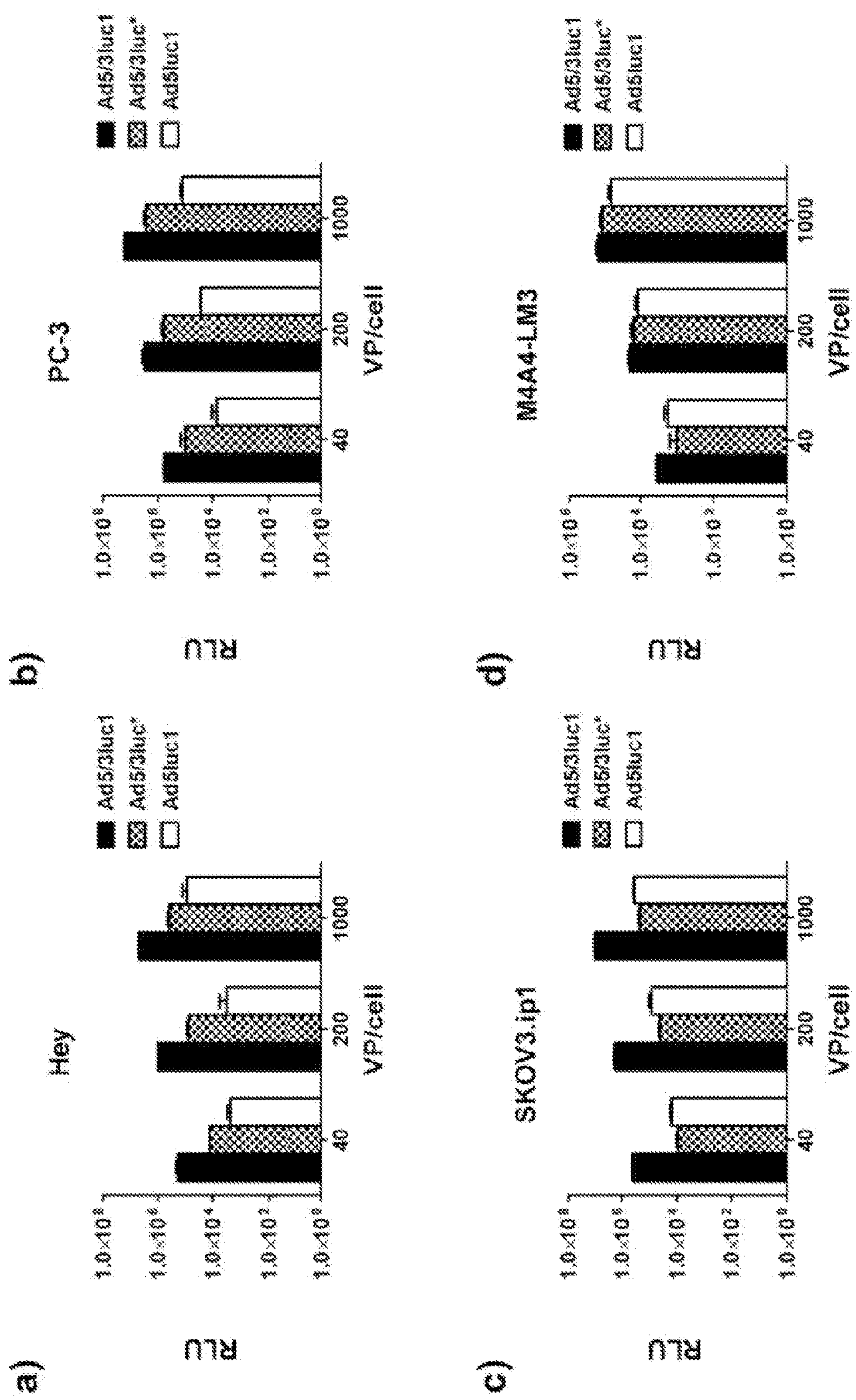
FIG. 16 shows that the mutation of the KKTK motif of a 5/3 chimeric virus results in transduction of cancer cell lines Hey (a), PC-3 (b), SKOV3.ip1 and M4A4-LMN3 (c) to similar degree as a virus with an unmodified capsid and in some case to similar degree as Ad5/3 Luc1.

To further verify that the KKTK mutation does not hinder viral transduction to cancer cells, in vitro transduction to various cancer cell lines was assessed (FIG. 16). Hey (ovarian adenocarcinoma), PC-3 (prostate cancer), Skov3.ip1 (ovarian adenocarcinoma), and M4A4-LM3 (breast ductal carcinoma) were infected with 200 VP/cell. Unbound virus was washed out after 1 h incubation and regular growth media was added. Cells were lysed and frozen after a total of 24 hours of incubation. Luciferase transgene activity was quantified as relative light units (RLU) by measuring luminosity emitted from cell lysates after addition of luciferin, the substrate for luciferase transgene. Capped bar indicates standard deviation of mean. The results show that the mutation in the fiber KKTK motif does not hamper viral transduction to cancer cell lines in vitro.

Example 9

The Effect of CpG

Figure 17:
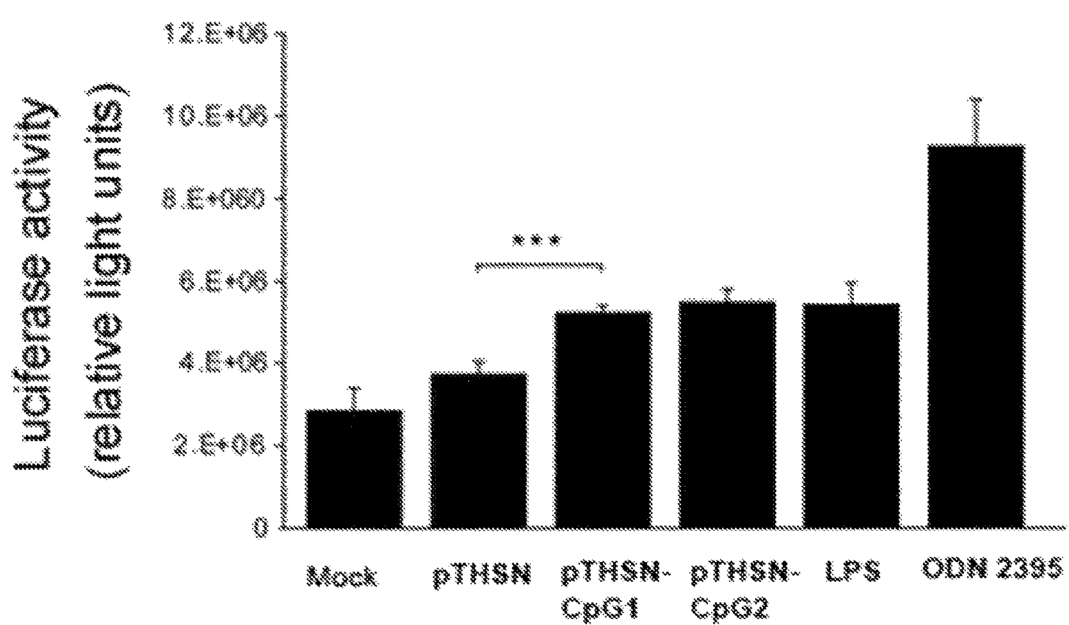
FIG. 17 shows that the CpG island induces NFkB activation via TLR-9 in 293-hTLR9 cells. A represents the actual luciferase signal from the imaging and B shows the results in a bar graph.
Figure 18A:
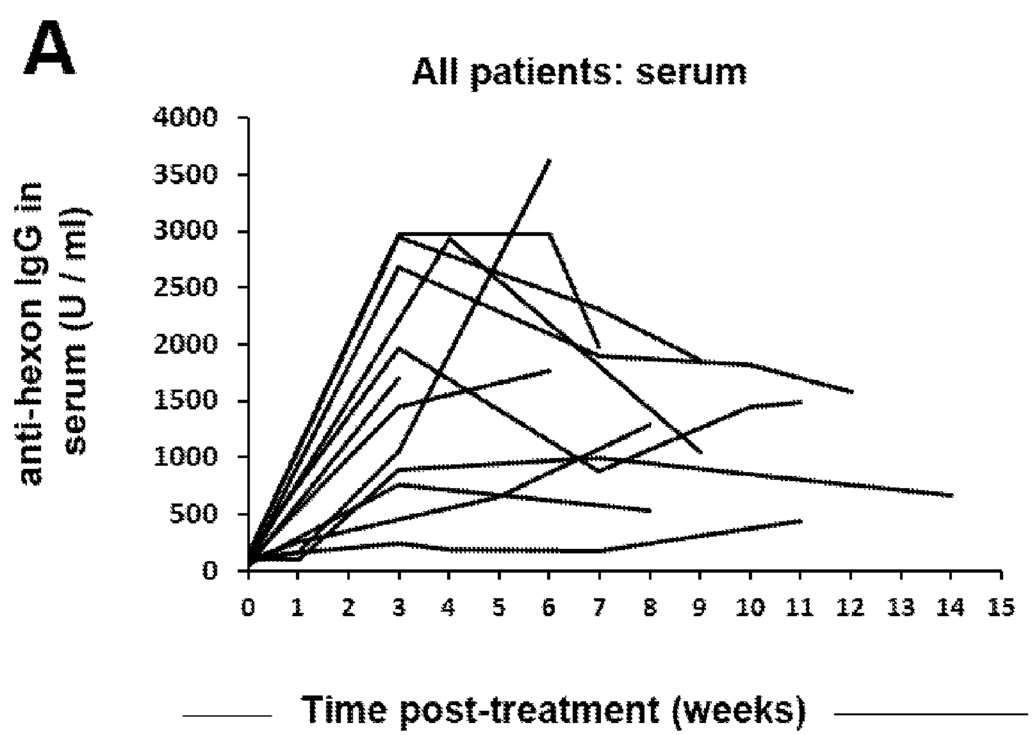
FIG. 18 shows antibody levels against serotype 5 hexon analyzed from serum of all patients (a) and ascites cells and fluid of patient O314 (b) before and after viral treatment. (a) In all patients, serum levels were above weakly positive value of 35 U/ml value before treatment but were dramatically elevated after treatment. (b) Ascites cells from patient O314 showed a value of 43 U/100 mg before and 471 U/100 mg after treatment, suggesting presence of CGTG-602 virus in the malignant cells. Ascites fluid values were elevated from 58 U/ml before treatment to 758 U/ml after treatment.
Figure 18B:
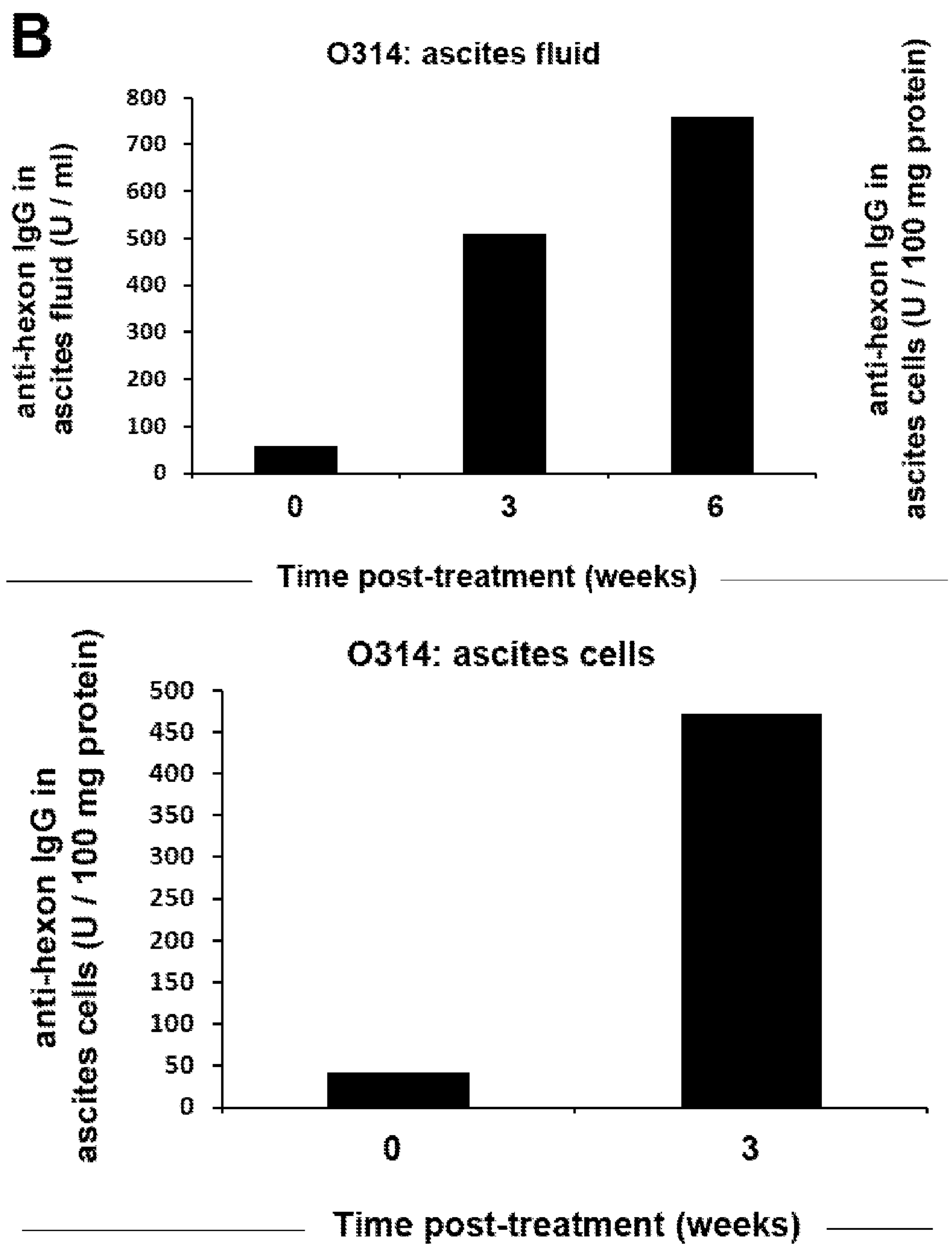

To analyze the feasibility of CpG islands in human cells, NFkB activation by pTHSN plasmid containing either one or two CpG islands was analyzed in 293-hTLR9 (Invivogen) cell line. 293hTLR9 is a cell line that expresses exclusively TLR9. Cells were transfected with a plasmid expressing luciferase driven by an NFkB-inducible promoter. 24 hours later pTSHN, pTSHN-CpG1 (with 1 island) and pTSHN-CpG2 (with 2 islands) were added to the media and 12 hours later luciferase was measured (FIG. 17). The luciferase activity was dependent on NFkB activation. Binding of CpG to TLR9 causes a conformational shift in the receptor, causing activation of NFkB. pTHSN without CpG was used as a negative control plasmid, lipopolysaccharide (LPS), a frequently used stimulator of signaling pathways and NFkB was used as a positive control and luciferase signal from mock treated cells were subtracted as background. The results indicate that the insertion of CpG to the viral genome functions through TLR9 to activate NFkB of the responding cell.

Example 10

Statistical Analysis

Two-tailed student's T-test was used to analyze the in vitro efficacy as well as the infective virus load in hepatocytes. One way analysis of variance (ANOVA) was used to assess tumor volume for hamster experiments. Survival data was processed with Kaplan-Meier analysis.

TABLE 1

Patients at baseline

| Patient ID | Age (y) | Sex | Diagnosis | Prior therapies | WHO |
|---|---|---|---|---|---|
| O314 | 62 | F | Ovarian cancer | surgery, docetaxel + carboplatin (x2), doxorubicin, weekly-paclitaxel, carboplatin, gemcitabine, topotecan | 1 |
| O337 | 69 | F | Ovarian cancer | surgery x 2, carboplatin + paclitaxel, carboplatin (x2), radiotherapy, carboplatin, topotecan, doxorubicin, tamoxifen | 2 |
| O340 | 74 | F | Ovarian cancer | surgery (x5), bleomycin, etoposide, cisplatin, letrozole | 0 |
| O351 | 72 | F | Ovarian cancer | surgery, paclitaxel + carboplatin (x3), gemcitabine + carboplatin, gemcitabine, doxorubicin, topotecan, etoposide, oxaliplatin, vinorelbin, tamoxifen | 2 |
| C312 | 54 | M | Rectum cancer | capecitabine, capecitabine + oxaliplatin, capecitabine + oxaliplatin + bevacizumab, irinotecan + bevacizumab, bevacizumab, cetuximab +5-FU-irinotecan (x2), oxaliplatin + SFU, bevacizumab | 1 |
| C332* | 49 | F | Colon cancer | surgery x 2, capecitabine + oxaliplatin + bevacizumab, capecitabine + irinotecan + bevacizumab, capecitabine + bevacizumab | 0 |
| H192 | 54 | M | Pancreatic cancer | gemcitabine, capecitabine, gemcitabine chemoradiation, gemcitabine + erlotinib | 1 |
| H344 | 58 | F | Pancreatic cancer | surgery, gemcitabine + erlotinib, gemcitabine + capecitabine; gemcitabine + oxaliplatin + capesitabine gemcitabine + erlotinib | 1 |
| I347 | 51 | M | Melanoma | surgery, DTIC + interferon, paclitaxel + carboplatin | 2 |
| R319 | 67 | F | Breast cancer | docetaxel (multiple), gemcitabine, cyclophosphamide + epirubicin + fluorouracil, capecitabine, vinorelbine + epirubicin + 5-FU, doxorubicin, tomerifene, letrozole, fulvestrant, exemestane medroxyprogesterone acetate | 1 |
| R342 | 54 | F | Breast cancer | surgery x2, cyclophosphamide, epirubicin, 5-FU, radiotherapy, docetaxel + capecitabine, capecitabine, doxorubicin, cisplatin + gemcitabine | 2 |
| R356 | 40 | F | Breast cancer | surgery x4, radiotherapy x 2, cyclophosphamide + epirubicin + 5-FU, vinoreibine + trastuzumab, capecitabine + lapatinib, paclitaxel + bevacizumab, docetaxel + epirubicin + capecitabine + bevacizumab, paclitaxel + gemcitabine | 1 |
| S352 | 59 | F | Sarcoma | surgery x 2 | 1 |
| S354 | 50 | F | Fibrosarcoma | surgery, ifosfamide + doxorubicin (x6), radiotherapy | 2 |

*patient C332 received only 1 CGTG-602 treatment prior to other virus treatments and is not included in all analysis

TABLE 2

| Treatment dose, number of treatments and virus sensitizers | | |
|---|---|---|
| Patient ID | Treatment dose, no. of treatments | Virus sensitizers |
| O314 | $1 \times 10^{11}$(1)<br>$3 \times 10^{11}$(2) | cyclophosphamide |
| O337 | $5 \times 10^{11}$(3) | cyclophosphamide |
| O340 | $5 \times 10^{11}$(3) | cyclophosphamide |
| O351 | $3 \times 10^{11}$(3) | cyclophosphamide |
| C312 | $1 \times 10^{11}$(1)<br>$3 \times 10^{11}$(2) | cyclophosphamide |
| C332 | $8 \times 10^{11}$(1) | — |
| H192 | $3 \times 10^{11}$(2) | cyclophosphamide, temozolomide, erlotinib |
| H344 | $8 \times 10^{11}$(3) | cyclophosphamide, temozolomide |
| I347 | $5 \times 10^{11}$(3) | cyclophosphamide, temozolomide |
| R319 | $3 \times 10^{11}$(1)<br>$5 \times 10^{11}$(2) | cyclophosphamide |
| R342 | $3 \times 10^{11}$(2) | cyclophosphamide |
| R356 | $1 \times 10^{12}$(4) | cyclophosphamide |
| S352 | $3 \times 10^{11}$(1)<br>$1 \times 10^{12}$(2) | cyclophosphamide, temozolomide |
| S354 | $3 \times 10^{11}$(4) | cyclophosphamide, temozolomide |

TABLE 4-continued

| Adverse events (occurring in percentage of 39 rounds of therapy in 14 patients) | | | | |
|---|---|---|---|---|
| | Grade 1 | Grade 2 | Grade 3 | Grade 4-5 |
| Chills | 8 | 3 | — | — |
| Rigors | 8 | 3 | — | — |
| Gastrointestinal | | | | |
| Anorexia | 5 | 10 | — | — |
| Nausea | 13 | 15 | — | — |
| Vomiting | 13 | 5 | — | — |
| Heartburn | 8 | — | — | — |
| Diarrhea | 3 | 5 | — | — |
| Constipation | 5 | 3 | — | — |
| Distension | 5 | 3 | — | — |
| Ileus | — | 3 | — | — |
| Feel of satietas | — | 3 | — | — |
| Neurologic and Ocular | | | | |
| Neuropathy | 5 | — | 3 | — |
| Muscle cramps | 3 | — | — | — |
| Pain | | | | |
| Injection site | 13 | 3 | — | — |
| Abdominal | 18 | 21 | 3 | — |
| Limbs | 3 | 13 | — | — |
| Back | — | 5 | — | — |
| Chest wall | 3 | — | 3 | — |

TABLE 3

| | Virus load in serum | | | | | | | | | | Treatment responses | | | |
|---|---|---|---|---|---|---|---|---|---|---|---|---|---|---|
| | Days post treatment | | | | | | | | | | | | | |
| Patient | after 1st | | | after 2nd | | | after 3rd | | | | PET or | | | Survival |
| ID | 0 | 1 | 3-8 | 0 | 1 | 3-8 | 0 | 1 | 3-10 | 14-55 | (%) | Marker | Other benefit | (days) |
| O314 | 0 | 0 | | 0 | <500 | | | 0 | 0 | | | mPR | | 71 |
| O337 | 0 | <500 | | | 0 | | 0 | <500 | | | | mSD | | 273* |
| O340 | 0 | 1141 | 3608 | 0 | <500 | 0 | 0 | <500 | 0 | 0 | MMR (−10.3%) | mCR | | 258* |
| O351 | | 0 | | 0 | <500 | 0 | 0 | 0 | 0 | | | mMR | | 87 |
| C312 | 0 | <500 | | 0 | <500 | | | <500 | | | SMD (+23%) | mPD | | 349* |
| H192 | 0 | 0 | | 0 | <500 | | | | | | | mPD | | 80 |
| H344 | 0 | <500 | 11523 | 0 | <500 | 0 | 0 | <500 | 0 | 0 | PMD | mPD | | 133 |
| I347 | 0 | <500 | 0 | 0 | <500 | 0 | 0 | <500 | | | | | | 106 |
| R319 | 0 | 0 | 0 | 0 | 0 | | 0 | <500 | | | PMR (−49.1%) | mPR | CR: non-injected mediastinal lesion | 332 |
| R342 | 0 | <500 | | | <500 | | | | | | | mPD | | 76 |
| R356 | 0 | <500 | | <500 | 876 | | | <500 | | | | mPR | | 102 |
| S352 | 0 | 0 | | 0 | <500 | 0 | 0 | 0 | | 0 | SMD (+6.1%) | | | 112 |
| S354 | 0 | 789 | | 0 | 0 | | | <500 | | 0 | CMR (−39%)[a] | | 39% reduction in tumor volume symptoms: clear improvement | 135* |

blanks indicate sample not available

*patient still alive

MMR: minor metabolic response; PMR: partial metabolic response; SMD; stable metabolic disease; PMD: progressive metabolic disease; CMR: complete metabolic response; mMR: marker minor response; mPR: marker partial response; mSD: marker stable disease; mPD: marker progressive disease; mCR: marker complete response

TABLE 4

| Adverse events (occurring in percentage of 39 rounds of therapy in 14 patients) | | | | |
|---|---|---|---|---|
| | Grade 1 | Grade 2 | Grade 3 | Grade 4-5 |
| Constitutional | | | | |
| Fever | 28 | 28 | 5 | — |
| Fatigue | 10 | 46 | — | — |

TABLE 4-continued

| Adverse events (occurring in percentage of 39 rounds of therapy in 14 patients) | | | | |
|---|---|---|---|---|
| | Grade 1 | Grade 2 | Grade 3 | Grade 4-5 |
| Headache | 8 | 3 | — | — |
| Flank | — | 5 | 3 | — |
| Others | 18 | 15 | 5 | — |

TABLE 4-continued

| Adverse events (occurring in percentage of 39 rounds of therapy in 14 patients) | | | | |
|---|---|---|---|---|
| | Grade 1 | Grade 2 | Grade 3 | Grade 4-5 |
| Pulmonary/Upper respiratory | | | | |
| Pneumothorax | 3 | — | — | — |
| Dyspnea | 5 | 5 | 3 | — |
| Cough | 3 | 3 | — | — |
| Lung infection | — | — | 3 | — |
| Hematological | | | | |
| Anemia | 13 | 26 | 5 | — |
| Leukocytopenia | 10 | 8 | 3 | — |
| Thrombocytopenia | 18 | — | — | — |
| Metabolic/Laboratory | | | | |
| AST elevation | 26 | 3 | — | — |
| Hypokalemia | 3 | — | — | — |
| Hyponatremia | 15 | — | 5 | — |
| Creatinine elevation | — | — | 3 | — |
| INR elevation | 3 | — | — | — |
| Other | | | | |
| Oedema | 8 | 8 | 3 | — |
| Urine incontinence | — | 3 | — | — |
| Hemorrhage | 5 | — | — | — |
| Flu-like symptoms | 3 | 5 | — | — |
| Flushing | — | — | 3 | — |
| Alopecia | 3 | — | — | — |
| Pruritus | — | 3 | — | — |
| Voice changes | 3 | — | — | — |

The invention claimed is:

1. A recombinant serotype 5 (Ad5) adenovirus comprising:
   a) a nucleic acid sequence encoding an E2F-1 promoter replacing the natural E1A adenoviral promoter;
   b) at least a 24 bp deletion (D24) in the Rb binding constant region 2 of E1;
   c) at least a deletion in gp19k/6.7K in E3; and
   d) a nucleic acid sequence encoding an immunostimulatory transgene inserted in the deletion in gp19k/6.7K.

2. The recombinant Ad5 adenovirus according to claim 1, further comprising a capsid modification.

3. The recombinant Ad5 adenovirus according to claim 2, wherein the capsid modification is a substitution wherein a region encoding Ad5 adenoviral fiber knob is replaced by the corresponding region from another adenovirus serotype.

4. The recombinant Ad5 adenovirus according to claim 1, further comprising a nucleic acid element which activates TLR9 comprising a CpG island inserted in an E3 region downstream of the immunostimulatory transgene.

5. The recombinant Ad5 adenovirus according to claim 2, wherein when the recombinant Ad5 adenovirus fiber knob region comprises Ad5 adenoviral fiber knob the adenovirus genome further comprises an RGD motif (Arg-Gly-Asp) inserted in the HI loop of the adenoviral fiber knob.

6. The recombinant Ad5 adenovirus according to claim 2, wherein when the recombinant Ad5 adenovirus fiber knob region comprises Ad5 adenoviral fiber knob the adenovirus genome comprises a polylysine motif introduced in the C terminus of the adenovirus fiber knob.

7. The recombinant Ad5 adenovirus according to claim 2, wherein when the recombinant Ad5 adenovirus fiber knob region comprises Ad3 adenoviral fiber knob, the nucleic acid modification in a fiber shaft region comprises a GAGA (SEQ ID NO: 28) motif substituted for the KKTK (SEQ ID NO: 29) motif.

8. The recombinant Ad5 adenovirus according to claim 1, wherein the virus genome further comprises at least one element selected from the group consisting of adenoviral immediate early genes, intermediate genes, and late genes.

9. A method of treating a cancer comprising administering to a subject suffering from the cancer the recombinant Ad5 adenovirus of claim 1, thereby treating the cancer.

10. A recombinant Ad5 adenovirus comprising the nucleic acid sequence according to SEQ ID NO: 1, 2, 3, 4, 5, 6, or 7.

11. A method of producing and recovering infectious recombinant Ad5 adenovirus articles comprising the steps of
   a) providing a recombinant Ad5 adenovirus comprising
      i) a nucleic acid sequence encoding an E2F-1 promoter replacing the natural EIA adenoviral promoter;
      ii) at least a 24 bp deletion (D24) in the Rb binding constant region 2 of E1;
      iii) at least a deletion in gp19k/6.7K in E3; and
      iv) a nucleic acid sequence encoding an immunostimulatory transgene inserted in the deletion in gp19k/6.7K,
   b) culturing the host cell under conditions allowing said recombinant Ad5 adenovirus to propagate and to produce infectious recombinant Ad5 adenovirus particles, and
   c) recovering said infectious recombinant Ad5 adenovirus particles.

12. A pharmaceutical composition comprising the recombinant Ad5 adenovirus according to claim 1 and a pharmaceutically acceptable carrier.

13. A virus particle comprising the recombinant Ad5 adenovirus according to claim 1.

14. An isolated host cell comprising the recombinant Ad5 adenovirus according to claim 1.

15. A method for inducing immunity directed against a cancer or treating a tumor in a subject comprising administering to the subject the recombinant Ad5 adenovirus of claim 1, wherein the immunostimulatory transgene encodes a tumor specific antigen that is expressed, and thereby induces immunity directed against the cancer or treating the tumor.

16. The method of claim 9 comprising administering the recombinant Ad5 adenovirus several times.

17. A method of treating a cancer comprising sequentially administering recombinant Ad5 adenoviruses, each adenovirus comprising:
   a) a nucleic acid sequence encoding E2F-1 promoter replacing the natural EIA adenoviral promoter;
   b) at least a 24 bp deletion (D24) in the Rb binding constant region 2 of E1;
   c) at least a deletion in gp19k/6.7K in E3;

d) a nucleic acid sequence encoding an immunostimulatory transgene inserted in the deletion in gp19k/6.7K; and e) a nucleic acid element which activates TLR9 comprising a CpG island inserted in an E3 region downstream of the immunostimulatory transgene;

wherein to avoid neutralizing antibodies in a subject a subsequent administration comprises a recombinant Ad5 adenovirus having a different fiber knob of the capsid compared to the recombinant Ad5 adenovirus used in the first administration, thereby treating the cancer.

18. The method of claim 17 comprising one or several administrations of the recombinant Ad5 serotype adenovirus and radiotherapy, surgery, or administering one or more agent selected from the group consisting of a virus sensitizer, chemotherapeutic agent, verapamil, calcium channel blocker, anti-CD20 therapy, and autophagy inducing agent.

19. The recombinant Ad5 adenovirus according to claim 3, wherein the other adenovirus serotype is Ad3.

20. The method of claim 1, wherein the immunostimulatory transgene is hGM-CSF.

21. A method of treating a cancer comprising administering to a subject, at the site of the cancer, the recombinant Ad5 adenovirus of claim 10, thereby treating the cancer.

22. The method of claim 21 comprising administering the recombinant Ad5 adenovirus several times.

23. The method of claim 21 comprising administering the recombinant Ad5 adenovirus several times, wherein to avoid neutralizing antibodies in a subject a subsequent administration comprises a recombinant Ad5 adenovirus having a different fiber knob of the capsid compared to the recombinant Ad5 adenovirus used in the first administration.

24. The method of claim 21 comprising one or several administrations of the recombinant Ad5 serotype adenovirus and radiotherapy, surgery, or administering one or more agent selected from the group consisting of a virus sensitizer, chemotherapeutic agent, verapamil, calcium channel blocker, anti-CD20 therapy, and autophagy inducing agent.

25. A method of producing and recovering infectious recombinant Ad5 adenovirus particles comprising the steps of a) providing a recombinant adenovirus comprising the nucleic acid sequence according to SEQ ID NO: 1, 2, 3, 4, 5, 6, or 7 inside a host cell permissive for adenovirus replication, b) culturing the host cell under conditions allowing said recombinant Ad5 adenovirus to propagate and to produce infectious recombinant Ad5 adenovirus particles, and c) recovering said infectious recombinant Ad5 adenovirus particles.

26. A pharmaceutical composition comprising the recombinant Ad5 adenovirus according to claim 10 and a pharmaceutically acceptable carrier.

27. A virus particle comprising the recombinant Ad5 adenovirus according to claim 10.

28. An isolated host cell comprising the recombinant Ad5 adenovirus according to claim 10.

29. A method for inducing immunity directed against a cancer or treating a tumor in a subject comprising administering to the subject the recombinant Ad5 adenovirus of claim 10, thereby inducing immunity directed against the cancer or treating the tumor.

* * * * *